United States Patent
Wilson et al.

(10) Patent No.: US 10,973,928 B2
(45) Date of Patent: *Apr. 13, 2021

(54) ADENO-ASSOCIATED VIRUS (AAV) CLADES, SEQUENCES, VECTORS CONTAINING SAME, AND USES THEREFOR

(71) Applicant: The Trustees of the University of Pennsylvania, Philadelphia, PA (US)

(72) Inventors: James M. Wilson, Philadelphia, PA (US); Guangping Gao, Westborough, MA (US); Mauricio R. Alvira, Philadelphia, PA (US); Luc H. Vandenberghe, Weston, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 160 days.

This patent is subject to a terminal disclaimer.

(21) Appl. No.: 16/045,043

(22) Filed: Jul. 25, 2018

(65) Prior Publication Data

US 2019/0015527 A1 Jan. 17, 2019

Related U.S. Application Data

(63) Continuation of application No. 15/227,418, filed on Aug. 3, 2016, now Pat. No. 10,265,417, which is a continuation of application No. 13/023,918, filed on Feb. 9, 2011, now abandoned, which is a continuation of application No. 10/573,600, filed as application No. PCT/US2004/028817 on Sep. 30, 2004, now Pat. No. 7,906,111.

(60) Provisional application No. 60/566,546, filed on Apr. 29, 2004, provisional application No. 60/508,226, filed on Sep. 30, 2003.

(51) Int. Cl.

| | |
|---|---|
| *C12N 15/864* | (2006.01) |
| *C12N 7/00* | (2006.01) |
| *C12N 15/37* | (2006.01) |
| *C12N 15/11* | (2006.01) |
| *A61K 48/00* | (2006.01) |
| *A61K 39/42* | (2006.01) |
| *C07K 14/005* | (2006.01) |
| *C12N 15/86* | (2006.01) |
| *C07K 14/705* | (2006.01) |
| *C12N 9/64* | (2006.01) |

(52) U.S. Cl.
CPC ............ *A61K 48/00* (2013.01); *C07K 14/005* (2013.01); *C07K 14/705* (2013.01); *C12N 7/00* (2013.01); *C12N 9/644* (2013.01); *C12N 15/86* (2013.01); *C12Y 304/21022* (2013.01); *C12N 2750/14121* (2013.01); *C12N 2750/14122* (2013.01); *C12N 2750/14142* (2013.01); *C12N 2750/14143* (2013.01); *C12N 2750/14151* (2013.01); *C12N 2830/008* (2013.01); *C12N 2830/48* (2013.01); *C12N 2830/85* (2013.01)

(58) Field of Classification Search
None
See application file for complete search history.

(56) References Cited

U.S. PATENT DOCUMENTS

| | | | |
|---|---|---|---|
| 5,866,552 A | 2/1999 | Wilson et al. | |
| 6,156,303 A | 12/2000 | Russell et al. | |
| 6,498,244 B1 | 12/2002 | Patel et al. | |
| 6,759,237 B1 | 7/2004 | Wilson et al. | |
| 7,056,502 B2 | 6/2006 | Hildinger et al. | |
| 7,198,951 B2 | 4/2007 | Gao et al. | |
| 7,282,199 B2 | 10/2007 | Gao | |
| 7,588,772 B2 | 9/2009 | Kay et al. | |
| 7,790,449 B2 | 9/2010 | Gao | |
| 7,906,111 B2 * | 3/2011 | Wilson .................... | A61P 7/00 424/93.2 |
| 8,318,480 B2 | 11/2012 | Gao | |
| 8,524,446 B2 | 9/2013 | Gao | |
| 8,628,966 B2 | 1/2014 | Chatterjee et al. | |
| 8,906,675 B2 | 12/2014 | Gao | |
| 8,962,330 B2 | 2/2015 | Gao | |
| 8,962,332 B2 | 2/2015 | Gao | |
| 9,677,088 B2 | 6/2017 | Nakai et al. | |
| 10,265,417 B2 * | 4/2019 | Wilson ..................... | C12N 7/00 |
| 10,406,173 B2 * | 9/2019 | Wilson .................. | A61K 38/47 |
| 10,485,883 B2 * | 11/2019 | Wilson ..................... | A61P 7/04 |
| 2003/0138772 A1 | 7/2003 | Gao et al. | |
| 2003/0228282 A1 | 12/2003 | Gao et al. | |
| 2004/0057931 A1 | 3/2004 | Wilson et al. | |
| 2004/0057932 A1 | 3/2004 | Wilson et al. | |
| 2004/0057933 A1 | 3/2004 | Wilson et al. | |
| 2005/0014262 A1 | 1/2005 | Gao et al. | |
| 2007/0243526 A1 | 10/2007 | Kay et al. | |
| 2009/0197338 A1 | 8/2009 | Vandenberghe et al. | |
| 2015/0176027 A1 | 6/2015 | Gao | |

FOREIGN PATENT DOCUMENTS

| | | |
|---|---|---|
| EP | 1310571 | 2/2006 |
| WO | WO-1998/009657 A2 | 3/1998 |

(Continued)

OTHER PUBLICATIONS

Lee et al., Adeno-Associated Virus (AAV) Vectors: Rational Design Strategies for Capsid Engineering, Curr Opin Biomed Eng., vol. 7: 58-63, Sep. 2018.

(Continued)

*Primary Examiner* — Maria Marvich
(74) *Attorney, Agent, or Firm* — Howson & Howson LLP; Colleen M. Schaller

(57) ABSTRACT

Sequences of novel adeno-associated virus capsids and vectors and host cells containing these sequences are provided. Also described are methods of using such host cells and vectors in production of rAAV particles. AAV-mediated delivery of therapeutic and immunogenic genes using the vectors of the invention is also provided.

11 Claims, 125 Drawing Sheets

Specification includes a Sequence Listing.

(56) References Cited

FOREIGN PATENT DOCUMENTS

| WO | WO-1998/011244 | 3/1998 |
|---|---|---|
| WO | WO-1999/061601 | 12/1999 |
| WO | WO-2000/028061 | 5/2000 |
| WO | WO-2001/083692 A3 | 11/2001 |
| WO | WO-2003/042397 A2 | 5/2003 |
| WO | WO-2003-052051 A2 | 6/2003 |
| WO | WO-2003/052052 A2 | 6/2003 |
| WO | WO-2016/049230 A1 | 3/2016 |
| WO | WO-2018/160582 | 9/2018 |

OTHER PUBLICATIONS

Kondylis et al., Analytical Techniques to Characterize the Structure, Properties and Assembly of Virus Capsids, Anal. Chem., vol. 91:622-636, Jan. 2019.
Bell et al., Identification of the Galactose Binding Domain of the Adeno Associated Virus Serotype 9 Capsid, Journal of Virology, vol. 86(13): 7326-7333, Jul. 2012.
Hinderer et al, Severe Toxicity in nonhuman primates and piglets following hi-dose intravenous administration of an adeno-associated virus vector expressing human SMN, Human Gene Therapy, 29(3):285-98 (Jan. 29, 2018).
Flotte and Buning, Severe Toxicity in Nonhuman Primates and Piglets with Systemic High-Dose Administration of Adeno-Associated Virus Serotype 9—Like Vectors: Putting Patients First, Human Gene Therapy, 29(3):283-4 (Jan. 29, 2018).
Daley, J., Severe Toxicity Reported in High-Dose AAV Gene Therapy in Animals, The Scientist, Jan. 31, 2018, printed from https://www.the-scientist.com/the-nutshell/severe-toxicity-reported-in-high-dose-aav-gene-therapy-in-animals-30348.
Sheridan, C., Gene therapy rescues newborns with spinal muscular atrophy, Nature Biotechnology, 36(8): 669-70 (Aug. 2018).
Nzilambi et al., The prevalence of infection with human immunodeficiency virus over a 10-year period in rural zaire, NE J Med, 318(5):276-279, Feb. 1988.
Kawamura et al., Hiv-2 in West Africa in 1966, The Lancet, Feb. 1989, 385.
Le Guenno, HIV1 and HIV2: two ancient viruses for a new disease? Transactions of the Royal Society of Tropical Medicine and Hygiene, 1989, 83, 847.
Faria et al., The early spread and epidemic ignition of HIV-1 in human populations, Science, Oct. 2014, 346(6205):56-61.
F. Gao et al., Origin of HIV-1 in the chimpanzee Pan troglodytes troglodytes, Nature, Feb. 1999, 397 :436-440.
Moskaleno et al., Epitope Mapping of Human Anti-Adeno-Associated Virus Type 2 Neutralizing Antibodies: Implications for Gene Therapy and Virus Structure, J Virol, Feb. 2000, 74(4):1761-6.
Wobus et al., Monoclonal Antibodies against the Adeno-Associated Virus Type 2 (AAV-2) Capsid: Epitope Mapping and identification of Capsid Domains Involved in AAV-2-Cell Interaction and Neutralization of AAV-2 Infection, J Virol, Oct. 2000, 74(19) :9281-93.
Nam et al., Structure of Adeno-Associated Virus Serotype 8, a Gene Therapy Vector, J Virol, 81(22) :12260-71, Nov. 2007.
Shen et al., Characterization of the Relationship of AAV Capsid Domain Swapping to Liver Transduction Efficiency, Mol Ther, Aug. 2007, 15(11):1955-62.
Wang et al., Comparative Study of Liver Gene Transfer With AAV Vectors Based on Natural and Engineered AAV Capsids, Molecular Therapy, Dec. 2015, 23(12): 1877-87.
Hu et al., RH10 provides superior transgene expression in mice when compared with natural AAV serotypes for neonatal gene therapy, J. Gene Med, Sep. 2010, 12(9): 766-778.
Girod et al., The VP1 capsid protein of adeno-associated virus type 2 is carrying a phospholipase A2 domain required for virus infectivity, J. General Virol, 2002, 83:973-978.
Grieger et al, Surface-Exposed Adeno-Associated Virus Vpl-NLS Capsid Fusion Protein Rescues Infectivity of Noninfectious Wild-Type Vp2/Vp3 and , Vp3—Only Capsids but Not That of Fivefold Pore Mutant Virions, J. Virol, 81(15):7833-7483, Aug. 2007.
Warrington et al, Adeno-Associated Virus Type 2 VP2 Capsid Protein Is Nonessential and Can Tolerate Large Peptide Insertions at Its N Terminus, J Virol, 78(1):6595-6609, Jun. 2004.
Li et al, 2015, Site-Directed Mutagenesis of Surface-Exposed Lysine Residues Leads to Improved Transduction by AAV2,But Not AAV8, Vectors in Murine Hepatocytes In Vivo, Hum Gene Ther Methods. Oct. 2015;26(6):211-20.
Grosse et al, Relevance of Assembly-Activating Protein for Adeno-associated Virus Vector Production and Capsid Protein Stability in Mammalian and Insect Cells, J Virol 91:e01198-17, Aug. 2017.
Sonntag et al, A viral assembly factor promotes AAV2 capsid formation in the nucleolus, PNAS, 107(22):10220-5, Jun. 2010.
Liu et al, Neutralizing antibodies against AAV2, AAV5 and AAV8 in healthy and HIV-1-infected subjects in China: implications for gene therapy using AAV vectors, Gene Therapy, 21:732-738, May 2014.
Mimuro et al, The Prevalence of Neutralizing Antibodies Against Adeno-Associated Virus Capsids Is Reduced in Young Japanese Individuals, J. Med Virol, 86:1990-7 Oct. 2013.
Mao, et al. Angiotensin 1-7 Overexpression Mediated by a Capsid-optimized AAV8 Vector Leads to Significant Growth Inhibition of Hepatocellular Carcinoma In vivo, Int. J. Biol. Sci, 14, Jan. 2018.
Ling et al., Human Hepatocyte Growth Factor Receptor is a Cellular Coreceptor for Adeno-Associated Virus Serotype 3, Human Gene Therapy, 21:1741-1747 (Dec. 2010).
Suhy et al. Safe, Long-term Hepatic Expression of Anti-HCV shRNA in a Nonhuman Primate Model, Mol Ther. Sep. 2012;20(9):1737-49. doi:. 10.1038/mt.2012.119. Epub Jun. 26, 2012.
Ling et al, Selective In Vivo Targeting of Human Liver Tumors by Optimized AAV3 Vectors in a Murine Xenograft Model, Hum Gene Ther. Dec. 2014;25(12):1023-34.
Vercauteren, Superior In vivo Transduction of Human Hepatocytes Using Engineered AAV3 Capsid, Mol Therapy, 24(6):1042-1049, Jun. 2016.
Chirmule et al., Immune responses to adenovirus and adeno-associated virus in humans, Gene Therapy, 6:1574-1583, Sep. 1999.
Bevan et al, Systemic Gene Delivery in Large Species for Targeting Spinal Cord, Brain, and Peripheral Tissues for Pediatric Disorders, Mol Ther. Nov. 2011;19(11):1971-80. doi: 10.1038/mt.2011.157. Epub Aug. 2, 2011.
Messina et al., 2012, Repeat Transduction in the Mouse Lung by Using Adeno-Associated Virus Vectors with Different Serotypes.
Halbert et al., Repeat Transduction in the Mouse Lung by Using Adeno-Associated Virus Vectors with Different Serotypes, J. Virol, 74(3):1524-1532, Feb. 2000.
Wu, Asokan & Samulski, Adeno-associated Virus Serotypes: Vector Toolkit for Human Gene Therapy, Molecular Therapy, 14(3):316-327, Sep. 2006.
Chen et al., Epidemiology of hepatitis B virus infection in the Asia-Pacific region, J Gastroenterol Hepatol. May 2000;15 Suppl:E3-6.
Looker et al., An estimate of the global prevalence and incidence of herpes simplex virus type 2, Bull World Health Organ. Oct. 2008;86(10):805-12, A.
Hamilton et al., Adenoviral-Mediated Gene Transfer to Murine Small Intestine Is More Efficient in Neonates Than Adults, J Pediatr Surg. Feb. 1997;32(2):373-7.
Ellis et al, Virology Journal, Mar. 2013, A survey of ex vivo/in vitro transduction efficiency of mammalian primary cells and cell lines with Nine natural adeno-associated virus (AAV1-9) and one engineered adeno-associated virus serotype, 10:74.
Giles et al, Deamidation of Amino Acids on the Surface of Adeno-Associated Virus Capsids Leads to Charge Heterogeneity and Altered Vector Function, Mol Ther, 26(12), Dec. 2018.
Adachi K et al., Drawing a high-resolution functional map of adeno-associated virus capsid by massively parallel sequencing, Nat Commun, 5:3075, Jan. 17, 2014.

(56) References Cited

OTHER PUBLICATIONS

Afione SA et al., In vivo model of adeno-associated virus vector persistence and rescue, Journal of Virology, vol. 70(5):3235-3241, May 1996.
Black A et al., Adeno-associated virus 8-mediated gene therapy for choroideremia: preclinical studies in in vitro and in vivo models, The Journal of Gene Medicine, vol. 16:122-130, Jun. 24, 2014.
Brown KE et al., Cloning and sequencing of the simial parvovirus genome, Virology, vol. 210:314-322, May 1995.
Büning et al., Receptor targeting of adeno-associated virus vectors, Gene Therapy, vol. 10, pp. 1142-1151, (Jan. 2003).
Muzyczka and Berns, Chapter 69—Parvoviridae: The Viruses and Their Replication, Fields Virology—4th Ed., pp. 2327-2359, 2001.
Charan RA et al., Adeno-associated Virus Serotype 8 (AAV8) Delivery of Recombinant A20 to Skeletal Muscle Reduces Pathological Activation of Nuclear Factor (NF)-kB in Muscle of mdx Mice, Molecular Medicine, vol. 18:1527-35, Feb. 2013. (Epub Nov. 6, 2012).
Childers MK et al., Gene Therapy Prolongs Survival and Restores Function in Murine and Canine Models of Myotubular Myopathy, Sci Transl Med, vol. 6(220):1-31, Jan. 22, 2014.
ClinicalTrials.org, "AAV8 Vector Trials", Nov. 2017.
Dai X et al., Long-term retinal cone rescue using a capsid mutant AAV8 vector in a mouse model of CNGA3-achromatopsia, PLOS One, vol. 12(11):e0188032, Nov. 13, 2017.
Dimattia MA et al., Structural insight into the unique properties of Adeno-Associated Virus Serotype 9, J. Virol, 86(12):6947-58, Jun. 2012. (Epub Apr. 11, 2012).
Durigon EL et al., Multiple primer pairs for polymerase chain reaction (PCR) amplification of human parvovirus B19 DNA, Journal of Virological Methods, vol. 44:155-65, Feb. 1993.
Fischer MD et al., Codon-Optimized RPGR Improves Stability and Efficacy of AAV8 Gene Therapy in Two Mouse Models of X-Linked Retinitis Pigmentosa, Molecular Therapy, vol. 25(8):1854-65, Aug. 2, 2017. (Epub May 24, 2017).
Gao G et al., Adeno-Associated Viruses Undergo Substantial Evolution in Primates During Natural Infections, PNAS, vol. 100(10):6081-86, May 13, 2003. (Epub Apr. 25, 2003).
Gao G et al., Clades of Adeno-Associated Viruses are Widely Disseminated in human Tissues, Journal of Virology, vol. 78(12):6381-6388, Jun. 2004.
Gao G et al., Erythropoietin Gene Therapy Leads to Autoimmune Anemia in Macaques, Blood, vol. 103(9):3300-2, May 2004.
Gao GP et al., Novel adeno-associated viruses from rhesus monkeys as vectors for human gene therapy, PNAS, vol. 99(18):11854-59, Sep. 2002. (Epub Aug. 21, 2002).
Gao GP et al., Biology of Adenovirus vectors with E1 and E4 deletions for liver-directed gene therapy, Journal of Virology, vol. 70(12):8934-8943, Dec. 1996.
GenBank entry AF513851, Sep. 2002.
GenBank entry AF513852, Sep. 2002.
Gilkes JA et al., Mucopolysaccharidosis IIIB confers enhanced neonatal intracranial transduction by AAV8 but not by 5, 9 or rh10, Gene Therapy, vol. 23(3):263-271, Mar. 2016. (Epub Dec. 16, 2015).
Girod A et al. Genetic capsid modifications allow efficient retargeting of adeno-associated virus type 2. Nat Med. 5(9):1052-6. Sep. 1999.
Govindasamy L et al., Structural insights into adeno-associated virus serotype 5, Journal of Virology. 87(20):11187-99, Oct. 2013. (Epub Aug. 7, 2013).
Green SW et al., Rhesus and pig-tailed macaque parvoviruses: identification of two new members of the erythrovirus genus in monkeys, Virology, vol. 269:105-12, Mar. 30, 2000.
Grifman M et al., Incorporation of Tumor-Targeting Peptides into Recombinant Adeno-Associated Virus Capsids, Molecular Therapy, 3(6):964-75, Jun. 2001.

Grimm D and Kay MA, From Virus Evolution to Vector Revolution: Use of Naturally Occurring Serotypes of Adeno-Associated Virus (AAV) as Novel Vectors for Human Gene Therapy, Current Gene Therapy, 3(4)281-304, Aug. 2003.
Guo HH et al., Protein tolerance to random amino acid change, PNAS, 101(25):9205-10, Jun. 22, 2004. (Epub Jun. 14, 2004).
Gurda BL et al., Capsid antibodies to different adeno-associated virus serotypes bind common regions, Journal of Virology, 87(16):9111-24, Aug. 2013. (Epub Jun. 12, 2013).
Hernandez YJ et al., Latent Adeno-associated virus infection elicits humoral but no cell-mediated immune responses in a nonhuman primate model, Journal of Virology, vol. 73(10):8549-58, Oct. 1999.
Kotin RM, Prospects for the Use of Adeno-Associated Virus as a Vector for Human Gene Therapy, Human Gene Therapy, 5(7):793-801, Jul. 1994.
Lesk AM and Whisstock JC, Prediction of protein function from protein sequence and structure, Quarterly Reviews of Biophysics, 36(3):27-8, Aug. 2003.
Lochrie MA et al., Mutations on the External Surfaces of Adeno-Associated Virus Type 2 Capsids that Affect Transduction and Neutralization, Journal of Virology, 80(2):821-34, Jan. 2006.
Lytle AM et al., Effects of FVIII immunity on hepatocyte and hematopoietic stem cell-directed gene therapy of murine hemophilia A, Methods & Clinical Development, vol. 3:15056, Feb. 10, 2016.
Molecular Therapy, "Information for Authors", pp. 1-13.
Mountz JD et al., Monkey See, Monkey Do, Gene Therapy, vol. 10(3):194-6, Feb. 2003.
Davidson AR, "Chapter 8—Multiple Sequence Alignment as a Guideline for Protein Engineering Strategies" in Protein Design Methods and Applications, Eds., R Guerois & M Lopez de la Paz, Human Press, Totowa, New Jersey, 2006.
Pignataro D et al., Adeno-Associated Viral Vectors Serotype 8 for Cell-Specific Delivery of Therapeutic Genes in the Central Nervous System, Frontiers in Neuroanatomy, vol. 11(2):1-13, Feb. 10, 2017.
Rabinowitz JE et al., Cross-Packaging of a Single Adeno-Associated Virus (AAV) Type 2 Vector Genome into Multiple AAV Serotypes Enables Transduction with Broad Specificity, J Virol., 76(2):791-801, Jan. 2002.
Richards FM, Protein stability: still an unsolved problem, Cellular and Molecular Life Sciences, 53(10):790-802, Oct. 1997.
Ruffing M et al., Assembly of viruslike particles by recombinant structural proteins of adeno-associated virus type 2 in insect cells, J Virol., vol. 66(12):6922-30, Dec. 1992.
Rutledge EA et al., Infectious clones and vectors derived from adeno-associated virus (AAV) serotypes other than AAV type 2, Journal of Virology, vol. 72(1):309-319, XP-002137089, Jan. 1998.
Schnell MA et al., Activation of innate immunity in nonhuman primates following intraportal administration of adenoviral vectors, Molecular Therapy, vol. 3(5):708-722, May 2001.
Smith LJ et al., Gene transfer properties and structural modeling of human stem cell-derived AAV, Mol. Ther., 22(9):1625-34, Sep. 2014. (Epub Jun. 13, 2014).
UniProtKB/Swiss-Prot: Q6JC13, (downloaded Aug. 10, 2012).
Van Vliet KM et al., The role of the adeno-associated virus capsid in gene transfer, Methods Mol Biol, 437:51-91, 2008.
Wang L et al., Enhancing Transgene Expression from Recombinant AAV8 Vectors in Different Tissues Using Woodchuck Hepatitis Virus Post-Transcriptional Regulatory Element, International Journal of Medical Sciences, vol. 13(4):286-291, Apr. 1, 2016.
Weitzman MD et al., Adeno-associated virus (AAV) Rep proteins mediate complex formation between AAV DNA and its integration site in human DNA, PNAS, vol. 91:5808-5812, Jun. 21, 1994.
Wu P et al. Mutational analysis of the adeno-associated virus type 2 (AAV2) capsid gene and construction of AAV2 vectors with altered tropism. J Virol. 74(18):8635-47, Sep. 2000.
Xiao W et al., Gene therapy vectors based on adeno-associated virus type 1, Journal of Virology, 73(5):3994-4003, May 1999.
Xie Q et al., The atomic structure of adeno-associated virus (AAV-2), a vector for human gene therapy, PNAS, 99(16):10405-10, Jul. 22, 2002.

(56) References Cited

OTHER PUBLICATIONS

Xie Q et al., Towards the atomic structure of the adeno-associated virus 2 capsid, Infectious Disease Review, from the VIIIth Parvbovirus Workshop, Mont Tremblant, Quebec, Canada, vol. 2(3):136, (Jun. 28-Jul. 20, 2000).

Xie Q et al., Structure-function analysis of receptor-binding in adeno-associated virus 6 (AAV-6), Virology, 420(1):10-9, Nov. 10, 2011. (Epub Sep. 13, 2011).

Zadori Z et al., A viral phospholipase A2 is required for parvovirus infectivity, Developmental Cell, vol. 1:291-302, Aug. 2001.

Zhang HG et al., Addition of Six-His-Tagged Peptide to the C Terminus of Adeno-Associated Virus VP3 Does Not Affect Viral Tropism or Production, Journal of Virology, 76(23):12023-31, Dec. 2002.

Zhu T et al., Sustained Whole-Body Functional Rescue by Systemic Delivery of AAV8 Vectors in Heart Failure and Muscular Dystrophy Hamsters, Molecular Therapy, vol. 11(suppl 1):916, May 2005.

* cited by examiner

Fig. 2A

| hu.27-B | 1 | MAADGYLPDWLEDTLSEGIRQWWKLKPGPPPPKPAERHKDDSRGLVLPGYKYLGPFNGLDKGEPVNEADA |
| hu.21-B | 1 | MAADGYLPDWLEDTLSEGIRQWWKLKPGPPPPKPAERHKDDSRGLVLPGYKYLGPFNGLDKGEPVNEADA |
| hu.22-B | 1 | MAADGYLPDWLEDTLSEGIRQWWKLKPGPPPPKPAERHKDDSRGLVLPGYKYLGPFNGLDKGEPVNEADA |
| hu.23-B | 1 | MAADGYLPDWLEDTLSEGIRQWWKLKPGPPPPKPAERHKDDSRGLVLPGYKYLGPFNGLDKGEPVNEADA |
| hu.7-C | 1 | MAADGYLPDWLEDTLSEGIRQWWKLKPGPPPPKPAERHKDDSRGLVLPGYKYLGPFNGLDKGEPVNEADA |
| hu.61-C | 1 | MAADGYLPDWLEDTLSEGIRQWWKLKPGPPPPKPAERHKDDSRGLVLPGYKYLGPFNGLDKGEPVNEADA |
| hu.56-C | 1 | MAADGYLPDWLEDTLSEGIRQWWKLKPGPPPPKPAERHKDDSRGLVLPGYKYLGPFNGLDKGEPVNEADA |
| rh.56-C | 1 | MAADGYLPDWLEDTLSEGIRQWWKLKPGPPPPKPAERHKDDSRGLVLPGYKYLGPFNGLDKGEPVNEADA |
| hu.9-C | 1 | MAADGYLPDWLEDTLSEGIRQWWKLKPGPPPPKPAERHQDNSRGLVLPGYKYLGPFNGLDKGEPVNEADA |
| hu.54-C | 1 | MAADGYLPDWLEDTLSEGIRQWWKLKPGPPPPKPAERHKDDSRGLVLPGYKYLGPFNGLDKGEPVNEADA |
| hu.53-C | 1 | MAADGYLPDWLEDTLSEGIRQWWKLKPGPPPPKPAERHKDDSRGLVLPGYKYLGPFNGLDKGEPVNEADA |
| hu.60-C | 1 | MAADGYLPDWLEDTLSEGIRQWWKLKPGPPPPKPAERHKDDSRGLVLPGYKYLGPFNGLDKGEPVNEADA |
| hu.55-C | 1 | MAADGYLPDWLEDTLSEGIRQWWKLKPGPPPPKPAERHKDDSRGLVLPGYKYLGPSNGLDKGEPVNEADA |
| hu.2-C | 1 | MAADGYPPDWLEDTLSEGIRQWWKLKPGPPPPKPAERHKDDSRGLVLPGYKYLGPFNGLDKGEPVNEADA |
| hu.1-C | 1 | MAADGYLPDWLEDTLSEGIRQWWKLKPGPPPPKPAERHKDDSRGLVLPGYKYLGPFNGLDKGEPVNEADA |
| hu.18-C | 1 | MAADGYLPDWLEDTLSEGIRQWWKLKPGPPPPKPAERHKDDSRGLVLPGYKYLGPFNGLDKGEPVNEADA |
| hu.3-C | 1 | MAADGYLPDWLEDTLSEGIRQWWKLKPGPPPPKPAERHKDDSRGLVLPGYKYLGPFNGLDKGEPVNEADA |
| hu.25-C | 1 | MAADGYLPDWLEDTLSEGIRQWWKLKPGPPPPKPAERHKDGSRGLVLPGYKYLGPFNGLDKGEPVNEADA |
| hu.15-C | 1 | MAADGYLPDWLEDTLSEGIRQWWKLKPGPPPPKPAERHKDDSRGLVLPGYKYLGPFNGLDKGEPVDEADA |
| hu.16-C | 1 | MAADGYLPDWLEDTLSEGIRQWWKLKPGPPPPKPAERHKDDSRGLVLPGYKYLGPFNGLYKGEPVNEADA |
| hu.11-C | 1 | MAADGYLPDWLEDTLSEGIRQWWKLKPGPPPPKPAERHQDDSRGLVLPGYKYLGPFNGLDKGEPVNEADA |
| hu.10-C | 1 | MAADGYLPDWLEDTLSEGIRQWWKLKPGPPPPKPAERHQDDSRGLVLPGYKYLGPFNGLDKGEPVNEADA |
| hu.4-C | 1 | MAADGYLPDWLEDTLSEGIRQWWKLKPGPPPPKPLAERHQDDSRGLVLPGYKYLGPFNGLDKGEPVNEADA |
| rh.54-D | 1 | MAADGYLPDWLEDNLSEGIREWWDLKPGAPKPKANQQKQDDGRGLVLPGYKYLGPFNGLDKGEPVNEADA |
| rh.48-D | 1 | MAADGYLPDWLEDNLSEGIREWWDLKPGAPKPKANQQKQDDGRGLVLPGYKYLGPFNGLDKGEPVNEADA |
| rh.55-D | 1 | MAADGYLPDWLEDNLSEGIREWWDLKPGAPKPKANQQKQDDGRGLVLPGYKYLGPFNGLDKGEPVNEADA |
| rh.62-D | 1 | MAADGYLPDWLEDNLSEGIREWWDLKPGAPKPKANQQKQDNGRGLVLPGYKYLGPFNGLDKGEPVNEADA |
| AAV7-D | 1 | MAADGYLPDWLEDNLSEGIREWWDLKPGAPKPKANQQKQDDGRGLVLPGYKYLGPFNGLDKGEPVNAADA |
| rh.52-E | 1 | MAADGYLPDWLEDNLSEGIREWWDLKPGAPKPKANQQKQGDGRGLVLPGYKYLGPFNGLDKGEPVNAADA |
| rh.51-E | 1 | MVADGYLPDWLEDNLSEGIREWWDLKPGAPKPKANQQKQGDGRGLVLPGYKYLGPFNGLDKGEPVNAADA |
| hu.39-E | 1 | MAADGYLPDWLEDNLSEGIREWWDLKPGAPKPKANQQKQDDGRGLVLPGYKYLGPFNGLDKGEPVNAADA |

Fig. 2B

```
rh.53-E   1  MAADGYLPDWLEDNLSEGIREWWDLKPGAPKPKANQQKQDDGRGLVLPGYKYLGPFNGLDKGEPVNAADA
hu.37-E   1  MAADGYLPDWLEDNLSEGIREWWDLKPGAPKPKANQQKQDDGRGLIVLPGYKYLGPFNGLDKGEPVNAADA
rh.43-E   1  MAADGYLPDWLEDNLSEGIREWWDLKPGAPKPKANQQKQDDGRGLVLPGYKYLGPFNGLDKGEPVNAADA
rh.50-E   1  MAADGYLPDWLEDNLSEGIREWWDLKPGAPKPKANQQKQDDGRGLVLPGYKYLGPFNGLDKGEPVNAADA
rh.49-E   1  MAADGYLPDWLEDNLSEGIREWWDLKPGAPKPKANQQKQDDGRGLVLPGYKYLGPFNGLDKGEPVNAADA
rh.61-E   1  MAADGYLPDWLEDNLSEGIREWWDLKPGAPKPKANQQKQDDGRGLVLPGYKYLGPFNGLDKGEPVNAADA
rh.64-E   1  MAADGYLPDWLEDNLSEGIREWWDLKPGAPKPKANQQKQDDGRGLVLPGYKYLGPFNGLDKGEPVNAADA
hu.41-E   1  MAADGYLPDWLEDNLSEGIREWWDLKPGAPKPKANQQKQDDGRGLIVLPGYKYLGPFNGLDKGEPVNAADA
hu.42-E   1  MAADGYLPDWLEDNLSEGIREWWDLKPGAPKPKANQQKQDDGRGLIVLPGYKYLGPFNGLDKGEPVNAADA
rh.57-E   1  MAADGYLPDWLEDNLSEGIREWWALKPGAPKPKANQQKQDDGRGLVLPGYKYLGPFNGLDKGEPVNAADA
rh.40-E   1  MAADGYLPDWLEDNLSEGIREWWDLKPGAPKPKANQQKQDDGRGLVLPGYKYLGPFNGLDKGEPVNAADA
AAV8-E    1  MAADGYLPDWLEDNLSEGIREWWALKPGAPKPKANQQKQDDGRGLVLPGYKYLGPFNGLDKGEPVNAADA
rh.58-E   1  MAADGYLPDWLEDNLSEGIREWWDLKPGAPKPKANQQKQDDGRGLVLPGYKYLGPFNGLDKGEPVNAADA
rh.40-E   1  MAADGYLPDWLEDNLSEGIREWWDLKPGAPKPKANQQKQDDGRGLIVLLGYKYLGPFNGLDKGEPVNAADA
rh.67-E   1  MAADGYLPDWLEDNLSEGIREWWDLKPGAPKPKANQQKQDDGRGLIVLPGCKYLGPFNGLDKGEPVNAADA
hu.17-E   1  MAADGYLPDWLEDNLSEGIREWWDLKPGAPKPKANQQKQDDGRGLVLPGYKYLGPFNGLDKGEPVNAADA
hu.6-E    1  MAADGYLPDWLEDNLSEGIREWWDLKPGAPKPKANQQKQDDGRGLVLPGYKYLGPFNGLDKGEPVNAADA
hu.66-E   1  MAADGYLPDWLEDNLSEGIREWWDLKPGAPKPKANQQKQDDGRGLVLPGYKYLGPFNGLDKGEPVNAADA
rh.38-E   1  MAADGYLPDWLEDNLSEGIREWWDLKPGAPKPKPAERHKDDSRGLVLPGYKYLGPGNLDKGEPVNAADA
hu.32-F   1  MAADGYLPDWLEDTLSEGIREWQWWKLKPGPPPPKANQPKANQPGPPPKPGYKYLGPGNGLDKGEPVNAADA
AAV9/hu   1  MAADGYLPDWLEDTLSEGIREWWALKPGAPQPKANQPGPPPKPGYKYLGPGNGLDKGEPVNAADA
hu.31-F   1  MAADGYLPDWLEDTLSEGIRQWWKLKPGPPPPKPAERHKDDSRGLVLPGYKYLGPGNGLDKGEPVNAADA 80         90        100        110        120        130        140
                ....|....|....|....|....|....|....|....|....|....|....|....|....|....|

AAV5      70  VAREHDISYNEQLEAGDNPYLKYNHADAEFQEKLADDTSFGGNLGKAVFQAKKRVLEPFG-LVEEGAKTA
AAV3-3    71  AALEHDKAYDQQLKAGDNPYLKYNHADAEFQERLQEDTSFGGNLGRAVFQAKKRILEPLG-LVEEAAKTA
AAV4-4    70  AALEHDKAYDQQLKAGDNPYLKYNHADAEFQQRLQGDTSFGGNLGRAVFQAKKRVLEPLG-LVEQAGETA
AAV1-A    71  AALEHDKAYDQQLKAGDNPYLRYNHADAEFQERLQEDTSFGGNLGRAVFQAKKRVLEPLG-LVEEGAKTA
hu.46-A   71  AALEHDKAYDRQLDSGDNPYLKYNHADAEFQERLKEDTSFGGNLGRAVFQAKKRVLEPLG-LVEEGAKTA
```

| | | |
|---|---|---|
| hu.9-C | 71 | AALEHDKAYDRQLDSGDNPYLKYNHADAEFQERLKEDTSFGGNLGRAVFQAKKRVLEPLG-LVEEPVKTA |
| hu.54-C | 71 | AALEHDKAYDRQLDSGDNPYLKYNHADAEFQERLKEDTSFGGNLGRAVFQAKKRVLEPLG-LVEEPVKTA |
| hu.53-C | 71 | AALEHDKAYDRQLDSGDNPYLKYNHADAEFQERLKEDTSFGGNLGRAVFQAKKRVLEPLG-LVEEPVKTA |
| hu.60-C | 71 | AALEHDKAYDRQLDSGDNPYLKYNHADAEFQERLKEDTSFGGNLGRAVFQAKKRVLEPLG-LVEEPVKTA |
| hu.55-C | 71 | AALEHDKAYDRQLDSGDNPYLKYNHADAEFQERLKEDTSFGGNLGRAVFQAKKRVLEPLG-LVEEPVKTA |
| hu.2-C | 71 | AALEHDKAYDRQLDSGDNPYLKYNHADAEFQERLKEDTSFGGNLGRAVFQAKKRVLEPLG-LVEEPVKTA |
| hu.1-C | 71 | AALEHDKAYDRQLDSGDNPYLKYNHADAEFQERLKEDTSFGGNLGRAVFQAKKRVLEPLG-LVEEPVKTA |
| hu.18-C | 71 | AALEHDKAYDRQLESGDNPYLKYNHADAEFQERLKEDTSFGGNLGRAVFQAKKRVLEPLG-LVEEPVKTA |
| hu.3-C | 71 | AALEHDKAYDRQLDSGDNPYLKYNHADAEFQERLKEDTSFGGNLGRAVFQAKKRVLEPLRPGLRKPVKTA |
| hu.25-C | 71 | AALEHDKAYDRQLNSGDNPYLKYNHADAEFQERLKEDTSFGGNLGRAVFQAKKRVLEPLG-LVEEPVKTA |
| hu.15-C | 71 | AALEHDKAYDRQLDSGDNPYLKYNHADAEFQERLKEDTSFGGNLGRAVFQAKKRVLEPLG-LVGEPVKTA |
| hu.16-C | 71 | AALEHDKAYDRQLDSGDNPYLKYNHAGAEFQERLKEDTSFGGNLGRAVFQAKKRVLEPLG-LVEEPVKTA |
| hu.11-C | 71 | AALEHDKAYDRQLDSGDNPYLKYNHADAEFQERLKEDTSFGGNLGRAVFQAKKRVLEPLG-LVEEPVKTA |
| hu.10-C | 71 | AALEHDKAYDRQLDSGDNPYLKYNHADAEFQERLKEDTSFGGNLGRAVFQAKKRVLEPLG-LVEEPVKTA |
| hu.4-C | 71 | AALEHDKAYDRQLDSGDNPYLKYNHADAEFQERLKEDTSFGGNLGRAVFQAKKRVLEPLG-LVEEPVKTA |
| rh.54-D | 71 | AALEHDKAYDQQLKAGDNPYLRYNHADAEFQERLQEDTSFGGNLGRAVFQAKKRVLEPLG-LVEEAAKTA |
| rh.48-D | 71 | AALEHDKAYDQQLKAGDNPYLRYNHADAEFQERLQEDTSFGGNLGRAVFQAKKRVLEPLG-LVEEAAKTA |
| rh.55-D | 71 | AALEHDKAYDQQLKAGDNPYLRYNHADAEFQERLQEDTSFGGNLGRAVFQAKKRVLEPLG-LVEEGAKTA |
| rh.62-D | 71 | AALEHDKAYDQQLKAGDNPYLRYNHADAEFQERLQEDTSFGGNLGRAVFQAKKRVLEPLG-LAEEAAKTA |
| AAV7-D | 71 | AALEHDKAYDQQLKAGDNPYLRYNHADAEFQERLQEDTSFGGNLGRAVFQAKKRVLEPLG-LVEEGAKTA |
| rh.52-E | 71 | AALEHDKAYDQQLKAGDNPYLRYNHADAEFQERLQEDTSFGGNLGRAVFQAKKRVLEPLG-LVEEGAKTA |
| rh.51-E | 71 | AALEHDKAYDQQLKAGDNPYLRYNHADAEFQERLQEDTSFGGNLGRAVFQAKKRVLEPLG-LVEEGAKTA |
| hu.39-E | 71 | AALEHDKAYDQQLKAGDNPYLRYNHADAELQERLQEDTSFGGNLGRAVFQAKKRVLEPLG-LVEEGAKTA |
| rh.53-E | 71 | AALEHDKAYDQQLKAGDNPYLRYNHADAEFQERLQEDTSFGGNLGRAVFQAKKRVLEPLG-LVEEGAKTA |
| hu.37-E | 71 | AALEHDKAYDQQLKAGDNPYLRYNHADAEFQERLQEDTSFGGNLGRAVFQAKKRVLEPLG-LVEEGAKTA |
| rh.43-E | 71 | AALEHDKAYDQQLKAGDNPYLRYNHADAEFQERLQEDTSFGGNLGRAVFQAKKRVLEPLG-LVEEGAKTA |
| hu.50-E | 71 | AALEHDKAYDQQLKAGDNPYLRYNHADAEFQERLQEDTSFGGNLGRAVFQAKKRVLEPLG-LVEEGAKTA |
| rh.49-E | 71 | AALEHDKAYDQQLKAGDNPHLRYNHADAEFQERLQEDTSFGGNLGRAVFQAKKRVLEPLG-LVEEGAKTA |
| rh.61-E | 71 | AALEHDKAYDQQLKAGDNPYLRYNHADAEFQERLQEDTSFGGNLGRAVFQAKKRVLEPLG-LVEEGAKTA |
| hu.41-E | 71 | AALEHDKAYDQQLKAGDNPYLRYNHADAEFQERLQEDTSFGGNLGRAVFQAKKRVLEPLG-PVEEAAKTA |

Fig. 2E

| | | |
|---|---|---|
| rh.64-E | 71 | AALEHDKAYDQQLKAGDNPYLRYNHADAEFQERLQEDTSFGGNLGRAVFQAKKRVLEPLG-LVEEGAKTA |
| hu.42-E | 71 | AALEHDKAYDQQLKAGDNPYLRYNHADAEFQERLQEDTSFGGNLGRAVFQAKKRVLEPLG-LVEEAAKTA |
| rh.57-E | 71 | AALEHDKAYDQQLQAGDNPYLRYNHADAEFQERLQEDTSFGGNLGRAVFQAKKRVLEPLG-LVEEGAKTA |
| hu.40-E | 71 | AALEHDKAYDQQLQAGDNPYLRYNHADAEFQERLQEDTSFGGNLGRAVFQAKKRVLEPLG-LVEEAAKTA |
| AAV8-E | 71 | AALEHDKAYDQQLKAGDNPYLRYNHADAEFQERLQEDTSFGGNLGRAVFQAKKRVLEPLG-LVEEGAKTA |
| rh.58-E | 71 | AALEHDKAYDQQLKAGDNPYLRYNHADAEFQERLQEDTSFGGNLGRAVFQAKKRVLEPLG-LVEEAAKTA |
| rh.40-E | 71 | AALEHDKAYDQQLKAGDNPYLRYNHADAEFQERLQEDTSFGGNLGRAVFQAKKRVLEPLG-LVEEAAKTA |
| hu.67-E | 71 | AALEHDKAYDQQLKAGDNPYLRYNHADAEFQERLQEDTSFGGNLGRAVFQAKKRVLEPLG-LVEEGAKTA |
| hu.17-E | 71 | AALEHDKAYDQQLKAGDNPYLRYNHADAEFQERLQEDTSFGGNLGRAVFQAKKRVLEPLG-LVEEAAKTA |
| hu.6-E | 71 | AALEHDKAYDQQLKAGDNPYLRYNHADAEFQERLQEDTSFGGNLGRAVFQAKKRVLEPLG-LVEEGAKTA |
| hu.66-E | 71 | AALEHDKAYDQQLKAGDNPYLRYNHADAEFQERLQEDTSFGGNLGRAVFQAKKRVLEPLG-LVEEAAKTA |
| rh.38-E | 71 | AALEHDKAYDQQLKAGDNPYLRYNHADAEFQERLKEDTSFGGNLGRAVFQAKKRVLEPLG-LVEEAAKTA |
| hu.32-F | 71 | AALEHDKAYDQQLKAGDNPYLKYNHADAEFQERLKEDTSFGGNLGRAVFQAKKRLLEPLG-LVEEAAKTA |
| AAV9/hu | 71 | AALEHDKAYDQQLKAGDNPYLRYNHADAEFQERLQEDTSFGGNLGRAVFQAKKRVLEPLG-LVEEAAKTA |
| hu.31-F | 71 | AALEHDKAYDQQLKAGDNPYLKYNHADAEFQERLKEDTSFGGNLGRAVFQAKKRLLEPLG-LVEEAAKTA |

|  |  | 150 | 160 | 170 | 180 | 190 | 200 | 210 |
|---|---|---|---|---|---|---|---|---|

| | | |
|---|---|---|
| AAV5 | 139 | PTGKRIDDHFP------KRKKARTEEDSKPSTSSDAEAGPSGSQQLQIPAQPASSLGADTMSAGG |
| AAV3-3 | 140 | PGKKGAVDQSPQ-EPDSSSGVGKSGKQPARKRLNFGQTGDSESVPD-PQPLGEPPAAPTSLGSNTMASGG |
| AAV4-4 | 139 | PGKKRPLIESPQ-QPDSSTGIGKKGKQPAKKKLVFEDETGAGDGP----PEGSTSGAMS--DDSEMRAAA |
| AAV1-A | 140 | PGKKRPVEQSPQ-EPDSSSGIGKTGQQPAKKRLNFGQTGDSESVPD-PQPLGEPPATPAAVGPTTMASGG |
| hu.46-A | 140 | PGKKRPVEQSPQ-EPDSPSGIGKTGQQPAKKRLNFGQTGDSESVPD-PQPLGEPPATPAAVGPTTMASGG |
| hu.48-A | 140 | PGKKRPVEQSPQ-EPDSSSGIGKTGQQPAKKRLNFGQTGDSESVPD-PQPLGEPPATPAAVGPTTMASGG |
| hu.44-A | 140 | PGKKRPVEQSPQ-GPDSSSGIGKTGQQPAKKRLNFGQTGDSESVPD-PQPLGEPPATPAAVGPTTMASGG |
| hu.43-A | 140 | PGKKRPVEPSPQRSPDSSGIGKKGQQPAKKRLNFGQTGDSESVPD-PQPIGEPPAGPSGLGSGTMAAGG |
| AAV6-A | 140 | PGKKRPVEQSPQ-EPDSSSGIGKTGQQPARKRLNFGQTGDSESVPD-PQPLGEPPATPAAVGPTTMASGG |
| hu.34-B | 140 | PGKKRPVEHSPV-EPDSSSGIGKAGQQPARKRLNFGQTGDADSVPD-PQPLGQPPAAPSGLGTNTMATGS |
| hu.47-B | 140 | PGKKRPVEHSPV-EPDSSSGTGKAGQQPARKRLNFGQTGDADSVPD-PQPLGQPPAAPSGLGTNTMATGS |
| hu.29-B | 140 | PGKKRPVEHSPA-EPDSSSGTGKSGNQPARKRLNFGQTGDSDSVPD-PQPLGQPPAAPSGLGTNTMATGS |

Fig. 2F

| | | |
|---|---|---|
| hu.63-B | 140 | PGKKRPVEHSPA-EPDSSSSGTGKAGQQPARKRLNFGQTGDADSVPD-PQPLGQPPAAPSGLGTNTMATGS |
| hu.56-B | 140 | PGKKRPVEHSPV-EPDSSSSGTGKAGNQPARKRLNFGQTGDADSVPD-PQPLGQPPASPSGLGTNTMATGS |
| hu.45-B | 140 | PGKKRPVEHSPV-EPDSSSSGTGKAGQQPARKRLNFGQTGDADSVPD-PQPLGQPPAAPSGLGTNTMATGS |
| hu.57-B | 139 | PGKKRPVEHSPV-EPDSSSSGTGKAGQQPARKRLNFGQTGDADSVPD-PQPLGQPPAAPSGLGTNTMATGS |
| hu.35-B | 140 | PGKKRPVEHSPV-EPDSSSSGTGKAGNQPARKRLNFGQTGDADSVPD-PQPLGQPPAAPSGLGTNTMATGS |
| hu.58-B | 140 | PGKKRPVEHSPA-EPDSSSSGTGKAGQQPARKRLNFGQTGDADSVPD-PQPLGQPPAAPSGLGTNTMATGS |
| hu.28-B | 140 | PGKKRPVEHSPV-EPDSSSSGTGKAGNQPARKRLNFGQTGDSDSVPD-PQPLGQPPAAPSGLGTNTMATGS |
| hu.51-B | 140 | PGKKRPVEHSPA-EPDSSSSGTGKSGNQPARKRLNFGQTGDADSVPD-PQPLGQPPAAPSGLGTNTMATGS |
| hu.19-B | 140 | PGEKRPVEHSPA-EPDSSSSGTGKAGQQPARKRLNFGQTGDADSVPD-PQPLGQPPAAPSGLGTNTMASGS |
| hu.49-B | 140 | PGKKRPVEHSPV-EPDSSSSGTGKAGQQPARKRLNFGQTGDADSVPD-PQPLGQPPAAPSGLGTNTMATGS |
| hu.52-B | 140 | PGKKRPVEHSPV-EPDSSSSGTGKAGQQPARKRLNFGQTGDADSVPD-PQPLGQPPAAPSGLGTNTMASGS |
| hu.13-B | 140 | PGKKRPVEHSPA-EPDSSSSGTGKAGQQPARKRLNFGQTGDADSVPD-PQPLGQPPAAPSGLGTNTMASGS |
| AAV2-B | 140 | PGKKRPVEHSPV-EPDSSSSGTGKAGQQPARKRLNFGQTGDADSVPD-PQPLGQPPAAPSGLGTNTMATGS |
| hu.20-B | 140 | PGEKRPVEHSPV-EPDSSSSGTGKAGQQPARKRLNFGQTGDADSVPD-PQPLGQPPAAPSGLGTNTMASGS |
| hu.24-B | 140 | PGKKRPVEHSPA-EPDSSSSGTGKAGQQPARKRLNFGQTGDADSVPD-PQPLGQPPAAPSGLGTNTMATGS |
| hu.64-B | 140 | PGKKRPVEHSLA-EPDSSSSGTGKAGQQPARRRLNFGQTGDADSVPD-PRPLGQPPAAPSGLGTNTMATGS |
| hu.27-B | 140 | PGKKRPVEHSPA-EPDSSSSGTGKAGQQPARKRLNFGQTGDADSVPD-PQPLGQPPAAPSGLGTNTMASGS |
| hu.21-B | 140 | PGKKRPVEHSPV-EPDSSSSGTGKAGQQPARKRLNFGQTGDADSVPD-PRPLGQPPAAPSGLGTNTMASGS |
| hu.22-B | 140 | PGKKRPVEHSPV-EPDSSSSGTGKAGQQPARKRLNFGQTGDADSVPD-PQPLGQPPAAPSGLGTNTMASGS |
| hu.23-B | 140 | PGKKRPVEHSPA-EPDSSSSGTGKAGQQPARKRLNFGQTGDADSVPD-PQPLGQPPAAPSGLGTNTMASGS |
| hu.7-C | 140 | PGKKRPVEHSPA-EPDSSSSGTGKAGQQPARKRLNFGQTGDADSVPD-PQPLGQPPAAPSGLGSTTMATGS |
| hu.61-C | 140 | PGKKRPVEHPPV-EPDSSSSGTGKAGQQPARKRLNFGQTGDADSVPD-PQPLGQPPAAPSGLGSTTMATGS |
| rh.56-C | 140 | PGKKRPVEHSPA-EPDSSSSGTGKAGQQPARKRLNFGQTGDADSVPD-PQPLGQPPAAPSGLGSTTMATGS |
| hu.9-C | 140 | PGKKRPVEHSPV-EPDSSSSGTGKAGHQPARKRLNFGQTGDADSVPD-PQPLGQPPAAPTSLGSTTMATGS |
| hu.54-C | 140 | PGKKRPVEHSPA-EPDSSSSGTGKAGQQPARKRLNFGQTGDADSVPD-PQPLGQPPAAPTSLGSTTMATGS |
| hu.53-C | 140 | PGKKRPVEHSPA-EPDSSSSGTGKAGQQPARKRLNFGQTGDADSVPD-PQPLGQPPAAPTSLGSTTMATGS |
| hu.60-C | 140 | PGKKRPVEHSPA-EPDSSSSGTGKAGQRPARKRLNFGQTGDADSVPD-PQPLRQPPAAPSGLGSTTMATGS |
| hu.55-C | 140 | PGKKRPVEHSPA-EPDSSSSGTGKAGQQPARKRLNFGQTGDADSVPD-PQPLGQPPAAPSGLGSTTMATGS |
| hu.2-C | 140 | PGKKRPVEHSPV-EPDSSSSGTGKAGQRPARKRLNFGQTGDADSVPD-PQPLGQPPAAPTSLGSTTMATGS |
| hu.1-C | 140 | PGKKRPVEHSPV-EPDSSSSGTGKAGQQPARKRLNFGQTGDADSVPD-PQPLGQPPAAPSGLGSTTMATGS |

Fig. 2G

```
hu.18-C  140  PGKKRPVEHSPV-EPDSSSGTGKAGQQPARKRLNFGQTGDADSVPD-PQPLGQPPAAPSGLGSTTMASGS
hu.3-C   141  PGKKRPVEHSPV-EPDSSSGTGKAGQQPARKRLNFGQTGDADSVPD-PQPLGQPPAAPSGLGSTTMATGS
hu.25-C  140  PGKKRPVEHSPA-EPDSSSGTGKAGQQPARKRLNFGQTGDADSVPD-PQPLGQPPAAPSGLGSTTMATGS
hu.15-C  140  PGKKRPVEHSPV-EPDSSSGTGKAGNQPARKRLNFGQTGDADSVPD-PQPLGQPPAAPSGLGSTTMATGS
hu.16-C  140  PGKKRPVEHSPV-EPDSSSGTGKAGNQPARKRLNFGQTGDADSVPD-PQPLGQPPAAPSGLGSTTMATGS
hu.11-C  140  PGKKRPVEHSPV-EPDSSSGTGKAGHQPARKRLNFGQTGDADSVPD-PQPLGQPPAAPTSLGSTTMATGS
hu.10-C  140  PGKKRPVEHSPV-EPDSSSGTGKAGHQPARKRLNFGQTGDADSVPD-PQPLGQPPAAPTSLGSTTMATGS
hu.4-C   140  PGKKRPVEHSPV-EPDSSSGTGKAGQQPARKRLNFGQTGDADSVPD-PQPLGQPPAAPSGLGSTTMATGS
rh.54-D  140  PGKKRPVEPSPQRSPDSSTGIGKKGQQPARKRLNFGQTGDSESVPD-PQPLGEPPAGPSGLGSGTMAAGG
rh.48-D  140  PGKKRPVEPSPQRSPDSSTGIGKKGQQPARKRLNFGQTGDSESVPD-PQPIGEPPAGPSGLGSGTMAAGG
rh.55-D  140  PGKKRPVEPSPQRSPDSSTGIGKKGQQPARKRLNFGQTGDSESVPD-PQPIGEPPAAPSSVGSGTMAAGG
rh.62-D  140  PGKKRPVEPSPQRSPDSSTGIGKKGQQPARKRLNFGQTGDSESVPD-PQPIGEPPAGPSGLGSGTMAAGG
AAV7-D   140  PAKKRPVEPSPQRSPDSSGIGKKGQQPARKRLNFGQTGDSESVPD-PQPLGEPPAAPSSVGSGTVAAGG
rh.52-E  140  PGKKRPVEPSPQRSPDSSTGIGKKGQQPAGKRLNFGQTGDSESVPD-PQPIGEPPAAPSSVGSGTMAAGG
rh.51-E  140  PGKKRPVEPSPQRSPDSSTGIGKKGQQPARKRLNFGQTGDSESVPD-PQLIGEPPAAPSSVGSGTMAAGG
rh.39-E  140  PGKKRPVEPSPQRSPDSSTGIGKKGQQPARKRLNFGQTGDSESVPD-PQPIGEPPAAPSSVGSGTMAAGG
rh.53-E  140  PGKKRPVEPSPQRSPDSSTGIGKKGQQPARKRLNFGRTGDSESVPD-PQPIGEPPAAPSSVGSGTMAAGG
hu.37-E  140  PGKKRPVEPSPQRSPDSSTGIGKKGQQPARKRLNFGQTGDSESVPD-PQPIGEPPAAPSSVGSGTMAAGG
hu.43-E  140  PGKKRPVEPSPQRSPDSSTGIGKKGQQPAKKRLNFGQTGDSESVPD-PQPIGEPPAGPSGLGSGTMAAGG
hu.50-E  140  PGKKRPVEQSPQ-EPDSSSGIGKKGQQPARKRLNFGQTGDSESVPD-PQPLGEPPAAPSSVGSGTMAAGG
hu.49-E  140  PGKKRPVEPSPQRSPDSSTGIGKKGQQPARKRLNFGQTGDSESVPD-PQPIGEPPAAPSSVGSGTMAAGG
rh.61-E  140  PGKKRPVEPSPQRSPDSSTGIGKKGQQPARKRLNFGQTGDSESVPD-PQPIGEPPAAPSSVGSGTMAAGG
hu.41-E  140  PGKKRPVEPPPQRSPDSSTGIGKKGQQPARKRLNFGQTGDSESVPD-PQPIGEPPAAPSSVGSGTMAAGG
hu.64-E  140  PGKKRPVEPSPQRSPDSSTGIGKKGQQPARKRLNFGQTGDSESVPD-PQPIGEPPAGPSGLGSGTMAAGG
rh.42-E  140  PGKKRPVEPSPQRSPDSSTGIGKKGQQPARKRLNFGQTGDSESVPD-PQPIGEPPAAPSSVGSGTMAAGG
hu.57-E  140  PGKKRPVEPSPQRSPDSSTGIGKKGQQPARKRLSFGQTGDSESVPD-PQPLGEPPAAPSSVGSGTMAAGG
hu.40-E  140  PGKKRPVEPSPQRSPDSSTGIGKKGQQPAKKRLNFGQTGDSESVPD-PQPIGEPPAGPSGLGSGTMAAGG
AAV8-E   140  PGKKRPVEPSPQRSPDSSTGIGKKGQQPARKRLNFGQTGDSESVPD-PQPLGEPPAAPSGVGPNTMAAGG
rh.58-E  140  PGKKRPVEPSPQRSPDSSTGIGKKGQQPARKRLNFGQTGDSESVPD-PQPIGEPPAAPSSVGSGTMAAGG
rh.40-E  140  PGKKRPVEPSPQRSPDSSTGIGKKGQQPAKKRLNFGQTGDSESVPD-PQPIGEPPAGPSGVGPNTMAAGG
```

Fig. 2H

```
hu.67-E   140 PGKKRPVEPSPQRSPDSSTGIGKKGQQPAKKRLNFGQTGDSESVPD-PQPIGEPPAGPSGLGSGTMAAGG
hu.17-E   140 PGKKRPVEPSPQRSPDSSTGIGKKGQQPAKKRLNFGQTGDSESVPD-PQPIGEPPAGPSGLGSGTMAAGG
hu.6-E    140 PGKKRPVEPSPQRSPDSSTGIGKTGQQPAKKRLNFGQTGDSESVPD-PQPIGEPPAGPSGLGSGTMAAGG
hu.66-E   140 PGKKRPVEPSPQRSPDSSTGIGKTGQQPAKKRLNFGQTGDSESVPD-PQPIGEPPAGPSGLGSGTMAAGG
rh.38-E   140 PGKKRPVEPSPQRSPDSSAGIGKKGQQPAKKRLNFGQTGDSESVPD-PQPIGEPPAGPSGLGSGTMAAGG
hu.32-F   140 PGKKRPVEPSPQRSPDSSTGIGKKGQRPAKKRLNFGQTGDSESVPD-PQPIGEPPAAPSGVGSLTMASGG
AAV9/hu   140 PGKKRPVEQSPQ-EPDSSAGIGKSGSQPAKKKLNFGQTGDTESVPD-PQPIGEPPAAPSGVGSLTMASGG
hu.31-F   140 PGKKRPVEQSPQ-EPDSSAGIGKSAGIGKSAQPAKKRLNFGQTGDTESVPD-PQPIGEPPAAPSGVGSLTMASGG 220         230         240         250         260         270         280
                                    |....|....|....|....|....|....|....|....|....|....|....|....|....|

AAV5      198 GGPLGDNNQGADGVGNASGDWHCDSTWMGDRVVTKSTRTWVLPSYNNHQYREIKS-GSVDGSNANAYFGY
AAV3-3    208 GAPMADNNEGADGVGNSSGNWHCDSTWLGDRVITTSTRTWALPTYNNHLYKQIS--SQSGASNDNHYFGY
AAV4-4    202 GGAAVEGGQGADGVGNSSGNWHCDSTWSEGHVTTSTRTWVLPTYNNHLYKRLG---ESLQSNTYNGF
AAV1-A    208 GAPMADNNEGADGVGNASGNWHCDSTWLGDRVITTSTRTWALPTYNNHLYKQISS-ASTGASNDNHYFGY
hu.46-A   208 GAPMADNNEGADGVGNASGNWHCDSTWLGDRVITTSTRTWALPTYNNHLYKQISS-ASTGASNDNHYFGY
hu.48-A   208 GAPMADNNEGADGVGNASGNWHCDSTWLGDRVITTSTRTWALPTYNNHLYKQISS-TSTGASNDNHYFGY
hu.44-A   208 GAPMADNNEGADGVGNASGNWHCDSTWLGDRVITTSTRTWALPTYNNHLYKQISS-ASTGASNDNHYFGY
hu.43-A   209 GAPMADNNEGADGVGNASGNWHCDSTWLGDRVITTSTRTWALPTYNNHLYKQISS-ASTGASNDNHYFGY
AAV6-A    208 GAPMADNNEGADGVGNASGNWHCDSTWMGDRVITTSTRTWALPTYNNHLYKQIS--SQSGASNDNHYFGY
hu.34-B   208 GAPMADNNEGADGVGNASGNWHCDSTWMGDRVITTSTRTWALPTYNNHLYKQIS--SQSGASNDNHYFGY
hu.47-B   208 GAPMADNNEGADGVGNSSGNWHCDSTWMGDRVITTSTRTWALPTYNNHLYKQIS--SQSGASNDSHYFGY
hu.29-B   208 GAPMADNNEGADGVGNSSGNWHCDSTWMGDRVITTSTRTWALPTYNNHLYKQIS--SQSGASNDNHYFGY
hu.63-B   208 GAPMADNNEGADGVGNSSGNWHCDSTWMGDRVITTSTRTWALPTYNNHLYKQIS--SQSGASNDNHYFGY
hu.56-B   208 GAPMADNNEGADGVGNSSGNWHCDSTWMGDRVITTSTRTWALPTYNNHLYKQIS--SQSGASNDNHYFGY
hu.45-B   208 GAPMADNNEGADGVGNSSGDWHCDSTWMGDRVITTSTRTWALPTYNNHLYKQIS--SQSGASNDNHYFGY
hu.57-B   207 GAPMADNNEGADGVGNSSGDWHCDSTWMGDRVITTSTRTWALPTYNNHLYKQIS--SQSGASNDNHYFGY
hu.35-B   208 GAPMADNNEGADGVGNSSGNWHCDSTWMGDRVITTSTRTWALPTYNNHLYKQIS--SQSGASNDNHYFGY
hu.58-B   208 GAPMADNNDGADGVGNSSGNWHCDSTWMGDRVITTSTRTWALPTYNNHLYKQIS--SQSGASNDNHYFGY
hu.28-B   208 GAPMADNNEGADGVGNSSGNWHCDSTWMGDRVITTSTRTWALPTYNNHLYKQIS--SQSGASNDNHYFGY
```

Fig. 2I

| | | |
|---|---|---|
| hu.51-B | 208 | GAPMADNNEGADGVGNSSSGNWHCDSTWMGDRVITTSTRTWALPTYNNHLYKQIS--SQSGASNDNHYFGY |
| hu.19-B | 208 | GAPMADNNEGADGVGNSSSGNWYCDSTWMGDRVITTSTRTWALPTYNNHLYKQIS--SQSGASNDNHYFGY |
| hu.49-B | 208 | GAPMADNNEGADGVGNSSGSWHCDSTWMGDRVITTSTRTWALPTYNNHLYKQIS--SQSGASNDNHYFGY |
| hu.52-B | 208 | GAPMADNNEGADGVGNSSSGNRHCDSTWMGDRVITTSTRTWALPTYNNHLYKQIS--SQSGASNDNHYFGY |
| hu.13-B | 208 | GAPMADNNEGADGVGNSSSGNWHCDSTWMGDRVITTSTRTWALPTYNNHLYKQIS--SQSGASNDNHYFGY |
| AAV2-B | 208 | GAPMADNNEGADGVGNSSSGNWHCDSTWMGDRVITTSTRTWALPTYNNHLYKQIS--SQSGASNDNHYFGY |
| hu.20-B | 208 | GAPMADNNEGADGVGNSSSGNWHCDSTWMGDRVITTSTRTWALPTYNNHLYKQIS--SQSGASNDNHYFGY |
| hu.24-B | 208 | GAPMADNNEGADGVGNSSSGNWHCDSTWMGDRVITTSTRTWALPTYNNHLYKQIS--SQSGASNDNHYFGY |
| hu.64-B | 208 | GAPMADNNEGADGVGNSSSGNWHCDSTWMGDRVITTSTRTWALPTYNNHLYKQIS--SQSGASNDNHYFGY |
| hu.27-B | 208 | GAPMADNNEGADGVGNSSSGNWHCDSTWMGDRVITTSTRTWALPTYNNHLYKRQIS--SQSGASNDNHYFGY |
| hu.21-B | 208 | GAPMADNNEGADGVGNSSSGNWHCDSTWMGDRVITTSTRTWALPTYNNHLYKQIS--SQSGASNDNHYFGY |
| hu.22-B | 208 | GAPMADNNEGADGVGNSSSGNWHCDSTWMGDRVITTSTRTWALPTYNNHLYKQIS--SQSGASNDNHYFGY |
| hu.23-B | 208 | GAPMADNNEGADGVGNSSSGNWHCDSTWMGGRVITTSTRTWALPTYNNHLYKQIS--SQSGASNDNHYFGY |
| hu.7-C | 208 | GAPMADNNEGADGVGNSSSGNWHCDSTWMGDRVITTSTRTWALPTCNNHLYKQIS--SQSGASNDNHYFGY |
| hu.61-C | 208 | GAPMADNNEGADGVGNSSSGNWHCDSQWLGDRVITTSTRTWALPTYNNHLYKQIS--SQSGASNDNHYFGY |
| rh.56-C | 208 | GAPMADNNEGADGVGNSSSGNWHCDSQWLGDRVITTSTRTWALPTYNNHLYKQIS--SQSGASNDNHYFGY |
| hu.9-C | 208 | GAPMADNNEGADGVGNSSSGNWHCDSQWLGDRVITTSTRTWAQPTYNNHLYKQIS--SQSGASNDNHYFGC |
| hu.54-C | 208 | GAPMADNNEGADGVGNSSSGNWHCDSQWLGDRVITTSTRTWALPTYNNHLYKQIS--SQSGASNDNHYFGY |
| hu.53-C | 208 | GAPMADNNEGADGVGNSSSGNWHCDSQWLGDRVITTSTRTWALPTYNNHLYKQIS--SQSGASNDNHYFGY |
| hu.60-C | 208 | GAPMADNNEGADGVGNSSSGNWHCDSQWLGDRVITTSTRTWALPTYNNHLYKQIS--SQSGASNDNHYFGY |
| hu.55-C | 208 | GAPMADNNEGADGVGNSSSGNWHCDSQWLGDRVITTSTRTWALPTYNNHLYKQIS--SQSGASNDNHYFGY |
| hu.2-C | 208 | GAPMADNNEGADGVGNSSSGNWHCDSQWLGDRVITTSTRTWALPTYNNHLYKQIS--SQSGASNDNHYFGY |
| hu.1-C | 208 | GAPMADNNEGADGVGNSSSGNWHCDSQWLGDRVITTSTRTWALPTYNNHLYKQIS--SQSGASNDNHYFGY |
| hu.18-C | 208 | GAPVADNNEGADGVGNSSSGNWHCDSQWLGDRVITTSTRTWALPTYNNHLYKQIS--SQSGASNDNHYFGY |
| hu.3-C | 209 | GAPVADNNEGADGVGNSSSGNWHCDSQWLGDRVITTSTRTWALPTYNNHLYKQIS--SQSGASNDNHYFGY |
| hu.25-C | 208 | GAPMADNNEGADGVGNSSSGNWHCDSQWLDDRVIATSTRTWALPTYNNHLYKQIS--SQSGASNDNHYFGY |
| hu.15-C | 208 | GAPVADNNEGADGVGNSSSGNWHCDSQWLGDRVITTSTRTWALPTYNNHLYKQIS--SQSGASNDNHYFGY |
| hu.16-C | 208 | GAPVADNNEGADGVGNSSSGNWHCDSQWLGDRVITTSTRTWALPTYNNHLYKQIS--SQSGACNDNHYFGY |
| hu.11-C | 208 | GAPMADNNEGADGVGNSSSGNWHCDSQWLGDRVITTSTRTWALPTYNNHLYKQIS--SQSGASNDNHYFGY |
| hu.10-C | 208 | GAPMADNNEGADGVGNSSSGNWHCDSQWLGDRVITTSTRTWALPTYNNHLYKQIS--SQSGASNDNHYFGY |

Fig. 2J

| | | |
|---|---|---|
| hu.4-C | 208 | GAPMADNNEGADGVGNSSGNWHCDSQWLGDRVITTSTRTWALPTYNNHLYKQIS--SQSGASNDNHYFGY |
| rh.54-D | 209 | GAPMADNNEGADGVGNASGNWHCDSTWLGDRVITTSTRTWALPTYNNHLYKQISS-QSAGSTNDNVYFGY |
| rh.48-D | 209 | GAPMADNNKGADGVGNASGNWHCDSTWLGDRVITTSTRTWALPTYNNHLYKQISS-QSAGSTNDNVYFGY |
| rh.55-D | 209 | GAPMADNNEGADGVGNASGNWHCDSTRLGDRVITTSTRTWALPTYNNHLYKQISS-QSAGSTNDNVYFGY |
| rh.62-D | 209 | GAPMADNNKGADGVGNASGNWHCDSTWLGDRVITTSTRTWALPTYNNHLYKQISS-QSAGSTNDNVYFGY |
| AAV7-D | 209 | GAPMADNNEGADGVGNASGNWHCDSTWLGDRVITTSTRTWALPTYNNHLYKQISS-ETAGSTNDNTYFGY |
| rh.52-E | 209 | GAPMADNNEGADGVGSSSGNWHCDSTWLGDRVITTSTRTWALPTYNNHLYKQISNGTSGGSTNDNTYFGY |
| rh.51-E | 209 | GAPMADNNEGADGVGSSSGNWHCDSTWLGDRVITTSTRTWALPTYNNHLYKQISNGTSGGSTNDNTYFGY |
| rh.39-E | 209 | GAPMADNNEGADGVGSSSGNWHCDSTWLGDRVITTSTRTWALPTYNNHLYKQISNGTSGGSTNDNTYFGY |
| rh.53-E | 209 | GAPMADNNEGADGVGSSSGNWHCDSTWLGDRVITTSTRTWALPTYNNHLYKQISNGTSGGSTNDNTYFGY |
| hu.37-E | 209 | GAPMADNNEGADGVGSSSGNWHCDSTWLGDRVITTSTRTWALPTYNNHLYKQISNGTSGGSTNDNTYFGY |
| rh.43-E | 208 | GAPMADNNEGADGVGSSSGNWHCDSTWLGDRVITTSTRTWALPTYNNHLYKQISNGTSGGATNDNTYFGY |
| rh.50-E | 209 | GAPMADNNEGADGVGSSSGNWHCDSTWLGDRVITTSTRTWALPTYNNHLYKQISNGTSGGSTNDNTYFGY |
| rh.49-E | 209 | GAPMADNNEGADGVGSSSGNWHCDSTWLGDRVITTSTRTWALPTYNNHLYKQTSNGTSGGSTNDNTYFGY |
| rh.61-E | 209 | GAPMADNNEGADGVGSSSGNWHCDSTWLGDRVITTSTRTWALPTYNNHLYKQISNGTSGGSTNDNTYFGY |
| rh.41-E | 209 | GAPMADNNEGADGVGSSSGNWHCDSTWLGDRVITTSTRTWALPTYNNHLYKQISNGTSGGSTNDNTYFGY |
| rh.64-E | 209 | GAPMADNNEGADGVGSSSGNWHCDSTWLGDRVITTSTRTWALPTYNNHLYKQISNGTSGGSTNDNTYFGY |
| hu.42-E | 209 | GAPMADNNEGADGVGSSSGNWHCDSTWLGDRVITTSTRTWALPTYNNHLYKQISNGTSGGSTNDNTYFGY |
| rh.57-E | 209 | GAPMADNNEGADGVGSSSGNWHCDSTWLGDRVITTSTRTWALPTYNNHLYKQISNGTSGGSTNDNTYFGY |
| hu.40-E | 209 | GAPMADNNEGADGVGSSSGNWHCDSTWLGDRVITTSTRTWALPTYNNHLYKQISNGTSGGSTNDNTYFGY |
| AAV8-E | 209 | GAPMADNNEGADGVGSSSGNWHCDSTWLGDRVITTSTRTWALPTYNNHLYKQISNGTSGGATNDNTYFGY |
| rh.58-E | 209 | GAPMADNNEGADGVGSSSGNWHCDSTWLGDRVITTSTRTWALPTYNNHLYKQISNGTSGGSTNDNTYFGY |
| rh.40-E | 209 | GAPMADNNEGADGVGSSSGNWHCDSTWLGDRVITTSTRTWALPTYNNHLYKQISNGTSGGSTNDNTYFGY |
| hu.67-E | 209 | GAPMADNNEGADGVGSSSGNWHCDSTWLGDRVITTSTRTWALPTYNNHLYKQISNGTSGGSTNDNTYFGY |
| hu.17-E | 209 | GAPMADNNEGADGVGSSSGNWHCDSTWLGDRVITTSTRTWALPTYNNHLYKQISNGTSGGSTNDNTYFGY |
| hu.6-E | 209 | GAPMADNNEGADGVGSSSGNWHCDSAWLGDRVITTSTRTWALPTYNNHLYKQISNGTSGGSTNDNTYFGY |
| hu.66-E | 209 | GAPMADNNEGADGVGSSSGNWHCDSTWLGDRVITTSTRPWALPTYNNHLYKQISNGTSGGSTNDNTYFGY |
| rh.38-E | 209 | GAPMADNNEGADGVGSSSGNWHCDSTWLGDRVITTSTRTWALPTYNNHLYKQISNGTSGGSTNDNTYFGY |
| hu.32-F | 208 | GAPVADNNEGADGVGSSSGNWHCDSQWLGDRVITTSTRTWALPTYNNHLYKQISNSTSGGSSNDNAYFGY |
| AAV9/hu | 208 | GAPVADNNEGADGVGSSSGNWHCDSQWLGDRVITTSTRTWALPTYNNHLYKQISNSTSGGSSNDNAYFGY |

Fig. 2K

```
hu.31-F  208 GAPVADNNEGADGVGSSSGNWHCDSQWLGDRVITTSTRTWALPTYNNHLYKQISNSTSGGSSNDNAYFGY
                      290       300       310       320       330       340       350
                 ....|....|....|....|....|....|....|....|....|....|....|....|....|....|
AAV5     267 STPWGYFDFNRFHSHWSPRDWQRLINNYWGFRPRSLRVKIFNIQVKEVTVQDSTTTIANNLTSTVQVFTD
AAV3-3   276 STPWGYFDFNRFHCHFSPRDWQRLINNNWGFRPKKLSFKLFNIQVRGVTQNDGTTIANNLTSTVQVFTD
AAV4-4   267 STPWGYFDFNRFHCHFSPRDWQRLINNNWGFRPKRLNFKLFNIQVKEVTTSNGETTVANNLTSTVQIFAD
AAV1-A   277 STPWGYFDFNRFHCHFSPRDWQRLINNNWGFRPKRLNFKLFNIQVKEVTTNDGVTTIANNLTSTVQVFSD
hu.46-A  277 STPWGYFDFNRFHCHFSPRDWQRLINNNWGFRPKRLNFKLFNIQVKEVTTNDGVTTIANNLTSTVQVFSD
hu.48-A  277 GTPWGYFDFNRFHCHFSPRDWQRLINNNWGFRPKRLNFKLFNIQVEEVTTNDGVTTIANNLTSTVQVFSD
hu.44-A  277 STPWGYFDFNRFHCHFSPRDWQRLINNNWGFRPKRLNFKLFNIQVKEVTTNDGVTTIANNLTSTVQVFSD
hu.43-A  278 STPWGYFDFNRFHCHFSPRDWQRLINNNWGFRPKRLNFKLFNIQVKEVTTNDGVTTIANNLTSTVQVFSD
AAV6-A   277 STPWGYFDFNRFHCHFSPRDWQRLINNNWGFRPKRLNFKLFNIQVKEVTTNDGVTTIANNLTSTVQVFSD
hu.34-B  276 STPWGYFDFNRFHCHFSPRDWQRLINNNWGFRPKRLNFKLFNIQVKEVTQNDGTTTIANNLTSTVQVFTD
hu.47-B  276 STPWGYFDFNRFHCHFSPRDWQRLINNNWGFRPKRLNFKLFNIQVKEVTQNDGTTTIANNLTSTVQVFTD
hu.29-B  276 STPWGYFDFNRFHCHFSPRDWQRLINNNWGFRPKRLNFKLFNIQVKEVTQNDGTTTIANNLTSTVQVFTD
hu.63-B  276 STPWGYFDFNRFHCHFSPRDWQRLINNNWGFRPKRLNFKLFNIQVKEVTQNDGTTTIANNLTSTVQVFTD
hu.56-B  276 STPWGYFDFNRFHCHFSPRDWQRLINNNWGFRPKRLNFKLFNIQVKEVTQNDGTTTIANNLTSTVQVFTD
hu.45-B  276 STPWGYFDFNRFHCHFSPRDWQRLINNNWGFRPKRLNFKLFNIQVKEVTQNDGTTTIANNLTSTVQVFTD
hu.57-B  275 STPWGYFDFNRFHCHFSPRDWQRLINNNWGFRPKRLNLKLFNIQVKEVTQNDGTTTIANNLTSTVQVFTD
hu.35-B  276 STPWGYFDFNRFHCHFSPRDWQRLINNNWGFRPKRLNFKLFNIQVKEVTQNDGTTTIANNLTSTVQVFTD
hu.58-B  276 STPWGYFDFNRFHCHFSPRDWQRLINNNWGFRPKRLNFKLFNIQVREVTQNDGTTTIANNLTSTVQVFTD
hu.28-B  276 STPWGYFDFNRFHCHFSPRDWQRLINNNWGFRPKRLNFKLFNIQVKEVTQNDGTTTIANNLTSTVQVFTD
hu.51-B  276 STPWGYFDFNRFHCHFSPRDWQRLINNNWGFRPKRLNFKLFNIQVKEVTQNDGTTTIANNLTSTVQVFTD
hu.19-B  276 STPWGYFDFNRFHCHFSPRDWQRLINNNWGFRPKRLNFKLFNIQVKEVTQNDGTTTIANNLTSTVQVFTD
hu.49-B  276 STPWGYFDFNRFHCHFSPRDWQRLINNNWGFRPKRLNFKLFNIQVKEVTQNDGTTTIANNLTSTVQVFTD
hu.52-B  276 STPWGYFDFNRFHCHFSPRDWQRLINNNWGFRPKRLNFKLFNIQVKEVTQNDGTTTIANNLTSTVQVFTD
hu.13-B  276 STPWGYFDFNRFHCHFSPRDWQRLINNNWGFRPKRLNFKLFNIQVKEVTQNDGTTTIANNLTSTVQVFTD
AAV2-B   276 STPWGYFDFNRFHCHFSPRDWQRLINNNWGFRPKRLSFKLFNIQVKEVTQNDGTTTIANNLTSTVQVFTD
hu.20-B  276 STPWGHFDFNRFHCHFSPRDWQRLINNNWGFRPKRLSFKLFNIQVKEVTQNDGTTTIANNLTSTVQVFTD
```

Fig. 2L

| | | |
|---|---|---|
| hu.24-B | 276 | STPWGYFDFNRFHCHFSPRDWQRLINNNWGFRPKRLSFKLFNIQVKEVTQNDGTTTIANNLTSTVQVFTD |
| hu.64-B | 276 | STPWGYFDFNRFHCHFSPRDWQRLINNNWGSRPKRLNFKLFNIQVKEVTQNDGTTTIANNLTSTVQVFTD |
| hu.27-B | 276 | STPWGYFDFNRFHCHFSPRDWQRLINNNWGFRPKRLSFKLFNIQVKEVTQNDGTTTIANNLTSTVQVFTD |
| hu.21-B | 276 | STPWGYFDFNRFHCHFSPRDWQRLINNNWGFRPKRLSFKLFNIQVKEVTQNDGTTTIANNLTSTVQVFTD |
| hu.22-B | 276 | STPWGYFDFNRFHCHFSPRDWQRLINNNWGFRPKRLSFKLFNIQVKEVTQNDGTTTIANNLTSTVQVFTD |
| hu.23-B | 276 | STPWGYFDFNRFHCHFSPRDWQRLINNNWGFRPKRLSFKLFNIQVKEVTQNDGTTTIANNLTSTVQVFTD |
| hu.7-C | 276 | STPWGYFDFNRFHCHFSPRDWQRLINNNWGFRPKRLNFKLFNIQVKEVTQNDGTTTIANNLTSTVQVFTD |
| hu.61-C | 276 | STPWGYFDFNRFHCHFSPRDWQRLINNNWGFRPKRLNFKLFNIQVKEVTQNDGTTTIANNLTSTVQVFTD |
| rh.56-C | 276 | STPWGYFDFNRFHCHFSPRDWQRLINNNWGFRPKRLNFKLFNIQVKEVTQNDGTTTIANNLTSTVQVFTD |
| hu.9-C | 276 | STPWGYFDFNRFHCHFSPRDWQRLINNNWGFRPKRLNFKLFNIQVKEVTQNDGTTTIANNLTSTVQVFTD |
| hu.54-C | 276 | STPWGYFDFNRFHCRFSPRDWQRLINNNWGFRPKRLNFKLFNIQVKEVTQNDGTTTIANNLTSTVQVFTD |
| hu.53-C | 276 | STPWGYFDFNRFHCHFSPRDWQRLINNNWGFRPKRLNFKLFNIQVKEVTQNDGTTTIANNLTSTVQVFTD |
| hu.60-C | 276 | STPWGYFDFNRFHCHFSPRDWQRLINNNWGFRPKRLNFKLFNIQVKEVTQNDGTTTIANNLTSTVQVFTD |
| hu.55-C | 276 | STPWGYFDFNRFHCHFSPRDWQRLINNNWGFRPKRLNFKLFNIQVKEVTQNDGTTTIANNLTSTVQVFTD |
| hu.2-C | 276 | STPWGYFDFNRFHCHFSPRDWQRLINNNWGFRPKRLNFKLFNIQVKEVTQNGGTTTIANNLTSTVQVFTD |
| hu.1-C | 276 | STPWGYFDFNRFHCHFSPRDWQRLINNNWGFRPKRLNFKLFNIQVKEVTQNDGTTTIANNLTSTVQVFTD |
| hu.18-C | 276 | STPWGYFDFNRFHCHFSPRDWQRLINNSWGFRPKRLNFKLFNIQVKEVTQNDGTTTIANNLTSTVQVFTD |
| hu.3-C | 277 | STPWGYFDFNRFHCHFSPRDWQRLINSNWGFRPKRLNFKLFNIQVKEVTQNDGTTTIANNLTSTVQVFTD |
| hu.25-C | 276 | STPWGYFDFNRFHCHFSPRDRQRLINNNWGFRPKRLNFKLFNIQVKEVTQNDGTTTIANNLTSTVQVFTD |
| hu.15-C | 276 | STPWGYFDFNRFHCHFSPRDWQRLINNNWGFRPKRLNFKLFNIQVKEVTQNDGTTTIANNLTSTVQVFTD |
| hu.16-C | 276 | STPWGYFDFNRFHCHFSPRDWQRLINNNWGFRPKRLNFKLFNIQVKEVTQNDGVTTIANNLTSTVQVFTD |
| hu.11-C | 276 | STPWGYFDFNRFHCHFSPRDWQRLINNNWGFRPKKLNFKLFNIQVKEVTQNDGVTTIANNLTSTVQVFTD |
| hu.10-C | 276 | STPWGYFDFNRFHCHFSPRDWQRLINNNWGFRPKKLNFKLFNIQVKEVTQNDGVTTIANNLTSTVQVFTD |
| hu.4-C | 276 | STPWGYFDFNRFHCHFSPRDWQRLINNNWGFRPKRLNFKLFNIQVKEVTQNDGTTTIANNLTSTVQVFTD |
| rh.54-D | 278 | STPWGYFDFNRFHCHFSPRDWQRLVNNNWGFRPKRLINNNWGVTTIANNLTSTVQVFSD |
| rh.48-D | 278 | STPWGYFDFNRFHCHFSPRDWQRLINNNWGFRPKRLNFKLFNIQVKEVTTNDGVTTIANNLTSTVQVFSD |
| rh.55-D | 278 | STPWGYFDFNRFHCHFSPRDWQRLINSNWGFRPKRLNFKLFNIQVKEVTTNDGVTTIANNLTSTVQVFSD |
| rh.62-D | 278 | STPWGYFDFNRFHCHFSPRDWQRLINNNWGFRPKRLNFKLFNIQVKEVTTGDGVTTIANNLTSTVQVFSD |
| AAV7-D | 278 | STPWGYFDFNRFHCHFSPRDWQRLINNNWGFRPKKLRFKLFNIQVKEVTTNDGVTTIANNLTSTIQVFSD |
| rh.52-E | 279 | STPWGYFDFNRFHCHFSPRDWQRLINNNWGFRPKRLSFKLFNIQVKEVTQNEGTKTIANSLTSTIQVFTD |

Fig. 2M

```
rh.51-E  279  STPWGYFDFNRFHCHFSPRDWQRLINNNWGFRPKRLSFKLFNIQVKEVTQNEGTKTIANNLTSTIQVFTD
hu.39-E  279  STPWGYLDFNRFHCHFSPRDWQRLINNNWGFRPKRLSFKLFNIQVKEVTQNEGTKTIANNLASTIQVFTD
rh.53-E  279  STPWGYFDFNRFHCHFSPRDWQRLINNNWGFRPKRLSFKLFNIQVKEVTQNEGTKTIANNLTSTIQVFTD
hu.37-E  278  STPWGYFDFNRFHCHFSPRDWQRLINNNWGFRPKRLSFKLFNIQVKEVTQNEGTKTIANNLTSTIQVFTD
rh.43-E  279  STPWGYFDFNRFHCHFSPRDWQRLINNNWGFRPKRLSFKLFNIQVKEVTQNEGTKTIANNLTSTIQVFTD
rh.50-E  279  STPWGYFDFNRFHCHFSPRDWQRLINNNWGFRPKRLSFKLFNIQVKEVTQNEGTKTIANNLTSTIQVFTD
rh.49-E  279  STPWGYFDFNRFHCHFSPRDWQRLINNNWGFRPKRLSFKLFNIQVKEVTQNEGTKTIANNLTSTIQVFTD
rh.61-E  279  STPWGYFDFNRFHCHFSPRDWQRPINNNWGFRPKRLSFKLFNIQVKEVTQNEGTKTVANNLTSTIQVFTD
hu.41-E  279  STPWGYFDFNRFHCHFSPRDWQRLINNNWGFRPKRLSFKLFNIQVKEVTQNEGTKTIANNLTSTIQVFTD
rh.64-E  279  STPWGYFDFNRFHCHFSPRDWQRLINNNWGFRPKRLSFKLFNIQVKEVTQNEGTKTIANNLTSTIQVFTD
hu.42-E  279  STPWGYFDFNRFHCHFSPRDWQRLINNNWGFRPKRLSFKLFNIQVKEVTQDEGTKTIANNLTSTIQVFTD
rh.57-E  279  STPWGYFDFNRFHCHFSPRDWQRLINNNWGFRPKRLSFKLFNIQVKEVTQNEGTKTIANNLTSTIQVFTD
rh.40-E  279  STPWGYFDFNRFHCHFSPRDWQRLINNNWGFRPKRLSFKLFNIQVKEVTQNEGTKTIANNLTSTIQVFTD
AAV8-E   279  STPWGYFDFNRFHCHFSPRDWQRLINNNWGFRPKRLSFKLFNIQVKEVTQNEGTKTIANNLTSTIQVFTD
rh.58-E  279  STPWGYFDFNRFHCHFSPRDWQRLINNNWGFRPKRLNFKLFNIQVKEVTQNEGTETIANNLTSTIQVFTD
hu.40-E  279  STPWGYFDFNRFHCHFSPRDWQRLINNNWGFRPKRLSFKLFNIQVKEVTQNEGTKTIANNLTSTIQVFTD
rh.67-E  279  STPWGYFDFNRFHCHFSPRDWQRLINNNWGFRPKRLSFKPFNIQVKEVTQNEGTKTIANNLTSTIQVFTD
hu.17-E  279  STPWGYFDFNRFHCHFSPRDWQRLINNNWGFRPKRLNFKLFNIQVKEVTDNNGVKTIANNLTSTVQVFTD
hu.6-E   279  STPWGYFDFNRFHCHFSPRDWQRLINNNWGFRPKRLNFKLFNIQVKEVTDNNGVKTIANNLTSTVQVFTD
hu.66-E  279  STPWGYFDFNRFHCHFSPRDWQRLINNNWGFRPKRLNFKLFNIQVKEVTDNNGVKTIANNLTSTIQVFTD
rh.38-E  279  STPWGYFDFNRFHCHFSPRDWQRLINNNWGFRPKRLNFKLFNIQVKEVTDNNGVKTIANNLTSTVQVFTD
hu.32-F  279  STPWGYFDFNRFHCHFSPRDWQRLINNNWGFRPKRLSFKLFNIQVKEVTQNEGTKTIANNLTSTVQVFTD
AAV9/hu  278  STPWGYFDFNRFHCHFSPRDWQRLINNNWGFRPKRLNFKLFNIQVKEVTDNNGVKTIANNLTSTVQVFTD
hu.31-F  278  STPWGYFDFNRFHCHFSPRDWQRLINNNWGFRPKRLNFKLFNIQVKEVTDNNGVKTIANNLTSTVQVFTD 360       370       380       390       400       410       420

AAV5     337  DDYQLPYVVGNGTEGCLPAFPPQVFTLPQYGYATLNRD-NTENPTERSSFFCLEYFPSKMLRTGNNFEFT
AAV3-3   346  SEYQLPYVLGSAHQGCLPPFPADVFMVPQYGYLTLNNG---SQAVGRSSFYCLEYFPSQMLRTGNNFQFS
AAV4-4   337  SSYELPYVMDAGQEGSLPPFPNDVFMVPQYGYCGLVTGNTSQQQTDRNAFYCLEYFPSQMLRTGNNFEIT
```

Fig. 2N

| | | | | |
|---|---|---|---|---|
| AAV1-A | 347 | SEYQLPYVLGSAHQGCLPPFPADVFMIPQYGYLTLNNG---- | SQAVGRSSFYCLEYFPSQMLRTGNNFTFS |
| hu.46-A | 347 | SEYQLPYVLGSAHQGRLPPFPADVFMIPQYGYLTLNNG---- | SQAVGRSSSYCLEYFPSQMLRTGNNFTFS |
| hu.48-A | 347 | SEYQLPYVLGSAHQGCLPPFPADVFMIPQYGYLTLNNG---- | SQAVGRSSFYCLEYFPSQMLRTGNNFTFS |
| hu.44-A | 347 | SEYQLPYVLGSAHQGCLPPFPADVFMIPQYGYLTLNNG---- | SQAVGRSSFYCLGYFPSQMLRTGNNFTFS |
| hu.43-A | 348 | SEYQLPYVLGSAHQGCLPPFPADVFMIPQYGYLTLNNG---- | SQAVGRSSFYCLEYFPSQMLRTGNNFTFS |
| AAV6-A | 347 | SEYQLPYVLGSAHQGCLPPFPADVFMIPQYGYLTLNNE---- | SQAVGRSSFYCLEYFPSQMLRTGNNFTFS |
| hu.34-B | 346 | SEYQLPYVLGSAHQGCLPPFPADVFMVPQYGYLTLNNG---- | SQAVGRSSFYCLEYFPSQMLRTGNNFTFS |
| hu.47-B | 346 | SEYQLPYVLGSAHQGCLPPFPADVFMVPQYGYLTLNNG---- | SQAVGRSSFYCLEYFPSQMLRTGNNFTFS |
| hu.29-B | 346 | SEYQLPYVLGSAHQGCLPPFPADVFMVPQYGYLTLNNG---- | SQAVGRSSFYCLEYFPSQMLRTGNNFTFS |
| hu.63-B | 346 | SEYQLPYVLGSAHQGCLPPFPADVFMVPQYGYLTLNNG---- | SQAVGRSSFYCLEYFPSQMLRTGNNFTFS |
| hu.56-B | 346 | LEYQLPYVLGSAHQGCLPPFPADVFMVPQYGYLTLNNG---- | SQAVGRSSFYCLEYFPSQMLRTGNNFTFS |
| hu.45-B | 346 | SGYQLPYVLGSAHQGCLPPFPADVFMVPQYGYPTLNNG---- | SQAVGRSSFYCLEYFPSQMLRTGNNFTFS |
| hu.57-B | 345 | LEYQLPYVLGSAHQGCLPPFPADVFMVPQYGYLTLNNG---- | SQAVGRSSFYCLEYFPSQMLRTGNNFTFS |
| hu.35-B | 346 | SEYQLPYVLGSAHQGCLPPFPADVFMVPQYGYLTLNNG---- | SQAVGRSSFYCLEYFPSQMLRTGNNFTFS |
| hu.58-B | 346 | SEYQLPYVLGSAHQGCLPPFPADVFMVPQYGYLTLNNG---- | SQAVGRSSFYCLEYFPSQMLRTGNNFTFS |
| hu.28-B | 346 | SEYQLPYVLGSAHQGCLPPFPADVFMVPQYGYLTLNNG---- | SQAVGRSSFYCLEYFPSQMLRTGNNFTFS |
| hu.51-B | 346 | SEYQLPYVLGSAHQGCLPPFPADVFMVPQYGYLTLNNG---- | SQAVGRSSFYCLEYFPSQMLRTGNNFTFS |
| hu.19-B | 346 | SEYQLPYVLGSAHQGCLPPFPADVFMVPQYGYLTLNNG---- | SQAVGRSSFYCLEYFPSQMLRTGNNFTFS |
| hu.49-B | 346 | SEYQLPYVPGSAHQGCLPPFPADVFMVPQYGYLTLNNG---- | SQAVGRSSFYCLEYFPSQMLRTGNNFTFS |
| hu.52-B | 346 | SEYQLPYVLGSAHQGCLPPFPADVFMVPQYGYLTLSNG---- | SQAVGRSSFYCPEYFPSQMLRTGNNFTFS |
| hu.13-B | 346 | SEYQLPYVLGSAHQGCLPPFPADVFMVPQYGYLTLNNG---- | SQAVGRSSFYCLEYFPSQMLRTGNNFTFS |
| AAV2-B | 346 | SEYQLPYVLGSAHQGCLPPFPADVFMVPQYGYLTLNNG---- | SQAVGRSSFYCLEYFPSQMLRTGNNFTFS |
| hu.20-B | 346 | SEYQLPYVLGSAHQGCLPPFPADVFMVPQYGYLTLNNG---- | SQAVGRSSFYCLEYFPSQMLRTGNNFTFS |
| hu.24-B | 346 | SEYQLPYVLGSAHQGCLPPFPADVFMVPQYGYLTLNNG---- | SQAVGRSSFYCLEYFPSQMLRTGNNFTFS |
| hu.64-B | 346 | SEYQLPYVLGSAHQGCLPPFPADVFMVPQYGYLTLNNG---- | SQAVGRSSFYCLEYFPSQMLRTGNNFTFS |
| hu.27-B | 346 | SGYQLPYVLGSAHQGCLPPFPADVFMVPQYGYLTLNNG---- | SQAVGRSSFYCLEYFPSQMLRTGNNFTFS |
| hu.21-B | 346 | SEYQLPYVLGSAHQGCLPPFPADVFMVPQYGYLTLNNG---- | SQAVGRSSFYCLEYFPSQMLRTGNNFTFS |
| hu.22-B | 346 | SEYQLPYVLGSAHQGCLPPFPADVFMVPQYGYLTLNNG---- | SQAVGRSSFYCLEYFPSQTLRTGNNFTFS |
| hu.23-B | 346 | SEYQLPYVLGSAHQGCLPPFPADVFMVPQYGYLTLNNG---- | SQAVGRSSFYCLEYFPSQMLRTGNNFTFS |
| hu.7-C | 346 | SEYQLPYVLGSAHQGCLPPFPADVFMVPQYGYLTLNNG---- | SQAVGRSSFYCLEYFPSQMLRTGNNFQFS |

Fig. 20

| | | |
|---|---|---|
| hu.61-C | 346 | SEYQLPYVLGSAHQGCLPPFPADVFMVPQYGYLTLNNG----SQAVGRSSFYCLEYFPSQMLRTGNNFQFS |
| rh.56-C | 346 | SEYQLPYVLGSAHQGCLPPFPADVFMVPQYGYLTLNNG----SQAVGRSSFYCLEYFPSQMLRTGNNFQFS |
| hu.9-C | 346 | SEYPLPYVLGSAHQGCLPPFPADVFMVPQYGYLTLNNG----SQAVGRSSFYCLEYFPSQMLRTGNNFTFS |
| hu.54-C | 346 | SEYQLPYVLGSAHQGCLPPFPADVFMVPQYGYLTLNNG----SQAVGRSSFYCLEYFPSQMLRTGNNFTFS |
| hu.53-C | 346 | SEYQLPYVLGSAHQGCLPPFPADVFMVPQYGYLTLNNG----SQAVGRSSFYCLEYFPSQMLRTGNNFQFS |
| hu.60-C | 346 | SEYQLPYVLGSAHQGCLPPFPADVFMVPQYGYLTLNNG----SQAVGRSSFYCLEYFPSQMLRTGNNFQFS |
| hu.55-C | 346 | SEYQLPYVLGSAHQGCLPPFPADVFMVPQYGYLTLNNG----SQAVGRSSFYCLECFPSQMLRTGNNFQFS |
| hu.2-C | 346 | SEYQLPYVLGSAHQGCLPPFPADVFMVPQYGYLTLNNG----SQAVGRSSFYCLEYFPSQMLRTGNNFQFS |
| hu.1-C | 346 | SEYQLPYVLGSAHQGCLPPFPADVFMVPQYGYLTLNNG----SQAVGRSSFYCLEYFPSQMLRTGNNFQFS |
| hu.18-C | 346 | SEYQLPYVLGSAHQGCLPPFPADVFMVPQYGYLTLNNG----SQAVGRSSFYCLEYFPSQMLRTGNNFQFS |
| hu.3-C | 347 | SEYQLPYVPGSAHQGCLPPFPADVFMVPQYGYLTLNNG----SQAVGRSPFYCLEYFPSQMLRTGNNFQFS |
| hu.25-C | 346 | SGYQLPYVLGSAHQGCLPPFPADVFMVPQYGYLTLNNG----SQAVGRSSFYCLEYFPSQMLRTGNNFQFS |
| hu.15-C | 346 | SEYQLPYVLGLAHQGCLPPFPADVFMVPQYGYLTLNNG----SQAVGRSSFYCLEYFPSQMLRTGNNFQFS |
| hu.16-C | 346 | SEYQLPYVLGSAHQGCLPPFPADVFMVPQYGYLTLNNG----SQAVGRSSFYCLEYFPSQMLRTGNNFTFS |
| hu.11-C | 346 | SEYQLPYVLGSAHQGCLPPFPADVFTVPQYGYLTLNNG----SQAVGRSSFYCLEYFPSQMLRTGNNLTFS |
| hu.10-C | 346 | SEYQLPYVLGSAHQGCLPPFPADVFMVPQYGYLTLNNG----SQAVGRSSFYCLEYFPSQMLRTGNNFQFS |
| hu.4-C | 346 | SEYQLPYVLGSAHQGCLPPFPADVFMVPQYGYLTLNNG----SQAVGRSSFYCLEYFPSQMLRTGNNFTFS |
| rh.54-D | 348 | SEYQLPYVLGSAHQGCLPPFPADVFMIPQYGYLTLNNG----SQSVGRSSFYCLEYFPSQVLRTGNNFTFS |
| rh.48-D | 348 | SEYQLPYVLGSAHQGCLPPFPADVFMIPQYGYLTLNNG----SQSVGRSSFYCLEYFPSQMLRTGNNFTFS |
| rh.55-D | 348 | SEYQLPYVLGSAHQGCLPPFPADVFMIPQYGYLTLNND----SQSVGRSSFYCLEYFPSQMLRTGNNFTFS |
| rh.62-D | 348 | SEYQLPYVLGSAHQGCLPPFPADVFMIPQYGYLTPNNG----SQAVGRSSFYCLEYFPSQMLRTGNNFEFS |
| AAV7-D | 348 | SEYQLPYVLGSAHQGCLPPFPADVFMIPQYGYLTLNNG----SQAVGRSSFYCLEYFPSQMLRTGNNFEFS |
| rh.52-E | 349 | SEYQLPYVLGSAHQGCLPPFPADVFMIPQYGYLTLNNG----SQAVGRSSFYCLEYFPSQMLRTGNNFSFS |
| rh.51-E | 349 | SEYQPPYVLGSAHQGCQPPFPADVFMIPQYGYLTLNNG----SQAVGRSSFYCLEYFPSQMLRTGNNFSFS |
| hu.39-E | 349 | SEYQLPYVLGSAHQGCLPPFPADVFMIPQYGYLTLNNG----SQAVGRSSFYCLEYFPSQMLRTGNNFSFS |
| rh.53-E | 349 | SEYQLPYVLGSAHQGCLPPFPADVFMIPQYGYLTLNNG----SQAVGRSSFYCLEYFPSQMLRTGNNFEFS |
| hu.37-E | 349 | SEYQLPYVLGSAHQGCLPPFPADVFMIPQYGYLTLNNG----SQAVGRSSFYCLEYFPSQMLRTGNNFEFS |
| rh.43-E | 348 | SEYQLPYVLGSAHQGCLPPFPADVFMIPQYGYLTLNNG----SQAVGRSSFYCLEYFPSQMLRTGNNFQFT |
| rh.50-E | 349 | SEYQLPYVLGSAHQGCLPPFPADVFMIPQYGYLTLNNG----SQAVGRSSFYCLEYFPSQMLRTGNNFSFS |
| rh.49-E | 349 | SEYQLPYVLGSAHQGCLPPFPADVFMIPQYGNLTLNNG----SQAVGRSSFYCLEYFPSQMLRTGNNFSFS |

| | | |
|---|---|---|
| hu.47-B | 413 | YTFEDVPFHSSYAHSQSLDRLMNPLIDQYLYYLSTTN-TPSGTTTQSRLQFSQAGASDIRDQSRNWLPGP |
| hu.29-B | 413 | YTFEDVPFHSSYAHSQSLDRLMNPLIDQYLYYLSRTN-TPSGTTTQSRLQFSQAGASDIRDQSRNWLPGP |
| hu.63-B | 413 | YTFEDVPFHSSYAHSQSLDRLMNPLIDQYLYYLSRTN-TPSGTTTQSRLQFSQAGASDIRDQSRNWLPGP |
| hu.56-B | 413 | YTFEDVPFHSSYAHSQSLDRLMNPLIDQYLYYLSRTN-TPSGTTTQSRLQFSQAGASDIRDQSRNWLPGP |
| hu.45-B | 413 | YTFEDVPFHSSYAHSQSLDRLMNPLIDQYLYYLSTTN-TPSGTTTQSRLQFSQAGASDIRDQSRNWLPGP |
| hu.57-B | 412 | YTFEDVPFHSSYAHSQSLDRLMNPLIDQYLYYLSRTN-TPSGTTTQSRLQFSQAGASDIRDQSRNWLPGP |
| hu.35-B | 413 | YTFEDVPFHSSYAHSQSLGRLMNPLIDQYLYYLSRTN-TPSGTTTQSRLQFSQAGASDIRDQSRNWLPGP |
| hu.58-B | 413 | YTFEDVPFHSSYAHSQSLDRLMNPLIDQYLYYLSRTN-TPSGTTTQSRLQFSQAGASDIRDQSRNWLPGP |
| hu.28-B | 413 | YTFEDVPFHSSYAHSQSLDRLMNPLIDQYLYYLSRTN-TPSGTTTQSRLQFSQAGASDIQDQSRNWLPGP |
| hu.51-B | 413 | YTFEDVPFHSSYAHSQSLDRLMNPLIDQYLYYLSTTN-TPSGTTTQSRLQFSQAGASDIRDQSRNWLPGP |
| hu.19-B | 413 | YTFEDVPFHSSYAHSQSLDRLMNPLIDQYLYYLSRTN-TPSGTTTQSRLQFSQAGASDIRDQSRNWLPGP |
| hu.49-B | 413 | YTFEDVPFHSSYAHSQSLDRLMNPLIDQYLYYLSRTN-TPSGTTTMSRLQFSQAGASDIRDQSRNWLPGP |
| hu.52-B | 413 | YTFEDVPFHSSYAHSQSLDRLMNPLIDQYLYYLSTTN-TPSGTTTQSRLQFSQAGASDIRDQSRNWLPGP |
| hu.13-B | 413 | YTFEDVPFHSSYAHSQSLDRLMNPLIDQYLYYLSRTN-TPSGTTTQSRLQFSQAGASDIRDQSRNWLPGP |
| AAV2-B | 413 | YTFEDVPFHSSYAHSQSLDRLMNPLIDQYLYYLSRTN-TPSGTTTQSRLQFSQAGASDIRDQSRNWLPGP |
| hu.20-B | 413 | YTFEDVPFHSSYAHSQSLDRLMNPLVDQYLYYLSRTN-TPSGTTTMSRLQFSQAGASDIRDQSRNWLPGP |
| hu.24-B | 413 | YTFEDVPFHSSYAHSQSLDRLMNPLIDQYLYYLSRTN-TPSGTTTMSRLQFSQAGASDIRDQSRNWLPGP |
| hu.64-B | 413 | YTFEDVPFHSSYAHSQSLDRLMNPLIDQYLYYLSRTN-TPSGTTTMSRLQFSQAGASDIRDQSRNWLPGP |
| hu.27-B | 413 | YTFEDVPFHSSYAHGQSLDRLMNPLIDQYLYYLSRTN-TPSGTTTMSRLQFSQAGASDVRDQSRNWLPGP |
| hu.21-B | 413 | YTFEDVPFHSSYAHSQSLDRLMNPLIDQYLYYLSRTN-TPSGTTTMSRLQFSQAGASDIRDQSRNWLPGP |
| hu.22-B | 413 | YTFEDVPFHSSYAHSQSLDRLMNPLIDQYLYYLSRTN-TPSGTTTMSRLQFSQAGASDIRDQSRNWLPGP |
| hu.23-B | 413 | YTFEDVPFHSSYAHSQSLDRLMNPLIDQYLYYLSRTN-TPSGTTTMSRLQFSQAGASDIRDQSRNWLPGP |
| hu.7-C | 413 | YTFEDVPFHSSYAHSQSLDRLMNPLIDQYLYYLNKTQ-SNSGTLQQSRLLFSQAGPTSMSLQAKNWLPGP |
| hu.61-C | 413 | YTFEDVPFHSSYAHSQSLDRLMNPLIDQYLYYLNKTQ-TNSGTLQQSRLLFSQAGPTSMSLQAKNRLPGP |
| rh.56-C | 413 | YTFEDVPFHSSYAHSQSLDRLMNPLIDQYLYYLNKTQ-SNSGALQQSRLLFSQAGPTSMSLQAKNWLPGP |
| hu.9-C | 413 | YTFEDVPFHSSYAHSQSLDRLMNPLIDQYLYYLNRTQ-TASGT-QQSRLLFSQAGPTSMSLQAKNWLPGP |
| hu.54-C | 413 | YTFEDVPFHSSYAHSQGLDRLMNPLIDQYLYYLNRTQ-TASGT-QQSRLLFSQAGPTSMSLQAKNWLPGP |
| hu.53-C | 413 | YTFEDVPFHSSYAHSQSLDRLMNPLIDQYLYYLNRTQ-TASGT-QQSRLLFSQAGPTSMSLQAKNWLPGP |
| hu.60-C | 413 | YTFEDVPFHSSYAHSQSLDRLMNPLVDQYLYYLNKTQ-TNSGTLQQSRLLFSQAGPTSMSLQAKNWLPGP |
| hu.55-C | 413 | YTFEDVPFHSSYAHSQSLDRLMNPLIDQYLYYLNRTQ-TASGT-QQSRLLFSQAGPTSMSLQAKNWLPGP |

Fig. 2R

| | | |
|---|---|---|
| hu.2-C | 413 | YTFEDVPFHSSYAHSQSLDRLMNPLIDQYLYYLNKTQ-TNSGTLQQSRLLFSQAGPTNMSLQAKNWLPGP |
| hu.1-C | 413 | YTFEDVPFHSSYAHSQSLDRLMNPLIDQYLYYLNKTQ-TNSGTLQQSRLLFSQAGPTNMSLQAKNWLPGP |
| hu.18-C | 413 | YTFEDVPFHSSYAHSQSLDRLLNPLIDQYLYYLNKTQ-SNSGTLQQSRLLFSQAGPTSMSLQAKNWLPGP |
| hu.3-C | 414 | YTFEDVPFHSSYAHCQSLDRLMNPLIDQYLYYLNKTQ-TNSGTLQQSRLLFSQAGPTNMSLQAKNWLPGP |
| hu.25-C | 413 | YTFEDVPFHSSYAHSQSLDRLMNPLIDQYLYYLNKTQ-TNSGTLQQSRLLFSQAGPTNMSLQAKNWLPGP |
| hu.15-C | 413 | YTFEDVPFHSSYAHSQSLDRLMNPLIDQYLYYLNKTQ-SNSGTLQQSRLLFSQAGPTSMSLQAKNWLPGP |
| hu.16-C | 413 | YTFEDVPFHSSYAHSQSLDRLMNPLIDQYLYYLNKTQ-SNSGTLQQSRLLFSQAGPTSMSLQAKNWLPGP |
| hu.11-C | 413 | YTFEDVPFHSSYAHSQSLDRLMNPLIDQYLYYLNRTQ-SNSGTLQQSRLLFSQAGPTSMSLQAKNWLPGP |
| hu.10-C | 413 | YTFEDVPFHSSYAHSQSLDRLMNPLIDQYLYYLNRTQ-SNSGTLQQSRLLFSQAGPTSMSLQAKNWLPGP |
| hu.4-C | 413 | YTFEDVPFHSSYAHSQSLDRLMNPLIDQYLYYLNKTQ-TNSGTLQQSRLLFSQAGPTNMSLQAKNWLPGP |
| rh.54-D | 415 | YTFEDVPFHSSYAHSQSLDRLMNPLIDQYLYYLARTQSNPGGTSGNRELQFYQGGPSTMAEQAKNWLPGP |
| rh.48-D | 415 | YTFEDVPFHSSYAHSQSLDRLMNPLIDQYLYYLARTQSNAGGTAGNRELQFYQGGPTTMAEQAKNWLPGP |
| rh.55-D | 415 | YTFEDVPFHSSYAHSQSLDRLMNPLIDQYLYYLARTQSNAGGTAGNRELQFYQGGPTTMAEQAKNWLPGP |
| rh.62-D | 415 | YTFEDVPFHSSYAHSQSLDRLMNPLIDQYLYYLARTQSNAGGTAGNRELQFYQGGPTTMAEQAKNWLPGP |
| AAV7-D | 415 | YSFEDVPFHSSYAHSQSLDRLMNPLIDQYLYYLARTQSNPGGTAGNRELQFYQGGPSTMAEQAKNWLPGP |
| rh.52-E | 416 | YTFEDVPFHSSYAHSQSLDRLMNPLIDQYLYYLYLSRTQS-TGGTAGTQQLLSSQAGPSNMSAQARNWLPGP |
| rh.51-E | 416 | YTFEDVPFHSSYAHSQSLDRLMNPLIDQYLYYLYLSRTQS-TGGTAGTQQLLFSQAGPSNMSAQARNWLPGP |
| rh.39-E | 416 | YTFEDVPFHSSYAHSQSLDRLMNPLIDQYLYYLYLSRTQS-TGGTAGTQQLLFSRAGPSNMSAQARNWLPGP |
| rh.53-E | 416 | YTFEDVPFHSSYAHSQSLDRLMNPLIDQYLYYLYLSRTQS-TGGTAGTQQLLFSQAGPSNMSAQARNWLPGP |
| rh.37-E | 416 | YTFEDVPFHSSYVHSQSLDRLMNPLIDQYLYYLYLSRTQS-TGGTQGTQQLLFSQAGPANMSAQAKNWLPGP |
| hu.43-E | 415 | YTFEDVPFHSSYAHSQSLDRLMNPLVDQYLYYLYLSRTQT-TGGTANTQTLGFSQGGPNTMANQAKNWLPGP |
| rh.50-E | 416 | YTFEDVPFHSSYAHSQSLDRLMNPLIDQYLYYLYLSRTQS-TGGTAGTQQLLFSQAGPSNMSAQARNWLPGP |
| hu.49-E | 416 | YTFEDVPFHSSYAHSQSLDRLMNPLIDQYLYYLYLSRTQS-TGGTAGTQQLLFSQAGPSNMSAQARNWLPGP |
| rh.61-E | 416 | YPFEDVPFHSSYAHSQSLDRLMNPLIDQYLYYLYLSRTQS-TGGTAGTQQLLFSQAGPSNMSAQARNWLPGP |
| hu.41-E | 416 | YTFEDVPFHSSYAHSQSLDRLMNPLIDQYLYYLYLSRTQS-TGGTQGTQQLLFSQAGPANMSAQAKNWLPGP |
| hu.64-E | 416 | YTFEDVPFHSSYAHSQSLDRLMNPLIDQYLYYLYLSRTQS-TGGTQGTQQLLFSQAGPANMSAQAKNWLPGP |
| rh.42-E | 416 | YTFEDVPFHSSYAHSQSLDRLMNPLIDQYLYYLYLSRTQS-TGGTQGTQQLLFSQAGPANMSAQAKNWLPGP |
| rh.57-E | 416 | YTFEDVPFHSSYAHSQSLDRLMNPLIDQYLYYLYLSRTQS-TGGTQGTQQLLFSQAGPANMSAQAKNWLPGP |
| hu.40-E | 416 | YTFEDVPFHSSYAHSQSLDRLMNPLIDQYLYYLYLSRTQT-TGGTANTQTLGFSQGGPNTMANQAKNWLPGP |
| AAV8-E | 416 | YTFEDVPFHSSYAHSQSLDRLMNPLIDQYLYYLSRTQT-TGGTANTQTLGFSQGGPNTMANQAKNWLPGP |

```
                       500         510         520         530         540         550         560
                         .    |    .    |    .    |    .    |    .    |    .    |    .    |
rh.58-E    416  YTFEDVPFHSSYAHSQSLDRLMNPLIDQYLYYLSRTQS-TGGTAGTQQLLFSQAGPSNMSAQARNWLPGP
rh.40-E    416  YTFEDVPFHSSYAHSQSLDRLMNPLIDQYLYYLSRTQS-TGGTQGTQQLLFSQAGPANMSARAKNWLPGP
hu.67-E    416  YTFEDVPFHSGYAHSQSLDRLMNPLIDQYLYYLSRTQS-TGGTQGTQQLLFSQAGPANMSAQAKNWLPGP
hu.17-E    416  YQFEDVPFHSSYAHSQSLDRLMNPLIDQYLYYLSRTQS-TGGTQGTQQLLFSQAGPNNMSAQAKNWLPGP
hu.6-E     416  YQFEDVPFHSSYAHSQSLDRLMNPLIDQYLYYLSRTQS-TGGTAGTQQLLFSQAGPNNMSAQAKNWLPGP
hu.66-E    416  YTFEDVPFHSSCAHSQSLDRLMNPLIDQYLYYLSRTQS-TGGTAGTQQLLFSQAGPANMSAQAKNWLPGP
rh.38-E    416  YTFEDVPFHSSYAHSQSSDRLMNPLIDQYLYYLSRTRS-TGGTQGTQQLLFSQAGPANMSAQAKNWLPGP
hu.32-F    415  YEFENVPFHSSYAHSQSLDRLMNPLIDQYLHYLYYLSRTQS-TGGTQGTQQLLFSQAGPANMSAQAKNWLPGP
AAV9/hu    415  YEFENVPFHSSYAHSQSLDRLMNPLIDQYLYYLSKTINGSG---QNQQTLKFSVAGPSNMAVQGRNYIPGP
hu.31-F    415  YEFENVPFHSSYAHSQSLDRLMNPLIDQYLYYLSKTINGSG---QNQQTLKFSVAGPSNMAVQGRNYIPGP

AAV5       469  MGRTQGWNLGSGVN------RASVSAFATTNRMELEGASYQVPPQPNGMTNNLQGSNTYALENTMIFNSQP
AAV3-3     483  CYRQQRLSKTANDN------NNSNFPWTAASKYHLNSTLDGRWSALTPGPMATAGPADSKFS-NSQLIFAGPKQ
AAV4-4     477  SIKQQGFSKTANQNYKIPATGSDSLIKYETHSTLDGRWSALTPGPMATAGPADSKFS-NSQLIFAGPKQ
AAV1-A     483  CYRQQRVSKTKTDN------NNSNFTWTGASKYNLNGRESIINPGTAMASHKDDEDKFFPMSGVMIFGKES
hu.46-A    483  CYRQQRVSKTKTDN------NNSNFTWTGASKYNLNGRESIINPGTAMASHKDDEDKFFPMSGVMIFGKES
hu.48-A    483  CYRQQRVSKTKTDN------NNSNFTWTWTGASKYNLNGRESIINPGTAMASHKDDEDKFFPMSGVMIFGKES
hu.44-A    483  CYRQQRVSKTKTDN------NNSNFTWTWTGASKYNLNGRESIINPGTAVASHKDDEDKFFPMSGVMIFGKES
hu.43-A    484  CYRQQRVSKTKTDN------NNSNFTWTWTGASKYNLNGRESIINPGTAMASHKDDEDKFFPMSGVMIFGKES
AAV6-A     483  CYRQQRVSKTKTDN------NNSNFTWTGASKYNLNGRESIINPGTAMASHKDDEDKFFPMSGVMIFGKES
hu.34-B    482  CYRQQRVSKTSADN------NNSEYSWTGATKYHLNGRDSLVNPGPAMASHKDDEEKFFPQSGVLIFGKQG
hu.47-B    482  CYRQQRVSKTSADN------NNSEYSWTGATKYHLNGRDSLVNPGPAMASHKDNEEKFFPQSGVLIFGKQG
hu.29-B    482  CYRQQRVSKTSADN------NNSEYSWTGATKYHLNGRDSLVNPGPAMASHKDDEEKFFPQSGVLIFGKQG
hu.63-B    482  CYRQQRVSKTSADN------NNSEYSWTGATKYHLNGRDSLVNPGPAMASHKDDEEKFFPQSGVLIFGKQD
hu.56-B    482  CYRQQRVSKTAADN------NNSEYSWTGATKYHLNGRDSLVNPGPAMASHKDDEEKFFPQSGVLIFGKQG
hu.45-B    482  CYRQQRVSKTSADN------NNSEYSWTGATKYHLNGRDSLVNPGPAVASHKDDEEKFFPQSGVLIFGKQG
hu.57-B    481  CYRQQRVSKTAADN------NNGEYSWTGATKYHLNGRDSLVNPGPAMASHKDDEEKFFPQSGVLIFGKQG
hu.35-B    482  CYRQQRVSKTSADN------NNSEYSWTGATKYHLNGRDSLVNPGPAMASHKDDEEKFFPQSGVLIFGKQG
```

| Name | Pos | Sequence |
|---|---|---|
| hu.58-B | 482 | CYRQQRVSKTSADN-----NNSEYSWIGATKYHLNGRDSLVNPGPAMASHKDDEEKFFPQSGVLIFGKQG |
| hu.28-B | 482 | CYRQQRVSKTSADN-----NNSEYSWTGATKYHLNGRDSLVNPGPAMASHKDDEEKFFPQSGVLIFGKQG |
| hu.51-B | 482 | CYRQQRVSKTSADN-----NNSEYSWTGATKYHLNGRDSLVNPGPAMASHKDNEEKFFPQSGVLIFGKQG |
| hu.19-B | 482 | CYRQQRVSKTAADN-----NNSDYSWTGATKYHLNGRDSLVNPGPAMASHKDDEEKYFPQSGVLIFGKQD |
| hu.49-B | 482 | CYRQQRVSKTSADN-----NNSEYSWTGATKYHLNGRDSLVNPGPAMASHKDDEEKFFPQSGVLIFGKQD |
| hu.52-B | 482 | CYRQQRVSKTSADN-----NNSEYSWTGATKYHLNGRDSLVNPGPAMASHKDDEEKFFPQSGVLIFGKQG |
| hu.13-B | 482 | CYRQQRVSKTSADN-----NNSEYSWTGATKYHLNGRDSLVNPGPAMASHKDNEEKFFPQSGVLIFGKQG |
| AAV2-B | 482 | CYRQQRVSKTSADN-----NNSEYSWTGATKYHLNGRDSLVNPGPAMASHKDDEEKFFPQSGVLIFGKQG |
| hu.20-B | 482 | CYRQQRVSKTAADN-----NNSDYSWTGATKYHLNGRDSLVNPGPAMASHKDDEEKYFPQSGVLIFGKQD |
| hu.24-B | 482 | CYRQQRVSKTAADN-----NNSEYSWTGATKYHLNGRDSLVNPGPAMASHKDDEEKYFPQSGVLIFGKQD |
| hu.64-B | 482 | CYRQQRVSKTSADN-----NNSDYSWTGATKYHLNGRDSLVNPGPAMASHKDDEEKYFPQSGVLIFGKQD |
| hu.27-B | 482 | CYRQQRVSKTAADN-----NNSEYSWTGATKYHLNGRDSLVNPGPAMASHKDDEEKYFPQSGVLVFGKQD |
| hu.21-B | 482 | CYRQQRVSKTAADN-----NNSDYSWTGATKYHLNGRDSLVNPGPAMASHKDDEEKYFPQSGVLIFGKQD |
| hu.22-B | 482 | CYRQQRVSKTSADN-----NNSDYSWTGATKYHLNGRDSLVNPGPAMASHKDDEEKYFPQSGVLIFGKQD |
| hu.23-B | 482 | CYRQQRVSKTAADN-----NNSDYSWTGATKYHLNGRDSLVNPGPAMASHKDDEEKYFPQSGVLIFGKQD |
| hu.7-C | 482 | CYRQQRLSKQANDN-----NNSNFPWTAATKYHLNGRDSLVNPGPAMASHKDDEEKFFPMHGTLIFGKQG |
| hu.61-C | 482 | CYRQQRLSKQANDN-----NNSNFPWTAATKYHLNGRDSLVNPGPAMASHKDDEEKFFPMHGTLIFGKQG |
| rh.56-C | 482 | CYRQQRLSKQANDN-----NNSNFPWTAATKYHLNGRDSLVNPGPAMASHKDDEEKFFPMHGTLIFGKQG |
| hu.9-C | 482 | CYRQQRLSKQANDN-----NNSNFPWTAATKYHLNGRDSLVNPGPAMASHKDDEEKFFPMHGTLIFGKEG |
| hu.54-C | 481 | CYRQQRLSKQANDN-----NNSNFPWTGATKYHLNGRDSLVNPGPAMASHKDDEEKFFPMHGTLIFGKEG |
| hu.53-C | 481 | CYRQQRLSKQANDN-----NNSNFPWTAATKYYLNGRDSLVNPGPAMASHKDDEEKFFPMHGTLIFGKQG |
| hu.60-C | 481 | CYRQQRLSKQANDN-----NNSNFPWTAATKYHLNGRDSLVNPGPAMASHKDDEEKFFPMHGTLIFGKQG |
| hu.55-C | 481 | CYRQQRLSKQANDN-----NNSNFPWTGATKYHLNGRDSLVNPGPAMASHKDDEEKFFPMHGTLIFGKEG |
| hu.2-C | 482 | CYRQQRLSKQANDN-----NNSNFPWTAATKYHLNGRDSLVNPGPAMASHKDDEEKFFPMHGTLIFGKQG |
| hu.1-C | 482 | CYRQQRLSKQANDN-----NNSNFPWTAATKYHLNGRDSLVNPGPAMASHKDDEEKFFPMHGTLIFGKQG |
| hu.18-C | 482 | CYRQQRLSKQANGN-----NNSNFPWTAATKYHLNGRDSLVNPGPAMASHKDDEEKFFPMHGTLIFGKQG |
| hu.3-C | 483 | CYRQQRLSKQANDN-----NNCNFPWTAATKYHLNGRDSLVNPGPAMASHKDDEEKFFPMHGTLIFGKQG |
| hu.25-C | 482 | CYRQQRLSKQANDN-----NNSNFPWTAATKYHLNGRDSLVNPGPAMASHKDDEEKFFPMHGTLIFGKQG |
| hu.15-C | 482 | CYRQQRLSKQANDN-----NNSNFPWTAATKYHLNGRDSLVNPGPAMASHKDDEEKFFPMHGTLIFGKQG |
| hu.16-C | 482 | CYRQQRLSKQANDN-----NNSNFPWTAATKYHLNGRDSLVNPGPAMASHKDDEEKFFPMHGTLIFGKQG |

Fig. 2U

| | | | | |
|---|---|---|---|---|
| hu.11-C | 482 | CYRQQRLSKQANDN------ | ----NNSNFPWTAATKYRLNGRDSLVNPGPAMASHKDDEEKFFPMHGTLIFGKQG |
| hu.10-C | 482 | CYRQQRLSKQANDN------ | ----NNSNFPWTAATKYHLNGRDSLVNPGPAMASHKDDEEKFFPMHGTLIFGKQG |
| hu.4-C | 482 | CYRQQRLSKQANDN------ | ----NNSNFPWTAATKYHLNGRDSLVNPGPAMASHKDDEEKFFPMHGTLIFGKQG |
| rh.54-D | 485 | CFRQQRVSKTLDQN------ | ----NNSNFAWTGATKYHLNGRDSLVNPGVAMATHKDDEERFFPSSGVLIFGKTG |
| rh.48-D | 485 | CFRQQRVSKTLDQN------ | ----NNSNFAWTGATKYHLNGRDSLVNPGVAMATHKDDEERFFPSSGVLIFGKTG |
| rh.55-D | 485 | CFRRRVSKTLDQN------ | ----NNSNFAWTGATKYHLNGRNSLVNPGVAMATHKDDEERFFPSSGVLIFGKTG |
| rh.62-D | 485 | CFRQQRVSKTLDQN------ | ----NNSNFAWTGATKYHLNGRNSLVNPGVAMATHKDDEERFFPSSGVLIFGKTG |
| AAV7-D | 485 | CFRQQRVSKTLDQN------ | ----NNSNFAWTGATKYHLNGRNSLVNPGVAMATHKDDEERFFPSSGVLIFGKTG |
| rh.52-E | 485 | CYRQQRVSTTLSQN------ | ----NNSNFAWTGATKYHLNGRDSLVNPGVAMATNKDDEDRFFPSSGILMFGKQG |
| rh.51-E | 485 | CYRQQRVSTTLSQN------ | ----NNSNFAWTGATKYHLNGRDSLVNPGVAMATNKDDEDRFFPSSGILMFGKQG |
| rh.39-E | 485 | CYRQQRVSTTLSQN------ | ----NNSNFAWTGATKYHLNGRDSLVNPGVAMATNKDDEDRFFPSSGILMFGKQG |
| rh.53-E | 485 | CYRQQRVSTTLSQN------ | ----NNSNFAWTGATKYHLNGRDSLVNSGVAMATNKDDEERFFPSSGVLMFGKQG |
| rh.37-E | 485 | CYRQQRVSTTLSQN------ | ----NNSNFAWTGATKYHLNGRDSLVNPGVAMATHKDDEERFFPSSGVLMFGKQG |
| rh.43-E | 484 | CYRQQRVSTTTGQN------ | ----NNSNFAWTAGTKYHLNGRNSLANPGIAMATHKDDEERFFPVTG-SCFWQQN |
| rh.50-E | 485 | CYRQQRVSTTLSQN------ | ----NNSNFAWTGATKYHLNGRDSLVNPGVAMATNKDDEDRFFPSSGILMFGKQG |
| rh.49-E | 485 | CYRQQRVSTTLSQN------ | ----NNSNFAWTGATKYHLNGRDSLVNPGVAMATHKDDEDRFFPSSGILMFGKQG |
| rh.61-E | 485 | CYRQQRVSTTLSQN------ | ----NNSNFAWTGATKYHLNGRDSLVNPGVAMATHKDDEERFFPSSGVLMFGKQG |
| rh.41-E | 485 | CYRQQRVSTTLSQN------ | ----NNSNFAWTGATKYHLNGRDSLVNPGVAMATNKDDEERFFPSSGVLMFGKQG |
| rh.64-E | 485 | CYRQQRVSTTLSQN------ | ----NNSNFAWTGATKYHLNGRDSLVNPGVAMATHKDDEERFFPSSGVLMFGKQG |
| hu.42-E | 485 | CYRQQRVSTTLSQN------ | ----NNSNFAWTGATKYHLNGRDSLVNPGVAMATHKDDEERFFPSSGILMFGKQG |
| rh.57-E | 485 | CYRQQRVSTTLSQS------ | ----NNSNFAWTGATKYHLNGRDSLVNPGVAMATHKDDEERFFPSSGILMFGKQG |
| hu.40-E | 485 | CYRQQRVSTTLSQN------ | ----NNSNFAWTGATKYHLNGRDSLVNPGVAMATHKDDEDRFFPSSGILMFGKQG |
| AAV8-E | 485 | CYRQQRVSTTTGQN------ | ----NNSNFAWTGATKYHLNGRDSLVNPGIAMATHKDDEERFFPSNGILIFGKQN |
| rh.58-E | 485 | CYRQQRVSTTLSQN------ | ----NNSNFAWTGATKYHLNGRDSLVNPGVAMATNKDDEDRFFPSSGILMFGKQG |
| rh.40-E | 485 | CYRQQRVSTTLSQN------ | ----NNSNFAWTGATKYHLNGRDSLVNPGVAMATNKDDEERFFPSSGVLMFGKQG |
| hu.67-E | 485 | CYRQQRVSTTLSQN------ | ----NNSNFAWTGATKYHLNGRDSLVNPGVAMATHKDDEERFFPSSGVLMFGKQG |
| hu.17-E | 485 | CYRQQRVSTTLSQN------ | ----NNSNFAWTGATKYHLNGRDSLVNPGVAMATHKDDEERFFPSSGVLMFGKQG |
| hu.6-E | 485 | CYRQQRVSTTLSQN------ | ----NNSNFAWTGATKYHLNGRDSLVNPGVAMATHKDDEERFFPSSGVLMFGKQG |
| hu.66-E | 485 | CYRQQRVSTTLSQN------ | ----NNSNFAWTGATKYHLNGRDSLVNPGVAMATHKDDEERFFPSSGVLMFGKQG |
| rh.38-E | 485 | CYRQQRVSTTLSQN------ | ----NNSNFAWTGATKYHLNGRDSLVNPGVAMATHKDDEERFFPSSGVLMFGKQG |

Fig. 2V

```
hu.32-F    483 SYRQQRVSTTVTQN-----NNSEFAWPGASSWALNGRNSLMNPGPAMASHKEGEDRFFPLSGSLIFGKQG
AAV9/hu    483 SYRQQRVSTTVTQN-----NNSEFAWPGASSWALNGRNSLMNPGPAMASHKEGEDRFFPLSGSLIFGKQG
hu.31-F    483 SYRQQRVSTTVTQN-----NNSEFAWPGASSWALNGRNSLMNPGPAMASHKEGEDRFFPLSGSLIFGKQG 570       580       590       600       610       620       630
                ....|....|....|....|....|....|....|....|....|....|....|....|....|....|

AAV5       534 ANPGTTATYLEGNMLITSESETQPVNRVAYNVGGQMATNNQSSTTAPATGTYNLQEIVPGSVWMERDVYL
AAV3-3     548 T--TASNAELD-NVMITDEEEIRTTNPVATEQYGTVANNLQSSNTAPTTGTVNHQGALPGMVWQDRDVYL
AAV4-4     546 N--GNTATVPG-TLIFTSEEELAATNATDTDMWGNLPGGDQSNSNLPTVDRLTALGAVPGMVWQNRDIYY
AAV1-A     548 A--GASNTALD-NVMITDEEEIKATNPVATERFGTVAVNFQSSSTDPATGDVHAMGALPGMVWQDRDVYL
hu.46-A    548 A--GASNTALD-NVMITDEEEIKATNPVATERFGTVAVNFQSSSTDPATGDVHAMGALPGMVWQDRDVYL
hu.48-A    548 A--GASSTALD-NVMITDEEEIKATNPVATERFGTVAVNFQSSSTDPATGDVHAMGALPGMVWQDRDVYL
hu.44-A    548 A--GASNTALD-NVMITDEEEIKATNPVATERFGTVAVNFQSSSTDPATGDVHAMGALPGMVWQGRDVYL
hu.43-A    549 A--GASNTALD-NVMITDEEEIKATNPVATERFGTVAVNFQSSSTDPATGDVHVMGALPGMVWQDRDVYL
AAV6-A     548 A--GASNTALD-NVMITDEEEIKATNPVATERFGTVAVNLQSSSTNLQRGNRQAATADVNTQGVLPGMVWQDRDVYL
hu.34-B    547 S--EKTNVDIE-KVMITDEEEIRTTNPVATEQYGSVSTNLQRGNRQAATADVNTQGVLPGMVWQDRDVYL
hu.47-B    547 S--EKTNVDIE-KVMITDEEEIRTTNPVATEQYGSVSTNLQRGNRQAATADVNTQGVLPGMVWQDRDVYL
hu.29-B    547 P--EKTNVDIE-KVMITDEEEIRTTNPVATEQYGSVSTNLQSGNTQAATSDVNTQGVLPGMVWQDRDVYL
hu.63-B    547 S--GKTNVDIE-KVMITDEEEIRTTNPVATEQYGSVSTNLQSGNTQAATSDVNTQGVLPGMVWQDRDVYL
hu.56-B    547 S--EKTNVDIE-KVMITDEEEIRTTNPVATEQYGSVSTNLQSGNTQAATSDVNTQGVLPGMVWQDRDVYL
hu.45-B    547 S--EKTNVDIE-KVMITDEEEIRTTNPVATEQYGSVSTNLQRGNRQAATADVNTQGVLPGMVWQDRDVYL
hu.57-B    547 S--EKTNVDIE-KVMITDEEEIRTTNPVATEQYGSVSTNLQSGNTRAATSDVNTQGVLPGMVWQDRDVYL
hu.35-B    546 S--EKTNVDIE-KVMITDEEEIRTTNPVATEQYGSVSTNLQRGNRQAATADVNTQGVLPGMVWQDRDVYL
hu.58-B    547 S--EKTNVDIE-KVMITDEEEIRTTNPVATEQYGSVSTNLQSGNTQASTADVNTQGVLPGMVWQDRDVYL
hu.28-B    547 S--EKTNVDIE-KVMITDEEEIRTTNPVATEQYGSVSTNLQSGNTQAATADVNTQGVLPGMVWQGRDVYL
hu.51-B    547 S--EKTNVDIE-KVMITDEEEIRTTNPVATEQYGSVSTNLQRGNRQAATADVNTQGVLPGMVWQDRDVYL
hu.19-B    547 S--EKTNVDIE-KVMITDEEEIRTTNPVATEQYGSVSTNLQSGNTQAATSDVNTQGVLPGMVWQDRDVYL
hu.49-B    547 S--GKTNVDIE-KVMITDEEEIRTTNPVATEQYGSVSTNLQSGNTQAATADVNTQGVLPGMVWQDRDVHL
hu.52-B    547 S--EKTNVDIE-KVMITDEEEIRTTNPVATEQYGSVSTNLQRGNRQAATADVNTQGVLPGMVWQDRDVYL
hu.13-B    547 S--EKTNVDIE-KVMITDEEEIRTTNPVATEQYGSVSTNLQGGNTQAATADVNTQGVLPGMVWQDRDVYL
```

Fig. 2W

| | | |
|---|---|---|
| AAV2-B | 547 | S--EKTNVDIE-KVMITDEEEIRTTNPVATEQYGSVSTNLQRGNRQAATADVNTQGVLPGMVWQDRDVYL |
| hu.20-B | 547 | S--GKTNVDIE-KVMITDEEEIRTTNPVATEQYGSVSTNLQSGNTQAATSDVNTQGVLPGMVWQDRDVYL |
| hu.24-B | 547 | S--GKTNVDIE-KVMITDEEEIRTTNPVATEQYGSVSTNLQSGNTQAATSDVNTQGVLPGMVWQDRDVYL |
| hu.64-B | 547 | S--GKTNVDIE-KVMITDEEEIRTTNPVATEQYGSVSTNLQSGNTQAATSDVNTQGVLPGMVWQDRDVYL |
| hu.27-B | 547 | S--GKTNVDIE-KVMITDEEEIRTTNPAATEQYGSVSTNLQSGNTQAATSDVNTQGVLPGMVWQDRDVYL |
| hu.21-B | 547 | S--GKTNVDIE-KVMITDEEEIRTTNPVATEQYGSVSTNLQSGNTQAATSDVNTQGVLPGMVWQDRDVYL |
| hu.22-B | 547 | S--GKTNVDIE-KVMITDEEEIRTTNPVATEQYGSVSTNLQSGNTQAATSDVNTQGVLPGMVWQDRDVYL |
| hu.23-B | 547 | S--GKTNVDIE-KVMITDEEEIRTTNPVATEQYGSVSTYLQSGNTQAATSDVNTQGVLPGMVWQDRDVYL |
| hu.7-C | 547 | T--NANDADLD-NVMITDEEEIRTTNPVATEQYGVSNNLQNSNTGPTTGTVNHQGALPGMVWQDRDVYL |
| hu.61-C | 547 | T--NANDADLE-NVMITDEEEIRTTNPVATEQYGTVSNNLQNSNTGPTTGTVNHQGALPGMVWQDRDVYL |
| rh.56-C | 547 | T--NANDADLE-NVMITDEEEIRTTNPVATEQYGTVSNNLQNSNTGPTTGTVNHRGALPGMVWQDRDVYL |
| hu.9-C | 547 | T--NANDADLE-HVMITDEEEIRTTNPVATEQYGNVSNNLQNSNTGPTTENVNHQGALPGMVWQDRDVYL |
| hu.54-C | 546 | T--NATNAELE-NVMITDEEEIRTTNPVATEQYGYVSNNLQNSNTAASTETVNHQGALPGMVWQDRDVYL |
| hu.53-C | 546 | T--NATNAELE-NVMITDEEEIRTTNPVATEQYGYVSNNLQNSNTAASTETVNHQGALPGMVWQDRDVYL |
| hu.60-C | 547 | T--NANDADLE-NVMITDEEEIRTTNPVATEQYGTVSNNLQNSNTGPTTGTVNHQGALPGMVWQDRDVYL |
| hu.55-C | 546 | T--NATNAELE-NVMITDEEEIRTTNPVATEQYGYVSNNLQNSNTAASTETVNHQGALPGMVWQDRDVYL |
| hu.2-C | 547 | T--NANDADLE-NVMITDEEEIRTTNPVATEQYGYVSNNLQDSNTGPTTGTVNHQGALPGMVWQDRDVYL |
| hu.1-C | 547 | T--NANDADLE-NVMITDEEEIRATNPVATEQYGTVSNNLQNSNTGPTTGTVNHQGALPGMVWQDRDVYL |
| hu.18-C | 547 | T--NANDADLD-NVMITDEEEIRATNPVATEQYGYVSNNLQNSNTGPTTGTVNHQGALPGMVWQDRDVYL |
| hu.3-C | 548 | T--NANDADLE-NVMITDEEEIRPTNPVATEQYGYVSNNLQNSNTGPTTGTVNHQGALPGMVWQDRDVYL |
| hu.25-C | 547 | T--NANDADLE-NVMITDEEEIRTTNPVATEQYGTVSNNLQNSNTGPTTGTVNHQGALPGMVWQDRDVYL |
| hu.15-C | 547 | T--NANDADLD-NVMITDEEEIRPTNPVATEEYGTVSSNLQAANTAAQTQVVNNQGALPGMVWQNRDVYL |
| hu.16-C | 547 | T--NANDADLD-NVMITDEEEIRPTNPVATEEYGTVSSNLQAANTAAQTQVVNNQGALPGMVWQNRDVYL |
| hu.11-C | 547 | T--NANDADLE-HVMITDEEEIRTTNPVATEQYGYVSNNLQNSNTGPTTENVNHQGALPGMVWQDRDVYL |
| hu.10-C | 547 | T--NANDADLE-HVMITDEEEIRTTNPVATEQYGYVSNNLQNSNTGPTTENVNHQGALPGMVWQDRDVYL |
| hu.4-C | 547 | T--NANDADLE-NVMITDEEEIRATNPVATEQYGTVSNNLQNSNTGPTTGTVNHQGALPGMVWQDRDVYL |
| rh.54-D | 550 | A--TN-KTTLE-NVLMTNEEEIRPTNPVATEEYGIVSSNLQAANTAAQTQVVNNQGALPGMVWQNRDVYL |
| rh.48-D | 550 | A--AN-KTTLE-NVLMTNEEEIRPTNPVATEEYGTVSSNLQAANTAAQTQVVNNQGALPGMVWQNRDVYL |
| rh.55-D | 550 | A--AN-KTTLE-NVLMTNEEEIRPTNPVATEEYGTVSSNLQAANTAAQTQVVNNQGALPGMVWQNRDVYL |
| rh.62-D | 550 | A--AN-KTTLE-NVLMTNEEEIRPTNPVATEEYGTVSSNLQAANTAAQTQVVNNQGALPGMVWQNRDVYL |

Fig. 2X

```
AAV7-D   550 A--TN-KTTLE-NVLMTNEEIRPTNPVATEEYGIVSSNLQAANTAAQTQVVNNQGALPGMVWQNRDVYL
rh.52-E  550 A--GKDNVDYS-NVMLTSEEEIKTTNPVATEQYGVVADNLQQQNTAPIVGAVNSQGALPGMVWQNRDVYL
rh.51-E  550 A--GKDNVDYS-NVMLTSEEEIKTTNPVATEQYGVVADNLQQQNTAPIVGAVNSQGALPGMVWQNRDVYL
hu.39-E  550 A--GKDNVDYS-NVMLTSEEEIKTTNPVATEQYGVVADNLQQQNTAPTVGAVNSQGALPGMVWQNRDVYL
hu.53-E  550 A--GKDNVDYS-NVMLTSEEEIKTTNPVATEQYGVVADNLQQQNTAPTVGAVNSQGALPGMVWQNRDVYL
hu.37-E  550 A--GRDNVDYS-NVMLTSEEEIKTTNPVATEQYGVVADNLQQTNTGPIVGNVNSQGALPGMVWQNRDVYL
rh.43-E  548 A--ARDNADYS-DVMLTSEEEIKTTNPVATEEYGIVADNLQQTNTAPQIGTVNSQGALPGMVWQNRDVYL
hu.50-E  550 A--GKDNVDYS-NVMLTSEEEIKTTNPVATEQYGVVADNLQQQNTAPIVGAVNSQGALPGMVWQNRDVYL
rh.49-E  550 A--GKDNMGYS-NVMLTSEEEIKTTNPVATEQYGVVADNLQQQNTAPIVGAVNSQGALPGMVWQNRDVYL
rh.61-E  550 A--GKDNVDYS-NVMLTSEEEIKTTNPVATEQYGVVADNLQQQDTAPIVGAVNSQGALPGMVWQNRDVYL
hu.41-E  550 A--GRDNVDYS-NVMLTSEEEIKTTNPVATEQYGVVADNLQQTNTGPIVGNVNSQGALPGMVWQNRDVYL
hu.64-E  550 A--GRDNVDYS-NVMLTSEEEIKTTNPVATEQYGVVADNLQQTNTGPIVGNVNSQGALPGMVWQNRDVYL
hu.42-E  550 A--GRDNVDYS-SVMLTSEEEIKTTNPVATEQYGVVADNLQQTNTAPQIGTVNSQGALPGMVWQNRDVYL
rh.57-E  550 A--GRDNVDYS-SVMLTSEEEIKTTNPVATEQYGVVADNLQQTNTAPIVGAVNSQGALPGMVWQNRDVYL
rh.40-E  550 A--GRDNVDYS-SVMLTSEEEIKTTNPVATEQYGVVADNLQQTNTGPIVGNVNSQGALPGMVWQNRDVYL
AAV8-E   550 A--ARDNADYS-DVMLTSEEEIKTTNPVATEEYGIVADNLQQQNTAPIVGAVNSQGALPGMVWQNRDVYL
rh.58-E  550 A--GKDNVDYS-NVMLTSEEEIKTTNPVATEQYGVVADNLQQQNTAPIVGAVNSQGALPGMVWQNRDVYL
rh.40-E  550 A--GRDNVDYS-NVMLTSEEEIKTTNPVATEQYGVVADNLQQTNTGPIVGNVNSQGALPGMVWQNRDVYL
rh.67-E  550 A--GRDNVDYS-NVMLTSEEEIKTTNPVATEQYGVVADNLQQANTGPIVGNVNSQGALPGMVWQNRDVYL
hu.17-E  550 A--GKDNVDYS-NVMLTSEEEIKTTNPVATEQYGVVADNLQQNAAPIVGAVNSQGALPGMVWQNRDVYL
hu.6-E   550 A--GKDNVDYS-NVMLTSEEEIKTTNPVATEQYGVVADNLQQNAAPIVGAVNSQGALPGMVWQNRDVYL
hu.66-E  550 A--GRDNVDYS-SVMLTSEEEIKTTNPVATEQYGVVADNLQQTNTGPIVGNVNSQGALPGMVWQNRDVYL
rh.38-E  550 A--GRDNVDYS-SVMLTSEEEIKTTNPVATEQYGVVADNLQQTNTGPIVGNVNSQGALPGMVWQNRDVYL
hu.32-F  548 T--GRDNVDAD-KVMITNEEEIKTTNPVATESYGQVATNHQSAQAQAQTGWVQNQGILPGMVWQDRDVYL
AAV9/hu  548 T--GRDNVDAD-KVMITNEEEIKTTNPVATESYGQVATNHQSAQAQAQTGWVQNQGILPGMVWQDRDVYL
hu.31-F  548 T--GRDNVDAD-KVMITNEEEIKTTNPVATESYGQVATNHQSAQAQAQTGWVQNQGILPGMVWQDRDVYL
                640        650        660        670        680        690        700
                 .    |    .    |    .    |    .    |    .    |    .    |    .    |

AAV5     604 QGPIWAKIPETGAHFHPSPAMGGFGLKHPPPMMLIKNTPVPGN-ITSFSDVPVSSFITQYSTGQVTVEME

Fig. 2Y
```

| | | |
|---|---|---|
| AAV3-3 | 615 | QGPIWAKIPHTDGHFHPSPLMGGFGLKHPPPQIMIKNTPVPANPPTTFSPAKFASFITQYSTGQVSVEIE |
| AAV4-4 | 613 | QGPIWAKIPHTDGHFHPSPLIGGFGLKHPPPQIFIKNTPVPANPATTFSSTPVNSFITQYSTGQVSVQID |
| AAV1-A | 615 | QGPIWAKIPHTDGHFHPSPLMGGFGLKNPPPQILIKNTPVPANPPAEFSATKFASFITQYSTGQVSVEIE |
| hu.46-A | 615 | QGPIWAKIPHTDGHFHPSPLMGGFGLKNPPPQILIKNTPVPANPPAEFSATKFASFITQYSAGQVSVEIE |
| hu.48-A | 615 | QGPIWAKIPHTDGHFHPSPLMGGFGLKNPPPQILIKNTPVPANPPAEFSATKFASFITQYSTGQVSVEIE |
| hu.44-A | 615 | QGPIWAKIPHTDGHFHPSPLMGGFGLKNPPPQILIKNTPVPANPPAEFSATKFASFITQYSTGQVSVEIE |
| hu.43-A | 616 | QGPIWAKIPHTDGHFHPSPLMGGFGLKNPPPQILIKNTPVPANPPAEFSATKFASFITQYSTGQVSVEIE |
| hu.6-A | 615 | QGPIWAKIPHTDGHFHPSPLMGGFGLKHPPPQILIKNTPVPANPSTTFSAAKFASFITQYSTGQVSVEIE |
| hu.34-B | 614 | QGPIWAKIPHTDGHFHPSPLMGGFGLKHPPPQILIKNTPVPANPSTTFSAAKFASFITQYSTGQVSVEIE |
| hu.47-B | 614 | QGPIWAKIPHTDGHFHPSPLMGGFGLKHPPPQILIKNTPVPANPSTTFSAAKFASFITQYSTGQVSVEIE |
| hu.29-B | 614 | QGPIWAKIPHTDGHFHPSPLMGGFGLKHPPPQILIKNTPVPANPSTTFSAAKFASFITQYSTGQVSVEIE |
| hu.63-B | 614 | QGPIWAKIPHTDGHFHPSPLMGGFGLKHPPPQILIKNTPVPANPSTTFSAAKFASFITQYSTGQVSVEIE |
| hu.56-B | 614 | QGPIWAKIPHTDGHFHPSPLMGGFGLKHPPPQILIKNTPVPANPSTTFSAAKFASFITQYSTGQVSVEIE |
| hu.45-B | 614 | QGPIWAKIPHTDGHFHPSPLMGGFGLKHPPPQILIKNTPVPANPSTTFSAAKFASFITQYSTGQVSVEIE |
| hu.57-B | 613 | QGPIWAKIPHTDGHFHPSPLMGGFGLKHPPPQILIKNTPVPANPSTTFSAAKFASFITQYSTGQVSVEIE |
| hu.35-B | 614 | QGPIWAKIPHTDGHFHPSPLMGGFGLKHPPPQILIKNTPVPANPSTTFSAAKFASFITQYSTGQVSVEIE |
| hu.58-B | 614 | QGPIWAKIPHTDGHFHPSPLMGGFGLKHPPPQILIKNTPVPANPSTTFSAAKFASFITQYSTGQVSVEIE |
| hu.28-B | 614 | QGPIWAKIPHTDGHFHPSPLMGGFGLKHPPPQILIKNTPVPANPSTTFSAAKFASFITQYSTGQVSVEIE |
| hu.51-B | 614 | QGPTWAKIPHTDGHFHPSPLMGGFGLKHPPPQILIKNTPVPANPSTTFSAAKFASFITQYSTGQVSVEIE |
| hu.19-B | 614 | QGPIWAKIPHTDGHFHPSPLVGGFGLKHPPPQILIKNTPVPANPSTTFSAAKFASFITQYSTGQVSVEIE |
| hu.49-B | 614 | QGPIWAKIPHTDGHFHPSPLMGGFGLKHPPPQILIKNTPVPANPSTTFSAAKFASFITQYSTGQVSVEIE |
| hu.52-B | 614 | QGPIWAKIPHTDGHFHPSPLMGGFGPKHPPPQILIKNTPVPANPSTTFSAAKFASFITQYSTGQVSVEIE |
| hu.13-B | 614 | QGPIWAKIPHTDGHFHPSPLMGGFGLKHPPPQILIKNTPVPANPSTTFSAAKFASFITQYSTGQVSVEIE |
| AAV2-B | 614 | QGPIWAKIPHTDGHFHPSPLMGGFGLKHPPPQILIKNTPVPANPSTTFSAAKFASFITQYSTGQVSVEIE |
| hu.20-B | 614 | QGPIWAKIPHTDGHFHPSPPMGGFGLKHPPPQILIKNTPVPANPSTTFSAAKFASFITQYSTGQVSVEIE |
| hu.24-B | 614 | QGPIWAKIPHTDGHFHPSPLMGGFGLKHPPPQILIKNTPVPANPSTTFSAAKFASFITQYSTGQVSVEIE |
| hu.64-B | 614 | QGPIWAKIPHTDGHFHPSPLMGGFGLKHPPPQILIKNTPVPANPSTTFSAAKFASFITQYSTGRVSVEIE |
| hu.27-B | 614 | QGPIWAKIPHTDGHFHPSPLMGGFGLKHPPPQILIKNTPVPANPSTTFSAAKFVSFITQYSTGQVSVEIE |
| hu.21-B | 614 | QGPIWAKIPHTDGHFHPSPLMGGFGLKHPPPQILIKNTPVPANPSTTFSAAKFASFITQYSTGQVSVEIE |
| hu.22-B | 614 | QGPIWAKIPHTDGHFHPSPLMGGFGLKHPPPQILIKNTPVPANPSTTFSAAKFASFITQYSTGQVSVEIE |

Fig. 2Z

| | | |
|---|---|---|
| hu.23-B | 614 | RGPIWAKIPHTDGHFHPSPLMGGFGLKHPPPQILIKNTPVPANPSTTFSAAKFASFITQYSTGQVSVEIE |
| hu.7-C | 614 | QGPIWAKIPHTDGHFHPSPLMGGFGLKHPPPQIMIKNTPVPANPPTNFSSAKFASFITQYSTGQVSVEIE |
| hu.61-C | 614 | QGPIWAKIPHTDGHFHPSPLVGGFGLKHPPPQIMIKNTPVPANPPTNFSSAKFASFITQYSTGQVSVEIE |
| rh.56-C | 614 | QGPIWAKIPHTDGHFHPSPLMGGFGLKHPPPQIMIKNTPVPANPPTNFSSAKFASFITQYSTGQVSVEIE |
| hu.9-C | 614 | QGPIWAKIPHADGHFHPSPLMGGFGLKHPPPQIMIKNTPVPANPPTNFSSAKFASFITQYSTGQVSVEIE |
| hu.54-C | 613 | RGPIWAKIPHTDGHFHPSPLMGGFGLKHPPPQIMIKNTPVPANPPTNFSSAKFASFITQYSTGQVSVEIE |
| hu.53-C | 613 | QGPIWAKIPHTDGHFHPSPLMGGFGLKHPPPQIMIKNTPVPANPPTNFSSAKFASFITQYSTGQVSVEIE |
| hu.60-C | 614 | QGPIWAKIPHTDGHFHPSPLMGGFGLKHPPPQIMIKNTPVPANPPTNFSSAKFASFITQYSTGQVSVEIE |
| hu.55-C | 613 | QGPIWAKIPHTDGHFHPSPLMGGFGLKHPPPQIMIKNTPVPANPPTNFSSAKFASFITQYSTGQVSVEIE |
| hu.2-C | 614 | QGPIWAKIPHTDGHFHPSPLMGGFGLKHPPPQIMIKNTPVPANPPTNFSSAKFASFITQYSTGQVSVEIE |
| hu.1-C | 614 | QGPIWAKIPHTDGHFHPSPLMGGFGLKHPPPQIMIKNTPVPANPPTNFSSAKFASFITQYSTGQVSVEIE |
| hu.18-C | 614 | QGPIWAKIPHTDGHFHPSPLMGGFGLKHPPPQIMIKSTPVPANPPTNFSSSKFASFASSITQYSTGQVSVEIE |
| hu.3-C | 615 | QGPIWAKIPHTDGHFHPSPLTGGFGLKHPPPQIMIKNTPVPANPPTNFSSAKFASFITQYSTGQVSVEIE |
| hu.25-C | 614 | QGPIWAKIPHTDGHFHPSPLMGGFGLKHPPPQIMIKNTPVPANPPTNFSSAKFASFITQYSTGQVSVEIE |
| hu.15-C | 614 | QGPIWAKIPHTDGHFHPSPLMGGFGLKHPPPQIMIKNTPVPANPPTNFSSAKFASFITQYSTGQVSVEIE |
| hu.16-C | 614 | QGPIWAKIPHTDGHFHPSPLMGGFGLKHPPPQIMIKNTPVPANPPTNFSSAKFASFITQYSTGQVSVEIE |
| hu.11-C | 614 | QGPIWAKIPHTDGHFHPSPLMGGFGLKHPPPQIMIKNTPVPANPPTNYSSAKFASFITQYSTGQVSVEIE |
| hu.10-C | 614 | QGPIWAKIPHTDGHFHPSPLMGGFGLKHPPPQIMIKNTPVPANPPTNFSSAKFASFITQYSTGQVSVEIE |
| hu.4-C | 614 | QGPIWAKIPHTDGHFHPSPLMGGFGLKHPPPQIMIKNTPVPANPPTNFSSAKFASFITQYSTGQVSVEIE |
| rh.54-D | 616 | QGPIWAKIPHTDGNFHPSPLMGGFGLKHPPPQILIKNTPVPANPPEVFTPAKFASFITQYSTGQVSVEIE |
| rh.48-D | 616 | QGPIWAKIPHTDGNFHPSPLMGGFGLKHPPPQILIKNTPVPANPPEVFTPAKFASFITQYSTGQVSVEIE |
| rh.55-D | 616 | QGPIWAKIPHTDGNFHPSPLMGGFGLKHPPPQILIKNTPVPANPPEVFTPAKFASFITQYSTGQVSVEIE |
| rh.62-D | 616 | QGPIWAKIPHTDGNFHPSPLMGGFGLKHPPPQILIKNTPVPANPPEVFTPAKFASFITQYSTGQVSVEIE |
| AAV7-D | 616 | QGPIWAKIPHTDGNFHPSPLMGGFGLKHPPPQILIKNTPVPADPPTAFNQAKLNSFITQYSTGQVSVEIE |
| rh.52-E | 617 | QGPIWAKIPHTDGNFHPSPLMGGFGLKHPPPQILIKNTPVPADPPTAFNQAKLNSFITQYSTGQVSVEIE |
| rh.51-E | 617 | QGPIWAKIPHTDGNFHPSPLMGGFGLKHPPPQILIKNTPVPADPPTAFNQAKLNSFIAQYSTGQVSVEIE |
| hu.39-E | 617 | QGPIWAKIPHTDGNFHPSPLMGGFGLKHPPPQILIKNTPVPADPPTAFNQAKLNSFITQYSTGQVSVEIE |
| rh.53-E | 617 | QGPIWAKIPHTDGNFHPSPLMGGFGLKHPPPQILIKNTPVPADPPTTFSQAKLASFITQYSTGQVSVEIE |
| hu.37-E | 617 | QGPIWAKIPHTDGNFHPSPLMGGFGLKHPPPQILIKNTPVPADPPTTENQSKLNSFITQYSTGQVSVEIE |
| rh.43-E | 615 | QGPIWAKIPHTDGNFHPSPLMGGFGLKHPPPQILIKNTPVPADPPTTENQSKLNSFITQYSTGQVSVEIE |

Fig. 2AA

```
rh.50-E   617  QGPIWAKIPHTDGNFHPSPLMGGFGLKHPPPQILIKNTPVPADPPTAFNQAKLNSFITQYSTGQVSVEIE
rh.49-E   617  QGPIWAKIPHTDGNFHPSPLMGGFGLKHPPPQILIKNTPVPADPPTAFNQAKLNSFITQYGTGQVSVEIE
rh.61-E   617  QGPIWAKIPHTDGNFHPSPLMGGFGLKHPPPQVLIKNTPVPADPPTAFNQAKLNSFITQYSTGQVSVEIE
hu.41-E   617  QGPIWAKIPHTDGNFHPSPLMGGFGLKHPPPQILIKNTPVPADPPTTFSQAKLASFITQYSTGQVSVEIE
rh.64-E   617  QGPIWAKIPHTDGNFHPSPLMGGFGLKHPPPQILIKNTPVPADPPTTFSQAKLASFITQYSTGQVSVEIV
hu.42-E   617  QGPIWAKIPHTDGNFHPSPLMGGFGLKHPPPQILIKNTPVPADPPTTFSQAKLASFITQYSTGQVSVEIE
rh.57-E   617  QGPIWAKIPHTDGNFHPSPLMGGLGLKHPPPQILIKNTPVPADPPTTFSQAKLASFITQYSTGQVSVEIE
hu.40-E   617  QGPIWAKIPHTDGNFHPSPLMGGFGLKHPPPQILIKNTPVPADPPTTFSQAKLASFITQYSTGQVSVEIE
AAV8-E    617  QGPIWAKIPHTDGNFHPSPLMGGFGLKHPPPQILIKNTPVPADPPTTFNQSKLNSFITQYSTGQVSVEIE
rh.58-E   617  QGPIWAKIPHTDGNFHPSPLMGGFGLKHPPPQILIKSTPVPADPPTTFSQAKLASFITQYSTGQVSVEIE
rh.40-E   617  QGPIWAKIPHTDGNFHPSPLMGGFGLKHPPPQILIKNTPVPADPPTTFSQAKLASFITQYSTGQVSVEIE
hu.67-E   617  QGPIWAKIPHTDGNFHPSPLMGGFGLKHPPPQILIKNTPVPADPPTTFSQAKLASFITQYSTGQVSVEIE
hu.17-E   617  QGPIWAKIPHTDGNFHPSPLMGGFGLKHPPPQILIKNTPVPADPPTTFSQAKLASFITQYSTGQVSVEIE
hu.6-E    617  QGPIWAKIPHTDGNFHPSPLMGGFGLKHPPPQILIKNTPVPADPPTTFSQAKLASFITQYSTGQVSVEIE
hu.66-E   617  QGPIWAKIPHTDGNFHPSPLMGGFGMKHPPPQILIKNTPVPADPPTAFNKDKLNSFITQYSTGQVSVEIE
rh.38-E   617  QGPIWAKIPHTDGNFHPSPLMGGFGMKHPPPQILIKNTPVPADPPTAFNKDKLNSFITQYSTGQVSVEIE
hu.32-F   615  QGPIWAKIPHTDGNFHPSPLMGGFGMKHPPPQILIKNTPVPADPPTAFNKDKLNSFITQYSTGQVSVEIE
AAV9/hu   615  QGPIWAKIPHTDGNFHPSPLMGGFGMKHPPPQILIKNTPVPADPPTAFNKDKLNSFITQYSTGQVSVEIE
hu.31-F   615  QGPIWAKIPHTDGNFHPSPLMGGFGMKHPPPQILIKNTPVPADPPTAFNKDKLNSFITQYSTGQVSVEIE 710        720        730        740        750
                         |          |          |          |          |
AAV5      673  WELKKENSKRWNPEIQYTNNYNDPQFVDFAPDSTGEYRTTRPIGTRYLTRPL*
AAV3-3    685  WELQKENSKRWNPEIQYTSNYNKSVNVDFTVDTNGVYSEPRPIGTRYLTRNL*
AAV4-4    683  WEIQKERSKRWNPEVQFTSNYGQQNSLLWAPDAAGKYTEPRAIGTRYLTHHL*
AAV1-A    685  WELQKENSKRWNPEVQYTSNYAKSANVDFTVDNNGLYTEPRPIGTRYLTRPL*
hu.46-A   685  WELQKENSKRWNPEVQYTSNYAKSANVDFTVDNNGLYTEPRPIGTRYLTRPL*
hu.48-A   685  WELQKENSKRWNPEVQYTSNYAKSANVDFTVDNNGLYTEPRPIGTRYLTRPL*
hu.44-A   685  WELQKENSKRWNPEVQYTSNYAKSANVDFTVDNNGLYTEPRPIGTRYLTRPL*
hu.43-A   686  WELQKENSKRWNPEVQYTSNYAKSASVDFTVDNNGLYTEPRPIGTRYLTRPL*
```

Fig. 2AB

| | | |
|---|---|---|
| AAV6-A | 685 | WELQKENSKRWNPEVQYTSNYAKSANVDFTVDNGLYTEPRPIGTRYLTRPL* |
| hu.34-B | 684 | WELQKENSKRWNPEIQYTSNYNKSVNVDFTVDTNGVYSEPRPIGTRYLTRNL* |
| hu.47-B | 684 | WELQKENSKRWNPEIQYTSNYNKSVNVDFTVDTNGVYSEPRPIGTRYLTRNL* |
| hu.29-B | 684 | WELQKENSKRWNPEIQYTSNYNKSVNVDFTVDTNGVYSEPRPIGTRYLTRNL* |
| hu.63-B | 684 | WELQKENSKRWNPEIQYTSNYNKSVNVDFTVDTNGVYSEPRPIGTRYLTRNL* |
| hu.56-B | 684 | WELQKENSKRWNPEIQYTSNYNKSVNVDFTVDTNGVYSEPRPIGTRYLTRNL* |
| hu.45-B | 684 | WELQKENSKRWNPEIQYTSNYNKSVNVDFTVDTNGVYSEPRPIGTRYLTRNL* |
| hu.57-B | 683 | WELQKENSKRWNPEIQYTSNYNKSVNVDFTVDTNGVYSEPRPIGTRYLTRNL* |
| hu.35-B | 684 | WELQKENSKRWNPEIQYTSNYNKSVNVDFTVDTNGVYSEPRPIGTRYLTRNL* |
| hu.58-B | 684 | WELQKENSKRWNPEIQYTSNYNKSVNVDFTVDTNGVYSEPRPIGTRYLTRNL* |
| hu.28-B | 684 | WELQKENSKRWNPEIQYTSNYNKSVNVDFTVDTNGVYSEPRPIGTRYLTRNL* |
| hu.51-B | 684 | WELQKENSKRWNPEIQYTSNYNKSVNVDFTVDTNGVYSEPRPIGTRYLTRNL* |
| hu.19-B | 684 | WELQKENSKRWNPEIQYTSNYNKSVNVDFTVDTNGVYSEPRPIGTRYLTRNL* |
| hu.49-B | 684 | WELQKENSKRWNPEIQYTSNYNKSVNVDFTVDTNGVYSEPRPIGTRYLTRNL* |
| hu.52-B | 684 | WELQKENSKRWNPEIQYTSNYNKSVNVDFTVDTNGVYSEPRPIGTRYLTRNL* |
| hu.13-B | 684 | WELQKENSKRWNPEIQYTSNYNKSVNVDFTVDTNGVYSEPRPIGTRYLTRNL* |
| AAV2-B | 684 | WELQKENSKRWNPEIQYTSNYNKSVNVDFTVDTNGVYSEPRPIGTRYLTRNL* |
| hu.20-B | 684 | WELQKENSKRWNPEIQYTSNYNKSVNVDFTVDTNGVYSEPRPIGARYLTRNL* |
| hu.24-B | 684 | WELQKENSKRWNPEIQYTSNYNKSVNVDFTVDTNGVYSEPRPIGTRYLTRNL* |
| hu.64-B | 684 | WELQKENSKRWNPEIQYTSNYNKSVNVDFTVDTNGVYSEPRPIGTRYLTRNL* |
| hu.27-B | 684 | WELQKENSKRWNPEIQYTSNYNKSVNVDFTVDTNGVYSEPRPIGTRYLTRNL* |
| hu.21-B | 684 | WELQKENSKRWNPEIQYTSNYNKSVNVDFTVDTNGVYSEPRPIGTRYLTRNL* |
| hu.22-B | 684 | WELQKENSKRWNPEIQYTSNYNKSVNVDFTVDTNGVYSEPRPIGTRYLTRNL* |
| hu.23-B | 684 | WELQKENSKRWNPEIQYTSNYNKSVNVDFTVDTNGVYSEPRPIGTRYLTRNL* |
| hu.7-C | 684 | WELQKENSKRWNPEIQYTSNYNKSVNVDFTVDTNGVYSEPRPIGTRYLTRNL* |
| hu.61-C | 684 | WELQKENSKRWNPEIQYTSNYNKSVNVDFTVDTNGVYSEPRPIGTRYLTRNL* |
| rh.56-C | 684 | WELQKENSKRWNPEIQYTSNYNKSVNVDFTVDTNGVYSEPRPIGTRYLTRNL* |
| hu.9-C | 684 | WELQKENSKRWNPEIQYTSNYNKSVNVDFTVDTNGVYSEPCPIGTRYLTRNL* |
| hu.54-C | 683 | WELQKENSKRWNPEIQYTSNYNKSVNVDFTVDTNGVYSEPRPIGTRYLTRNL* |
| hu.53-C | 683 | WELQKENSKRWNPEIQYTSNYNKSVNVDFTVDTNGVYSEPRPIGTRYLTRNL* |

Fig. 2AC

| | | |
|---|---|---|
| hu.60-C | 684 | WELQKENSKRWNPEIQYTSNYNKSVNVDFTVDTNGVYSEPRPIGTRYLTRNL* |
| hu.55-C | 683 | WELQKENSKRWNPEIQYTSNYNKSVNVDFTVDTNGVYSEPRPIGTRYLTRNL* |
| hu.2-C | 684 | WELQKENSKRWNPEIQYTSNYNKSVNVDFTVDTNGVYSEPRPIGTRYLTRNL* |
| hu.1-C | 684 | WELQKENSKRWNPEIQYTSNYNKSVNVDFTVDTNGVYSEPRPIGTRYLTRNL* |
| hu.18-C | 684 | WELQKENSKRWNPEIQYTSNYNKSVNVDFTVDTNGVYSEPRPIGTRYLTRNL* |
| hu.3-C | 685 | WELQKENSKRWNPEIQYTSNYNKSVNVDFTVDTNGVYSEPRPIGTRYLTRNL* |
| hu.25-C | 684 | WELQKENSKRWNPEIQYTSNYNKSVNVDFTVDNNGVYSEPRPIGTRYLTRNL* |
| hu.15-C | 684 | WELQKEDSKRWNPEIQYTSNYNKPVNVDFTVDTNGVYSEPRPIGTRYLTRNL* |
| hu.16-C | 684 | WELQKENSKRWNPEIQYTSNYNKSVNVDFTVDTNGVYSEPRPIGTRYLTRNL* |
| hu.11-C | 684 | WELQKENSKRWNPEIQYTSNYNKSVNVDFTVDTNGVYSEPRPIGTRYLTRNL* |
| hu.10-C | 684 | WELRKENSKRWNPEIQYTSNYNKSVNVDFTVDTNGVYSEPRPIGTRYLTRNL* |
| hu.4-C | 684 | WELQKENSKRWNPEIQYTSNFDKQTGVDFAVDSQGVYSEPRPIGTRYLTRNL* |
| rh.54-D | 686 | WELQKENSKRWNPEIQYTSNFDKQTGVDFAVDSQGVYSEPRPIGTRYLTRNL* |
| rh.48-D | 686 | WELQKENSKRWNPEIQYTSNFDKQTGVDFAVDSQGVYSEPRPIGTRYLTRNL* |
| rh.55-D | 686 | WELQKENSKRWNPEIQYTSNFDKQTGVDFAVDSQGVYSEPRPIGTRYLTRNL* |
| rh.62-D | 686 | WELQKENSKRWNPEIQYTSNFEKQTGVDFAVNTEGVYSEPRPIGTRYLTRNL* |
| AAV7-D | 686 | WELQKENSKRWNPEIQYTSNYYKSTNVDFAVNTEGVYSEPRPIGTRYLTRNL* |
| rh.52-E | 687 | WELQKENSKRWNPEIQYTSNYYKSTNVDFAVNTEGVYSEPRPIGTRYLTRNL* |
| rh.51-E | 687 | WEPQKENSKRWNPEIQYTSNYYKSTNADFAVNTEGVYSEPRPIGTRYLTRNL* |
| rh.39-E | 687 | WELQKENSKRWNPEIQYTSNYYKSTNVDFAVNTEGVYSEPRPIGTRYLTRNL* |
| rh.53-E | 687 | WELQKENSKRWNPEIQYTSNYYKSTNVDFAVNTEGVYSEPRPIGTRYPTRNL* |
| rh.37-E | 687 | WELQKENSKRWNPEIQYTSNYYKSTNVDFAVNTEGTYSEPRPIGTRYLTRNL* |
| rh.43-E | 685 | WELQKENSKRWNPEIQYTSNYYKSTSVDFAVNTEGVYSEPRPIGTRYLTRNL* |
| rh.50-E | 687 | WELQKENSKRWSPEIQYTSNYYKSTNVDFAVNTEGVYSEPRPIGTRYLTRNL* |
| rh.49-E | 687 | WELQKENSKRWNPEIQYTSNYYKSTNVDFAVNTEGVYSEPRPIGTRYLTRNL* |
| rh.61-E | 687 | WELQKENSKRWNPEIQYTSNYYKSTNVDFAVNTEGTYSEPRPIGTRYLTRNL* |
| rh.41-E | 687 | WELQKENSKRRNPEIQYTSNYYKSTNVDFAVNTEGTYSEPRPIGTRYLTRNL* |
| rh.64-E | 687 | WELQKENSKRWNPEIQYTSNYYKSTNVDFAVNTEGTYSEPRPIGTRYLTRNL* |
| hu.42-E | 687 | WELQKENSKRWNPEIQYTSNYYKSTNVDFAVNTEGVYSEPRPIGTRYLTRNL* |
| rh.57-E | 687 | WELQKENSKRWNPEIQYTSNYYKSTNVDFAVNTEGVYSEPRPIGTRYLTRNL* |

Fig. 2AD

| | | |
|---|---|---|
| hu.40-E | 687 | WELQKENSKRWNPEIQYTSNYYKSTNVDFAVNTEGTYSEPRPIGTRYLTRNL* |
| AAV8-E | 687 | WELQKENSKRWNPEIQYTSNYYKSTSVDFAVNTEGVYSEPRPIGTRYLTRNL* |
| rh.58-E | 687 | WELQKENSKCWNPEIQYTSNYYKSTNVDFAVNTEGVYSEPRPIGTRYLTRNL* |
| rh.40-E | 687 | WELQKENSKRWNPEIQYTSNYYKSTNVDFAVNSEGTYSEPRPIGTRYLTRNL* |
| hu.67-E | 687 | WELQKENSKRWNPEIQYTSNYYKSTNVDFAVNTEGTYSEPRPIGTRYLTRNL* |
| hu.17-E | 687 | WELQKENSKRWNPEIQYTSNYNKSVNVDFTVDTNGVYSEPRPIGTRYLTRNL* |
| hu.6-E | 687 | WELQKENSKRWNPEIQYTSNYYKSTNVDFAVNTEGTYSEPRPIGTRYLTRNL* |
| hu.66-E | 687 | WELQKENSKRWNPEIQYTSNYYKSTNVDFAVNTEGTYSEPRPIGTRYLTRNL* |
| rh.38-E | 687 | WELQKENSKRWNPEIQYTSNYYKSTNVDFAVNTEGTYSEPRPIGTRYLTRNL* |
| hu.32-F | 685 | WELQKENSKRWNPEIQYTSNYYKSNNVEFAVNTEGVYSEPRPIGTRYLTRNL* |
| AAV9/hu | 685 | WELQKENSKRWNPEIQYTSNYYKSNNVEFAVNTEGVYSEPRPIGTRYLTRNL* |
| hu.31-F | 685 | WELQKENSKRWNPEIQYTSNYYKSNNVEFAVSTEGVYSEPRPIGTRYLTRNL* |

Fig. 2AE

```
AAV5       1 ATGTCTTTTGTTGTTTGATCACCCTCCAGATTGGTTGGAAGAA---GTTGGTGAAGGTCTTCGCGAGTTTTGG
AAV3-3     1 ATGGCTGCTGACGGTTATCTTCCAGATTGGCTCGAGGACAACCTTCTGAAGGCATTCGTGAGTGGTGGG
AAV4-4     1 ---ATGACTGACGGTTACCTTCCAGATTGGCTGGAGGACAACCTCTCTGAAGGCGTTCGAGAGTGGTGGG
AAV1-A     1 ATGGCTGCCGATGGTTATCTTCCAGATTGGCTCGAGGACACTCTCTCTGAGGCATTCGCGAGTGGTGGG
hu.46-A    1 ATGGCTGCCGATGGTTATCTTCCAGATTGGCTCGAGGACACAACTCTCTGAGGCATTCGCGAGTGGTGGG
hu.48-A    1 ATGGCTGCCGATGGTTATCTTCCAGATTGGCTCGAGGACAACTCTCTGAGGCATTCGCGAGTGGTGGG
hu.44-A    1 ATGGCTGCCGATGGTTATCTTCCAGATTGGCTCGAGGACACTCTCTGAAGGAATAAGACAGTGGTGGA
hu.43-A    1 ATGGCTGCTGACGGTTATCTTCCAGATTGGCTCGAGGACACTCTCTGAAGGCATTCGCGAGTGGTGGG
AAV6-A     1 ATGGCTGCCGATGGTTATCTTCCAGATTGGCTCGAGGACACTCTCTGAAGGAATAAGACAGCGGTGGA
hu.34-B    1 ATGGCTGCCGATGGTTATCTTCCAGATTGGCTCGAGGACACTCTCTGAAGGAATAAGACAGTGGTGGA
hu.47-B    1 ATGGCTGCCGATGGTTATCTTCCAGATTGGCTCGAGGACACTCTCTGAAGGAATAAGACAGTGGTGGA
hu.29-B    1 ATGGCTGCCGATGGTTATCTTCCAGATTGGCTCGAGGACACTCTCTGAAGGAATAAGACAGTGGTGGA
hu.63-B    1 ATGGCTGCCGATGGTTATCTTCCAGATTGGCTCGAGGACACTCTCTGAAGGAATAAGACAGTGGTGGA
hu.56-B    1 ATGGCTGCCGATGGTTATCTTCCAGATTGGCTCGAGGACACTCTCTGAAGGAATAAGACAGTGGTGGA
hu.45-B    1 ATGGCTGCCGATGGTTATCTTCCAGATTGGCTCGAGGACACTCTCTGAAGGAATAAGACAGTGGTGGA
hu.57-B    1 ATGGCTGCCGATGGTTATCTTCCAGATTGGCTCGAGGACACTCTCTGAAGGAATAAGACAGTGGTGGA
hu.35-B    1 ATGGCTGCCGATGGTTATCTTCCAGATTGGCTCGAGGACACTCTCTGAAGGAATAAGACAGTGGTGGA
hu.58-B    1 ATGGCTGCCGATGGTTATCTTCCAGATTGGCTCGAGGACACTCTCTGAAGGAATAAGACAGTGGTGGA
hu.28-B    1 ATGGCTGCCGATGGTTATCTTCCAGATTGGCTCGAGGACACTCTCTGAAGGAATAAGACAGTGGTGGA
hu.51-B    1 ATGGCTGCCGATGGTTATCTTCCAGATTGGCTCGAGGACACTCTCTGAAGGAATAAGACAGTGGTGGA
hu.19-B    1 ATGGCTGCCGATGGTTATCTTCCAGATTGGCTCGAGGACACTCTCTGAAGGAATAAGACAGTGGTGGA
hu.49-B    1 ATGGCTGCCGATGGTTATCTTCCAGATTGGCTCAAGGACACTCTCTGAAGGAATAAGACAGTGGTGGA
hu.52-B    1 ATGGCTGCCGATGGTTATCTTCCAGATTGGCTCGAGGACACTCTCTGAAGGAATAAGACAGTGGTGGA
hu.13-B    1 ATGGCTGCCGATGGTTATCTTCCAGATTGGCTCGAGGACACTCTCTGAAGGAATAAGACAGTGGTGGA
AAV2-B     1 ATGGCTGCCGATGGTTATCTTCCAGATTGGCTCGAGGACACTCTCTGAAGGAATAAGACAGTGGTGGA
hu.20-B    1 ATGGCTGCCGATGGTTATCTTCCAGATTGGCTCGAGGACACACCCTCTCTGAAGGAATAAGACAGTGGTGGA
hu.24-B    1 ATGGCTGCCGATGGTTATCTTCCAGATTGGCTCGAGGACACACCCTCTCTGAAGGAATAAGACAGTGGTGGA
hu.64-B    1 ATGGCTGCCGATGGTTATCTTCCAGATTGGCTCGAGGACACACCCTCTCTGAAGGAATAAGACAGTGGTGGA
```

```
rh.53-E    1  ATGGCTGCCGATGGTTATCTTCCAGATTGGCTCGAGGACAACCTCTCTGAGGGCATTCGCGAGTGGTGGG
hu.37-E    1  ATGGCTGCTGACGGTTATCTTCCAGATTGGCTCGAGGACAACCTCTCTGAGGGCATTCGCGAGTGGTGGG
rh.43-E    1  ATGGCTGCCGATGGTTATCTTCCAGATTGGCTCGAGGACAACCTCTCTGAGGGCATTCGCGAGTGGTGGG
rh.50-E    1  ATGGCTGCCGATGGTTATCTTCCAGATTGGCTCGAGGACAACCTCTCTGAGGGCATTCGCGAGTGGTGGG
rh.49-E    1  ATGGCTGCCGATGGTTATCTTCCAGATTGGCTCGAGGACAACCTCTCTGAGGGCATTCGCGAGTGGTGGG
rh.61-E    1  ATGGCTGCCGATGGTTATCTTCCAGATTGGCTCGAGGACAACCTCTCTGAGGGCATTCGCGAGTGGTGGG
hu.41-E    1  ATGGCTGCTGACGGTTATCTTCCAGATTGGCTCGAGGACAACCTCTCTGAGGGCATTCGCGAGTGGTGGG
rh.64-E    1  ATGGCTGCCGATGCTTATCTTCCAGATTGGCTCGAGGACAACCTCTCTGAGGGCATTCGCGAGTGGTGGG
rh.42-E    1  ATGGCTGCCGATGGTTATCTTCCAGATTGGCTCGAGGACAACCTCTCTGAGGGCATTCGCGAGTGGTGGG
hu.40-E    1  ATGGCTGCCGATGGTTATCTTCCAGATTGGCTCGAGGACAACCTCTCTGAGGGCATTCGCGAGTGGTGGG
rh.57-E    1  ATGGCTGCTGACGGTTATCTTCCAGATTGGCTCGAGGACAACCTCTCTGAGGGCATTCGCGAGTGGTGGG
hu.40-E    1  ATGGCTGCTGACGGTTATCTTCCAGATTGGCTCGAGGACAACCTCTCTGAGGGCATTCGCGAGTGGTGGG
AAV8-E     1  ATGGCTGCCGATGGTTATCTTCCAGATTGGCTCGAGGACAACCTCTCTGAGGGCATTCGCGAGTGGTGGG
rh.58-E    1  ATGGCTGCTGACGGTTATCTTCCAGATTGGCTCGAGGACAACCTCTCTGAGGGCATTCGCGAGTGGTGGG
rh.40-E    1  ATGGCTGCTGACGGTTATCTTCCAGATTGGCTCGAGGACAACCTCTCTGAGGGCATTCGCGAGTGGTGGG
hu.67-E    1  ATGGCTGCCGATGGTTATCTTCCAGATTGGCTCGAGGACAACCTCTCTGAGGGCATTCGCGAGTGGTGGG
hu.17-E    1  ATGGCTGCCGATGGTTATCTTCCAGATTGGCTCGAGGACAACCTCTCTGAGGGCATTCGCGAGTGGTGGG
hu.6-E     1  ATGGCTGCCGATGGTTATCTTCCAGATTGGCTCGAGGACAACCTCTCTGAGGGCATTCGCGAGTGGTGGG
hu.66-E    1  ATGGCTGCCGATGGTTATCTTCCAGATTGGCTCGAGGACAACCTCTCTGAGGGCATTCGCGAGTGGTGGG
rh.38-E    1  ATGGCTGCCGATGGTTATCTTCCAGATTGGCTCGAGGACAACCTCTCTGAAGGAATAAGCGAGTGGTGGG
hu.32-F    1  ATGGCTGCCGATGGTTATCTTCCAGATTGGCTCGAGGACAACCTTAGTGAAGGAATTCGCGAGTGGTGGG
hu.9/hu    1  ATGGCTGCCGATGGTTATCTTCCAGATTGGCTCGAGGACAACCTCTCTGAAGGAGATAAGACAGTGGTGGA
AAV9/hu    1  ATGGCTGCCGATGGTTATCTTCCAGATTGGCTCGAGGACAACCTCTCTGAAGGAATAAGACAGTGGTGGA
hu.31-F    1  ATGGCTGCCGATGGTTATCTTCCAGATTGGCTCGAGGACAACCTCTCTGAAGGAATAAGACAGTGGTGGA

....|....|....|....|....|....|....|....|....|....|....|....|....|....|
                  80         90        100        110        120        130        140

AAV5      68  GCCTTGAAGCGGGCCCACCAGGAAACCAATCAGCAGCATCAAGATCAAGCCCGTGGTGTTGTGTCTTGCT
AAV3-3    71  CTCTGAAACCTGAGTCCCTCAACCCAAAGCAACGACCAACCGTTCGGGGTCTTGTGCT
AAV4-4    68  CGCTGCAACCTGGAGCCCCGGAGCCCCAAACCTAAACCCAAGCCCAAATCAACAACATCAGGACCTCGGGGCTCGGGTGCT
AAV1-A    71  ACTTGAAACCTGGAGCCCCGGAGCCCCAAAGCCCAAAGCCAACAAGCAGGACAGGACCAGCCGCCGGGGTCTTGTGCT
hu.46-A   71  AGCTCAACCTGGCCCACCACCAAGCCCGGCATAAGGACCAGGAATAAGACGACAGACAGGGGGTCTTGTGCT
```

```
hu.67-E    141  TCTTGGCTACAAGTACCTCGGACCCTTCAACGGACTCGACAAGGGGGAGCCCGTCAATGCGGCGGACGCA
hu.17-E    141  TCCTGGCTGCAAGTACCTCGGACCCTTCAACGGACTCGACAAGGGGGAGCCCGTCAACGCGGCGGACGCA
hu.6-E     141  TCCTGGCTACAAGTACCTCGGACCCTTCAACGGACTCGACAAGGGGGAGCCCGTCAACGCGGCGGACGCA
hu.66-E    141  TCCTGGCTACAAGTACCTCGGACCCTTCAACGGACTCGACAAGGGGGAGCCCGTCAACGCGGCGGACGCA
rh.38-E    141  TCCTGGCTACAAGTACCTCGGACCCTTCAACGGACTCGACAAGGGGGAGCCGGTCAACGCGGCGGACGCA
rh.32-F    141  TCCTGGCTACAAGTACCTCGGACCCCGGACCGGCAACGCACGGGTCGACAAGGGGGAGCCGGTCAACGCGGCAGACGCG
AAV9/hu    141  TCCGGGTTACAAATACCTTGACAATGGACAACGGGCAACGCACGGACAAGGGAGAGCCGGTCAACGCAGCAGACGCG
hu.31-E    141  TCCTGGGTACAAGTACCTCGGACCCAACGGCAACGCACGGGACAAGGGAGAGCCGGTCAACGCAGCAGACGCG

....|....|....|....|....|....|....|....|....|....|....|....|....|
                        220         230         240         250         260         270         280

AAV5       208  GTCGGCGGAGAGCACGACAATCTCGTACAACGAGCAGCTTGAGGCGGAGACAACCCTACCTCAAGTACA
AAV3-3     211  GCAGCCCTCGAGAACGACACGACAAAGCTTACGACCAGCAGCAGCTCAAGGCCGGTGACAACCCGTACCTCAAGTACA
AAV4-4     208  GCAGCCCTCGAGCACGACACGACAAAGGCCTACGACCAGCAGCAGCTCAAGGCCGGTGACAATCCGTACCTCAAGTACA
AAV1-A     211  GCAGCCCTCGAGCACGACACGACAAAGGCCTACGACCAGCAGCAGCTCAAAGCGGGTGACAATCCGTACCTCAAGTACA
hu.46-A    211  GCGGCCCTCGAGCACGACACGACAAAGGCCTACGACCAGCAGCAGCTCGACAGCGGTGACAATCCGTACCTCAAGTACA
hu.48-A    211  GCGGCCCTCGAGCACGACACGACAAAGGCCTACGACCAGCAGCAGCTCGACAGCGGTGACAATCGTACCTGCGGTATA
hu.44-A    211  GCGGCCCTCGAGCACGACACGACAAAGGCCTACGACCAGCAGCAGCTCAAAGCGGGTGACAATCCGTACCTCAAGTACA
hu.43-A    211  GCGGCCCTCGAGCACGACACGACAAAGGCCTACGACCAGCAGCAGCTCAAAGCGGGTGACAATCCGTACCTCAAGTACA
AAV6-A     211  GCGGCCCTCGAGCACGACACGACAAAGGCCTACGACCAGCAGCAGCTCGACAGCGGGTGACAATCCGTACCTGCGGTATA
hu.34-B    211  GCGGCCCTCGAGCACGACACGACAAAGGCCTACGACCAGCAGCAGCTCGACAGCGGAGACAACCCGTACCTCAAGTACA
hu.47-B    211  GCGGCCCTCGAGCACGACACGACAAAGGCCTACGACCAGCAGCAGCTCGACAGCGGAGACAACCCGTACCTCAAGTACA
hu.29-B    211  GCGGCCCTCGAGCACGACACGACAAAGGCCTACGACCAGCAGCAGCTCGACAGCGGAGACAACCCGTACCTCAAGTACA
hu.63-B    211  GCGGCCCTCGAGCACGACACGACAAAGGCCTACGACCAGCAGCAGCTCGACAGCGGAGACAACCCGTACCTCAAGTACA
hu.56-B    211  GCGGCCCTCGAGCACGACACGACAAAGGCCTACGACCAGCAGCAGCTCGACAGCGGAGACAACCCGTACCTCAAGTACA
hu.45-B    211  GCGGCCCTCGAGCACGACACGACAAAGGCCTACGACCAGCAGCAGCTCGACAGCGGAGACAACCCGTACCTCAAGTACA
hu.57-B    208  GCGGCCCTCGAGCACGACACGACAAAGGCCTACGACCAGCAGCAGCTCGACAGCGGAGACAACCCGTACCTCAAGTACA
hu.35-B    211  GCGGCCCTCGAGCACGACACGACAAAGGCCTACGACCAGCAGCAGCTCGACAGCGGAGACAACCCGTACCTCAAGTACA
hu.58-B    211  GCGGCCCTCGAGCACGACACGACAAAGGCCTACGACCAGCAGCAGCTCGACAGCGGAGACAACCCGTACCTCAAGTACG
hu.28-B    211  GCGGCCCTCGAGCACGACACGACAAAGGCCTACGACCAGCAGCAGCTCGACAGCGGAGACAACCCGTACCTCAAGTACA
```

FIG. 3I

| | | |
|---|---|---|
| hu.51-B | 211 | GCGGCCCTCGAGCACGACAAAGCCTACGACCGGCAGCTCGACAGCGGAGACAACCCGTACCTCAAGTACA |
| hu.19-B | 211 | GCGGCCCTCGAGCACGACAAGCCTACGACCGGCAGCTCGACAGCGGAGACAACCCGTACCTCAAGTACA |
| hu.49-B | 211 | GCGGCCCTCGAGCACGACAAGCCTACGACCGGCAGCTCGACAGCGGAGACAACCCGTACCTCAAGTACA |
| hu.52-B | 211 | GCGGCCCTCGAGCACGACAAGCCTACGACCGGCAGCTCGACAGCGGAGACAACCCGTACCTCAAGTACA |
| hu.13-B | 211 | GCGGCCCTCGAGCACGACAGAGCCTACGACCGGCAGCTCGACAGCGGAGACAACCCGTACCTCAAGTACA |
| AAV2-B | 211 | GCGGCCCTCGAGCACGACAAAGCCTACGACCGGCAGCTCGACAGCGGAGACAACCCGTACCTCAAGTACA |
| hu.20-B | 211 | GCGGCCCTCGAGCACGACAAGCCTACGACCGGCAGCTCGACAGCGGAGACAACCCGTACCTCAAGTACA |
| hu.24-B | 211 | GCGGCCCTCGAGCACGACAAGCCTACGACCGGCAGCTCGACAGCGGAGATAACCCGTACCTCAAGTACA |
| hu.64-B | 211 | GCGGCCCTCGAGCACGACAAGCCTACGACCGGCAGCTCGACAGCGGAGACAACCCGTACCTCAAGTACA |
| hu.27-B | 211 | GCGGCCCTCGAGCACGACAAGGCCTACGACCGGCAGCTCGACAGCGGAGACAACCCGTACCTCAAGTACA |
| hu.21-B | 211 | GCGGCCCTCGAGCACGACAAGGCCTACGACCGGCAGCTCGACAGCGGAGATAACCCGTACCTCAAGTACA |
| hu.22-B | 211 | GCGGCCCTCGAGCACGACAAGGCCTACGACCGGCAGCTCGACAGCGGAGACAACCCGTACCTCAAGTACA |
| hu.23-B | 211 | GCGGCCCTCGAGCACGACAAGGCCTACGACCGGCAGCTCGACAGCGGAGACAACCCGTACCTCAAGTACA |
| hu.7-C | 211 | GCGGCCCTCGAGCACGACAAGGCCTACGACCGGCAGCTCGACAGCGGAGACAACCCGTACCTCAAGTACA |
| hu.61-C | 211 | GCGGCCCTCGAGCACGACAAGGCCTACGACCGGCAGCTCGACAGCGGAGACAACCCGTACCTCAAGTACA |
| rh.56-C | 211 | GCGGCCCTCGAGCACGACAAGGCCTACGACCGGCAGCTCGACAGCGGAGACAACCCGTACCTCAAGTACA |
| hu.9-C | 211 | GCGGCCCTCGAGCACGACAAGGCCTACGACCGGCAGCTCGACAGCGGAGACAACCCGTACCTCAAGTACA |
| hu.54-C | 211 | GCGGCTCTCGAGCACGACAAGGCCTACGACCGGCAGCTCGACAGCGGAGACAACCCGTACCTCAAGTACA |
| hu.53-C | 211 | GCGGCCCTCGAGCACGACAAGGCCTACGACCGGCAGCTCGACAGCGGAGACAACCCGTACCTCAAGTACA |
| hu.60-C | 211 | GCGGCCCTCGAGCACGACAAGGCCTACGACCGGCAGCTCGACAGCGGAGACAACCCGTACCTCAAGTACA |
| hu.55-C | 211 | GCGGCCCTCGAGCACGACAAGGCCTACGACCGGCAGCTCGACAGCGGAGACAACCCGTACCTCAAGTACA |
| hu.2-C | 211 | GCGGCCCTCGAGCACGACAAGGCCTACGACCGGCAGCTCGACAGCGGAGACAACCCGTACCTCAAGTACA |
| hu.1-C | 211 | GCGGCCCTCGAGCACGACAAGGCCTACGACCGGCAGCTCGACAGCGGAAAGCAACCCGTACCTCAAGTACA |
| hu.18-C | 211 | GCGGCCCTCGAGCACGACAAGGCCTACGACCGGCAGCTCGACAGCGGAGACAACCCGTACCTCAAGTACA |
| hu.3-C | 211 | GCGGCCCTCGAGCACGACAAGGCCTACGACCGGCAGCTCAACAGCGGAGACAACCCGTACCTCAAGTACA |
| hu.25-C | 211 | GCGGCCCTCGAGCACGACAAGGCCTACGACCGGCAGCTCGACAGCGGAGACAACCCGTACCTCAAGTACA |
| hu.15-C | 211 | GCGGCCCTCGAGCACGACAAGGCCTACGACCGGCAGCTCGACAGCGGAGACAACCCGTACCTCAAGTACA |
| hu.16-C | 211 | GCGGCCCTCGAGCACGACAAGGCCTACGACCGGCAGCTCGACAGCGGAGACAACCCGTACCTCAAGTACA |
| hu.11-C | 211 | GCGGCCCTCGAGCACGACAAGGCCTACGACCGGCAGCTCGACACCGGAGACAACCCGTACCTCAAGTACA |
| hu.10-C | 211 | GCGGCCCTCGAGCACGACAAGGCCTACGACCGGCAGCTCGACAGCGGAGACAACCCGTACCTCAAGTACA |

| | | |
|---|---|---|
| hu.24-B | 281 | ACCACGCCGACGCGGAGTTTCAGGAGCGCCTTAAAGAGGATACGTCTTTTGGGGCAACCTCGGACGAGC |
| hu.64-B | 281 | ACCACGCCGACGCGGAGTTTCCAGGAGCGCCTCTTAAAGAAGAAGATACGTCTCTTTGGGGCAACCTCGGACGAGC |
| hu.27-B | 281 | ACCACGCCGACGCGGAGTTTCAGGAGCGTCGCCTCTTAAAGAAGAAGATACGTCTCTTTGGGGCAACCTCGGACGAGC |
| hu.21-B | 281 | ACCACGCCGACGCGGAGTTTCAGGAGCGCCTCTTAAAGAGGAAGATACGTCTCTTTTGGGGCAACCTCGGACGAGC |
| hu.22-B | 281 | ACCACGCCGACGCGGAGTTTCAGGAGCGCGCCTCTTAAAGAGGAGATACGTCTCTTTTGGGGCAACCTCGGACGAGC |
| hu.23-B | 281 | ACCACGCCGACGCGGAGTTTCAGGAGCGCGCCTCTTAAAGAGGAAGATACGTCTCTTTTGGGGCAACCTCGGACGAGC |
| hu.7-C | 281 | ACCACGCCGACGCGGAGTTTCAGGAGCGCCTCTTAAAGAAGAAGATACGTCTCTTTTGGGGCAACCTCGGACGAGC |
| hu.61-C | 281 | ACCACGCCGACGCGGAGTTTCAGGAGCGCCTCTTAAAGAAGAAGATACGTCTCTTTTGGGGCAACCTCGGACGAGC |
| rh.56-C | 281 | ACCACGCCGACGCGGAGTTTCAGGAGCGCCTCTTAAAGAAGAAGATACGTCTCTTTTGGGGCAACCTCGGACGAGC |
| hu.9-C | 281 | ACCACGCCGACGCGGAGTTTCAGGAGCGTCGCCTCTTAAAGAAGAAGATACGTCTCTTTTGGGGCAACCTCGGACGAGC |
| hu.54-C | 281 | ACCACGCCGACGCGGAGTTTCAGGAGCGTCGCCTCTTAAAGAAGAAGATACGTCTCTTTTGGGGCAACCTCGGACGAGC |
| hu.53-C | 281 | ACCACCCCGACGCGGAGTTTCAGGAGCGCCTCTTAAAGAAGAAGATACGTCTCTTTTGGGGCAACCTCGGACGAGC |
| hu.60-C | 281 | ACCACGCCGACGCGGAGTTTCAGGAGCGCCTCTTAAAGAAGAAGATACGTCTTTTGGGGCAACCTCGGACGAGC |
| hu.55-C | 281 | ACCACGCCGACGCGAGAGTTTCAGGAGCGCCTCTTAAAGAAGAAGATACGTCTCTTTTGGGGCAACCTCGGACGAGC |
| hu.2-C | 281 | ACCACGCCGACGCGAGAGTTTCAGGAGCGCCTCTTAAAGAAGAAGATACGTCTCTTTGGGGCAACCTCGGACGAGC |
| hu.1-C | 281 | ACCACGCCGACGCGGAGTTTCAGGAGCGCCTCTTAAAGAAGAAGATACGTCTCTTTTGGGGCAACCTCGGACGAGC |
| hu.18-C | 281 | ACCACGCCGACGCGGAGTTTCAGGAGCGCCTCTTAAAGAAGAAGATACGTCTTTTGGGGCAACCTCGGACGAGC |
| hu.3-C | 281 | ACCACGCCGACGCGGAGTTTCAGGAGCGCCTCTTAAAGAAGAAGATACGTCTCTTTTGGGGCAACCTCGGACGAGC |
| hu.25-C | 281 | ACCACCCCGACGCCGAGTTTCAGGAGCGCCTCTTAAAGAAGAAGATACGTCTCTTTGGGGCAACCTCGGACGAGC |
| hu.15-C | 281 | ACCACGCCGACGCCGAGTTTCAGGAGCGCCCTCTTAAAGAAGAAGATACGTCTCTTTTGGGGCAACCTCGGACGAGC |
| hu.16-C | 281 | ACCACGCCGACGCCGAGTTTCAGGAGCGCCCTCTTAAAGAAGAAGATACGTCTTTTGGGGCAACCTCGGACGAGC |
| hu.11-C | 281 | ACCACGCCGACGCCGAGTTTCAGGAGCGTCTGCCTCTTAAAGAAGAAGATACGTCTCTTTTGGGGCAACCTCGGACGAGC |
| hu.10-C | 281 | ACCACGCCGACGCCGAGTTTCAGGAGCGTCTGCCTCTTAAAGAAGAAGATACGTCTCTTTTGGGGCAACCTCGGACGAGC |
| hu.4-C | 281 | ACCACGCCGACGCCGAGTTTCAGGAGCGTCTGCCTCTTGCAAGAAGAAGATACGTCTCTTTTGGGGCAACCTCGGACGAGC |
| rh.54-D | 281 | ACCACGCCGACGCCGAGTTTCAGGAGCGTCTGCCTCTTGCAAGAAGAAGATACGTCTTTTGGGGCAACCTCGGACGAGC |
| rh.48-D | 281 | ACCACGCCGACGCCGAGTTTCAGGAGCGTCTGCCTCTTGCAAGAAGAAGATACGTCTCTTTTGGGGCAACCTCGGACGAGC |
| rh.55-D | 281 | ATCACGCCGACGCCGAGTTTCAGGAGCGTCTGCCTCTTGCAAGAAGAAGATACGTCTCTTTTGGGGCAACCTCGGGCGAGC |
| rh.62-D | 281 | ACCACGCCGACGCCGAGTTCCAGGAGCGTCTGCCTCTTGCAAGAAGAAGATACGTCTCTTTTGGGGCAACCTCGGGCGAGC |
| AAV7-D | 281 | ACCACGCCGACGCCGAGTTTCAGGAGCGTCTGCCTCTTGCAAGAAGAAGATACGTCATTGGGGCAACCTCGGGCGAGC |
| rh.52-E | 281 | ATCACGCCGACGCCGAGTTTCAGGAGCGTCTGCCTCTTGCAAGAAGAAGATACGTCTCTTTTGGGGCAACCTCGGGCGAGC |

```
AAV1-A    351  AGTCTTCCAGGCCAAGAAGCGGGTTCTCGAACCCTCTCGGT----CTGGTTGAGGAAGGCGCTAAGACGGCT
hu.46-A   351  AGTCTTCCAGGCCAAGAAGCGGGTTCTCGAACCCTCTCGGT----CTGGTTGAGGAAGGCGCTAAGACGGCT
hu.48-A   351  AGTCTTCCAGGCCAAGAAGCGGGTTCTCGAACCCTCTCGGT----CTGGTTGAGGAAGGCGCCTAAGACGGCT
hu.44-A   351  AGTCTTCCAGGCCAAGAAGCGGGTTCTCGAACCCTCTCGGT----CTGGTTGAGGAAGGCGCTGAGACGGCT
hu.43-A   351  AGTCTTCCAGGCCAAGAAGCGGGTTCTCGAACCCTCTCGGT----CTGGTTGAGGAAGGCGCTGAGACGGCT
AAV6-A    351  AGTCTTCCAGGCCAAGAAGAGAGGGTACTTGAACCCTCGGGT----CTGGTTGAGGAAGGTGCTAAGACGGCT
hu.34-B   351  AGTCTTCCAGGCCAAAAAGAGAGGGTCTTGAACCCTCTGGGC----CTGGTTGAGGAACCTGTTAAGACGGCT
hu.47-B   351  AGTCTTCCAGGCGAAAAAGAGAGGGTCTTGAACCCTCTGGGC----CTGGTTGGGGAACCTGTTAAGACGGCT
hu.29-B   351  AGTCTTCCAGGCGAAAAAGAGAGAGGGTCTTGAACCCTCTGGGC----CTGGTTGAGGAGCCTGTTAAGACGGCT
hu.63-B   351  AGTCTTCCAGGCGAAAAAGAGAGGGTCTTGAACCCTCTGGGC----CTGGTTGAGGAACCTGTTAAGACGGCT
hu.56-B   351  AGTCTTCCAGGCGAAAAAGAGAGGGTCTTGAACCCTCTGGGC----CTGGTTGAGGAACCTGTTAAGACGGCT
hu.45-B   351  AGTCTTCCAGGCGAAAAAGAGAGGGTCTTGAACCCTCTGGGC----CTGGTTGAGGAACCTGTTAAGACGGCT
hu.57-B   348  AGTCTTCCAGGCGAAAAAGAGAGGGTCTTGAACCCTCTGGGC----CTGGTTGAGGAACCTGTTAAGACGGCT
hu.35-B   351  AGTCTTCCAGGCGAAAAAGAGAGGGTACTTGAACCCTCTGAGC----CTGGTTGAGGAGCCTGTTAAGACGGCT
hu.58-B   351  AGTCTTCCAGGCGAAAAAGAGAGGGTCTTCTTGAACCCTCTGAGC----CTGGTTGAGGAACCTGTCAAGACGGCT
hu.28-B   351  AGTCTTCCAGGCGAAAAAGAGAGGGTCTTGAACCCTCTGGGC----CTGGTTGAGGAACCTGTTAAGACGGCT
hu.51-B   351  AGTCTTCCAGGCGAAAAAGAGAGGGTCTTGAACCCTCTGAGC----CTGGTTGAGGAACCTGTTAAGACGGCT
hu.19-B   351  AGTCTTCCAGGCGAAAAAGAGAGGGATTCTTGAACCCTCTGGGC----CTGGTTGAGGAACCTGTTAAGACGGCT
hu.49-B   351  AGTCTTCCAGGCGAAAAAGAGAGGGATTCTTGAACCCTCTGGGC----CTGGTTGAGGAACCTGTTAAGACGGCT
hu.52-B   351  AGTCTTCCAGGCGAAAAAGAGAGGGTCTTCTTGAACCCTCTGGGC----CTGGTTGGGGAACCTGTTAAGACGGCT
hu.13-B   351  AGTCTTCCAGGCGAAAAAGAGAGGGTCTTCTTGAACCCTCTGGGC----CTGGTTGAGGAACCTGTTAAAACGGCT
AAV2-B    351  AGTCTTCCAGGCGAAAAAGAGAGGGTCTTCTTGAACCCTCTGGGC----CTGGTTGAGGAACCTGTTAAGGCGGCT
hu.20-B   351  AGTCTTCCAGGCGAAAAAGAGAGGGATTCTTGAACCCTCTGGGC----CTGGTTGAGGAACCTGTTAAGACGGCT
hu.24-B   351  AGTCTTCCAGGCGAAAAAGAGAGGGATTCTTGAACCCTCTGGGC----CTGGTTGAGGAACCTGTTAAGACGGCT
hu.64-B   351  AGTCTTCCAGGCGAAAAAGAGAGGGATTCTTGAACCCTCTGGGC----CTGGTTGAGGAACCTGTTAAGACGGCT
hu.27-B   351  AGTCTTCCAGGCGAAAAAGAGAGGGATTCTTGAACCCTCTGGGC----CTGGTTGAGGAACCTGTTAAGACGGCT
hu.21-B   351  AGTCTTCCAGGCGAAAAAGAGAGGGATTCTTGAACCCTCTGGGC----CTGGTTGAGGAACCTGTTAAGACGGCT
hu.22-B   351  AGTCTTCCAGGCGAAAAAGAGAGGGATTCTTGAACCCTCTGGGC----CTGGTTGAGGAACCTGTTAAGACGGCT
hu.23-B   351  AGTCTTCCAGGCGAAAAAGAGAGGGTCTTGAACCCTCTGGGC----CTGGTTGAGGAACCTGTTAAGACGGCT
hu.7-C    351  AGTCTTCCAGGCCGAAAAAGAGAGGGTCTTGAACCCTCTGGGC----CTGGTTGAGGACCTGTTAAGACGGCT
```

```
rh.61-E  351 AGTCTTCCAGGCCAAGAAGAAGCGGGTTCTCGAACCCTCTCGGT----CTGGTTGAGGAAGGCGCTAAGACGGCT
hu.41-E  351 AGTCTTCCAGGCCAAGAAGAAGCGGGTTCTCGAACCCTCTCGGT----CCGGTTGAGGAAGCTGCTAAGACGGCT
rh.64-E  351 AGTCTTCCAGGCCAAGAAGAAGCGGGTTCTCGAACCCTCTCGGT----CTGGTTGAGGAAGGCGCTAAGACGGCT
hu.42-E  351 AGTCTTCCAGGCCAAGAAGAAGCGGGTTCTCGAACCCTCTCGGT----CTGGTTGAGGAAGGCGCTAAGACGGCT
rh.57-E  351 AGTCTTCCAGGCCAAGAAGAAGCGGGTTCTCGAACCCTCTCGGT----CTGGTTGAGGAAGGCGCTAAGACGGCT
rh.40-E  351 AGTCTTCCAGGCCAAGAAGAAGCGGGTTCTCGAACCCTCTCGGT----CTGGTTGAGGAAGGCGCTAAGACGGCT
hu.40-E  351 AGTCTTCCAGGCCAAGAAGAAGCGGGTTCTCGAACCCTCTCGGT----CTGGTTGAGGAAGGCGCTAAGACGGCT
AAV8-E   351 AGTCTTCCAGGCCAAGAAGAAGCGGGTTCTCGAACCCTCTCGGT----CTGGTTGAGGAAGGCGCTAAGACGGCT
rh.58-E  351 AGTCTTCCAGGCCAAGAAGAAGCGGGTTCTCGAACCCTCTCGGT----CTGGTTGAGGAAGCTGCTAAGACGGCT
rh.40-E  351 AGTCTTCCAGGCCAAGAAGAAGCGGGTTCTCGAACCCTCTCGGT----CTGGTTGAGGAAGCTGCTAAGACGGCT
hu.67-E  351 AGTCTTCCAGGCCAAGAAGAAGCGGGTTCTCGAACCCTCTCGGT----CTGGTTGAGGAAGCTGCTAAGACGGCT
hu.17-E  351 AGTCTTCCAGGCCAAGAAGAAGCGGGTTCTCGAACCCTCTCGGT----CTGGTTGAGGAAGCTGCTAAGACGGCT
hu.6-E   351 AGTCTTCCAGGCCAAGAAGAAGCGGGTTCTCGAACCCTCTCGGT----CTGGTTGAGGAAGCTGCTAAGACGGCT
hu.66-E  351 AGTCTTCCAGGCCAAGAAGAAGCGGGTTCTCGAACCCTCTCGGT----CTGGTTGAGGAAGCTGCTAAGACGGCT
rh.38-E  351 AGTCTTCCAGGCCAAGAAGAAGCGGGTTCTCGAACCTCTTCGGT----CTGGTTGAGGAAGCTGCTAAGACGGCT
hu.32-F  351 AGTCTTCCAGGCCAAGAAAAAGCGGGTTCTTGAACCTCTTTGGT----CTGGTTGAGGAAGCCGCTAAGACGGCT
AAV9/hu  351 AGTCTTCCAGGCCAAAAAAAAGAGGGCTTGAACCCTCTTGGT-----CTGGTTGAGGAAGCGCTAAGACGGCT
hu.31-F  351 AGTCTTCCAGGCCAAAAAAAAGAGGCTTGAACCCTCTTGGT-----CTGGTTGAGGAAGCGCTAAGACGGCT 430        440        450        460        470        480       490
             ....|....|....|....|....|....|....|....|....|....|....|....|....|....|
AAV5     415 CCTACCGGAAGCGGATAGACGGACCACTTTCCA---------------------------------AAAA
AAV3-3   418 CCTGGAAAGAAGAAGAGAGAAGGGCTGTAGATCAGTCGTCCTCAG---GAACCGGACTCATCATCTGGTGTTGGCAAAT
AAV4-4_  415 CCTGGAAAGAAGAAGAGAAACGTCCGTTCATTGAATCCCCCCCAG---CAGCCCAGACTCCTCCACGGTATCGGCAAAA
AAV1-A   418 CCTGGAAAGAAGAAGAGAAACGTCCGGTAGAGCAGTCGCCACAA----GAGCCAGACTCCTCCTCCGGCATCGGCAAGA
hu.46-A  418 CCTGGAAAGAAGAAGAGAAACGTCCGGTAGAGCAGTCGCCACAA----GAGCCAGACTCCTCCTCCGGCATCGGCAAGA
hu.48-A  418 CCTGGAAAGAAGAAGAGAAACGTCCGGTAGAGCAGTCGCCACAA----GAGCCAGACTCCTCCTCCGGCATCGGCAAGA
hu.44-A  418 CCTGGAAAGAAGAAGAGAAACGTCCGGTAGAGCAGTCGCCACAA----GGGCCAGACTCCTCCTCCGGCATCGGCAAGA
hu.43-A  418 CCTGGAAAGAAGAAGAGAAACGTCCGGTAGAGCAGTCGCCACCTCAGCGTTCCCCCCAGCCAGCCCTCCTCCACGGCATCGGCAAGA
AAV6-A   418 CCTGGAAAGAAGAAGAGAAACGTCCGGTAGAGCAGTCGCCACAA----GAGCCAGACTCCTCCTCCGGCATTGGCAAGA
hu.34-B  418 CGGGAAAAAGAAGAGAAGAGGCGGTAGAGCAGTCGCCACTCCTGTG---GAGCCAGACTCCTCCTCCGGGAACCGGAAAGG
```

```
                                                570              580              590              600              610              620          630
                                         ....|....|....|....|....|....|....|....|....|....|....|....|....|....|....|....|....|....|....|....|....|
hu.32-F     485  CGGGTTCACAGCCCGCTAAAAAGAAACTCAATTTCGGTCAGACTGGCGACACAGAGTCAGTCCCGAC---
AAv9/hu     485  CGGGTGCACAGCCCGCTAAAAAGAGAGACTCAATTTCGGTCAGACTGGCGACACAGAGTCAGTCCCAGAC---
hu.31-F     485  CGGGTTCACAGCCCGCTAAAAAGAAACTCAATTTCGGTCAGACTGGCGACACAGAGTCAGTCCCGAC---

AAV5        522  ATCCCAGCAGCTGCAAATCCCAGCCACCAGCCTCAAGTTTGGGAGCTGATACAATGTCTGCGGGAGGT
AAV3-3      552  -CCTCAACCTCTCGGAGAACAGCAGCCACCAGCCCCACAAGTTTGGGATCTAATACAATGGCTTCAGGCGGT
AAV4-4_     546  -------CCTGAGGGATCAACTTCCGGAGCCATGTCT------GATGACAGTGAGATGCGTCAGCAGCT
AAV1-A      552  -CCACAACCTCTCGGAGAACCTCCAGCAACCCCGCTGCTGGGGGACCTACTACAATGGCTTCAGGCGGT
hu.46-A     552  -CCACAACCTCTCGGAGAACCTCCAGCAACCCCAGCAACCCCGCTGTGTGGGGACCTACTACAATGGCTTCAGGCGGT
hu.48-A     552  -CCACAACCTCTCGGAGAACCTCCAGCAACCCCAGCAACCCCGCTGTGTGGGGACCTACTACAATGGCTTCAGGCGGT
hu.44-A     552  -CCACAACCTCTCGGAGAACCTCCAGCAACCCCAGCAACCCCGCTGTGTGGGGACCTACTACAATGGCTTCAGGCGGT
hu.43-A     555  -CCTCAACCATCGGAGAACCTCCAGCAACCCCAGGCCCCTCTGTGGGTCTGGGGACCTACTACAATGGCTTCAGGCGGT
AAV6-A      552  -CCACAACCTCTCGGAGAACCTCCAGCAACCCCAGGCCCCCGCTGCTGGGGACCTACTACAATGGCTTCAGGCGGT
hu.34-B     552  -CCCCAGCCTCTCGGACAGCAGCAGCAGCCCCAGCAGCCCCGCTCCTGGTCTGGGAACTAATACGATGGCTACAGGCAGT
hu.47-B     552  -CCCCAGCCTCTCGGACAGCAGCAGCAGCCCCAGCAGCCCCGCTCCTGGTCTGGGAACTAATACGATGGCTACAGGCAGT
hu.29-B     552  -CCCCAGCCTCTCGGACAGCAGCAGCAGCCCCAGCAGCCCCGCTCCTGGTCTGGGAACTAATACGATGGCTACAGGCAGT
hu.63-B     552  -CCCCAGCCTCTCGGACAGCAGCAGCAGCCCCAGCAGCCATCCGCCCCGCTCCTGGTCTGGGAACTAATACGATGGCTACAGGCAGT
hu.56-B     552  -CCCCAGCCTCTCGGACAGCAGCAGCAGCCCCAGCAGCCCCGCTCCTGGTCTGGGAACTAATACGATGGCTACAGGCAGT
hu.45-B     552  -CCCCAGCCTCTCGGACAGCAGCAGCAGCCCCAGCAGCCCCGCTCCTGGTCTGGGAACTAATACGATGGCTACAGGCAGT
hu.57-B     549  -CCCCAGCCTCTCGGACAGCAGCAGCAGCCCCAGCAGCCCCGCTCCTGGTCTGGGAACTAATACGATGGCTACAGGCAGT
hu.35-B     552  -CCCCAGCCTCTCGGACAGCAGCAGCAGCCCCAGCAGCCCCGCTCCTGGTCTGGGAACTAATACGATGGCTACAGGCAGT
hu.58-B     552  -CCCCAGCCTCTCGGACAGCAGCAGCAGCCCCAGCAGCCCCGCTCCTGGTCTGGGAACTAATACGATGGCTACAGGCAGT
hu.28-B     552  -CCCCAGCCTCTCGGACAGCAGCAGCAGCCCCAGCAGCCCCGCTCCTGGTCTGGGAACTAATACGATGGCTACAGGCAGT
hu.51-B     552  -CCCCAGCCTCTCGGACAGCAGCAGCAGCCCCAGCAGCCCCGCTCCTGGTCTGGGAACTAATACGATGGCTACAGGCAGT
hu.19-B     552  -CCCCAGCCTCTCGGACAGCAGCAGCAGCCCCAGCAGCCCCGCTCCTGGTCTGGGAACTAATACGATGGCTACAGGCAGT
hu.49-B     552  -CCCCAGCCTCTCGGACAGCAGCAGCAGCCCCAGCAGCCCCGCTCCTGGTCTGGGAACTAATACGATGGCTACAGGCAGT
hu.52-B     552  -CCCCAGCCTCTCGGACAGCAGCAGCAGCCCCAGCAGCCCCGCTCCTGGTCTGGGAACTAATACGATGGCTACAGGCAGT
hu.13-B     552  -CCCCAGCCTCTCGGACAGCAGCAGCAGCCCCAGCAGCCCCGCTCCTGGTCTGGGAACTAATACGATGGCTTCAGGCAGT
```

| | | |
|---|---|---|
| hu.23-B | 622 | GGCGCACCAATGGCAGACAATAACGAGGGCGCCGACGGAGTGGGTAATTCCTCCGGAAATTGGCATTGCG |
| hu.7-C | 622 | GGCGCACCAATGGCAGACAATAACGAGAGGGTGCCGATGGAGTGGGTAATTCCTCAGGAAATTGGCATTGCG |
| hu.61-C | 622 | GGCGCACCAATGGCAGACAATAACGAGAGGGTGCCGATGGAGTGGGTAATTCCTCAGGAAATTGGCATTGCG |
| rh.56-C | 622 | GGCGCACCAATGGCAGACAATAACGAGAGGGTGCCGATGGAGTGGGTAATTCTTCAGGAAATTGGCATTGCG |
| hu.9-C | 622 | GGCGCACCAATGGCAGACAATAACGAGAGGGTGCCGATGGAGTGGGTAATTCCTCAGGAAATTGGCATTGCG |
| hu.54-C | 622 | GGCGCACCAATGGCAGACAATAACGAGAGGGTGCCGATGGAGTGGGTAATTCCTCAGGAAATTGGCATTGCG |
| hu.53-C | 622 | GGCGCACCAATGGCAGACAATAACGAGAGGGTGCCGATGGAGTGGGTAATTCCTCAGGAAATTGGCATTGCG |
| hu.60-C | 622 | GGCGCACCAATGGCAGACAATAACGAGAGGGTGCCGATGGAGTGGGTAATTCCTCAGGAAATTGGCATTGCG |
| hu.55-C | 622 | GGCGCACCAATGGCAGACAATAACGAGAGGGTGCCGATGGAGTGGGTAATTCCTCAGGAAATTGGCATTGCG |
| hu.2-C | 622 | GGCGCACCAATGGCAGACAATAACGAGAGGGTGCCGATGGAGTGGGTAATTCCTCAGGAAATTGGCATTGCG |
| hu.1-C | 622 | GGCGCACCAATGGCAGACAATAACGAGAGGGTGCCGATGGAGTGGGTAATTCCTCAGGAAATTGGCATTGCG |
| hu.18-C | 622 | GGCGCACCAATGGCAGACAATAACGAGAGGGTGCCGATGGAGTGGGTAATTCCTCAGGAAATTGGCATTGCG |
| hu.3-C | 625 | GGCGCACCAGTGGCAGACAATAACGAGAGGGTGCCGATGGAGTGGGTAATTCCTCAGGAAATTGGCATTGCG |
| hu.25-C | 622 | GGCGCACCAATGGCAGACAATAACGAGAGGGTGCCGATGGAGTGGGTAATTCCTCAGGAAATTGGCATTGCG |
| hu.15-C | 622 | GGCGCACCAATGGCAGACAATAACGAGAGGGTGCCGATGGAGTGGGTAATTCCTCAGGAAATTGGCATTGCG |
| hu.16-C | 622 | GGCGCACCAATGGCAGACAATAACGAGAGGGTGCCGATGGAGTGGGTAATTCCTCAGGAAATTGGCATTGCG |
| hu.11-C | 622 | GGCGCACCAGTGGCAGACAATAACGAGAGGGTGCCGATGGAGTGGGTAATTCCTCAGGAAATTGGCATTGCG |
| hu.10-C | 622 | GGCGCACCAATGGCAGACAATAACGAGAGGGTGCCGATGGAGTGGGTAATTCCTCAGGAAATTGGCATTGCG |
| hu.4-C | 622 | GGCGCACCAATGGCAGACAATAACGAGAGGGTGCCGATGGAGTGGGTAATGCCTCAGGAAATTGGCATTGCG |
| rh.54-D | 625 | GGCGCTCCAATGGCAGACAATAACGAAGAGGGTGCCGACGGAGTGGGTAATGCCTCAGGAAATTGGCATTGCG |
| rh.48-D | 625 | GGCGCCAATGGCAGACAATAACAAGAGGGTGCCGACGGAGTGGGTAGTGCCTCCTCCGGAAATTGGCATTGCG |
| rh.55-D | 625 | GGCGCCACCAATGGCAGACAATAACAAGAGGGTGCCGACGGAGTGGGTAGTGCCTCAGGAAATTGGCATTGCG |
| rh.62-D | 625 | GGCGCCACCAATGGCAGACAATAACAAGAGGGTGCCGACGGAGTGGGTAGTGCCTCCTCCGGAAATTGGCATTGCG |
| AAV7-D | 625 | GGCGCACCAATGGCAGACAATAACAAGAAGGTGCCGACGGAGTGGGTAGTTCCTCCGGAAATTGGCATTGCG |
| rh.52-E | 625 | GGCGCCACCAATGGCAGACAATAACGAAGAAGGTGCCGACGGAGTGGGTAGTTCCTTCCGGAAATTGGCATTGCG |
| rh.51-E | 625 | GGCGCCACCAATGGCAGACAATAACGAAGAAGGTGCCGACGGAGTGGGTAGTTCCTCCGGAAATTGGCATTGCG |
| hu.39-E | 625 | GGCGCCACCAATGGCAGACAATAACGAAGAAGGTGCCGACGGAGTGGGTAGTTCCTCCGGAAATTGGCATTGCG |
| rh.53-E | 625 | GGCGCACCAATGGCAGACAATAACGAAGAAGGTGCCGACGGAGTGGGTAGTTCCTCCGGAAATTGGCATTGCG |
| hu.37-E | 625 | GGCGCTCCAATGGCAGACAATAACGAAGAAGGCGCCGACGGAGTGGGTAGTTCCTCCGGAAATTGGCATTGCG |
| rh.43-E | 622 | GGCGCACCAATGGCAGACAATAACGAAGAGGGCCGACGGAGTGGGTAGTTCCTCCGGAAATTGGCATTGCG |

| | | |
|---|---|---|
| AAV6-A | 692 | ATTCCACATGGCTGGGCGACAGAGTCATCACCAGCACCCGAACACATGGCCTTGCCCACCTATAACAA |
| hu.34-B | 692 | ATTCCACATGGATGGGCGACAGAGTCATCATCACCAGCACCCGAACCTGGGCCCTGCCCACCTACAACAA |
| hu.47-B | 692 | ATTCCACATGGATGGGCGACAGAGTCATCATCACCAGCACCCGAACCTGGGCCCTGCCCACCTACAACAA |
| hu.29-B | 692 | ATTCCACATGGATGGGCGACAGAGTCATCATCACCAGCACCCGAACCTGGGCCCTGCCCACCTACAACAA |
| hu.63-B | 692 | ATTCCACATGGATGGGCGACAGAGTCATCATCACCAGCACCCGAACCTGGGCTCTGCCCACCTACAACAA |
| hu.56-B | 692 | ATTCCACATGGATGGGCGACAGAGTCATCATCACCAGCACCCGAACCTGGGCCCTGCCCACCTACAACAA |
| hu.45-B | 692 | ATTCCACATGGATGGGCGACAGAGTCATCATCACCAGCACCCGAACCTGGGCCCTGCCCACCTACAACAA |
| hu.57-B | 689 | ATTCCACATGGATGGGCGACAGAGTCATCATCACCAGCACCCGAACCTGGGCCCTGCCCACCTACAACAA |
| hu.35-B | 692 | ATTCCACATGGATGGGCGACAGAGTCATCATCACCAGCACCCGAACCTGGGCCCTGCCCACCTACAACAA |
| hu.58-B | 692 | ATTCCACATGGATGGGCGACAGAGTCATCATCACCAGCACCCGAACCTGGGCTCTGCCCACCTACAACAA |
| hu.28-B | 692 | ATTCCACATGGATGGGCGACAGAGTCATCATCACCAGCACCCGAACCTGGGCCCTGCCCACCTACAACAA |
| hu.51-B | 692 | ATTCCACATGGATGGGCGACAGAGTCATCATCACCAGCACCCGAACCTGGGCCCTGCCCACCTACAACAA |
| hu.19-B | 692 | ATTCCACATGGATGGGCGACAGAGTCATCATCACCAGCACCCGAACCTGGGCCCTGCCCACCTACAACAA |
| hu.49-B | 692 | ATTCCACATGGATGGGCGACAGAGTCATCATCACCAGCACCCGAACCTGGGCTCTGCCCACCTACAACAA |
| hu.52-B | 692 | ATTCCACATGGATGGGCGACAGAGTCATCATCACCAGCACCCGAACCTGGGCCCTGCCCACCTACAACAA |
| hu.13-B | 692 | ATTCCACATGGATGGGCGACAGAGTCATCATCACCAGCACCCGAACCTGGGCCCTGCCCACCTACAACAA |
| AAV2-B | 692 | ATTCCACATGGATGGGCGACAGAGTCATCATCACCAGCACCCGAACCTTGGGCCCTGCCCACCTACAACAA |
| hu.20-B | 692 | ATTCCACATGGATGGGCGACAGAGTCATCATCACCAGCACCCGAACCTGGGCCCTGCCCACCTACAACAA |
| hu.24-B | 692 | ATTCCACATGGATGGGCGACAGAGTCATCATCACCAGCACCCGAACCTGGGCCCTGCCCACCTACAACAA |
| hu.64-B | 692 | ATTCCACATGGCTGGGCGACAGAGTCATCATCACCAGCACCCGAACCTGGGCTCTGCCCACCTACAACAA |
| hu.27-B | 692 | ATTCCACATGGCTGGGCGACAGAGTCATCATCACCAGCACCCGAACCTGGGCCCTGCCCACCTACAACAA |
| hu.21-B | 692 | ATTCCACATGGCTGGGCGACAGAGTCATCATCACCAGCACCCGAACCTGGGCCCTGCCCACCTACAACAA |
| hu.22-B | 692 | ATTCCACATGGATGGGCGACAGAGTCATCATCACCAGCACCCGAACCTGGGCCCTGCCCACCTACAACAA |
| hu.23-B | 692 | ATTCCACATGGATGGGCGACAGAGTCATCATCACCAGCACCCGAACCTGGGCCCTGCCCACCTACAACAA |
| hu.7-C | 692 | ATTCCCAATGGCTGGGCGACAGAGTCATCATCACCAGCACCCGAACCTGGGCCCTGCCCACCTGCAACAA |
| hu.61-C | 692 | ATTCCCAATGGCTGGGCGACAGAGTCATCATCACCAGCACCCGAACCTGGGCCCTGCCCACCTACAACAA |
| rh.56-C | 692 | ATTCCCAATGGCTGGGCGACAGAGTCATCATCACCAGCACCCGAACCTGGGCCAGCCCACCTACAACAA |
| hu.9-C | 692 | ATTCCCAATGGCTGGGCGACAGAGTCATCATCACCAGCACCCGAACCTGGGCCCTGCCCACCTACAACAA |
| hu.54-C | 692 | ATTCCCAATGGCTGGGCGACAGAGTCATCATCACCAGCACCCGAACCTGGGCCCTGCCCACCTACAACAA |
| hu.53-C | 692 | ATTCCCAATGGCTGGGCGACAGAGTCATCATCACCAGCACCCGAACCTGGGCCCTGCCCACCTACAACAA |

FIG. 3AC

```
hu.60-C  692  ATTCCCAATGGCTGGGCGACAGAGTCATCACCACCAGCACCCGCACCTGGGCCCTGCCCACCTACAACAA
hu.55-C  692  ATTCCCAATGGCTGGGCGACAGAGTCATCACCACCAGCACCCGAACCTGGGCCCTGCCCACCTACAACAA
hu.2-C   692  ATTCCCAATGGCTGGGCGACAGAGTCATCACCACCAGCACCCGAACCTGGGCCCTGCCCACATACAACAA
hu.1-C   692  ATTCCCAATGGCTGGGCGACAGAGTCATCACCACCAGCACCCGAACCTGGGCCCTGCCCACATACAACAA
hu.18-C  692  ATTCCCAATGGCTGGGCGACAGAGTCATCACCACCAGCACCCGAACCTGGGCCCTGCCCACCTACAACAA
hu.3-C   695  ATTCCCAATGGCTGGGCGACAGAGTCATCACCGCCAGCACCCGAACCTGGGCCCTGCCCACATACAACAA
hu.25-C  692  ATTCCCAATGGCTGGGCGACAGAGTCATCACCACCAAGCACTCGAACTCGGGCCCTGCCCACCTACAACAA
hu.15-C  692  ATTCCCAATGGCTGGGCGACAGAGTCATCACCACCAGCACCCGAACCTGGGCTCTGCCCACTTACAATAA
hu.16-C  692  ATTCCCAATGGCTGGGCGACAGAGTCATCACCACCAGCACCCGAACCTGGGCTCTGCCCACCTACAACAA
hu.11-C  692  ATTCCCAATGGCTGGGCGACAGAGTCATCACCACCAGCACCCGAACCTGGGCCCTGCCCACCTACAACAA
hu.10-C  692  ATTCCCAATGGCTGGGCGACAGAGTCATCACCACCAGCACCCGAACCTGGGCCCTGCCCACATACAACAA
hu.4-C   692  ATTCCCAATGGCTGGGCGACAGAGTCATCACCACCAGCACCCGAACCTGGGCCCTGCCCACCTACAACAA
rh.54-D  695  ATTCCACATGGCTGGGCGACAGAGTCATCACCACCAGCACCCGAACCTGGGCTTTGCCCACCTACAACAA
rh.48-D  695  ATTCCACATGGCTGGGCGACAGAGTCATCACCACCAGCACCCGAACCTGGGCTTTGCCCACCTACAACAA
rh.55-D  695  ATTCCACATGGCTGGGCGACAGAGTCATCACCACCAGCACCCGAACCTGGGCTTTGCCCACCTACAACAA
rh.62-D  695  ATTCCACATGGCTGGGCGACAGAGTCATTACCACCAGCACCCGAACCTGGGCCCTGCCCACCTACAACAA
AAV7-D   695  ATTCCACATGGCTGGGCGACAGAGTCATCACCACCAGCACCCGAACCTGGGCCCTGCCCACCTACAACAA
rh.52-E  695  ATTCCACATGGCTGGGCGACAGAGTCATCACCACCAGCACCCGAACCTGGGCCCTGCCCACCTACAACAA
rh.51-E  695  ATTCCACATGGCTGGGCGACAGAGTTATCACCACCAGCACCCGAACCTGGGCCCTGCCCACCTACAACAA
rh.39-E  695  ATTCCACATGGCTGGGCGACAGAGTCATCACCACCAGCACCCGAACCTGGGCCCTGCCCACCTACAACAA
rh.53-E  695  ATTCCACATGGCTGGGCGACAGAGTCATCACCACCAGCACCCGAACCTGGGCCCTGCCCACCTACAACAA
rh.37-E  695  ATTCCACATGGCTGGGCGACAGAGTCATCACCACCAGCACCCGAACCTGGGCCCTGCCCACCTACAACAA
rh.43-E  692  ATTCCCAATGGCTGGGCGACAGAGTCATCACCACCAGCACCCGAACCTGGGCCCTGCCCACCTACAACAA
rh.50-E  695  ATTCCACATGGCTGGGCGACAGAGTCATCACCACCAGCACCCGAACCTGGGCCCTGCCCACCTACAACAA
rh.49-E  695  ATTCCACATGGCTGGGCGACAGAGTCATCACCACCAGCACCCGAACCTGGGCCCTGCCCACCTACAACAA
rh.61-E  695  ATTCCACATGGCTGGGCGACAGAGTCATCACCACCAGCACCCGAACCTGGGCCCTGCCCACCTACAACAA
rh.41-E  695  ATTCCACATGGCTGGGCGACAGAGTCATCACCACCAGCACCCGAACCTGGGCCCTGCCCACCTACAACAA
rh.64-E  695  ATTCCACATGGCTGGGCGACAGAGTCATCACCACCAGCACCCGAACCTGGGCCCTGCCCACCTACAACAA
hu.42-E  695  ATTCCACATGGCTGGGCGACAGAGTCATCACCACCAGCACCCGAACCTGGGCCCTGCCCACCTACAACAA
rh.57-E  695  ATTCCACATGGCTGGGCGACAGAGTCATCACCACCAGCACCCGAACCTGGGCCCTGCCCACCTACAACAA
```

```
hu.57-B   759  CCACCTCTACAAGCAGAGATTTCC------AGCCAATCAGGAGGAGCCAGCCAATGACGACCAATGACGACCACTACTTTGGCTAC
hu.35-B   762  CCACCTCTACAAACAAGCAGATTTCC----AGCCAATCAGGAGCCTCGAACGACAATGACAACCACTACTTTGGCTAC
hu.58-B   762  CCATCTGTACAAGCAGATTTCC--------AGCCAATCAGGAGCCTCGAGCAGCAATGACAACCACTACTTTGGCTAC
hu.28-B   762  CCATCGTACAAGCAAATATCC---------AGCCAGTCTGGAGCAGCCAGCCAATCGACAACCACTACTTTGGCTAC
hu.51-B   762  CCACCTCTACAAACAAATTTCC--------AGCCAATCAGGAGCAGCCTGGAGCAGCCAGCAATGACAACCACTACTTTGGCTAC
hu.19-B   762  CCATCGTACAAGCAGATCTCC---------AGCCAGTCTGGAGCAGCCAGCAATGACAACCACTACTTTGGCTAC
hu.49-B   762  CCATCGTACAAGCAGATCTCC---------AGCCAATCAGGAGCAGCCTCGAGCAACGACAACCACTACTTTGGCTAC
hu.52-B   762  CCACCTCTACAAGCAGATATTCC-------AGCCAATCAGGAGCCTCGAACGACAATGACGACCACTACTTTGGCTAC
hu.13-B   762  CCATCTCTACAAGCAAATCTCC--------AGCCAATCAGGAGCCTCGAACAACGACAACCACTACTTTGGCTAC
AAV2-B    762  CCACCTCTACAAACAAATTCC---------AGCCAATCAGGAGCCTCGAACGACAACGACAACCACTACTTTGGCTAC
hu.20-B   762  CCATCGTACAAGCAAATCTCC---------AGCCAGTCTGGAGCAGCCAGCAATGACAACCACTACTTTGGCTAC
hu.24-B   762  CCATCGTACAAGCAAATCTCC---------AGCCAGTCTGGAGCAGCCAGCAATGACAACCACTACTTTGGCTAC
hu.64-B   762  CCACCTCTACAGGCAGATTTCC--------AGCCAATCAGGAGCAGCCAGCAATGACAACCACTACTTTGGCTAC
hu.27-B   762  CCATCGTACAAGCAAATCTCC---------AGCCAGTCTGGAGCAGCCAGCCAATGACAACCACTACTTTGGCTAC
hu.21-B   762  CCATCGTACAAGCAAATCTCC---------AGCCAGTCTGGAGCAGCCAGCAATGACAACCACTACTTTGGCTAC
hu.22-B   762  CCATCTGTACAAGCAAATCTCC--------AGCCAGTCTGGAGCAGCCAGCAATGACAACCACTACTTTGGCTAC
hu.23-B   762  CCATCGTACAAGCAAATCTCA---------AGCCAATCAGGAGCAGCCAGCAATGACAACCACTACTTTGGCTAC
hu.7-C    762  CCACCTCTACAAGCAAATCTCC--------AGCCAATCAGGAGCCTCAAACGACAATGACAACCACTACTTTGGCTAC
hu.61-C   762  CCACCTCTACAAGCAAATCTCC--------AGCCAATCAGGAGCCTCAAACGACAACGACAACCACTACTTTGGCTAC
rh.56-C   762  CCACCTCTACAAGCAAATCTCA--------AGCCAATCAGGAGCCTCAAACGACAACGACAACCACTACTTTGGCTAC
hu.9-C    762  CCACCTCTACAAGCAAATCTCC--------AGCCAATCAGGAGCCTCGAACGACAACGACAACCACTACTTGGCTGC
hu.54-C   762  CCACCTTTACAAGCAAATCTCC--------AGCCAATCAGGAGCAGCCTCGAACGACAACGACAACCACTACTTGGCTAC
hu.53-C   762  CCACCTTTACAAGCAAATCTCC--------AGCCAATCAGGAGCAGCCTCAAACGACAACGACAACCACTACTTTGGCTAC
hu.60-C   762  CCACCTCTACAAGCAAATCTCC--------AGCCAATCAGGAGCCTCAAACGACAACGACAACCACTACTTGGCTAC
hu.55-C   762  CCACCTTACAAGCAAATCTCC---------AGCCAATCAGGAGCCTCAAACGACAACGACAACCACTACTTTGGCTAC
hu.2-C    762  CCACCTCTACAAGCAAATCTCC--------AGCCAATCAGGAGCCTCAAACGACAACGACAACCACTACTTTGGCTAC
hu.1-C    762  CCACCTCTACAAGCAAATCTCC--------AGCCAATCAGGAGCCTCAAACGACAACGACAACCACTACTTTGGCTAC
hu.18-C   762  CCACCTCTACAAGCAAATCTCC--------AGCCAATCAGGAGCCTCAAACGACAACGACAACCACTACTTTGGCTAC
hu.3-C    765  CCACCTCTACAAGCAAATCTCC--------AGCCAATCAGGAGCCTGCAACGCAACGACAACCACTATTTGGCTAC
hu.25-C   762  CCACCTCTACAAGCAAATCTCC--------AGCCAATCAGGAGCCTCAAACGACAACGACAACCACTACTTTGGCTAC
```

FIG. 3AF

| | | |
|---|---|---|
| hu.15-C | 762 | CCACCCTCTACAAGCAAATCTCC------AGCCAATCAGGAGCCTCAAACGACAACCACTACTTTGGCTAC |
| hu.16-C | 762 | CCACCCTCTACAAGCAAATCTCC------AGCCAATCAGGAGCCTCAAACGACAACCACTACTTTGGCTAC |
| hu.11-C | 762 | CCACCCTCTACAAGCAAATCTCC------AGCCAATCAGGAGCCTCGAACGACAACCACTACTTTGGCTAC |
| hu.10-C | 762 | CCACCCTCTACAAGCAAATCTCC------AGCCAATCAGGAGCCCAGCAGCAACAACCACTACTTTGGCTAC |
| hu.4-C | 762 | CCACCCTCTACAAGCAAATCTCC------AGCCAATCAGGAGCCAGCAGCAACAACCACTACTTTGGCTAC |
| rh.54-D | 765 | CCACCCTCTACAAGCAAATCTCCCAGT---CAGTCAGCAGGTAGCACCAACGACAACGTCTACTTCGGCTAC |
| rh.48-D | 765 | CCACCCTCTACAAGCAAATCTCCCAGT---CAGTCAGCAGGTAGCACCAACGACAACGTCTACTTCGGCTAC |
| rh.55-D | 765 | CCACCCTCTACAAGCAAATCTCCCAGT---CAGTCAGCAGGTAGCACCAACGACAACGTCTACTTCGGCTAC |
| rh.62-D | 765 | CCACCCTCTACAAGCAAATCTCCCAGT---CAGTCAGCAGGTAGTACCAACGACAACACCTACTTCGGCTAC |
| AAV7-D | 765 | CCACCCTCTACAAGCAAATCTCCCAGT---GAAACTGCAGGTAGTACCAACGACAACACCTACTTTGGCTAC |
| rh.52-E | 765 | CCACCCTCTACAAGCAAATCTCCAACGGGACCCTCGGGAGGCAGCAGCAACGACAACACCTACTTCGGCTAC |
| rh.51-E | 765 | CCACCCTCTACAAGCAAATCTCCAACGGGACCCTCGGGAGGCAGCAGCAACGACAACACCTACTTTGGCTAC |
| rh.39-E | 765 | CCACCCTCTACAAGCAAATCTCCAACGGGACCCTCGGGAGGCAGCAGCAACGACAACACCTACTTTGGCTAC |
| rh.53-E | 765 | CCACCCTCTACAAGCAAATCTCCAACGGGACCCTCGGGAGGCAGCAGCAACGACAACACCTACTTCGGCTAC |
| rh.37-E | 762 | CCACCCTCTACAAGCAAATCTCCAACGGGACCCTCGGGAGGCAGCAGCAACGACAACACCTACTTCGGCTAC |
| rh.43-E | 765 | CCACCCTCTACAAGCAAATATCCAACGGGACCCTCGGGAGGACATCGGACACCAACGACAACACCTACTTCGGCTAC |
| rh.50-E | 765 | CCACCCTCTACAAGCAAATCTCCAACGGGACCCTCGGGAGGACATCGGACACCAACGACAACACCTACTTCGGCTAC |
| rh.49-E | 765 | CCACCCTCTACAAGCAAATCTCCAACGGGACCCTCGGGAGGACATCGGACACCAACGACAACACCTACTTCGGCTAC |
| hu.61-E | 765 | CCACCCTCTACAAGCAAATCTCCAACGGGACCCTCGGGAGGACATGGGACACCAACGACAACACCTACTTTGGCTAC |
| hu.41-E | 765 | CCACCCTCTACAAGCAAATCTCCAACGGGACCCTCGGGAGGACATGGGACACCAACGACAACACCTACTTCGGCTAC |
| rh.64-E | 765 | CCACCCTCTACAAGCAAATCTCCAACGGGACCCTCGGGAGGACATGGGACACCAACGACAACACCTACTTCGGCTAC |
| rh.42-E | 765 | CCACCCTCTACAAGCAAATCTCCAACGGGACCCTCGGGAGGACATGGGACACCAACGACAACACCTACTTGGCTAC |
| rh.57-E | 765 | CCACCCTCTACAAGCAAATATCCAACCTCCAATATCCAACGGGACCCTCGGGAGGAAGCAGCAGCAAGACAACACCTACTTCGGCTAC |
| hu.40-E | 765 | CCACCCTCTACAAGCAAATATCCAACCTCCAATATCCAACGGGACCCTCGGGAGGAAGCAGCAGCAAGACAACACCTACTTCGGCTAC |
| AAV8-E | 765 | CCACCCTCTACAAGCAAATCTCCAATATCCAACGGGACCCTCGGGAGGAAGCAGCAGCAAGACAACACCTACTTCGGCTAC |
| rh.58-E | 765 | CCACCCTCTACAAGCAAATCTCCAATATCCAACGGGACCCTCGGGAGGAAGCAGCAGCAAGACAACACCTACTTTGGCTAC |
| rh.40-E | 765 | CCACCCTCTACAAGCAAATCTCCAATCCAACGGGACCCTCGGGAGGAAGCAGCAGCAAGACAACACCTACTTCGGCTAC |
| hu.67-E | 765 | CCACCCTCTACAAGCAAATCTCCAATCCAACGGGACCCTCGGGAGGAAGCAGCAGCAAGACAACACCTACTTCGGCTAC |
| hu.17-E | 765 | CCACCCTCTACAAGCAAATCTCCAATCCAACGGGACCCTCGGGAGGAAGCAGCAGCAACGACAACACCTACTTCGGCTAC |
| hu.6-E | 765 | CCACCCTCTACAAGCAAATCTCCAACGGACGGGACCCTCGGGAGGAAGCAGCAGCAACGACAACACCTACTTCGGCTAC |

| | | |
|---|---|---|
| hu.52-B | 826 | AGCACCCCCTTGGGGGTATTTTGACTTCAACAGATTCCACTGCCACTTTTCACCACGTGACTGGCAAAGAC |
| hu.13-B | 826 | AGCACCCCCTTGGGGGTATTTTGACTTCAACAGATTCCACTGCCACTTTTCACCACGTGACTGGCAAAGAC |
| AAV2-B | 826 | AGCACCCCCTTGGGGGTATTTTGACTTCAACAGATTCCACTGCCACTTTTCACCACGTGACTGGCAAAGAC |
| hu.20-B | 826 | AGCACCCCCTTGGGGGCATTTTGACTTCAACAGATTCCACTGCCACTTCTCCCACCACGTGACTGGCAAAGAC |
| hu.24-B | 826 | AGCACCCCCTGGGGGTATTTTGACTTCAACAGATTCCACTGCCACTTCTCCCACCACGTGACTGGCAAAGAC |
| hu.64-B | 826 | AGCACCCCCTGGGGGTATTTTGACTTCAACAGATTCCACTGCCACTTTTCGCCACGTGACTGGCAAAGAC |
| hu.27-B | 826 | AGCACCCCCTGGGGGTATTTTCGACTTCAACAGATTCCACTGCCACTTCTCCCCACCACGTGACTGGCAAAGAC |
| hu.21-B | 826 | AGCACCCCCTGGGGGTATTTTGACTTCAACAGATTCCACTGCCACTTCTCCCCACCACGTGACTGGCAAAGAC |
| hu.22-B | 826 | AGCACCCCCTGGGGGTATTTTGACTTCAACAGATTCCACTGCCACTTTTCACCACGTGACTGGCAAAGAC |
| hu.23-B | 826 | AGCACCCCCTGGGGGTATTTTGACTTCAACAGATTCCACTGCCACTTTTCACCACGTGACTGGCAAAGAC |
| hu.7-C | 826 | AGCACCCCCTGGGGGTATTTTGACTTCAACAGATTCCACTGCCACTTTTCACCACGTGACTGGCAAAGAC |
| hu.61-C | 826 | AGCACCCCCTGGGGGTATTTTGACTTCAACAGATTCCACTGCCACTTTTCACCACGTGACTGGCAAAGAC |
| rh.56-C | 826 | AGCACCCCCTGGGGGTATTTTGACTTGACTTCAACAGATTCCACTGCCGCGTCACTTCTCCCACCACGTGACTGGCAAAGAC |
| hu.9-C | 826 | AGCACCCCCTGGGGGTATTTTGACTTCAACAGATTCCACTGCCACTGCCACTTTTCACCACGTGACTGGCAAAGAC |
| hu.54-C | 826 | AGCACCCCCTGGGGGTATTTTGACTTCAACAGATTCCACTGCCACTGCCACTTTTCACCACGTGACTGGCAAAGAC |
| hu.53-C | 826 | AGCACCCCCTGGGGGTATTTTGACTTCAACAGATTCCACTGCCACTGCCACTTTTCACCACGTGACTGATTGGCAAAGAC |
| hu.60-C | 826 | AGCACCCCCTGGGGGTATTTTGACTTCAACAGATTCCACTGCCACTGCCACTTTTCACCACGTGACTGGCAAAGAC |
| hu.55-C | 826 | AGCACCCCCTGGGGGTATTTTGACTTCAACAGATTCCACTGCCACTGCCACTTTTCACCACGTGACTGGCAAAGAC |
| hu.2-C | 826 | AGCACCCCCTGGGGGTATTTTGACTTCAACAGATTCCACTGCCACTGCCACTTTTCACCACGTGACTGGCAAAGAC |
| hu.1-C | 826 | AGCACCCCCTGGGGGTATTTTGACTTCAACAGATTCCACTGCCACTGCCACTTTTCACCACGTGACTGGCAAAGAC |
| hu.18-C | 826 | AGCACCCCCTGGGGGTATTTTGACTTCAACAGATTCCACTGCCACTGCCACTTTTCACCACGTGACTGGCAAAGAC |
| hu.3-C | 829 | AGCACCCCCTGGGGGTATTTTGACTTCAACAGATTCCACTGCCACTGCCACTTTTCACCACGTGACTGGCAAAGAC |
| hu.25-C | 826 | AGCACCCCCTGGGGGTATTTTGACTTCAACAGATTCCACTGCCACTGCCACTTTTCACCACGTGACCGGCAAAGAC |
| hu.15-C | 826 | AGCACCCCCTGGGGGTATTTTGACTTCAACAGATTCCACTGCCACTGCCACTTTTCACCACGTGACTGGCAAAGAC |
| hu.16-C | 826 | AGCACCCCCTGGGGGTATTTTGACTTCAACAGATTCCACTGCCACTGCCACTTTTCACCACGTGACTGGCAAAGAC |
| hu.11-C | 826 | AGCACCCCCTGGGGGTATTTTGACTTCAACAGATTCCACTGCCACTGTCACTTCTCCCACCACGTGACTGGCAAAGAC |
| hu.10-C | 826 | AGCACCCCCTGGGGGTATTTTGACTTCAACAGATTCCACTGCCACTGTCACTTCTCCCACCACGTGACTGGCAAAGAC |
| hu.4-C | 826 | AGCACCCCCTGGGGGTATTTTGACTTCAACAGATTCCACTGCCACTGTCACTTCTCCCACCACGTGACTGGCAGCGGC |
| rh.54-D | 832 | AGCACCCCCTGGGGGTATTTTGACTTCAACAGATTCCACTGCCACTGTCACTTCTCACTCACCACGTGACTGGCAGCGGC |
| rh.48-D | 832 | AGCACCCCCTGGGGGTATTTTGACTTCAACAGATTCCACTGCCACTGTCACTGTCACTTCTCACTCACCACGTGACTGGCAGCGGC |

| | | |
|---|---|---|
| AAV5 | 869 | TCATCAACAACTACTGGGCTTCAGACCCCGTCCCTCAGAGTCAAAATCTTCAACATTCAAGTCAAGA |
| AAV3-3 | 896 | TCATTAACAACAACTGGGATTCCGGCCAAGAACTCAGCTTCAGCGGGTCAAAATCTTCAACATCCAAGTTAGAGG |
| AAV4-4 | 869 | TCATCAACAACAACTGGGACTGGGGACCATGCGACCCAAGACCCAAGCCATGGGGTCAAACTCTTCAACATCCAGTCAAGGA |
| AAV1-A | 899 | TCATCAACAACAACAATTGGGGATTCCGGCCCAAGAGACTCAACTCAACTTCAAACTCTTCAACATTCAAGTCAAGGA |
| hu.46-A | 899 | TCATCAACAACAACAATTGGGGATTCCGGCCCAAGAGACTCAACTCAACTTCAAACTCTTCAACATTCAAGTCAAGGA |
| hu.48-A | 899 | TCATCAACAACAACAATTGGGGATTCCGGCCCAAGAGACTCAACTCAACTTCAAACTCTTCAACATTCAAGTCAAGGA |
| hu.44-A | 899 | TCATCAACAACAACAATTGGGGATTCCGGCCCAAGAGACTCAACTCAACTTCAAACTCTTCAACATTCAAGTCAAGGA |
| hu.43-A | 902 | TCATCAACAACAACAATTGGGGATTCCGGCCCAAGAGACTCAACTCAACTTCAAACTCTTCAACATTCAAGTCAAGGA |
| AAV6-A | 899 | TCATCAACAACAACAATTGGGGATTCCGGCCCAAGAGACTCAACTCAACTTCAAACTCTTCAACATTCAAGTCAAGGA |
| hu.34-B | 896 | TCATCAACAACAACAACTGGGGATTCCGACCCAAGAGACTCAACTCAACTTCAAGCTCTTTAACATTCAAGTCAAAGA |
| hu.47-B | 896 | TCATCAACAACAACAACTGGGGATTCCGACCCAAGAGACTCAACTCAACTTCAAGCTCTTTAACATTCAAGTCAAAGA |
| hu.29-B | 896 | TCATCAACAACAACAACTGGGGATTCCGACCCAAGAAAGACTCAACTCAACTTCAAGCTCTCTTAACATTCAAGTCAAAGA |
| hu.63-B | 896 | TCATCAACAACAACAACTGGGATTCCGACCCAAGAGACTCAACTCAACTTCAAGCTCTTTAACATTCAAGTCAAAGA |
| hu.56-B | 896 | TCATCAACAACAACAACTGGGATTCCGACCCAAGAGACTCAACTCAACTTCAAGCTCTTTAACATTCAAGTCAAAGA |
| hu.45-B | 896 | TCATCAACAACAACAACTGGGATTCCGACCCAAGAGACTCAACTCAACTTCAAGCTCTTTAACATTCAAGTCAAAGA |
| hu.57-B | 893 | TCATCAACAACAACAACTGGGATTCCGACCCAAGAGACTCAACTGTTAAGCTCTGTTAACATTCAAGTCAAAGA |
| hu.35-B | 896 | TCATCAACAACAACAACTGGGATTCCGACCCAAGAGACTCAACTCAACTTCAAGCTCTGTTAACATTCAAGTCAAAGA |
| hu.58-B | 896 | TCATCAACAACAACAACTGGGATTCCGACCCAAGAGACTCAACTCAACTTCAAGCTCTTTAACATTCAAGTCAAAGA |
| hu.28-B | 896 | TCATCAACAACAACAACTGGGATTCCGACCCAAGAGACTCAACTCAACTTCAAGCTCTTTAACATTCAAGTCAAAGA |
| hu.51-B | 896 | TCATCAACAACAACAACTGGGATTCCGACCCAAGAGACTCAACTCAACTTCAAGCTCTTTAACATTCAAGTCAAAGA |
| hu.19-B | 896 | TCATCAACAACAACAACTGGGATTCCGACCCAAGAGACTCAACTCAACTTCAAGCTCTTTAACATTCAAGTCAAAGA |
| hu.49-B | 896 | TCATCAACAACAACAACTGGGATTCCGACCCAAGAGACTCAACTCAACTTCAAGCTCTTTAACATTCAAGTCAAAGA |
| hu.52-B | 896 | TCATCAACAACAACAACTGGGATTCCGACCCAAGAGACTCAACTCAGCTTCAAGCTCTTTAACATTCAAGTCAAAGA |
| hu.13-B | 896 | TCATCAACAACAACAACTGGGATTCCGACCCAAGAGACTCAACTCAACTTCAAGCTCTTTAACATTCAAGTCAAAGA |
| AAV2-B | 896 | TCATCAACAACAACAACTGGGATTCCGACCCAAGAGACTCAACTCAACTTCAAGCTCTTTAACATTCAAGTCAAAGA |
| hu.20-B | 896 | TCATCAACAACAACAACTGGGATTCCGACCCAAGAGACTCAACTCAACTTCAAGCTCTTTAACATTCAAGTCAAAGA |
| hu.24-B | 896 | TCATCAACAACAACAACTGGGATTCCGACCCAAGAAAAGAGACTCAGCTTCAACTTCAAGCTCTTTAACATTCAAGTCAAAGA |
| hu.64-B | 896 | TCATCAACAACAACAACTGGGATTCCGGCCCAAGAGACTCAGCTTCAACTTCAAGCTCTTTAACATTCAAGTCAAAGA |
| hu.27-B | 896 | TCATCAACAACAACAACTGGGATTCCGGCCCAAGAGACTCAGCTTCAACTTCAAGCTCTTTAACATTCAAGTCAAAGA |

FIG. 3AK

```
hu.21-B   896  TCATCAACAACAACAACTGGGGATTCCGGCCCAAGAGACTCAGCTTCAAGCTCTTTAACATTCAAGTCAAGTCAAAGA
hu.22-B   896  TCATCAACAACAACAACTGGGGATTCCGGCCCAAGAGACTCAGCTTCAAGCTCTTTAACATTCAAGTCAAGTCAAAGA
hu.23-B   896  TCATCAACAACAACAACTGGGGATTCCGGCCCAAGAGACTCAGCTTCAAGCTCTTTAACATTCAAGTCAAGTCAAAGA
hu.7-C    896  TCATCAACAACAACAACTGGGGATTCCGACCCAAGAGACTCAACTTCAAGCTCTTTAACATTCAAGTCAAGTCAAAGA
hu.61-C   896  TCATCAACAACAACAACTGGGGATTCCGACCCAAGAGACTCAACTTCAAGCTCTTTAACATTCAAGTCAAGTCAAAGA
hu.56-C   896  TCATCAACAACAACAACTGGGGATTCCGACCCAAGAGACTCAACTTCAAGCTCTTTAACATTCAAGTCAAGTCAAAGA
rh.56-C   896  TCATCAACAACAACAACTGGGGATTCCGACCCAAGAGACTCAACTTCAAGCTCTTTAACATTCAAGTCAAGTCAAAGA
hu.9-C    896  TCATCAACAACAACAACTGGGGATTCCGACCCAAGAGACTCAACTTCAAGCTCTTTAACATTCAAGTCAAGTCAAAGA
hu.54-C   896  TCATCAACAACAACAACTGGGGATTCCGACCCAAGAGACTCAACTTCAAGCTCTTTAACATTCAAGTCAAGTCAAAGA
hu.53-C   896  TCATCAACAACAACAACTGGGGATTCCGACCCAAGAGACTCAACTTCAAGCTCTTTAACATTCAAGTCAAGTCAAAGA
hu.60-C   896  TCATCAACAACAACAACTGGGGATTCCGACCCAAGAGACTCAACTTCAAGCTCTTTAACATTCAAGTCAAGTCAAAGA
hu.55-C   896  TCATCAACAACAGCAACTGGGGATTCCGGCCCAAAGAGACTCAACTTCAAGCTCTTTAACATTCAAGTCAAGTCAAAGA
hu.2-C    896  TCATCAACAACAACAACTGGGGATTCCGGCCCAAAGAGACTCAACTTCAAGCTCTTTAACATTCAAGTCAAGTCAAAGA
hu.1-C    896  TCATCAACAACAACAACTGGGGATTCCGGCCCAAAGAGACTCAACTTCAAGCTCTTTAATATTCAAGTCAAGTCAAAGA
hu.18-C   899  TCATCAACAACAACAACTGGGGATTCCGGCCCAAAGAGACTCAACTTCAAGCTCTTTAATATTCAAGTCAAGTCAAAGA
hu.3-C    896  TCATCAACAACAACAACTGGGGATTCCGGCCCAAAGAGACTCAACTTCAAGCTCTTTAACATTCAAGTCAAGTCAAAGA
hu.25-C   896  TCATCAACAACAACAACTGGGGATTCCGGCCCAAAGAAGACTCAACTTCAAGCTCTTTAACATTCAAGTCAAGTCAAAGA
hu.15-C   896  TCATCAACAACAACAACTGGGGATTCCGGCCCAAAGAGACTCAACTTCAAGCTCTTTAACATTCAAGTCAAGTCAAAGA
hu.16-C   896  TCATCAACAACAACAACTGGGGATTCCGGCCCAAAGAGACTCAACTTCAAGCTCTTTAACATTCAAGTCAAGTCAAAGA
hu.11-C   896  TCATCAACAACAACAACTGGGGATTCCGGCCCAAAGAGACTCAACTTCAAGCTCTTTAACATTCAAGTCAAGTCAAAGA
hu.10-C   896  TCATCAACAACAACAACTGGGGATTCCGGCCCAAAGAGACTCAACTTCAAGCTCTTTAACATTCAAGTCAAGTCAAAGA
hu.4-C    896  TCGTCAACAACAACAACCGGGGATTCCGGCCCAAAGAGACTCAACTTCAAGCTCTTTAATATTCAAGTCAAGTCAAAGA
rh.54-D   902  TCATCAACAACAACAACTGGGGATTCCGGCCCAAAGAAGAGTCAGCTTCAAGCTCTTCAACATCCAAGTCCAGTCAAGGA
rh.48-D   902  TCATCAACAACAACAACTGGGGATTCCGGCCCAAGAAGAGTCAGCTTCAACTTGTTCAACATCCAGTCCAGTCAAGGA
rh.55-D   902  TCATCAACAACAACAACTGGGGATTCCGGCCCAAGAAGAGTCAGCTTCAACTTGTTCAACATCCAGTCCAGTCAAGGA
rh.62-D   902  TCATCAACAACAACAACTGGGGATTCCGGCCCAAGAAGAGTCAGCTGCGTTCAACTTCAACATCCAGTCCAGTCAAGGA
AAV7-D    902  TCATCAACAACAACAACTGGGGATTCCGGCCCAAGAAGAGTCAGCTGCGTTCAACTCTTCAACATCCAACATCCAGTCAAGGA
rh.52-E   905  TCATCAACAACAACAACTGGGGATTCCGGCCCAAGAGAGACTCAGCTTCAAGTTCAACATCCAACATCCAGTCAAGGA
rh.51-E   905  TCATCAACAACAACAACTGGGGATTCCGGCCCAAGAGAGACTCAGCTTCAAGCTCTTCAACATCCAACATCCAGTCAAGGA
rh.39-E   905  TCATCAACAACAACAACTGGGGATTCCGGCCCAAGAGAGACTCAGCTTCAAGCTCTTCAACATCCAACATCCAGTCAAGGA
rh.53-E   905  TCATCAACAACAACAACTGGGGATTCCGGCCCAAGAGAGACTCAGCTTCAAGCTCTTCAACATCCAACATCCAGTCAAGGA
```

| | | |
|---|---|---|
| hu.19-B | 1106 | TCTTCATGGTGCCACAGTATGGATACCCTCACCCTGAACAACGGC————————AGTCAGGCGGTAGGACG |
| hu.49-B | 1106 | TCTTCATGGTGCCACAGTATGGATACCCTCACCCTGAACAACGGG————————AGTCAGGCAGTAGGACG |
| hu.52-B | 1106 | TCTTCATGGTGCCACAGTATGGATACCCTCACCCTGAGCAACGGG————————AGTCAGGCAGTAGGACG |
| hu.13-B | 1106 | TCTTCATGGTGCCACAGTATGGATACCCTCACCCTGAACAACGGG————————AGTCAGGCAGTAGGACG |
| AAV2-B | 1106 | TCTTCATGGTGCCACAGTATGGATACCCTCACCCTGAACAACGGG————————AGTCAGGCAGTAGGACG |
| hu.20-B | 1106 | TCTTCATGGTGCCACAGTATGGATACCCTCACCCTGAACAACGGC————————AGTCAGGCGGTAGGACG |
| hu.24-B | 1106 | TCTTCATGGTGCCACAGTATGGATACCCTCACCCTGAACAACGGC————————AGTCAGGCGGTAGGACG |
| hu.64-B | 1106 | TCTTCATGGTGCCACAGTATGGATACCCTCACCCTGAACAACGGG————————AGTCAGGCAGTAGGACG |
| hu.27-B | 1106 | TCTTCATGGTGCCACAGTATGGATACCCTCACCCTGAACAACGGC————————AGTCAGGCGGTAGGACG |
| hu.21-B | 1106 | TCTTCATGGTGCCACAGTATGGATACCCTCACCCTGAACAACGGC————————AGTCAGGCGGTAGGACG |
| hu.22-B | 1106 | TCTTCATGGTGCCACAGTATGGATACCCTCACCCTGAACAACGGC————————AGTCAGGCGGTAGGACG |
| hu.23-B | 1106 | TCTTCATGGTGCCACAGTATGGATACCCTCACCCTGAACAACGGC————————AGTCAGGCGGTAGGACG |
| hu.7-C | 1106 | TCTTCATGGTCCCACAGTATGGATACCCTCACCCTGAACAACGGG————————AGTCAGGCAGTAGGACG |
| hu.61-C | 1106 | TCTTCATGGTCCCACAGTATGGATACCCTCACCCTGAACAACGGG————————AGTCAGGCGGTAGGACG |
| rh.56-C | 1106 | TCTTCATGGTCCCACAGTATGGATACCCTCACCCTGAACAACGGG————————AGTCAGGCGGTAGGACG |
| hu.9-C | 1105 | TCTTCATGGTCCCACAGTATGGATACCCTCACCCTGAACAACGGG————————AGTCAGGCGGTAGGACG |
| hu.54-C | 1106 | TCTTCATGGTCCCACAGTATGGATACCCTCACCCTGAACAACGGG————————AGTCAGGCGGTAGGACG |
| hu.53-C | 1106 | TCTTCATGGTCCCACAGTATGGATACCCTCACCCTGAACAACGGG————————AGTCAGGCGGTAGGACG |
| hu.60-C | 1106 | TCTTCATGGTCCCACAGTATGGATACCCTCACCCTGAACAACGGG————————AGTCAGGCGGTAGGACG |
| hu.55-C | 1106 | TCTTCATGGTCCCACAGTATGGATACCCTCACCCTGAACAACGGG————————AGTCAGGCGGTAGGACG |
| hu.2-C | 1106 | TCTTCATGGTCCCACAGTATGGATACCCTCACCCTGAACAACGGG————————AGTCAGGCGGTAGGACG |
| hu.1-C | 1106 | TCTTCATGGTCCCACAGTATGGATACCCTCACCCTGAACAACGGG————————AGTCAGGCGGTAGGACG |
| hu.18-C | 1106 | TCTTTATGGTCCCACAGTATGGATACCCTCACCCTGAACAACGGG————————AGTCAGGCGGTAGGACG |
| hu.3-C | 1109 | TCTTCATGGTCCCACAGTATGGATACCCTCACCCTGAACAACGGG————————AGTCAGGCGGTAGGACG |
| hu.25-C | 1106 | TCTTCATGGTCCCACAGTATGGATACCCTCACCCTGAACAACGGG————————AGTCAGGCGGTAGGACG |
| hu.15-C | 1106 | TCTTCATGGTCCCACAGTATGGATACCCTCACCCTGAACAACGGG————————AGTCAGGCGGTAGGACG |
| hu.16-C | 1106 | TCTTCATGGTCCCACAGTATGGATACCCTCACCCTGAACAACGGG————————AGTCAGGCGGTAGGACG |
| hu.11-C | 1106 | TCTTCATGGTCCCACAGTATGGATACCCTCACCCTGAACAACGGG————————AGTCAGGCGGTAGGACG |
| hu.10-C | 1106 | TCTTCACGGTCCCACAGTATGGATACCCTCACCCTGAACAACGGG————————AGTCAGGCGGTAGGACG |
| hu.4-C | 1106 | TCTTCATGGTCCCACAGTATGGATACCCTCACCCTGAACAACGGG————————AGTCAGGCGGTAGGACG |

FIG. 3AT

```
rh.54-D  1112 TCTTCATGATTCCTCAGTACGGCTACCTGACTCTGAACAATGGC------------AGCCAATCGGTGGGACG
rh.48-D  1112 TCTTCATGATTCCCCAGTACGGCTACCTGACTCTGAACAATGGC------------AGCCAATCGGTGGGTCG
rh.55-D  1112 TCTTCATGATTCCCCAGTACGGCTACCTGACTCTGAACAATGGC------------AGCCAATCGGTGGGTCG
rh.62-D  1112 TCTTCATGATTCCCCAGTACGGCTACCTGACTCTGAACAATGGC------------AGCCAATCGGTGGGTCG
AAV7-D   1112 TCTTCATGATTCCTCAGTACGGCTACCTGACTCTGAACAATGAC------------AGTCAGTCGTGTGGACG
rh.52-E  1115 TCTTCATGATTCCTCAGTACGGCTACCTGACTCTCAACAATGGC------------AGTCAGGCCGTGGGACG
rh.51-E  1115 TCTTCATGATTCCTCAGTACGGCTACCTGACTCTCAACAACGGT------------AGTCAGGCCGTGGGACG
hu.39-E  1115 TCTTCATGATTCCTCAGTACGGCTACCTGACTCTCAACAACGGT------------AGTCAGGCCGTGGGACG
rh.53-E  1115 TCTTCATGATTCCTCAGTACGGCTACCTGACTCTCAACAACGGT------------AGTCAGGCCGTGGGACG
hu.37-E  1115 TCTTCATGATTCCCCAGTACGGCTACCTGACTCTCAACAACGGT------------AGTCAAGCCGTAGGCCG
rh.43-E  1112 TGTTCATGATTCCCCAGTACGGCTACCTTACACTCTCAACAACGGT------------AGTCAGGCCGTGGGACG
hu.50-E  1115 TCTTCATGATTCCTCAGTACGGCAACCTGACTCTCAACAACGGT------------AGTCAGGCCGTGGGACG
rh.49-E  1115 TCTTCATGATTCCTCAGTACGGCTACCTGACTCTCAACAACGGT------------AGTCAGGCCGTGGGACG
rh.61-E  1115 TCTTCATGATTCCTCAGTACGGCTACCTGACTCTCAACAACGGT------------AGTCAGGCCGTAGGCCG
hu.41-E  1115 TCTTCATGATTCCTCAGTACGGCTACCTTACACTGAACAACGGT------------AGTCAAGCCGTAGGCCG
rh.64-E  1115 TCTTCATGATTCCCCAGTACGGCTACCTGACTCTCAACAACGGT------------AGTCAGGCCGTGGGACG
rh.42-E  1115 TCTTCATGATTCCCCAGTACGGCTACCTTACACTGAACAATGGA------------AGTCAAGCCGTAGGCCG
rh.57-E  1115 TCTTCATGATTCCCCAGTACGGCTACCTTACACTGAACAACGGT------------AGTCAGGCCGTGGGACG
hu.40-E  1115 TCTTCATGATTCCCCAGTACGGCTACCTTACACTGAACAATGGA------------AGTCAAGCCGTAGGCCG
AAV8-E   1115 TGTTCATGATTCCCCAGTACGGCTACCTGACTCTGAACAATGGT------------AGTCAGGCCGTGGGACG
rh.58-E  1115 TCTTCATGATTCCCCAGTACGGCTACCTGACTCTCAACAACGGT------------AGTCAAGCCGTAGGCCG
rh.40-E  1115 TCTTCATGATTCCCCAGTACGGCTACCTTACACTGAACAATGGA------------AGTCAAGCCGTAGGCCG
hu.67-E  1115 TCTTCATGATTCCCCAGTACGGGTACCTTACACTGAACAATGGA------------AGTCAAGCCGTAGGCCG
hu.17-E  1115 TCTTCATGATTCCTCAGTACGGGTACCTTACACTGAACAACGGC------------AGTCAAGCCGTGGGCCG
hu.6-E   1115 TCTTCATGATTCCCCAGTACGGGTACCTGACTCTGAACAACGGC------------AGTCAGGCCGTGGGCCG
hu.66-E  1115 TCTTCATGATTCCTCAGTACGGCTACCTTACTCTGAACAACGGC------------AGTCAGGCCGTAGGCCG
rh.38-E  1115 TCTTCATGATTCCCCAGTACGGCTACCTTACACTGAACAACGGA------------AGTCAAGCCGTAGGCCG
hu.32-F  1112 TTTTCATGATTCCTCAGTACGGGTATCGGGTATCTGACGCTTAATGATGGG------------AGCCAGGCCGTGGGTCG
AAV9/hu  1112 TTTTCATGATTCCTCAGTACGGGTATCTGACGCTTAATGATGA------------AGCCAGGCCGTGGGTCG
hu.31-F  1112 TTTTCATGATTCCTCAGTACGGGTATCTGACGCTTAATGATGGA------------GGCCAGGCCGTGGGTCG
```

```
hu.39-E   1176  TTCCTCCTCCTTCTACTGCCTGCCTGGAGTACTTCCCCTCTCAGATGCTGAGAACGGGCAACAACTTTCCTTCAGC
rh.53-E   1176  TTCCTCCTCCTTCTACTGCCTGCCTGGAGTACTTCCCCTCTCAGATGCTGAGAACGGGCAACAACTTTCCTTCAGC
hu.37-E   1176  TTCCTCCTCCTTCTACTGCCTGCCTGGAGTACTTCCCCTCTCAATGCTGCGAACTGGAAACAATTTGAATTCAGC
rh.43-E   1173  CTCCTCCTCCTTCTACTGCCTGCCTGGAATACTTTCCTTCGCAGATGCTGAGAACGGGCAACAACTTCCAGTTTACT
rh.50-E   1176  TTCCTCCTCCTTCTACTGCCTGCCTGGAGTACTTCCCCTCTCAGATGCTGAGAACGGGCAACAACTTTCCTTCAGC
rh.49-E   1176  TTCCTCCTCCTTCTACTGCCTGCCTGGAGTACTTCCCCTCTCAGATGCTGAGAACGGGCAACAACTTTCCTTCAGC
rh.61-E   1176  TTCCTCCTCCTTCTACTGCCTGCCTGGAGTACTTCCCCTCTCAGATGCTGAGAACGGGCAACAACTTTCCTTCAGC
hu.41-E   1176  TTCCTCCTCCTTCTACTGCCTGCCTGGAATATTTCCATCTCAAATGCTGCGAACTGGAGGGCAACAATTTGAATTCAGC
hu.64-E   1176  TTCCTCCTCCTTCTACTGCCTGCCTGGAGTACTTCCCCTCTCAGATGCTGAGAACGGGCAACAACTTTCCTTCAGC
rh.42-E   1176  TTCCTCCTCCTTCTACTGCCTGCCTGGAATATTTTCCATCTCAAATGCTGCGAACTGGAAACAATTTTGAATTCAGC
rh.57-E   1176  TTCCTCCTCCTTCTACTGCCTGCCTGGAGTACTTCCCCTCTCAGATGCTGCGAACTGGAAACGGGCAACAACTTTCCTTCAGC
hu.40-E   1176  TTCCTCCTCCTTCTACTGCCTGCCTGGAATATTTCCATCTCAAATGCTGAAACTCTGAAACTTCCAGTTTACT
AAV8-E    1176  CTCCTCCTCCTTCTACTGCCTGCCTGGAATACTTTCCTTCGCAGATGCTGAGAACGGGCAACAACTTTCCTTCAGC
rh.58-E   1176  TTCCTCCTCCTTCTACTGCCTGCCTGGAATATTTCCTTCTCAATCTCAAATGCTGAGAACGGGCAACAACTATTTGAATTCAGC
rh.40-E   1176  TTCCTCCTCCTTCTACTGCCTGCCTGGAATATTTCCTTCTCAATCTCAAATGCTGCGAACTGGAAACAACATTTGAATTCAGC
hu.67-E   1176  TTCCTCCTCCTTCTACTGCCTGCCT GGAGTACTTCCCTTCCGGAGAACAACGGGCAACAACTTTGAGTTCAGC
hu.6-E    1176  TTCCTCCTCCTTCTACTGCCTGCCTGGAGTACTTCCCTTCCGGAGAACAACGGGCAACAACTTTGAGTTCAGC
hu.66-E   1176  TTCCTCCTCCTTCTACTGCCTGCCTGGAGTACTTCCCTTCCATCTCAAATGCTGCGAACTGGAAACAACATTTGAATTCAGC
rh.38-E   1176  TTCGTCCTTTTACTGCCTGCCTGGAGTACTTCCCCTCTCAGATGCTGCGAACTGTAAGAACGGGTAACAACTTCCAGTTCAGC
hu.32-F   1173  TTCGTCCTTTTACTGCCTGCCTGGAGTACTTCCCCTCTCAGATGCTGCGAACTGTAAGAACGGGTAACAACTTCCAGTTCAGC
hu.31-F   1173  TTCGTCCTTTTACTGCCTGCCTGGAGTACTTCCCCTCTCAGATGCTGCGAACTGTAAGAACGGGTAACAACTTCCAGTTCAGC 1270      1280      1290      1300      1310      1320      1330
                ....|....|....|....|....|....|....|....|....|....|....|....|....|....|
AAV5     1216  TACAACTTTGAGGAGGAGTGTGCCTTCCACTCCAGCTTCGCTCCCAGTGCAGCCAGAACCTGTTCAAGCTGGCCAACC
AAV3-3   1237  TATACCTTCGAGGATGTAGTACCTTTTCACAGCAGCTACGCTCACAGCAGCCAGAGTTTGGATCGCTTGATGAATC
AAV4-4   1219  TACAGTTTGTGAGAAGGTGCCTTGCCTACTGCCTTTCCACTGCCGATGTAGCGCACAGCCAGAGCCTGGACCGGATGAACC
AAV9/hu  1240  TACACCTTTGAGGAAGTGCCTTTCCACAGCAGCTACGCCCACAGCCAGAGCCTGGACCGGCTGATGAACC
AAV1-A   1240  TACACCTTTGAGGAAGTGCCTTTCCACAGCAGCTACGCCCACAGCCAGAGCCTGGACCGGCTGATGAATC
```

FIG. 3AX

```
hu.46-A   1240  TACACCTTTGAGGAAGTGCCTCTCCACAGCAGCTGCGCGCACAGCCAGAGCCTGGACCGGCTGATGAATC
hu.48-A   1240  TACACCTTTGAGGAAGTGCCTCCTTTCCACAGCAGCTACGCGCACAGCCAGAGCCTGGACCGGCTGATGAATC
hu.44-A   1240  TACACCTTTGAGGAAGTGCCTCCTTTCCACAGCAGCTACGCGCACAGCCAGAGCCTGGACCGGCTGATGAATC
hu.43-A   1243  TACACCTTTGAGGAAGTGCCTCCTCTCCACAGCAGCTACGCGCACAGCCAGAGCCTGGACCGGCTGATGAATC
AAV6-A    1240  TACACCTTTGAGGAAGTGCCTCCTTTCCACAGCAGCTACGCGCACAGCCAGAGCCTGGACCGGCTGATGAATC
hu.34-B   1237  TACACTTTTGAGGAAGACGTTCCTTTCCACAGCAGCTACGCTCACAGCCAGAGTCTGGGCCGTCTCATGAATC
hu.47-B   1237  TACACTTTTGAGGAAGACGTTCCTTTCCACAGCAGCTACGCTCACAGCCAGAGTCTGGACCGTCTCATGAATC
hu.29-B   1237  TACACTTTTGAGGAAGACGTGCCTTTCCACAGCAGCTACGCTCACAGCCAGAGTTTGGACCGTCTCATGAATC
hu.63-B   1237  TACACTTTTGAGGAAGACGTTCCTTTCCACAGCAGCTACGCCCACAGCCAGAGTTTGGACCGTCTCATGAATC
hu.56-B   1237  TACACTTTTGAGAAGACGTTCCTTTCCACAGCAGCTACGCTCACAGTCCAGAGTCTGGACCGTCTCATGAATC
hu.45-B   1237  TACACTTTTGAGGACGTTCCTTTCCACAGCAGCTACGCTCACAGCCAGAGTCTGGACCGTCTCATGAATC
hu.57-B   1234  TACACTTTTGAGGAAGACGTTCCTTTCCACAGCAGCTACGCTCACAGCCAAAGTCTGGACCGTCTCATGAATC
hu.35-B   1237  TACACTTTTGAGGAAGACGTTCCTTTCCACAGCAGCTACGCTCACAGCCAGAGTCTGGGCCGTCTCATGAATC
hu.58-B   1237  TACACTTTTGAGGATGTTCCTTTCCACAGCAGCTACGCTCACAGCCAGAGTTTGGACCGTCTCATGAATC
hu.28-B   1237  TACACTTTTGAGGAAGACGTTCCTTTCCACAGCAGCTACGCTCACAGCCAGAGTCTGGACCGTCTCATGAATC
hu.51-B   1237  TACACTTTTGAGGAAGACGTTCCTTTCCACAGCGGCTACGCTCACAGCCAGAGTCTGGACCGTCTCATGAATC
hu.19-B   1237  TACACTTTTGAAGACGTTCCTTTCCACAGCAGCTACGCTCACAGCCAGAGTCTGGACCGTCTCATGAATC
hu.49-B   1237  TACACTTTTGAGGAAGACGTTCCTTTCCACAGCAGCTACGCTCACAGCCAGAGTTTGGACCGTCTCATGAATC
hu.52-B   1237  TACACTTTTGAGGAAGACGTTCCTTTCCACAGCAGCTACGCTCACAGCCAGAGTCTGGACCGTCTCATGAATC
hu.13-B   1237  TACACTTTTGAGGAAGACGTTCCTTTCCACAGCAGCTACGCTCACAGCCAGAGTTTGGACCGTCTCATGAATC
AAV2-B    1237  TACACTTTTGAAGACGTTCCTTTCCATAGCAGCTACGCTCACAGCCAGAGTCTGGACCGTCTCATGAATC
hu.20-B   1237  TACACTTTTGAAGACGTTCCTTTCCATAGCAGCTACGCTCACAGCCAAAGTCTGGACCGTCTCATGAATC
hu.24-B   1237  TACACTTTTGAAGACGTTCCTTTCCATAGCAGCTACGCTCACAGCCAAAGTCTGGACCGTCTCATGAATC
hu.64-B   1237  TACACTTTTGAAGACGTTCCTTTCCATAGCAGCTACGCCCACAGCCAGAGTTTGGACCGTCTCATGAATC
hu.27-B   1237  TACACTTTTGAAGACGTTCCTTTCCATAGCAGCTACGCTCACAGCCAAAGTCTGGACCGTCTCATGAATC
hu.21-B   1237  TACACTTTTGAAGACGTTCCTTTCCATAGCAGCTACGCTCACAGCCAAAGTCTGGACCGTCTCATGAATC
hu.22-B   1237  TACACTTTTGAAGACGTTCCTTTCCATAGCAGCTACGCTCACAGCCAAAGTCTGGACCGTCTCATGAATC
hu.23-B   1237  TACACTTTTGAAGACGTTCCTTTCCATAGCAGCTACGCTCACAGCCAAAGTCTGGACCGTCTCATGAATC
hu.7-C    1237  TACACTTTTGAAGACGTGCCTTTCCTTTCCACAGCAGCTACGCTCACAGCCAGAGTCTGGATCGGCTGATGAATC
hu.61-C   1237  TACACTTTTGAAGACGTCTGCCTTTCCACAGCAGCCAGAGTCTGGATCGGCTGATGAATC
```

FIG. 3AY

```
rh.56-C  1237  TACACCTTTGAAGACGTTCCTTTCCACAGCAGCTACGCTCACAGCCAGAGTCTGGATCGGCTGATGAATC
hu.9-C   1237  TACACCTTTGAAGACGTTCCTTTCCACAGCAGCTACGCTCACAGCCAGAGTCTGGATCGGCTGATGAATC
hu.54-C  1237  TACACTTTTGAAGACGTGCCTTTCCACAGCAGCTACGCTCACAGCCAGAGTTTGGATCGGCTGATGAATC
hu.53-C  1237  TACACTTTTGAAGACGTGCCTTTCCACAGCAGCTACGCTCACAGCCAGAGTTTGGATCGGCTGATGAATC
hu.60-C  1237  TACACTTTTGAAGACGTGCCTTTCCACAGCAGCTACGCTCACAGCCAGAGTTTGGATCGGCTGATGAATC
hu.55-C  1237  TACACTTTTGAAGACGTGCCTTTCCACAGCAGCTACGCTCACAGCCAGAGTTTGGATCGGCTGATGAATC
hu.2-C   1237  TACACTTTTGAAGACGTGCCTTTCCACAGCAGCTACGCTCACAGCCAGAGTCTGGATCGGCTGATGAATC
hu.1-C   1237  TACACTTTTGAAGACGTGCCTTTCCACAGCAGCTACGCTCACAGCCAGAGTCTGGATCGGCTGATGAATC
hu.1B-C  1237  TACACTTTTGAAGACGTGCCTTTCCACAGCAGCTACGCTCACAGCCAGAGTCTGGATCGGCTGATGAATC
hu.3-C   1240  TACACTTTTGAAGACGTGCCTTCCCACAGCAGCTACGCTCACTGCCAGAGTCTGGATCGGCTGATGAATC
hu.25-C  1237  TACACTTTTGAAGACGTGCCTGCCTCCTTCCACAGCAGCTACGCTCACAGCCAGAGTCTGGATCGGCTGATGAATC
hu.15-C  1237  TACACTTTTGAAGACGTGCCTGCCTTCCTTCCACAGCAGCTACGCTCACAGCCAGAGTCTGGATCGGCTGATGAATC
hu.16-C  1237  TACACTTTTGAAGACGTGCCTGCCTTCCTTCCACAGCAGCTACGCTCACAGCCAGAGTCTGGATCGGCTGATGAATC
hu.11-C  1237  TACACTTTTGAGGACGTTCCTTCCTTCCACAGCAGCTACGCTCACAGCCAGAGTTTGGACCGGCTGATGAATC
hu.10-C  1237  TACACTTTTGAGGACGTTCCTTCCTTCCACAGCAGCTACGCTCACAGCCAGAGTTTGGACCGGCTGATGAATC
hu.4-C   1237  TACACCTTTGAGGACGTTCCTGCCTTTCCACAGCAGCTACGCTCACAGCCAGAGTTTGGACCGGCTGATGAATC
rh.54-D  1243  TACACCTTCGAGGACGTGCCTGCCTTTCCACAGCAGCTACGCTACGCCACAGAGCCAGAGCCTAGACCGGCTGATGAATC
rh.48-D  1243  TACACCTTCGAGGACGTGCCTGCCTTCCTTCCACAGCAGCTACGCTACGCCACACAGCCAGAGCCTGGACCGGCTGATGAATC
rh.55-D  1243  TACACCTTCGAGGACGTGCCTGCCTTCCTTCCACAGCAGCTACGCTACGCCACACAGCCAGAGCCTGGACCGGCTGATGAATC
rh.62-D  1243  TACACCTTCGAGGACGTGCCTGCCTTCCTTCCACAGCAGCTACGCTACGCCACACAGCCAGAGCCTGGACCGGCTGATGAATC
AAV7-D   1243  TACAGCTTCGAGGACGTGCCTGCCTTCCTTCCACAGCAGCTACGCTACGCCACACAGCCAGAGCCTGGACCGGCTGATGAATC
rh.52-E  1246  TACACTTTCGAGGACGTGCCTGCCTTCCTTCCACAGCAGCAGCTACGCTACGCCACAGCCAGAGTTTGGACAGGCTGATGAATC
rh.51-E  1246  TACACCTTCGAGGACGTGCCTGCCTTCCTTCCACAGCAGCAGCTACGCTACGCCACAGCCAGAGTTTGGACAGGCTGATGAATC
hu.39-E  1246  TACACCTTCGAGGACGTGCCTGCCTTCCTTCCACAGCAGCAGCTACGCTACGCCACAGCCAGAGTTTGGACAGGCTGATGAATC
rh.53-E  1246  TACACCTTCGAGGACGTGCCTGCCTTCCTTCCACAGCAGCAGCTACGTACGCCACAGTGCCAGAGTTTGGACAGGCTGATGAATC
hu.37-E  1246  TACACCTTCGAGGACGTGCCTGCCTTCCTTCCACAGCAGCAGCTACGCTACGCCACAGCCAGAGTTTGGACAGGCTGATGAATC
hu.43-E  1243  TACAGCTTCGAGGACGTGCCTGCCTTTCCTTCCACAGCAGCAGCTACGCTACGCCACAGCCAGAGTTTGGACTTGGACAGGCTGATGAATC
rh.50-E  1246  TACACCTTTCGAGGACGTGCCTGCCTTCCTTCCACAGCAGCAGCTACGCTACGCCACAGCGGCACAGCCAGAGTTTGGACAGGCTGATGAATC
rh.49-E  1246  TACACTTTTCGAGGACGTGCCTGCCTTCCTTCCACAGCAGCAGCTACGCTACGCCACAGCGGCACAGCCAGAGTTTGGACAGGCTGATGAATC
rh.61-E  1246  TACCCTTTTCGAGGACGTGCCTGCCTTCCTTCCACAGCAGCAGCGAGCTACGCTACGCCACAGCCAGAGTTTGGACAGGCTGATGAATC
```

FIG. 3AZ

```
hu.41-E    1246  TACACCTTCGAGGACGTGCCTTTCCACAGCAGCTACGCCACACAGCCAGAGCTTGGACCGGACTGATGAATC
rh.64-E    1246  TACACTTTCGAGGACGTGCCTTTCCACAGCAGCTACGCCACACAGCCAGAGTTTGGACCAGGCTGATGAATC
hu.42-E    1246  TACACCTTCGAGGACGTGCCTTTCCACAGCAGCTACGCCACACAGCCAGAGCTTGGACCGGACTGATGAATC
rh.57-E    1246  TACACCTTCGAGGACGTGCCTTTCCACAGCAGCTACGCCACACAGCCAGAGTTTGGACCAGGCTGATGAATC
hu.40-E    1246  TACACCTTCGAGGACGTGCCTTTCCACAGCAGCTACGCCACACAGCCAGAGCTTGGACCGGACTGATGAATC
AAV8-E     1246  TACACCTTCGAGGACGTGCCTTTCCACAGCAGCTACGCCACACAGCCAGAGCTTGGACCGGACTGATGAATC
rh.58-E    1246  TACACCTTCGAGGACGTGCCTTTCCACAGCAGCTACGCCACACAGCCAGAGTTTGGACCAGGCTGATGAATC
rh.40-E    1246  TACACCTTCGAGGACGTGCCTTTCCACAGCAGCTACGCCACACAGCCAGAGCTTGGACCGGACTGATGAATC
hu.67-E    1246  TACACCTTCGAGGACGTGCCTTTCCACAGCAGCGGCTACGCCATAGCCAAAGCCAAAGCCTGGACCTGATGAACC
hu.17-E    1246  TACCAGTTTGAGGACGTGCCTGCCTTTCACAGCAGCGGCTACGCCATAGCCACAGCCAGAGCCTGGACCTGATGAACC
hu.6-E     1246  TACCAGTTTGAGGACGTGCCTGCCTTTCACAGCAGCGGCTACGCCATAGCCACAGCCAGAGCCTGGACCTGATGAACC
hu.66-E    1246  TACACCTTCGAGGACGTGCCTGCCTTTCCACAGCAGCTACGCTGCGCACACAGCCAGAGCTTGGACCGGACTGATGAATC
rh.38-E    1246  TACACCTTCGAGGACGTGCCTGCCTTTCCACAGCAGCTACGCTGCGCACACAGCCAGAGCTTGGACCGGACTGATGAATC
hu.32-F    1243  TACGAGTTTGAGAACGTACCTTTCCATAGCAGCTACGCTCACAGCCAGAGCTTGGACCGACTAATGAATC
AAV9/hu    1243  TACGAGTTTGAGAACGTACCCTTCCATAGCAGCTACGCTCACACAGCCAAAGCCAAAGCCTGGACCGACTAATGAATC
hu.31-F    1243  TACGAGTTTGAGAACGTACCCTTCCATAGCAGCTACGCTCACACAGCCAAAGCCAAAGCCTGGACCGACTAATGAATC 1340      1350      1360      1370      1380      1390      1400
                        ....|....|....|....|....|....|....|....|....|....|....|....|....|....|
AAV5       1286  CGCTGGTGGACCAGTACTTGTACCGCTTCGTGAACAGAAAT------------AACACTGG
AAV3-3     1307  CTCTTATTGATCAGTATCGTGTACTACCTGTGGGACTGCAATCAGAACGCAAGAACAACCTCTGGAACAACCAACCAATC
AAV4-4     1289  CTCTCATCGACCAGTACCTGTGGGGACTGCAATGCCGAACCACCTGAACCTGAATGCCGGGACTGC
AAV1-A     1310  CTCTCATCATCGACCAGTACCTGTATTACCTGTATTACCTGAACAGAACTCAA-----AATCAGTCCGGAAGTGCCCAAAACAG
hu.46-A    1310  CTCTCATCATCGACCAGTACCTGTATTACCTGTATTACCTGAACAGAACTCAA-----AATCAGTCCGGAAGTGCCCAAAACAA
hu.48-A    1310  CTCTCATCATCGACCAGTACCTGTATTACCTGTATTACCTGAACAGAACACAA-----AATCAGTCCGGAAGTGCCCAAAACAA
hu.44-A    1313  CTCTCATCATCGACCAGTACCTGTATTACCTGTATTACCTGAACAGAACTCAA-----AATCAGTCCGGAAGTGCCCAAAACAA
hu.43-A    1310  CTCTCATCATCGACCAGTACCTGTATTACCTGTATTACCTGAACAGAACTCAG-----AATCAGTCCGGAAGTGCCCAAAACAA
AAV6-A     1310  CTCTCATCATCGACCAGTACCTGTATTACCTGTATTACCTGAACAGAACTCAA-----AATCAGTCCGGAAGTGCCCAAAACAA
hu.34-B    1307  CTCTCATCATCGTCGACCAGTACCTGTATTACCTGTATTACTTGAGCACAACAAAC-----ACTCCAAGTGGAACCACCACGCAGTC
hu.47-B    1307  CTCTCATCATCGTCGACCAGTACCTGTATTACCTGTATTACTTGAGCACAACAAAC-----ACTCCAAGTGGAACCACCACGCAGTC
```

```
hu.1-C    1307  CTCTGATCGACCAGTACCCTGTATTATCTGAACAAGACACAA----ACAAATAGTGGAACTCTTCAGCAGTC
hu.18-C   1307  CTCTGATCGACCAGTACCAGTACCTATATTATTATCTGAACAAGACACAA----TCAAATAGTGGACTCTTCAGCAGTC
hu.3-C    1310  CTCTGATCGACCAGTACCAGTACCTGTATTATCTGAACAAGACACAA----ACAAATAGTGGAACTCTTCAGCAGTC
hu.25-C   1307  CTCTGATCGACCAGTACCAGTACCTGTATTATCTGAACAAGACACAA----ACAAATAGTGGAACTCTTCAGCAGTC
hu.15-C   1307  CTCTGATCGACCAGTACCAGTACCTGTATTATCTGAACAAGACACAA----TCAAATAGTGGAACCCTTCAGCAGTC
hu.16-C   1307  CTCTGATCGACCAGTACCAGTACCTGTATTATCTGAACAAGACACAA----TCAAATAGTGGAACTCTTCAGCAGTC
hu.11-C   1307  CTCTGATCGACCAGTATCTATATTATCTGAACAACAGGACACAA----TCAAATAGTGGACTGGAACTCTTCAGCAGTC
hu.10-C   1307  CTCTGATCGACCAGTATCTATATTATCTGAACAAGACACAA----TCAAATAGTGGAACTCTTCAGCAGTC
hu.4-C    1307  CTCTGATCGACCAGTACCAGTACCTGTATTATCTGAACAAGACACAA----ACAAATAGTGGAACTCTTCAGCAGTC
rh.54-D   1313  CCCTCATCGACCAGTACCAGTACCTGTATTACCTGGCTAGAACACAGAGTAACCCAGGAGGCACATCTGGCAATCG
rh.48-D   1313  CTCTTATCGACCAGTACCAGTACCTGTATTACCTGGCCCAGAACACAGAGCAACGCAGGAGGCACAGCTGGCAATCG
rh.55-D   1313  CTCTTATCGACCAGTACCAGTACCTGTATTACCTGGCCAGAACACAGAGCAACGCAGGAGGCACAGCTGGCAATCG
rh.62-D   1313  CTCTTATCGACCAGTACCAGTACCTGTATTACCTGGCCAGAACACAGAGCAACGCAGGAGGCACAGCTGGCAATCG
AAV7-D    1313  CCCTCATCGACCAGTACTTGTACTACCTGGCCAGAACAACAGAGTAACCCAGGAGGCACAGCTGGCAATCG
rh.52-E   1316  CTCTCATCGACCAGTACCAGTACCTGTACTACCTGTCAAGAACCCAGTCT----ACGGGAGGCACAGCGGGAACCCA
rh.51-E   1316  CTCTCATCGACCAGTACCAGTACCTGTACTACCTGTCAAGAACCCAGTCT----ACGGGAGGCACAGCGGGAACCCA
rh.39-E   1316  CTCTCATCGACCAGTACCAGTACCTGTACTACCTGTCAAGAACCCAGTCT----ACGGGAGGCACAGCGGGAACCCA
rh.53-E   1316  CTCTCATCGACCAGTACCAGTACCTGTACTACCTGTCAAGAACCCAGTCT----ACAGGAGGCACAGCGGGAACCCA
hu.37-E   1316  CTCTCATCGACCAGTACCAGTACCTGTACTACTTATCCAGAACTCAGTCC----ACAGGAGGAACTCAAGGTACCCA
hu.43-E   1313  CTCTGATTGACCAGTACCAGTACCTGTACTACTGTCTGACTCAGAAACA----ACAGGAGGCACGGCAAATACGCA
rh.50-E   1316  CTCTCGTGACCAGTACCAGTACCTGTACTACCTGTCAAGAACCCAGTCT----ACGGGAGGCACAGCGGGAACCCA
rh.49-E   1316  CTCTCATCGACCAGTACCAGTACCTGTACTACCTGTCAAGAACCCAGTCT----ACGGGAGGCACAGCGGGAACCCA
rh.61-E   1316  CTCTCATCGACCAGTACCAGTACCTGTACTACTTATCCAGAACCCAGTCC----ACAGGAGGAGACTCAAGGTACCCA
hu.41-E   1316  CTCTCATCGACCAGTACCAGTACCTGTACTACTTATCCAGAACTCAGTCC----ACAGGAGGCACAGCTCAAGGTACCCA
rh.64-E   1315  CTCTCATCGACCAGTACCAGTACCTGTCTGTACTACCTGTCAAGAACCCAGTCC----ACGGGAGGCACAGCGGGAACCCA
hu.42-E   1316  CTCTCATCGACCAGTACCAGTACCTGTACTACTTATCCAGAACTCAGTCT----ACAGGAGGAACTCAAGGTACCCA
rh.57-E   1316  CTCTCATCGACCAGTACCAGTACCTGTACTACTTATCCAGAACTCAGTCC----ACAGGAGGAACTCAAGGTACCCA
hu.40-E   1316  CTCTCATCGACCAGTACCAGTACCTGTACTACTTGTCTCGACTCAGAAACA----ACAGGAGGAACTCAAGGTACCCA
AAV8-E    1316  CTCTGATTGACCAGTACCAGTACCTGTACTACCTGTCTCGACTCAGAAACA----ACAGGAGGCACGGCAAATACGCA
rh.58-E   1316  CTCTCATCGACCAGTACCAGTACCTGTACTACCTGTCAAGAACCCAGTCT----ACGGGAGGCACGGCAACCCA
```

FIG. 3BC

```
rh.40-E  1316 CTCTCATCGACCAGTACCTGTACTACTTATCCAGAACTCAGTCC------ACAGGAGGAACTCAAGGTACCCA
hu.67-E  1316 CTCTCATCGACCAGTACCTGTACTACTTATCCAGAACTCAGTCC------ACAGGAGGAACTCAAGGTACCCA
hu.17-E  1316 CCCTCATCGACCAGTACCTGTACTACCTGTCTCGGACTCAGTCC------ACGGGAGGTACCGCAGGAACTCA
hu.6-E   1316 CCCTCATCGACCAGTACCTGTACTACCTGTCTCCGGACTCAGTCC------ACGGGAGGTACCGCAGGAACTCA
hu.66-E  1316 CTCTCATCGACCAGTACCTGTACTACTTATCCAGAACTCAGTCC------ACAGGAGGAACTCAAGGTACCCA
rh.38-E  1316 CTCTCATCGACCAGTACTTGTACTACTTATCCAGAACTCGGTCC------ACAGGAGGACTCAAGGTACCCA
hu.32-F  1313 CACTCATCGACCAATACTTGTACTACTCTCAAAGACTATTAACGGTTCTGGA------CAGAATCAACA
AAV9/hu  1313 CACTCATCGACCAATACTTGTACTACTCTCAAAGACTATTAACGGTTCTGGA------CAGAATCAACA
hu.31-F  1313 CACTCATCGACCAATACTTGTACTATCTCTCAAAGACTATTAACGGTTCTGGA------CAGAATCAACA 1410      1420      1430      1440      1450      1460      1470
              ....|....|....|....|....|....|....|....|....|....|....|....|....|....|

AAV5     1335 CGGAGTCCAGTTCAACAAGAACCTGGCCCGGGAGATACGCCAACCTACAAAAACTGGTTCCCGGGGCCC
AAV3-3   1377 ACGGCTGCTGTTTTAGCCAAGCCTGGGCCTGGGCCTCAGTCTTTGCAGGACCAGAAATTGGCTACCTGGGCCCCT
AAV4-4   1359 CACCACCAACTTTACCAAGCCGTGGGTCTCCAGCTGGACCGGCATGGGTCTGTTCTGTCTGTTCTGTCTGTTCAGCCCAAAACTGGCTACCTGGACCC
AAV1-A   1377 GGACTTGCTGTTGCTCAGCCGTGGGCCTCCCAGCTGGACTGGCATGGGCCATGGGCATGGGCCATGGGCATGGCATGGCATGGCATGGCATGGCATGGCATGGCATGGCATGGCATGGCATGGCATGGCATGGCATGGCATGGCATGGCATGGC
```
FIG. 3BD

| | | | |
|---|---|---|---|
| hu.20-B | 1444 | TGTTACCGCCAGCAGCGAGTATCAAAGACAGCTGCGGACAAC------ | AACAACAGTGATT |
| hu.24-B | 1444 | TGTTACCGCCAGCAGCGAGTATCAAAGACAGCTGCGGACAAC------ | AACAACAGTGATT |
| hu.64-B | 1444 | TGTTACCGCCAGCAGCGAGTATCAAAGACACATCTGCGGATAAC------ | AACAACAGTGAAT |
| hu.27-B | 1444 | TGTTACCGCCAGCAGCGAGTATCAAAGACAGCTGCGGACAAC------ | AACAACAGTGATT |
| hu.21-B | 1444 | TGTTACCGCCAGCAGCGAGTATCAAAGACAGCTGCGGACAAC------ | AACAACAGTGATT |
| hu.22-B | 1444 | TGTTACCGCCAGCAGCGAGTATCAAAGACAGCTGCGGACAAC------ | AACAACAGTGATT |
| hu.23-B | 1444 | TGTTACCGCCAGCAGCGAGTATCAAAGACAGCTGCGGACAAC------ | AACAACAGTGATT |
| hu.7-C | 1444 | TGCTACAGACAGCAGCGTCTGTCGTCAAAGCAGGCAAACGACAAC------ | AACAACAGCAACT |
| hu.61-C | 1444 | TGCTACAGACAGCAGCGTCTGTCGTCAAAGCAGGCAAACGACAAC------ | AACAACAGCAACT |
| rh.56-C | 1444 | TGCTACAGACAGCAGCGTCTGTCGTCAAAGCAGGCAAACGACAAC------ | AACAACAGCAACT |
| hu.9-C | 1444 | TGCTACAGACAGCAGCGTCTGTCTTCAAAGCAGGCAAACGACAAC------ | AACAACAGCAACT |
| hu.54-C | 1441 | TGTTATCGCCAGCAGCGTCTGTTTGTCAAAGCAGGCAAACGACAAC------ | AACAACAGCAACT |
| hu.53-C | 1441 | TGTTATCGCCAGCAGCGTCTGTTTGTCAAAGCAGGCAAACGACAAC------ | AACAACAGCAACT |
| hu.60-C | 1444 | TGCTACAGACAGCAGCGTCTGTCTGTCAAAGCAGCAAACGACAAC------ | AACAACAGCAACT |
| hu.55-C | 1444 | TGCTACAGACAGCAGCGTCTGTCTGTCAAAGCAGGCAAACGACAAC------ | AACAACAGCAACT |
| hu.2-C | 1441 | TGTTATCGCCAGCAGCGTTTGTCTGTCAAACCAAACGACAAC------ | AACAACTGCAACT |
| hu.1-C | 1444 | TGCTACAGACAGCAGCGTCTGTCTGTCAAACCAAACGACAAC------ | AACAACAGCAACT |
| hu.18-C | 1444 | TGCTACAGACAGCAGCGTCTGTCTGTCAAAGCAGGCAAACGGCAAC------ | AACAACAGCAACT |
| hu.3-C | 1497 | TGCTACAGACAGCAGCGTCTGTCTGTCAAAACAGCAGGCAAACGACAAC------ | AACAACAGCAACT |
| hu.25-C | 1444 | TGCTACAGACAGCAGCGTCTGTCTGTCAAAGCAGGCAAACGACAAC------ | AACAACAGCAACT |
| hu.15-C | 1444 | TGCTACAGACAGCAGCGTCTGTCTGTCAAAGCAGGCAAACGACAAC------ | AACAACAGCAACT |
| hu.16-C | 1444 | TGCTACAGACAGCAGCGTCTGTCTGTCAAAGCAGGCAAACGACAAC------ | AACAACAGCAACT |
| hu.11-C | 1444 | TGCTACAGACAGCAGCGTCTTTCAAAGCAGGCAAACGACAAC------ | AACAACAGCAACT |
| hu.10-C | 1444 | TGCTACAGACAGCAGCGTCGTCTGTCAAAGCAGGCAAACGACAAC------ | AACAACAGCAACT |
| hu.4-C | 1444 | TGCTACAGACAGCAGCGTCGTCTGTCAAACCAGGCAAACGACAAC------ | AACAACAGCAACT |
| rh.54-D | 1453 | TGCTTCCGGCAACAAAGAGTTTCCAAAACACTGGATCAAAAC | AACAACAGCAACT |
| rh.48-D | 1453 | TGCTTCCGGCAACAAAGAGTCTCCAAGACGCTGGATCAAAAC | AACAACAGCAACT |
| rh.55-D | 1453 | TGCTTCCGGCAACAAAGAGTCTCCAAGACGCTGGATCAAAAC | AACAACAGCAACT |
| rh.62-D | 1453 | TGCTTCCGGCAACAAAGAGTCTCCAAGACGCTGGATCAAAAC | AACAACAGCAACT |
| AAV7-D | 1453 | TGCTTCCGGCAACAAAGAGTCTCCAAAACGCTGGATCAAAAC | AACAACAGCAACT |

FIG. 3BH

```
rh.52-E  1453  TGCTACAGACAGCAGCGCGTCTCCACGACACTGTCGCAAAC------------AACAACAGCAACT
rh.51-E  1453  TGCTACAGACAGCAGCGCGTCGCGTCTCCACGACACTGTCGCAAAAC----------AACAACAGCAACT
rh.39-E  1453  TGCTACAGACAGCAGCAGCAGCGCGTCTCCACGACACTGTCGCAAAAC--------AACAACAGCAACT
hu.53-E  1453  TGCTACAGACAGCAGCAGCAGCGCGTCTCCACGACACTGTCGCAAAAC--------AACAACAGCAACT
rh.37-E  1453  TGCTACAGACAGCAGCAGCAGCGCGTCTCCACGACACTGTCGCAAAAC--------AACAATAGCAACT
rh.43-E  1450  TGTTACCGGCAGCAACAACGCAGTCCAACGACACCGGTGTCGCAAAAC--------AACAACAGCAACT
rh.50-E  1453  TGCTACAGACAGCAGCAGCGCGTCTCCACGACACTGTCGCAAAAC----------AACAACAGCAACT
hu.49-E  1453  TGCTACAGACAGCAGCAGCGCGCGTCTCCACGACACTGTCGCAAAAC---------AACAACAGCAACT
rh.61-E  1453  TGCTACAGACAGCAGCAGCGCGCGTCTCCACGACACTGTCGCAAAAC---------AACAACAGCAACT
hu.41-E  1453  TGCTACCGGCAGCAGCAGCGAGTCTCTACGACACTGTCGCAAAAC-----------AACAACAGCAACT
rh.64-E  1453  TGCTACAGACAGCAGCAGCGCGTCTCTACGACACTGTCGCAAAAC-----------AACAACAGCAACT
hu.42-E  1453  TGCTACCGGCAGCAGCAGCGAGTCTCTACGACACTGTCGCAAAGC-----------AACAACAGCAACT
rh.57-E  1453  TGCTACAGACAGCAGCAGCGCGTCTCCACGACACTGTCGCAAAAC-----------AACAACAGCAACT
hu.40-E  1453  TGCTACCGGCAGCAGCAGCGCGTCTCTACGACACTGTCGCAAAAC-----------AACAACAGCAACT
AAV8-E   1453  TGTTACCGGCCAACAACGCTCCAACAACCGTGTCAACCGGTGTCGCAAAAC------AACAATAGCAACT
rh.58-E  1453  TGCTACAGACAGCAGCAGCGCGTCTCCACGACACTGTCGCAAAAT-----------AACAACAGCAACT
rh.40-E  1453  TGCTACAGACAGCAGCAGCGCGTCTCTACGACACTGTCGCAAAAC-----------AACAACAGCAACT
hu.67-E  1453  TGCTACCGGCAGCAGCAGCGAGTCTCTACGACACTGTCGCAAAAC-----------AACAACAGCAACT
hu.17-E  1453  TGCTACCGGCAGCAGCAACGCAGTCTCCACGACACTGTCGCAAAAT-----------AACAACAGCAACT
hu.6-E   1453  TGCTACCGGCAGCAGCAACGCAGTCTCCACGACACTGTCGCAAAAT-----------AACAACAGCAACT
hu.66-E  1453  TGCTACCGGCAGCAGCAGCGAGTCTCTACGACACTGTCGCAAAAC-----------AACAACAGCAACT
rh.38-E  1453  TGCTACCGGCAGCAGCAGCGAGTCTCTACGACACTGTCGCAAAAC-----------AACAACAGCAACT
hu.32-F  1447  AGCTACCGGCAGCAACAACGTGTCTGTCTCAACCACTGTGACTGACTCAAAAC----AACAACAGCAACT
AAV9/hu  1447  AGCTACCGGCAGCAACAACGTGTCTGTCTCAACCACTGTGACTGACTCAAAAC----AACAACAGGAAT
hu.31-F  1447  AGCTACCGGACAACAACGTGTCTGTCTCCAACCACTGTGACTGACTCAAAAC-----AACAACAGGAAT 1550         1560         1570         1580         1590         1600         1610
                           ....|....|....|....|....|....|....|....|....|....|....|....|....|....|

AAV5     1460  GCGCCTTCGCCACGACCAATAGGATGGATGAGAGCTCGAGGGGCGAGTTACCAGGTTCCCCGCAGCCGGAACGG
AAV3-3   1502  TTCCTTGGACAGCGGCCAGCAACTCTCAATGCCCGACTCGCTGGTGAATCAGGACCAGCTAT

| | | |
|---|---|---|
| hu.55-C | 1566 | GGCCAGCCACAAGGACGATGAAGAAAAAGTTTTTCCCCATGCATGGAACCCTAATATTTGGTAAAGAAGGA |
| hu.2-C | 1569 | GGCCAGTCACAAGGATGACGAGAAAGAAGTTTTTCCCATGCATGGAACCCTGATATTTGGTAAACAAGGA |
| hu.1-C | 1569 | GGCCAGTCACAAGGATGACGAGAAAGAAGTTTTTCCCATGCATGGAACCCTGATATTTGGTAAACAAGGA |
| hu.18-C | 1569 | GGCCAGCCACAAGGATGACGAGAAAGAAGTTTTTCCCATGCATGGAACCCTGATATTTGGTAAACAAGGA |
| hu.3-C | 1572 | GGCCAGTCACAAGGATGACGAAGAAAAAGTTTTTCCCATGCATGGAACCCTGATATTTGGTAAACAAGGA |
| hu.25-C | 1569 | GGCCAGTCACAAGGATGACGAAGAAAGAAGTTTTTCCCATGCATGGAACCCTGATATTTGGTAAACAAGGA |
| hu.15-C | 1569 | GGCCAGCCACAAAGACGATGAAGAAAGAAGTTTTTCCCATGCATGGAACCCTGATATTTGGTAAACAAGGA |
| hu.16-C | 1569 | GGCCAGCCACAAAGACGATGAAGAAAGAAGTTTTTCCCATGCATGGAACCCTGATATTTGGTAAACAAGGA |
| hu.11-C | 1569 | GGCCAGCCACAAGGACGATGAAGAAAGAAGTTTTTCCCATGCATGGAACCCTGATATTTGGTAAACAAGGA |
| hu.10-C | 1569 | GGCCAGCCACAAGGACGATGAAGAAAGAAGTTTTTCCCATGCATGGAACCCTGATATTTGGTAAACAAGGA |
| hu.4-C | 1569 | GGCCAGTCACAAGGATGACGAAGAAGAAGTTTTTCCCATGCATGGAACCCTGATATTTGGTAAACAAGGA |
| rh.54-D | 1578 | GGCAACTCACAAGGACGACGAGGACCGCTTTTTCCCATCCCTTCGAGCGGAGTCCTGATTTTTGGAAAACTGGA |
| rh.48-D | 1578 | GGCAACCACAAGGACGACGAGGAACGCTTCTTCCCTTCCCTTCGAGCGGAGTCCTGATTTTTGGAAAACTGGA |
| rh.55-D | 1578 | GGCAACCACAAGGACGACGAGGAACGCTTCTTCCCTTCCCTTCGAGCGGAGTCCTGATTTTTGGAAAACTGGA |
| rh.62-D | 1578 | GGCAACCACAAGGACGACGAGGAACGCTTCTTCCCTTCCCTTCGAGCGGAGTCCTGATTTTTGGAAAACTGGA |
| AAV7-D | 1578 | GCCAACTCACAAGGACGACGAGGACGACCCGCTTTTCCCTTCCCATCCAGCGGAGTCCTGATTTTTGGAAAAACTGGA |
| rh.52-E | 1578 | GGCAACCACAACAAGGACGACGAGGAGGAGCCGCTGTTTTTCCCTTCCCATCCAGCGGCATGTTGGCAAGCAGGGA |
| rh.51-E | 1578 | GGCAACCACAACAAGGACGACGAGGAGGAGCCGCTTCTTCCCTTCCCATCCAGCGGCATGTTGGCAAGCAGGGA |
| rh.39-E | 1578 | GGCAACCACAACAAGGACGACGAGGAGGAGCCGCTTCTTCCCTTCCCATCCAGCGGCATGTTGGCAAGCAGGGA |
| rh.53-E | 1578 | GGCAACCACAACAAGGACGACGAGGAGGAGCCGCTTCTTCCCTTCCCATCCAGCGGCATGTTGGCAAGCAGGGA |
| hu.37-E | 1578 | GGCAACCACAACAAGGACGACGAGGAGGAGCCGCTTCTTCCCTTCCCATCCAGCGGCATGTTGGCAAGCAGGGA |
| rh.43-E | 1575 | GGCAACACACAACAAGACGACGAGGAGGAGCCGCTGTTTTTTCCTTCCCATCCAGTAACGGGA---TCCTGTTTTTGGCAACAAAT |
| rh.50-E | 1578 | GGCAACCACAACAAGACGACGAGGAGGAGCCGCTTCTTCCCTTCCCATCCAGCGGCATGTTGGCAAGCAGGGA |
| rh.49-E | 1578 | GGCAACCACAACAAGACGACGAGGAGGAGCCGCTTCTTCCCTTCCCATCCAGCGGCATGTTTGGCAAGCAGGGA |
| rh.61-E | 1578 | GGCAACCACAACAAGACGACGAGGAACGAGCCGCTTCTTCCCTTCCCATCCAGCGGAGTCCATGTTTGGCAAGCAGGGT |
| hu.41-E | 1578 | GGCAACCACAACAAGACGACGAGGAACGAGCCGCTTCTTCCCTTCCCATCCCGTCGAGTGGAGTCCATGTTTGGAAAACAGGGT |
| hu.64-E | 1578 | GGCAACCACAACAAGACGACGAGGAACGAGCCGCTTCTTCCCTTCCCATCCCGTCGAGTGGAGTCCATGTTTGGCAAGCAGGGT |
| hu.42-E | 1578 | GGCAACCACAACAAGACGACGAGGAACGAGCCGCTTCTTCCCTTCCCATCCCGTCGAGTGGAGTCCATGTTTGGAAAACAGGGT |
| rh.57-E | 1578 | GGCAACCACAACAAGACGACGAGGAACGAGCCGCTTCTTCCCTTCCCATCCCGTCGAGTGGAGTCCATGTTTGGCAAGCAGGGA |
| hu.40-E | 1578 | GGCAACCACAACAAGACGACGAGGAACGAGCCGCTTCTTCCCTTCCCATCCCGTCGAGTGGAGTCCTGATGTTTGGAAAACAGGGT |

| | | | | |
|---|---|---|---|---|
| hu.35-B | 1639 | TCA------ | ------GAGAAAAACAAAATGTGGACATTGAA--- | ---AAGGTCATGATTACAGACGAAGAGGAAATCAGGA |
| hu.58-B | 1639 | TCA------ | ------GAGAAAAACAAAATGTGGACATTGAA--- | ---AAGGTCATGATTACAGACGAAGAGGAAATCAGGA |
| hu.28-B | 1639 | TCA------ | ------GAGAAAAACAAAATGTGGATATTGAA--- | ---AAGGTCATGATTACAGACGAAGAGGAAATCAGGA |
| hu.51-B | 1639 | TCA------ | ------GAGAAAAACAAAATGTGGACATTGAA--- | ---AAGGTCATGATTACAGACGAAGAGGAAATCAGGA |
| hu.19-B | 1639 | TCG------ | ------GGAAAAAACAAAATGTGGACATTGAA--- | ---AAGGTCATGATTACAGACGAAGAGGAAATCAGGA |
| hu.49-B | 1639 | TCA------ | ------GAGAAAAACAAAATGTGGACATTGAA--- | ---AAGGTTATGATTACAGACGAAGAGGAAATCAGGA |
| hu.52-B | 1639 | TCA------ | ------GAGAAAAACAAAATGTGGACATTGAA--- | ---AAGGTCATGATTACAGACGAAGAGGAAATCAGGA |
| hu.13-B | 1639 | TCA------ | ------GAGAAAAACAAAATGTGGACATTGAA--- | ---AAGGTCATGATTACAGACGAAGAGGAAATCAGGA |
| AAV2-B | | TCA------ | ------GAGAAAAACAAAATGTGGACATTGAA--- | ---AAGGTCATGATTACAGACGAAGAGGAAATCAGGA |
| hu.20-B | 1639 | TCG------ | ------GGAAAAAACTAATGTGTGGACATTGAA--- | ---AAGGTTATGATTACAGACGAAGAGGAAATCAGGA |
| hu.24-B | 1639 | TCG------ | ------GGAAAAAACTAATGTGTGGATATTGAA--- | ---AAGGTTATGATTACAGACGAAGAGGAAATCAGGA |
| hu.64-B | 1639 | TCG------ | ------GGAAAAAACTAATGTGTGGACATTGAA--- | ---AAGGTCATGATTACAGACGAAGAGGAAATCAGGA |
| hu.27-B | 1639 | TCG------ | ------GGAAAAAACTAATGTGTGGACATTGAA--- | ---AAGGTTATGATTACAGACGAAGAGGAAATCAGGA |
| hu.21-B | 1639 | TCG------ | ------GGAAAAAACTAATGTGTGGACATTGAA--- | ---AAGGTCATGATTACAGACGAAGAGGAAATCAGGA |
| hu.22-B | 1639 | TCG------ | ------GGAAAAAACTAATGTGTGGACATTGAA--- | ---AAGGTTATGATTACAGACGAAGAGGAAATCAGGA |
| hu.23-B | 1639 | TCG------ | ------GGAAAAAACTAATGTGTGGACATTGGAC | ---AAGGTTATGATTACAGACGAAGAGGAAATCCGCA |
| hu.7-C | 1639 | ACA------ | ------AATGCTACGACGACGCGCGGGATTTGGAA | ---AATGTCATGATTACAGATGAAGATGAAGAATCAGGA |
| hu.61-C | 1639 | ACA------ | ------AATGCCAACGACGACGCGCGGGATTTGGAA | ---AATGTCATGATTACAGATGAAGATGAAGAATCCGCA |
| rh.56-C | 1639 | ACA------ | ------AATGCTAACGACGACGCGCGGGATTTGGAC | ---AATGTCATGATTACAGATGAAGATGAAGAATCAGGA |
| hu.9-C | 1636 | ACA------ | ------AATGCTAACGACCAACGCGCGGGAATTGGAG | ---CATGTTATGATTACAGATGAAGATGAAGAATCAGGA |
| hu.54-C | 1636 | ACA------ | ------AATGCTACCAACGACGCGCGGGAATTGGAA | ---AATGTCATGATTACAGATGAAGATGAAGAATCAGGA |
| hu.53-C | 1636 | ACA------ | ------AATGCTACCAACGACGCGCGGGATTTGGAA | ---AATGTCATGATTACAGATGAAGATGAAGAATCAGGA |
| hu.60-C | 1639 | ACA------ | ------AATGCTACCAACGACGCGCGGGAATTGGAA | ---AATGTCATGATTACAGATGAAGATGAAGAATCAGGA |
| hu.55-C | 1636 | ACA------ | ------AATGCTACCAACGACGCGCGGGAATTGGAA | ---AATGTCATGATTACAGATGAAGATGAAGAATCAGGA |
| hu.2-C | 1639 | ACA------ | ------AATGCTAACGACGCGCGGGATTTGGAA | ---AATGTCATGATTACAGATGAAGATGAAGAATCAGGG |
| hu.1-C | 1639 | ACA------ | ------AATGCCAACGACGACGCGCGGGATTTGGAA | ---AATGTCATGATTACAGATGAAGATGAAGAATCAGGG |
| hu.18-C | 1639 | ACA------ | ------AATGCTAACGACGACGCGCGGGATTTGGAA | ---AATGTCATGATTACAGATGAAGATGAAGAATCCGCA |
| hu.3-C | 1642 | ACA------ | ------AATGCCAACGACGACGCGCGGGATTTGGAA | ---AATGTCATGATTACAGATGAAGATGAAGAATCAGGC |
| hu.25-C | 1639 | ACA------ | ------AATGCCAACGACGACGCGCGGGATTTGGAA | ---AATGTCATGATTACAGATGAAGATGAAGAATCAGGA |
| hu.15-C | 1639 | ACA------ | ------AATGCTAACGACGACGCGCGGGATTTGGAC | ---AATGTCATGATTACAGATGAAGATGAAGAATCCGCA |

```
rh.38-E  1648  GCT------GGAAGAGACAATGTGGACTACAGC----AGCGTTATGCTAACCAGCGAAGAAGAAATTAAAA
hu.32-F  1642  ACT------GGAAGAGACAACGTGGATGCGGAC----AAAGTCATGATAACCAACGAAGAAGAAATTAAAA
AAV9/hu  1642  ACT------GGAAGAGACAACGTGGATGCGGAC----AAAGTCATGATAACCAACGAAGAAGAAATTAAAA
hu.31-F  1642  ACT------GGAAGAGACAACGTGGATGCGGAC----AAAGTCATGATAACCAACGAAGAAGAAATTAAAA 1760      1770      1780      1790      1800      1810      1820
                                ....|....|....|....|....|....|....|....|....|....|....|....|....|
AAV5     1670  CGGTGAACCGCCGTGGCTACGGCGTACCAACCTCGGCGGGCAGATGGCCACCACCAGAGCTCCACCACTGCCCC
AAV3-3   1703  CCACCAATCCTGTGGCCACCGATACGGACGGCAACAGAGCCAGTATGGAACTGTGGCAAATAACTTGCAGAGCTCAAATACAGCTCC
AAV4-4   1697  CCACCAACGCCACCGATACGGACGGCAACAGAGCCAGTATGGGGCAACCTACCTGGCGGTGACCAGCAGCACAGCAACCTGCC
AAV1-A   1703  CCACTAACCCTGTGGCCACCGATACGGACGGCAACAGAGATTTGGGACCCGTGGCAGTCAATTTCCAGACCAGCAGCACAGACCC
hu.46-A  1703  CCACTAACCCTGTGGCCACCGATACGGACGGCAACAGAGATTTGGGACCCGTGGCAGTCAATTTCCAGACCAGCAGCACAGACCC
hu.48-A  1703  CCACTAACCCTGTGGCCACCGATACGGACGGCAACAGAGATTTGGGACCCGTGGCAGTCAATTTCCAGACCAGCAGCACAGACCC
hu.44-A  1706  CCACTAACCCTGTGGCCACCGATACGGACGGCAACAGAGATTTGGGACCCGTGGCAGTCAATTTCCAGACCAGCAGCACAGACCC
hu.43-A  1703  CCACTAACCCTGTGGCCACCGATACGGACGGCAACAGAGATTTGGGACCCGTGGCAGTCAATTTCCAGACCAGCAGCACAGACCC
AAV6-A   1703  CAACTAACCCTGTGGCCACCGATACGGACGGCAACAGAGATTTGGGACTGTTCTGTATCTACAACCTCCAACAACAGAGCAGCAGC
hu.34-B  1700  CAACCAATCCCGTGGCTACGGCGTACCGACGGCAACAGAGATCAGCAGCAGTGTTCTGTATCTACAACCTCCAGAGAGGCAACAGACAAGC
hu.47-B  1700  CAACCAATCCCGTGGCTACGGCGTACCGACGGCAACAGAGATCAGCAGCAGTGTTCTGTATCTACAACCTCCAGAGAGGCAACAGACAAGC
hu.29-B  1700  CAACCAATCCCGTGGCTACGGCGTACCGACGGCAACAGAGATCAGCAGCAGTGTTCTGTATCTACAACCTCCAGAGAGGCAACAGACAAGC
hu.63-B  1700  CCACCAATCCCGTGGCTACGGCGTACCGACGGCAACAGAGATCAGCAGCAGTGTTCTGTATCTACAACCTCCAGAGAGGCAACAGACAAGC
hu.56-B  1700  CCACCAATCCCGTGGCTACGGCGTACCGACGGCAACAGAGATCAGCAGCAGTGTTCTGTATCTACAACCTCCAGAGAGGCAACAGACAAGC
hu.45-B  1700  CAACCAATCCCGTGGCTACGGCGTACCGACGGCAACAGAGATCAGCAGCAGTGTTCTGTATCTACAACCTCCAGAGAGGCAACAGACAAGC
hu.57-B  1697  CCACCAATCCCGTGGCTACGGCGTACCGACGGCAACAGAGATCAGCAGCAGTGTTCTGTATCTACAACCTCCAGAGAGGCAACAGACAAGC
hu.35-B  1700  CAACCAATCCCGTGGCTACGGCGTACCGACGGCAACAGAGATCAGCAGCAGTGTTCTGTATCTACAACCTCCAGAGAGGCAACAGACAAGC
hu.58-B  1700  CCACCAATCCCGTGGCCACCGGTACCGACGGCAACAGAGATCAGCAGCAGTGTTCTGTATCTACAACCTCCAGAGAGCGCAACAGACAAGC
hu.28-B  1700  CCACCAATCCCGTGGCCACCGGTACCGACGGCAACAGAGATCAGCAGCAGTGTTCTGTATCTACAACCTCCAGAGAGCGCAACAGACAAGC
hu.51-B  1700  CAACCAATCCCGTGGCTACGGCGTACCGACGGCAACAGAGATCAGCAGCAGTGTTCTGTATCTACAACCTCCAGAGAGGCAACAGACAAGC
hu.19-B  1700  CCACCAATCCCGTGGCTACGGCGTACCGACGGCAACAGAGACGATGGCTACCGGTTCTGTATCTACAACCTCCAGAGAGCCAACAGACAAGC
hu.49-B  1700  CCACCAATCCCGTGGCCACCGGTACCGACGGCAACAGAGATCAGCAGCAGTATGGTTCTGTATCTACAACCTCCAGAGAGCCAACACACAAGC
hu.52-B  1700  CAACCAATCCCGTGGCTACGGCGTACCGACGGCAACAGAGATCAGCAGCAGTATGGTTCTGTATCTACAACCTCCAGAGAGGCAACACACAAGC
```

```
rh.43-E   1773 TCAAAATTGGAACTGTCAACAGCCAGGGGCCTTACCCGGTATGGTCTGGCAGAACCGGGACGTGTACCTG
rh.50-E   1779 TATTGTGGGGGCCGTCAACAGCCAGGGAGCCTTACCTGGCATGGTCTGGCAGAACCGGGACGTGTACCTG
rh.49-E   1779 TATTGTGGGGGCCGTCAACAGCCAGGGAGCCTTACCTGGCATGGTCTGGCAGAACCGGGACGTGTACCTG
rh.61-E   1779 TATTGTGGGGGCCGTCAACAGCCAGGGAGCCTTACCTGGCATGGTCTGGCAGAACCGGGACGTGTACCTG
hu.41-E   1779 TATTGTGGGGGCCGTCAATGTCAACAGCCAAGGAGCCTTACCTGGCATGGTCTGGCAGAACCGGGACGTGTACCTG
hu.64-E   1779 TATTGTGGGGGCCGTCAACAGCCAGGGAGCCTTACCTGGCATGGTCTGGCAGAACCGGGACGTGTACCTG
hu.42-E   1779 TATTGTGGGGGGCCGTCAACAGCCAGGGAGCCTTACCTGGCATGGTCTGGCAGAACCGGGACGTGTACCTG
hu.57-E   1779 TATTGTGGGGCCGTCAACAGCCAGGGAGCCTTACCTGGCATGGTCTGGCAGAACCGGGACGTGTACCTG
hu.40-E   1779 TATTGTGGGGCCGTCAACAGCCAGGGAGCCTTACCTGGCATGGTCTGGCAGAACCGGGACGTGTACCTG
AAV8-E    1779 TCAAATTGGAACTGTCAACAGCCAGGGAGCCTTACCTGGCATGGTCTGGCAGAACCGGGACGTGTACCTG
rh.58-E   1779 TATTGTGGGCCGTCAACAGCCAGGGAGCCTTACCTGGCATGGTCTGGCAGAACCGGGACGTGTACCTG
rh.40-E   1779 TATTGTGGGGAAATGTCAACAGCCAGGGAGCCTTACCTGGCATGGTCTGGCAGAACCGGGACGTGTACCTG
hu.67-E   1779 TATTGTGGGGAAATGTCAACAGCCAGGGAGCCTTACCTGGCATGGTCTGGCAGAACCGGGACGTGTACCTG
hu.17-E   1779 TATTGTAGGGCCGTCAAGTCAAGGAGCCAAGCCTTACCTGGCATGGTCTGGCAGAACCGGGACGTGTACCTG
hu.6-E    1779 TATTGTAGGGCCGTCAACAGCCAAGGAGCCAAGCCTTACCTGGCATGGTCTGGCAGAACCGGGACGTGTACCTG
hu.66-E   1779 TATTGTGGGAAATGTCAACAGCCAAGGAGCCAAGCCTTACCTGGTATGGTTTGGCAGAACCGGGACGTGTACCTG
rh.38-E   1779 TATTCTGGGAAATGTCAACAGCCAAGGAGCCAAGCCTTACCTGGCATGGTCTGGCAGAACCGGGACGTGTACCTG
rh.32-F   1773 GCAAGACCGGCTGGTTCAAACCAAGGAATAACTTCCGGGTATGGTTTGGCAGGACAGAAACCGGGACGTGTACCTG
AAV9/hu   1773 GCAGACCGGCTGGTTCAAACCAAGGAATATCTCCGGGTATGGTATGGTATGGTTTGGCAGGACAGAGATGTGTACCTG
hu.31-F   1773 GCAGACCGGCTGGTTCAAACCAAGGAATACTCCGGGTATGGTTTGGCAGGACAGAGATGTGTACCTG
                         1900       1910       1920       1930       1940       1950       1960
               ....|....|....|....|....|....|....|....|....|....|....|....|....|....|

AAV5      1810 CAAGGACCCATCTGGCCAAGATCCCAGAGACGGCGCACTTTCACCCCTCCGGCCATGGCGGAT
AAV3-3    1843 CAAGGACCTATCTGGCCAAGAAGATTCCTCACACGGATGACACTTTCATCCTCCTCCTCCGGCCATGGGAGGCT
AAV4-4    1837 CAGGGTCCCATTTGGGCCAAGATTCCTCACACGGATGACACTTTCACCCCTCGATGGTGGCT
AAV1-A    1843 CAGGGTCCCATTTGGGCCAAAATTCCTCACACAGATGACACTTTCACCCCGTCGATTGGTGGCT
hu.46-A   1843 CAGGGTCCCATTTGGGCCAAAATTCCTCACACAGATGACACTTTCACCCCGTCCTTATGGGCGCT
hu.48-A   1843 CAGGGTCCCATTTGGGCCAAAATTCCTCACACAGATGACACTTTCACCCCGTCCTCTTATGGGCGCT
hu.44-A   1843 CAGGGTCCCATTTGGGCCAAAATTCCTCACACAGATGACACTTTCACCCCGTCCTCTTATGGGCGCT
```

FIG. 3BW

| | | |
|---|---|---|
| hu.43-A | 1846 | CAGGGTCCCCATTTGGGCCAAAATTCCTCACACAGATGGACACACTTTCACCCGTCTCCTCTTATGGGGCT |
| AAV6-A | 1843 | CAGGGTCCTATTTGGGCCAAAATTCCTCACACGATGGACACACTTTCACCCGTCTCCTCTCATGGGCGCT |
| hu.34-B | 1840 | CAGGGCCCATCTGGGCAAAGATTCCACACGACGGACACATTTCACCCCTCTCCCCTCATGGTGGAT |
| hu.47-B | 1840 | CAGGGCCCATCTGGGCAAAGATTCCACACGACGGACACATTTCACCCCTCTCCCCTCATGGTGGAT |
| hu.29-B | 1840 | CAGGGCCCATCTGGGCAAAGATTCCACACGACGGACACATTTCACCCCTCTCCCCTCATGGGCGAT |
| hu.63-B | 1840 | CAGGGCCCATCTGGGCAAAGATTCCACACGACGGACACATTTCACCCCTCTCCCCTCATGGGCGAT |
| hu.56-B | 1840 | CAGGGCCCATCTGGGCAAAGATTCCACACGACGGACACATTTCACCCCTCTCCCCTCATGGGCGAT |
| hu.45-B | 1840 | CAGGGCCCATCTGGGCAAAATTCCACACGACGGACACATTTCACCCCTCTCCCCTCATGGGCGAT |
| hu.57-B | 1837 | CAGGGCCCATCTGGGCAAAGATTCCACACGACGGACACATTTCACCCCTCTCCCCTCATGGGCGAT |
| hu.35-B | 1840 | CAGGGCCCATCTGGGCAAAGATTCCGCACGACGGACACATTTCACCCCTCTCCCCTCATGGGCGAT |
| hu.58-B | 1840 | CAGGGCCTACTGGGCAAAGATTCCACACGACGGACACATTTTCACCCCTCTCCCCTCATGGGCGAT |
| hu.28-B | 1840 | CAGGGCCTACTGGGCAAAGATTCCACACGACGGACACATTTTCACCCCTCTCCCCTCATGGGCGAT |
| hu.51-B | 1840 | CAGGGCCCATCTGGGCAAAGATTCCACACGACGGACACATTTCACCCCTCTCCCCTCGTGGCGAT |
| hu.19-B | 1840 | CAGGGCCCATCTGGGCAAAGATTCCACACGACGGACACATTTCACCCCTCTCCCCTCATGGGCGAT |
| hu.49-B | 1840 | CAGGGCCTATCTGGGCAAAGATTCCACACGACGGACACATTTCACCCCTCTCCCCTCATGGGCGAT |
| hu.52-B | 1840 | CAGGGCCCATCTGGGCAAAGATTCCACACGACGGACACATTTCACCCCTCTCCCCTCATGGGCGAT |
| hu.13-B | 1840 | CAGGGCCCATCTGGGCAAAGATTCCACACGACGGACACATTTCACCCCTCTCCCCTCATGGGCGAT |
| AAV2-B | 1840 | CAGGGCCCATCTGGGCAAAGATTCCACACGACGGACACATTTCACCCCTCTCCCCTCATGGGCGAT |
| hu.20-B | 1840 | CAGGGCCCATCTGGGCAAAGATTCCACACGACGGACACATTTCACCCCTCTCCCCTCATGGGCGAT |
| hu.24-B | 1840 | CAGGGCCCATCTGGGCAAAGATTCCACACGACGGACACATTTCACCCCTCTCCCCTCATGGGCGAT |
| hu.64-B | 1840 | CAGGGCCCATCTGGGCAAAGATTCCACACGACGGACACATTTCACCCCTCTCCCCTCATGGGCGAT |
| hu.27-B | 1840 | CAGGGCCCATCTGGGCAAAGATTCCACACGACGGACACATTTCACCCCTCTCCCCTCATGGGCGAT |
| hu.21-B | 1840 | CAGGGCCCATCTGGGCAAAGATTCCACACGACGGACACATTTCACCCCTCTCCCCTCATGGGCGAT |
| hu.22-B | 1840 | CAGGGCCCATCTGGGCAAAGATTCCACACGACGGACACATTTCACCCCTCTCCCCTCATGGGCGAT |
| hu.23-B | 1840 | CAGGGACCCATTTGGGCAAAGATTCCACACGACGGACACTTTCATCCTTCATCCTCATGATGGGAGTT |
| hu.7-C | 1840 | CAGGGACCCATTTGGGCCAAGATTCCTCACACGATGGACACTTTCATCCTTCATCCTCACTGGTGGGAGTT |
| hu.61-C | 1840 | CGGGGACCCATTTGGGCCAAGATTCCTCACACGATGGACACTTTCATCCTTCATCCTCACTGATGGGAGGTT |
| rh.56-C | 1840 | CAGGGACCCATTTGGGCCAAGATTCCTCACACGATGGACACTTTCATCCTTCATCCTCACTGATGGGAGGTT |
| hu.9-C | 1840 | CAGGGACCCATTGGGCCAAGATTCCTCACACGACGGACACTTTCATCCTTCATCCTCACTGATGGGAGGTT |
| hu.54-C | 1837 | CGGGGACCCATTGGGCCAAGATTCCTCAAGCCGATGGACACTTTCATCCTTCATCCTCACTGATGGGAGGTT |

```
hu.25-C    1910  TTGGACTCAAACACCCGCCTCCTCCGCCTCCTCAGATTATGATCAAAAACACTCCCGTTCCAGCCAATCCTCCTCCACAAA
hu.15-C    1910  TTGGACTCAAACACCCGCCTCCTCCGCCTCCTCAGATCATGATCATGATTAAAACACTCCCGTTCCAGCCAATCCTCCTCCACAAA
hu.16-C    1910  TTGGACTCAAACACCCGCCTCCTCCACCCGCCTCCTCAGATCATGATCATGATTAAAACACTCCCGTTCCAGCCAATCCTCCTCCACAAA
hu.11-C    1910  TTGGACTCAAACACCCGCCTCCTCCGCCTCCTCAGATCATGATCAAATCATGATCAAAACACTCCCGTTCCAGCCAATCCTCCTCCACAAA
hu.10-C    1910  TTGGACTCAAACACCCGCCTCCTCCGCCTCCTCAGATCATGATCAAATCATGATCAAAACACTCCCGTTCCAGCCAATCCTCCTCCACAAA
hu.4-C     1910  TTGGACTCAAACACCCGCCTCCTCCGCCTCCTCAGATCATGATCATGATCAAAACACTCCCGTTCCAGCCAATCCTCCTCCACAAA
rh.54-D    1916  TTGGACTGAAGCATCCGCCTCCTCCGCCTCCTCAGATCCTGATCCTGATCAAAACACTCCTGTTCCTGTTCCTAATCCCCGGAGGT
rh.48-D    1916  TTGGACTGAAGCATCCGCCTCCTCCGCCTCCTCAGATCCTGATCCTGATCAAAACACTCCTGTTCCTGTTCCTAATCCCCGGAGGT
rh.55-D    1916  TTGGACTGAAGCATCCGCCTCCTCCGCCTCCTCAGATCCTGATCCTGATCAAAACACTCCTGTTCCTGTTCCTAATCCCCGGAGGT
rh.62-D    1916  TTGGACTGAAGCATCCGCCTCCTCCGCCTCCTCAGATCCTGATCCTGATCAAAACACTCCTGTTCCTGTTCCTAATCCCCGGAGGT
AAV7-D     1916  TTGGACTTAAACATCCGCCTCCTCCGCCTCCTCAGATCCTGATCCTCATCAAAAACACTCCTGTTCCTGTTCCTCCTCCAACAGC
rh.52-E    1919  TTGGACTTAAACATCCGCCTCCTCCGCCTCCTCAGATCCTGATCCTCATCAAAAACACTCCTGTTCCTGCGATCCTCCTCCAACAGC
rh.51-E    1919  TTGGACTTAAACATCCGCCTCCTCCGCCTCCTCAGATCCTGATCCTCATCAAAAACACTCCTGTTCCTGCGATCCTCCTCCAACAGC
rh.39-E    1919  TTGGACTTAAACATCCGCCTCCTCCGCCTCCTCAGATCCTGATCCTCATCAAAAACACTCCTGTTCCTGCGATCCTCCTCCAACAGC
hu.39-E    1919  TTGGACTTAAACATCCGCCTCCTCCGCCTCCTCAGATCCTGATCCTCATCAAAAACACTCCTGTTCCTGCGATCCTCCTCCAACAGC
rh.53-E    1919  TTGGACTTAAACATCCGCCTCCTCCGCCTCCTCAGATCCTGATCCTCATCAAAAACACTCCTGTTCCTGCGATCCTCCTCCAACAGC
rh.37-E    1919  TTGGCCTGAAACATCCTCCGCCACCTCCGCCTCCTCAGATCCTGATCCTGATCAAGAACACGCCGCCTCCTGTTCCTGCGATCCTCCTCCAACAGC
rh.43-E    1913  TTGGCCTGAAACATCCTCCGCCACCTCCGCCTCCTCAGATCCTGATCCTCATCAAAAACACTCCTGTTCCTGCGATCCTCCTCCAACAGC
rh.50-E    1919  TTGGACTTAAACATCCGCCTCCTCCGCCTCCTCAGATCCTGATCCTCATCAAAAACACGCCGCCTCCTGTTCCTGCGATCCTCCTCCAACAGC
rh.49-E    1919  TTGGACTTAAACATCCGCCTCCTCCGCCTCCTCAGATCCTGATCCTCATCAAAAACACGCCGCCTCCTGTTCCTGCGATCCTCCTCCAACAAC
rh.61-E    1919  TTGGACTTAAACATCCGCCTCCTCCGCCTCCTCAGGTCCTGATCCTCATCAAAAACACGCCGCCTCCTGTTCCTGCGATCCTCCTCCAACAAC
hu.41-E    1919  TTGGACTGAAGCACCACCACTCCGCCTCCTCAGATCCTGATCCTCATCAAGAACACGCCGCCTCCTGTTCCTGCGGTACCTGCGATCCTCCAACAGC
hu.64-E    1919  TTGGACTGAAGCACCACCACTCCGCCTCCTCAGATCCTGATCCTCATCAAGAACACGCCGCCTCCTGTTCCTGCGGTACCTGCGATCCTCCAACAGC
hu.42-E    1919  TTGGACTGAAGCACCACCACTCCGCCTCCTCAGATCCTGATCCTCATCAAGAACACGCCGCCTCCTGTTCCTGCGGTACCTGCGATCCTCCAACAGC
rh.57-E    1919  TTGGACTGAAGCACCACCACTCCGCCTCCTCAGATCCTGATCCTCATCAAGAACACGCCGCCTCCTGTTCCTGCGGTACCTGCGATCCTCCAACAGC
hu.40-E    1919  TTGGACTGAAGCACCACCACTCCGCCTCCTCAGATCCTGATCCTCATCAAGAACACGCCGCCTCCTGTTCCTGCGGTACCTGCGATCCTCCAACAAC
AAV8-E     1919  TTGGCCTGAAACATCCGCCTCCTCCGCCACCTCCGCCTCCTCAGATCCTGATCCTCATCAAGAACACGCCGCCTCCTGTTCCTGCGGTACCTGCGATCCTCCAACAAC
rh.58-E    1919  TTGGACTTAAACATCCGCCACCACCTCCGCCTCCTCAGATCCTGATCCTCATCAAAAGACGCCTCCTGTTCCTGCGGATCCTCCGACCAC
rh.40-E    1919  TTGGACTGAAGCACCACCATCCGCCTCCTCAGATCCTGATCCTGATCAAGAATACGCCGCCTCCTGTTCCTGCGGATCCTCCAACAGC
hu.67-E    1919  TTGGACTGAAGCACCACCATCCGCCTCCTCAGATCCTGATCCTGATCAAGAACAACACGCCGCCTCCTGTTCCTGCGGATCCTCCAACAGC
hu.17-E    1919  TTGGACTGAAACACCCGCCTCCTCCGCCTCCTCAGATCCTGATTAAGAATACACCTGTTCCCGCGGATCCTCCAACTAC
```

FIG. 3CB

```
hu.6-E    1919  TTGGACTGAAACACCCGCCTCCTCCTCAGATCCTCAGATCCTGTTCCCGGGATCCTCCAACTAC
hu.66-E   1919  TTGGACTGAAGAACACCCCACCTCCTCCTCAGATCCTCAGATCCTCAGATCCTGCCGGTACCTCCAACAAC
rh.38-E   1919  TTGGACTGAAGAACACCCCACCTCCTCCTCAGATCCTCAGATCCTCAGATCCGCCGGTACCTCCAACAAC
rh.32-F   1913  TTGGAATGAAGAACACCCGCCCTCCTCCTCAGATCCTCAGATCCTCATCAGATCCTGTACCTCCTCCAACGGC
AAV9/hu   1913  TTGGAATGAAGAACACCCGCCCTCCTCCTCAGATCCTCATCATCAAAAACACAACCTGTACCTCCAACGGC
hu.31-F   1913  TTGGAATGAAGAACACCCGCCCTCCTCCTCAGATCCTCATCATCAAAAACAACACCTGTACCTCCAACGGC 2040      2050      2060      2070      2080      2090      2100
              ....|....|....|....|....|....|....|....|....|....|....|....|....|....|
AAV5      1947  CTTCTCGGACGTGCCCGTCAGCAGCTTCATCACCCAGTACTCACCGGGCAGGTCACCGTCAGCGAGATGGAG
AAV3-3    1983  TTTCAGCCCGGCCTACTCCGGTAAACTCCTTCATTGCTTCATTTATCACTCAGTACTCCACTGGACAGGTCAGCAGGTCAGCGTGGAAATTGAG
AAV4-4    1977  CTTCAGCTCTACTCCGGTAAACTCCTTCATTGCTTCATTTATCACTCAGTACTCCACTGGACACTGGACAGGTCAGCAGGTCAGCGTGGAAATTGAC
AAV1-A    1983  GTTTTCAGCTACAAAGTTTGCTTCATTCATCACCCAATACTCCGACAGGACACTGGACAGGACAAGGTCAGCAGGTCAGCGTGGAAATTGAA
hu.46-A   1983  GTTTTCAGCTACAAAGTTTGCTTCATTCATCACCCAATACTCCGACAGGACACTGGACAGGACAAGGTCAGCAGGTCAGCGTGGAAATTGAA
hu.48-A   1983  GTTTTCAGCTACAAAGTTTGCTTCATTCATCACCCAATACTCCGACAGGACACTGGACAGGACAAGGTCAGCAGGTCAGCGTGGAAATTGAA
hu.44-A   1983  GTTTTCAGCTACAAAGTTTGCTTCATTCATCACCCAATACTCCGACAGGACACTGGACAGGACAAGGTCAGCAGGTCAGCGTGGAAATTGAA
hu.43-A   1986  GTTTTCAGCTACAAAGTTTGCTTCATTCATCACCCAATACTCCGACAGGACACTGGACAGGACAAGGTCAGCAGGTCAGCGTGGAAATTGAA
AAV6-A    1983  GTTTTCGGCTACAAAGTTTGCTTCATTGCTTCATTCATCACCCAGTATTCCACACACAGACACTCCACAGGGACAGGACAAGGTCAGCGAGCGTGGAGATTGAA
hu.34-B   1980  CTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
hu.47-B   1980  CTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
hu.29-B   1980  CTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
hu.63-B   1980  CTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
hu.56-B   1980  CTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
hu.45-B   1980  CTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
hu.57-B   1977  CTTCAGTGCGGCGGCCAAAGTTTGCTTCCTTCCTTCATCATCATCACACAGACACACTATCCACAGACACACAGCGGACACAGGGACAGGACAGGACAGGTCAGCAGGTCAGCGAGCGTGGAGATCGAG
hu.35-B   1980  CTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
hu.58-B   1980  CTTCAGTGCGGCGGCCAAAGTTTGCTTCCTTCCTTCATCATTACACACAGACACACTACACAGACACACAGCGGACACAGGGGCAGGGTCAGCAGGTCAGCGAGCGTGGAGATCGAG
hu.28-B   1980  CTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
hu.51-B   1980  CTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
hu.19-B   1980  TTTCAGTGCGGCGGCCAAAGTTTGCTTCCTTCCTTCATCATCATCACACAGACACACTACACAGACACACAGCGGACACAGGGACAGGACAGGACAGGTCAGCAGGTCAGCGAGCGTGGAGATCGAG
```

```
rh.48-D   1986  GTTTACGCCCTGCCAAGTTTGCTTCTTTCATCACACAGTACAGCACCGGCCAGGTCAGCGCCAGCGTGGAGATCGAG
rh.55-D   1986  GTTTACGCCCTGCCAAGTTTGCTTCTTTCATCACACAGTACAGCACCGGCCAGGTCAGCGCCAGCGTGGAGATCGAG
rh.62-D   1986  GTTTACGCCCTGCCAAGTTTGCTTCTTTCATCACACAGTACAGCACCGGCCAGGTCAGCGCCAGCGTGGAGATCGAG
AAV7-D    1986  GTTTACTCCTGCCAAGTTTGCTTCTTTCGTTCTTCATCACACAGTACAGCACCGGACAAGTCAGCGCCAGCGTGGAGATCGAG
rh.52-E   1989  GTTCAACCAGGCCAAGCTGAATTCTTTCATCACGCAGTACAGCACCGGACAAGTCAGCGCCAGCGTGGAAATCGAG
rh.51-E   1989  GTTCAACCAGGCCAAGCTGAATTCTTTCATCACGCAGTACAGCACCGGACAAGTCAGCGCCAGCGTGGAGATCGAG
hu.39-E   1989  GTTCAACCAGGCCAAGCTGAATTCTTTCATCACGCGCAGTACAGCACCGGACAAGTCAGCGCCAGCGTGGAGATCGAG
rh.53-E   1989  GTTCAACCAGGCCAAGCTGAATTCTTTCATCACGCAGTACAGCACCGGACAAGTCAGCGCCAGCGTGGAGATCGAG
hu.37-E   1989  GTTCAACCAGGCGAAATTGGCTTCCTTCATTACGCAGTACAGCACCGGACAAGTCAGCGCCAGCGTGGAAATTGAA
rh.43-E   1983  CTTCAACCAGTCAAAGCTCAAACTCTTTCATCACGCAATACAGCACCGGACAAGTCAGCGTCAGCGTGGAGATCGAG
rh.50-E   1989  GTTCAACCAGGCCAAGCTGAATTCTTTCATCACGCAGTACAGCACCGGACAAGTCAGCGTCAGCGTGGAGATCGAG
rh.49-E   1989  GTTCAACCAGGCCAAGCTGAATTCTTTCATCACGCAGTACAGCACCGGACAAGTCAGCGTCAGCGTGGAGATCGAG
rh.61-E   1989  GTTCAGCCAGGCCAAGCTGAATTCTTTCCTTCATTACGCAGTACAGCACCGGACAAGTCAGCGTCAGCGTGGAAATCGAG
rh.41-E   1989  GTTCAGCCAGGCCAAGCTGAATTGGCTTCTTTCATCACGCAGTACAGCACCGGACAAGTCAGCGTCAGCGTGGAGATCGAG
rh.64-E   1989  GTTCAGCCAGGCCAAGCTGAATTGGCTTCTTTCATCACGCAGTACAGCACCGGACAAGTCAGCGTCAGCGTGGAGATCGTG
rh.42-E   1989  GTTCAGCCAGGCCAAGCTGAAATTGGCTTCTTTCATCACGCAGTACAGCACCGGACAAGTCAGCGTCAGCGTGGAGATCGAG
rh.57-E   1989  GTTCAGCCAGGCCAAGCTGAAATTGGCTTCTTTCATCACGCAGTACAGCACCGGACAAGTCAGCGCCAGCGTGGAAATCGAG
rh.40-E   1989  GTTCAGCCAGGCCAAGCTGAAATTGGCTTCTTTCATCACGCAGTACAGCACCGGACAAGTCAGCGCCAGCGTGGAAATCGAG
hu.42-E   1989  GTTCAGCCAGGCCAAGCTGAAATTGGCTTCTTTCATCACGCAGTACAGCACCGGACAAGTCAGCGCCAGCGTGGAAATCGAG
AAV8-E    1989  CTTCAACCAGTCAAGCTCAAAGCTCTTTCATCACGCAATACAGCACCGGACAAGTCAGCGCCAGCGTGGAATTGAA
rh.58-E   1989  CTTCAACCAGGCCAAGCTGAATTCTTTCATCACGCAGTACAGCACCGGACAAGTCAGCGCCAGCGTGGAGATCGAG
rh.40-E   1989  GTTCAGCCAGGCCAAATTGGCTTCCTTCCTTCATCACGCAGTACAGCACCGGCCAGCAAGTCAGCGCCAGCGTGGAGATCGAG
hu.67-E   1989  GTTCAGCCAGGCCAAATTGGCTTCTTTCATCACGCAGTACAGCACCGGACAAGTCAGCGCCAGCGTGGAAATCGAG
hu.17-E   1989  GTTCAGTCAGGCCAAGCTGGCGTCGTTCCTTCGTTCGTTCATCACGCAGTACAGCACCGGACAAGTCAGCGCCAGCGTGGAAATTGAA
hu.6-E    1989  CTTCAGTCAGGCCAAGCTGGCGTCGTTCCTTCGTTCGTCATCACGCAGTACAGCACCGGACAAGTCAGCGCCAGCGTGGAAATTGAA
hu.66-E   1989  GTTCAGCCAGGCGAAATTGGCTTCTTTCATCACGCAGTACAGCACCGGACAAGTCAGCGCCAGCGTGGAAATCGAG
rh.38-E   1989  GTTCAGCCAGGCGAAATTGGCTTCTTTCATCACGCAGTACAGCACCGGACAAGTCAGCGCCAGCGTGGAGATCGAG
hu.32-F   1983  TTTCAATAAGGACAAGCTGAACTCTTTCATCACCCAGTATTCTACTGGCCAAGTCAGCGCCAGCGTGGAGATTGAG
AAV9/hu   1983  CTTCAACAAGACAAGCTGAACTCTTTCATCACCCAGTATTCTACTGGCCAAGTCAGCGCCAGCGTGGAGATCGAG
hu.31-F   1983  TTTCAATAAGGACAAGCTGAACTCTTTCATCACCCAGTATTCTACTGGCCAAGTCAGCGCCAGCGTGGAGATTGAG
```

```
rh.53-E   2059  TGGGAGCTGCAGAAGGAGAACAGCAAGCGCTGGAACCCAGAGATTCAGTATACTTCCAACTACTACAAAT
hu.37-E   2059  TGGGAGCTGCAGAAGGAGAACAGCAAGCGCTGGAACCCAGAGATTCAGTACACTTCAAACTACTACAAAT
rh.43-E   2053  TGGGAGCTACAGAAGGAGAAGAAGCAAGCGCTGGAACCCAGAGATTCAGTACACTTCCAACTACTACAAAT
rh.50-E   2059  TGGGAGCTGCAGAAGGAGAACAGCAAGCGCTGGAACCCAGAGATTCAGTATACTTCCAACTACTACAAAT
rh.49-E   2059  TGGGAGCTGCAGAAGGAGAACAGCAAGCGCTGGAACCCAGAGATTCAGTATACTTCCAACTACTACAAAT
rh.61-E   2059  TGGGAGCTGCAGAAGGAGAACAGCAAGCGCTGGAACCCAGAGATTCAGTATACTTCCAACTACTACAAAT
hu.41-E   2059  TGGGAGCTGCAGAAGGAGAACAGCAAGCGTTGGAACCCAGAGATTCAGTACACTTCAAACTACTACAAAT
rh.64-E   2059  TGGGAGCTGCAGAAGGAGAACAGCAAACGCTGGAACCCAGAGATTCAGTACACTTCCAACTACTACAAAT
hu.42-E   2059  TGGGAGCTGCAGAAGGAGAACAGCAAGCGCTGGAACCCAGAGATTCAGTACACTTCAAACTACTACAAAT
hu.57-E   2059  TGGGAGCTGCAGAAGGAGAACAGCAAGCGCTGGAACCCAGAGATTCAGTACACTTCAAACTACTACAAAT
hu.40-E   2059  TGGGAGCTGCAGAAGGAGAACAGCAAACGCTGGAACCCAGATCCAGTACACTTCCAACTACTACAAAT
AAV8-E    2059  TGGGAGCTGCAGAAGGAGAAAACAGCAAGCGCTGGAACCCAGAGATTCAGTATACTTCCAACTACTACAAAT
rh.58-E   2059  TGGGAGCTGCAGAAGGAGAACAGCAAGTGCTGGAACCCAGAGATTCAGTACACTTCCAACTACTACAAAT
rh.40-E   2059  TGGGAGCTGCAGAAGGAGAACAGCGATGGAACGCTGGAACCCAGAGAAATTCAGTACACTTCCAACTACTACAAAT
hu.67-E   2059  TGGGAGCTGCAGAAGGAGAACAGCAAGCGCTGGAACCCAGAGATTCAGTACACTTCCAACTACTACAAAT
hu.17-E   2059  TGGGAGCTGCAGAAGGAGAGAGACAGCAAGCGCTGGAACCCAGAGATTCAGTACACTTCAAACTATAACAAAT
hu.6-E    2059  TGGGAGCTGCAGAAGGAGAACAGCAAGCGCTGGAACCCAGAGATTCAGTATACTTCCAACTACTACAAAT
hu.66-E   2059  TGGGAGCTGCAGAAGGAGAGAGACAGCAAGCGCTGGAACCCAGAACCGAGATTCAGTACACTTCAAACTACTACAAAT
rh.38-E   2059  TGGGAGCTGCAGAAGGAGAGAGACAGCAAGCGCTGGAACCCAGAACCGAGATCCAGTACACTTCCAACTACTACAAAT
rh.32-F   2053  TGGGAGCTGCAGAAGGAGAAAACAGCAAGCGCTGGAACCCAGATCCAGTACACTTCCAACTATTACAAGT
AAV9/hu   2053  TGGGAGCTGCAGAAGGAGAAAACAGCAAGCGCAAGCCAGCGCTGGAACCCGGAGATCCAGTACACTTCCAACTATTACAAGT
hu.31-F   2053  TGGGAGCTGCAGAAGGAGAAACAGCAAGCGCTGGAACCCGGAGATCCAGTACACTTCCAACTATTACAAGT

....|....|....|....|....|....|....|....|....|....|....|....|....|....|
                         2180          2190          2200          2210          2220          2230          2240

AAV5      2087  CCCAGTTTGTGGACTTTGCCCCGGACAGCAGCACCAGACCTATCGGAACCCGATA
AAV3-3    2123  CTGTTAATCTGGACTTTGTGGGCTCCCGATGCGGCTGGACAATACACTGAACCTAGAGCCTACCGAGCGCTA
AAV4-4    2117  AAAACTCTCGTTTGATTTTACTGTGGACAACAATGGACTTTATACTGAACCTCGCCCATTGCCACCCGTTA
AAV1-A    2123  CTGCCAACGTTGATTTTACTGTGGACAACAATGGACTTTATACTGAACCTCGCCCATTGGCACCCGTTA
hu.46-A   2123  CTGCCAACGTTGATTTTACTGTGGACAACAATGGACTTTATACTGAACCTCGCCCATTGGCACCCGTTA

| | | |
|---|---|---|
| rh.64-E | 2129 | CTACAAATGTGGACTTTGCTGTGTTAATACTGAGGGTGTTTACTCTGAGCCTCGCCCCCATTGGCACTCGTTA |
| hu.42-E | 2129 | CTACAAATGTGGACTTTGCTGTGTTAATACTGAGGGTGTTTACTCTGAGCCTCGCCCCCATTGGTACTCGTTA |
| rh.57-E | 2129 | CTACAAATGTGGACTTTGCTGTGTTAATACTGAGGGTGTTTACTCTGAGCCTCGCCCCCATTGGCACTCGTTA |
| hu.40-E | 2129 | CTACAAATGTGGACTTTGCTGTGTTAATACTGAGGGTGAACTTATTCTGAGCCTCGCCCCCATTGGTACTCGTTA |
| AAV8-E | 2129 | CTACAAGTGTGGACTTTGCTGTGTTAATACTGAGGGTGAACTTATTCTGAGCCTCGCCCCCATTGGCACCCGTTA |
| rh.58-E | 2129 | CTACAAATGTGGACTTTGCTGTGTTAATACTGAGGGTGAACTTATTCTGAGCCTCGAACCCCATTGGCACTCGTTA |
| rh.40-E | 2129 | CTACAAATGTGGACTTTGCTGTGTTAATACTGAGGGTGAACTTATTCTGAGCCTCGCCCCCATTGGCACTCGTTA |
| hu.67-E | 2129 | CTACAAATGTGGACTTTGCTGTGTCAATTCTGAGGGTGTTACTCTGAGCCTCGCCCCCATTGGTACTCGTTA |
| rh.40-E | 2129 | CTACAAATGTGGACTTTGCTGTGTCAATACAGACATATTCAGAGGGAACTTATTCTGAGCCTCGCCCCCATTGGTACTCGTTA |
| hu.17-E | 2129 | CTACAAATGTGGACTTTGCTGTGTCAATACAGAGGGAACTTATTGTGTGTATTCAGAACTAATGGTGTATTCTGAGCCTCGCCACCAGATA |
| hu.6-E | 2129 | CTGTTAATGTGGACTTTACTGTGCTGTCAATGTGGACACTTATTGTTGTATTCAGAACTCGACTCAAGTGCCTCGCCACCCGTTA |
| hu.66-E | 2129 | CTACAAATGTGGACTTTGCTGTGTCAATACAGAGGGAACTTATTCAGAACTTATTCTGAGCCTCGCCCCCATTGGTACTCGTTA |
| rh.38-E | 2129 | CTACAAATGTGGACTTTGCTGTGTCAATACAGAGGGAACTTATTCTGAGCCTCGCCCCCATTGGTACTCGCTA |
| hu.32-F | 2123 | CTAATAATGTTGAATTGCTGTTAATACTGAAGGTGTATATAGTGAACCCCGCCCCCATTGGCACCAGATA |
| AAV9/hu | 2123 | CTAATAATGTGAATTGCTGTTAATACTGAAGGTGTATATAGTGAACCCCGCCCCCATTGGCACCAGATA |
| hu.31-F | 2123 | CTACAATGTGAATTGCTGTTAGTACTGAAGGTGTATATATGTGAACCCCGCCCCCATTGGCACCAGATA |

```
                                   2250       2260
                              ....|....|....|....|
AAV5     2157   CCTTACCCGACCCCTT----
AAV3-3   2193   TCTCACACGAAACTTG----
AAV4-4   2187   CCTCACCCACCACCTGTAA-
AAV1-A   2193   CCTTACCCGTCCCCTGTAA-
hu.46-A  2193   CCTTACCCGTCCCCTGTAA-
hu.48-A  2193   CCTTACCCGTCCCCTGTAA-
hu.44-A  2193   CCTTACCCGTCCCCTGTAA-
hu.43-A  2196   CCTCACCCGTCCCCTGTAA-
AAV6-A   2193   CCTCACCCGTCCCCTGTAA-
hu.34-B  2190   CCTGACTCGTAATCTGTAA-
hu.47-B  2190   CCTGACTCGTAATCTGTAA-
hu.29-B  2190   CCTGACTCGTAATCTGTAA-
```

FIG. 3CK

| | | |
|---|---|---|
| hu.63-B | 2190 | CCTGACTCGTAATCTGTAA- |
| hu.56-B | 2190 | CCTGACTCGTAATCTGTAA- |
| hu.45-B | 2190 | CCTGACTCGTAATCTGTAA- |
| hu.57-B | 2187 | CCTGACTCGTAATCTGTAA- |
| hu.35-B | 2190 | CCTGACTCGTAATCTGTAA- |
| hu.58-B | 2190 | CCTGACTCGTAATCTGTAA- |
| hu.28-B | 2190 | CCTGACTCGTAATCTGTAA- |
| hu.51-B | 2190 | CCTGACTCGTAATCTGTAA- |
| hu.19-B | 2190 | CCTGACTCGTAATCTGTAA- |
| hu.49-B | 2190 | CCTGACTCGTAATCTGTAA- |
| hu.52-B | 2190 | CCTGACTCGTAATTTGTAA- |
| hu.13-B | 2190 | CCTGACTCGTAATCTGTAA- |
| AAV2-B | 2190 | CCTGACTCGTAATCTGTAA- |
| hu.20-B | 2190 | CCTGACTCGTAATCTGTAA- |
| hu.24-B | 2190 | CCTGACTCGTAATCTGTAA- |
| hu.64-B | 2190 | CCTGACTCGTAATCTGTAA- |
| hu.27-B | 2190 | CCTGACTCGTAATCTGTAA- |
| hu.21-B | 2190 | CCTGACTCGTAATCTGTAA- |
| hu.22-B | 2190 | CCTGACTCGTAATCTGTAA- |
| hu.23-B | 2190 | CCTGACTCGTAATCTGTAA- |
| hu.7-C | 2190 | CCTGACTCGTAATCTGTAA- |
| hu.61-C | 2190 | CCTGACTCGTAATCTGTAA- |
| rh.56-C | 2190 | CCTGACTCGTAATCTGTAA- |
| hu.9-C | 2190 | CCTGACTCGTAATCTGTAA- |
| hu.54-C | 2187 | CCTGACTCGTAATCTGTAA- |
| hu.53-C | 2187 | CCTGACTCGTAATCTGTAA- |
| hu.60-C | 2190 | CCTGACTCGTAATCTGTAA- |
| hu.55-C | 2187 | CCTGACTCGTAATCTGTAA- |
| hu.2-C | 2190 | CCTGACTCGTAATCTGTAAT |
| hu.1-C | 2190 | CCTGACTCGTAATCTGTAA- |

FIG. 3CL

| | | |
|---|---|---|
| hu.18-C | 2190 | CCCGACTCGTAATCTGTAA- |
| hu.3-C | 2193 | CCTGACTCGTAATCTGTAA- |
| hu.25-C | 2190 | CCTGACTCGTAATCTGTAA- |
| hu.15-C | 2190 | CCTGACTCGTAATCTGTAA- |
| hu.16-C | 2190 | CCTGACTCGTAATCTGTAA- |
| hu.11-C | 2190 | CCTGACTCGTAATCTGTAA- |
| hu.10-C | 2190 | CCTGACTCGTAATCTGTAA- |
| hu.4-C | 2190 | CCTGACTCGTAATCTGTAA- |
| rh.54-D | 2196 | CCTCACCCGTAATCTGTAA- |
| rh.48-D | 2196 | CCTCACCCGTAATCTGTAA- |
| rh.55-D | 2196 | CCTCACCCGTAATCTGTAA- |
| rh.62-D | 2196 | CCTCACCCGTAATCTGTAA- |
| AAV7-D | 2196 | CCTCACCCGTAATCTGTAA- |
| rh.52-E | 2199 | CCTCACCCGTAATCTGTAA- |
| rh.51-E | 2199 | CCTCACCCGTAATCTGTAA- |
| rh.39-E | 2199 | CCCCACCCGTAATCTGTAA- |
| rh.53-E | 2199 | CCTCACCCGTAATCTGTAA- |
| rh.37-E | 2199 | CCTCACCCGTAATCTGTAA- |
| rh.43-E | 2193 | CCTCACCCGTAATCTGTAA- |
| rh.50-E | 2199 | CCTCACCCGTAATCTGTAA- |
| rh.49-E | 2199 | CCTCACCCGTAATCTGTAA- |
| rh.61-E | 2199 | CCTCACCCGTAATCTGTAA- |
| hu.41-E | 2199 | CCTCACCCGTAATCTGTAA- |
| rh.64-E | 2199 | CCTCACCCGTAATCTGTAA- |
| hu.42-E | 2199 | CCTCACCCGTAATCTGTAA- |
| rh.57-E | 2199 | CCTCACCCGTAATCTGTAA- |
| hu.40-E | 2199 | CCTCACCCGTAATCTGTAA- |
| AAV8-E | 2199 | CCTCACCCGTAATCTGTAA- |
| rh.58-E | 2199 | CCTCACCCGTAATCTGTAA- |
| rh.40-E | 2199 | TCTGACACGTAATCTGTAA- |

FIG. 3CM

```
hu.67-E   2199  CCTCACCCGTAATCTGTAA-
hu.17-E   2199  CCTGACTCGTAATCTGTAA-
hu.6-E    2199  CCTCACCCGTAACCTGTAA-
hu.66-E   2199  CCTCACCCGTAATCTGTAA-
rh.38-E   2199  CCTCACCCGTAATCTGTAA-
hu.32-F   2193  CCTGACTCGTAATCTGTAA-
AAV9/hu   2193  CCTGACTCGTAATCTGTAA-
hu.31-F   2193  CCTGACTCGTAATCTGTAA-
```

FIG. 3CN

In Vitro

Liver

Lung

Muscle

ADENO-ASSOCIATED VIRUS (AAV) CLADES, SEQUENCES, VECTORS CONTAINING SAME, AND USES THEREFOR

CROSS REFERENCE TO RELATED APPLICATIONS

This application is a continuation of U.S. patent application No. 15/227,418, filed Aug. 3, 2016, now U.S. Pat. No. 10,265,417, which is a continuation of U.S. patent application No. 13/023,918, filed Feb. 9, 2011, now abandoned, which is a continuation of U.S. patent application No. 10/573,600, filed Mar. 24, 2006, now U.S. Pat. No. 7,906,111, issued Mar. 15, 2011, which is a national stage application under 35 USC § 371 of PCT/US04/028817, filed Sep. 30, 2004, which claims the benefit under 35 USC § 119(e) of the priority of U.S. patent application No. 60/508,226, filed Sep. 30, 2003, now expired, and U.S. patent application No. 60/566,546, filed Apr. 29, 2004, now expired. Each of these applications is hereby incorporated by reference in their entirety.

STATEMENT REGARDING FEDERALLY SPONSORED RESEARCH OR DEVELOPMENT

This application contains work supported by grants NIDDK P30 DK47757 and NHLBI P01 HL59407 from the National Institutes of Health (NIH). The US government may have certain rights in this invention.

BACKGROUND OF THE INVENTION

Adeno-associated virus (AAV), a member of the Parvovirus family, is a small nonenveloped, icosahedral virus with single-stranded linear DNA genomes of 4.7 kilobases (kb) to 6 kb. AAV is assigned to the genus, *Dependovirus*, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

Recent studies suggest that AAV vectors may be the preferred vehicle for gene delivery. To date, there have been several different well-characterized AAVs isolated from human or non-human primates (NHP).

It has been found that AAVs of different serotypes exhibit different transfection efficiencies, and also exhibit tropism for different cells or tissues. However, the relationship between these different serotypes has not previously been explored.

What is desirable are AAV-based constructs for delivery of heterologous molecules.

SUMMARY OF THE INVENTION

The present invention provides "superfamilies" or "clades" of AAV of phylogenetically related sequences. These AAV clades provide a source of AAV sequences useful for targeting and/or delivering molecules to desired target cells or tissues.

In one aspect, the invention provides an AAV clade having at least three AAV members which are phylogenetically related as determined using a Neighbor-Joining heuristic by a bootstrap value of at least 75% (based on at least 1000 replicates) and a Poisson correction distance measurement of no more than 0.05, based on alignment of the AAV vp1 amino acid sequence. Suitably, the AAV clade is composed of AAV sequences useful in generating vectors.

The present invention further provides a human AAV serotype previously unknown, designated herein as clone 28.4/hu.14, or alternatively, AAV serotype 9. Thus, in another aspect, the invention provides an AAV of serotype 9 composed of AAV capsid which is serologically related to a capsid of the sequence of amino acids 1 to 736 of SEQ ID NO: 123 and serologically distinct from a capsid protein of any of AAV1, AAV2, AAV3, AAV4, AAV5, AAV6, AAV7 or AAV8.

Vectors constructed with capsid of this huAAV9 have exhibited gene transfer efficacies similar to AAV8 in liver, superior to AAV1 in muscle and 200 fold higher than AAV 5 in lung. Further, this novel human AAV serotype shares less than 85% sequence identity to previously described AAV1 through AAV8 and is not cross-neutralized by any of these AAVs.

The present invention also provides other novel AAV sequences, compositions containing these sequences, and uses therefor. Advantageously, these compositions are particularly well suited for use in compositions requiring re-administration of AAV vectors for therapeutic or prophylactic purposes.

These and other aspects of the invention will be readily apparent from the following detailed description of the invention.

BRIEF DESCRIPTION OF THE DRAWINGS

FIGS. 2A-2AE are an alignment of the amino acid sequences of AAV vp1 capsid proteins of the invention, with the numbering of the individual sequences reported, and previously published AAV1 [SEQ ID NO: 219]; AAV2 [SEQ ID NO: 221]; AAV3-3 [SEQ ID NO: 217]; AAV4-4 [SEQ ID NO: 218]; AAV5 [SEQ ID NO: 216]; AAV6 [SEQ ID NO: 220]; AAV7 [SEQ ID NO: 222]; AAV8 [SEQ ID NO: 223], and; rh. 25/42-15; 29.3/bb.1; cy.2; 29.5/bb.2; rh.32, rh.33, rh.34, rh.10; rh.24; rh14, rh.16, rh.17, rh.12, rh.18, rh.21 (formerly termed 41.10); rh.25 (formerly termed 41.15); rh2; rh.31; cy.3; cy.5; rh.13; cy.4; cy.6; rh.22; rh.19; rh.35; rh.37; rh.36; rh.23; rh.8; and ch.5 [US Published Patent Application No. 2003/0138772 A1 (Jul. 24, 2003)]. The sequences of the invention include hu.14/AAV9 [SEQ ID NO: 123]; hu.17 [SEQ ID NO: 83], hu. 6 [SEQ ID NO: 84], hu.42 [SEQ ID NO: 85], rh.38 [SEQ ID NO: 86], hu.40 [SEQ ID NO: 87], hu.37 [SEQ ID NO: 88], rh.40 [SEQ ID NO: 92], rh.52 [SEQ ID NO: 96]; rh.53 [SEQ ID NO: 97]; rh.49 [SEQ ID NO: 103]; rh.51 [SEQ ID NO: 104]; rh.57 [SEQ ID NO: 105]; rh.58 [SEQ ID NO: 106], rh.61 [SEQ ID NO: 107]; rh.50 [SEQ ID NO: 108]; rh.43 [SEQ ID NO: 163]; rh.62 [SEQ ID NO: 114]; rh.48 [SEQ ID NO: 115];

Figure 1:
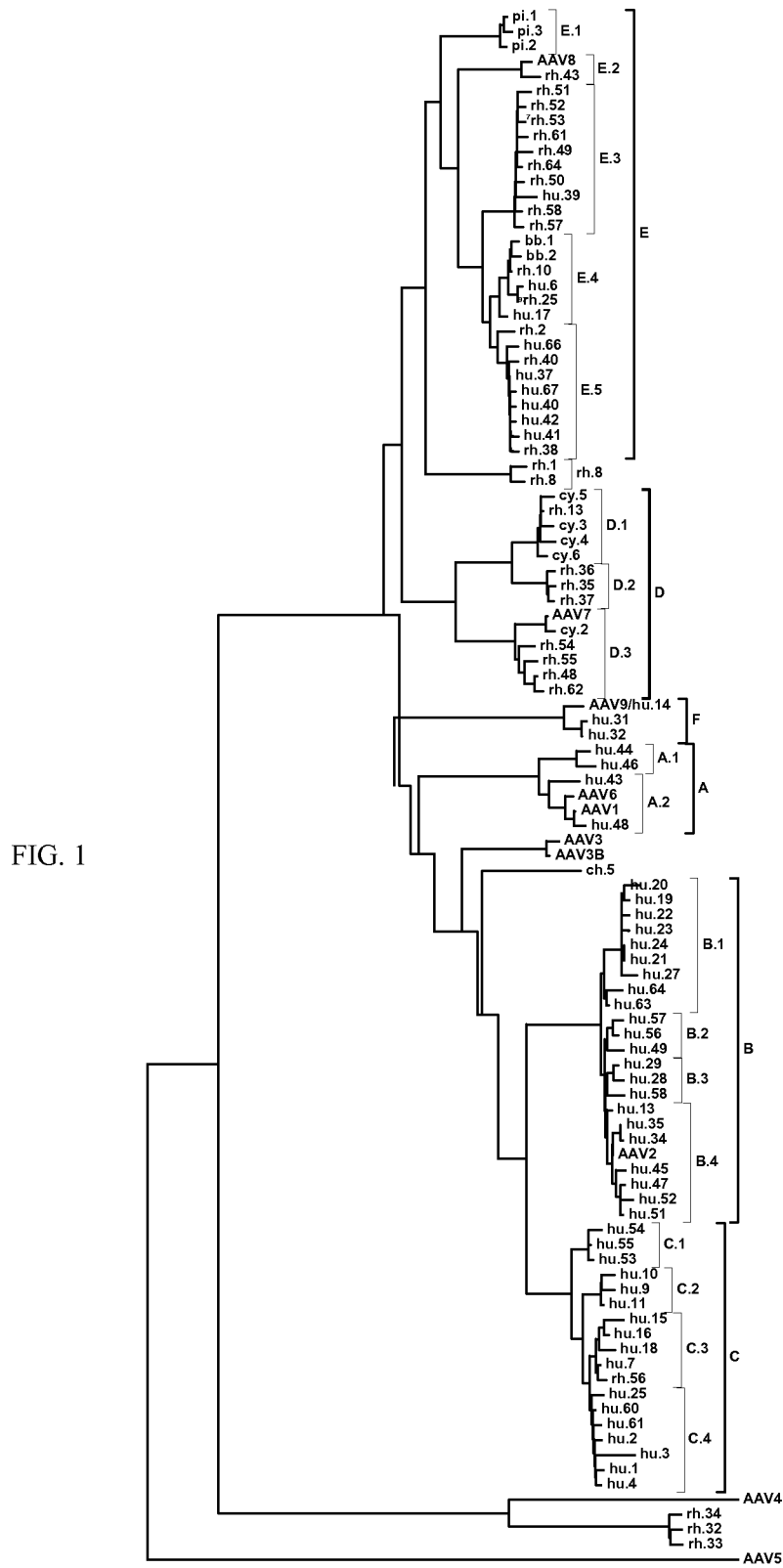
FIG. 1 is a tree showing the phylogenic relationship constructed using the Neighbor-Joining heuristic with Poisson correction distance measurement. The relationship was determined based on the isolated AAV vp1 capsid protein, with the isolated AAV grouped in clades. Groups of individual capsid clones are classified in clades based on their common ancestry. Clade nomenclature goes from A through F; subtypes are represented by the clade letter followed by a number.
Figure 4A:
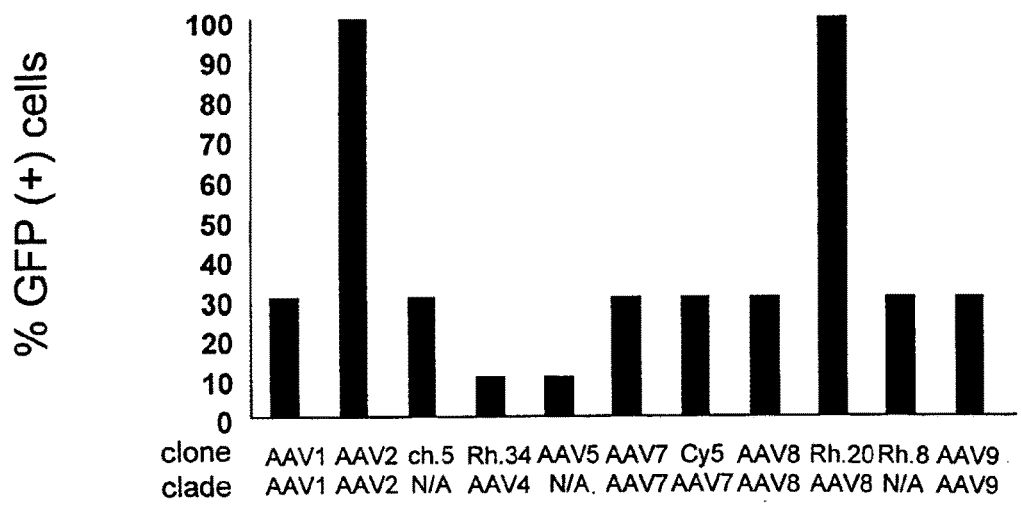
Figure 4B:
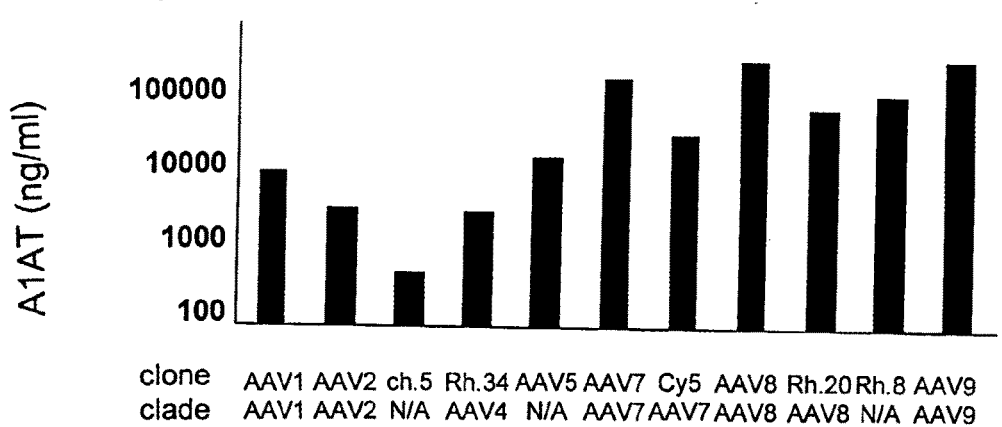
Figure 4C:
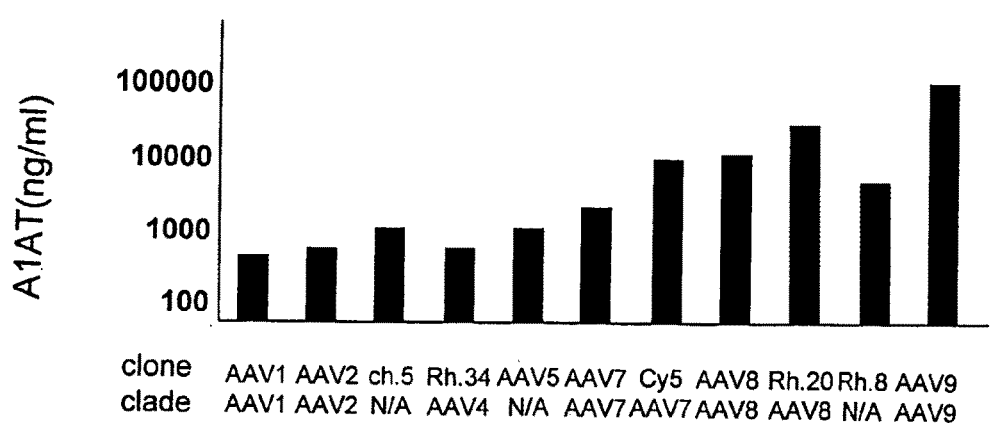
Figure 4D:
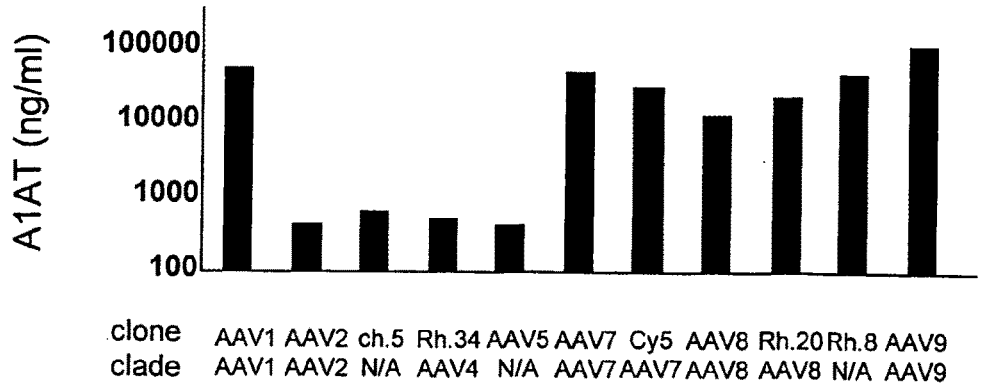

4-9/rh.54 (SEQ ID No: 116); and 4-19/rh.55 (SEQ ID Nos: 117); hu.31 [SEQ ID NO: 121]; hu.32 [SEQ ID NO: 122]; hu.34 [SEQ ID NO: 125]; hu.45 [SEQ ID NO: 127]; hu.47 [SEQ ID NO: 128]; hu.13 [SEQ ID NO: 129]; hu.28 [SEQ ID NO: 130]; hu.29 [SEQ ID NO:132]; hu.19 [SEQ ID NO: 133]; hu.20 [SEQ ID NO: 134]; hu.21 [SEQ ID NO: 135]; hu.23.2 [SEQ ID NO: 137]; hu.22 [SEQ ID NO: 138]; hu.27 [SEQ ID NO: 140]; hu.4 [SEQ ID NO: 141]; hu.2 [SEQ ID NO: 143]; hu.1 [SEQ ID NO: 144]; hu.3 [SEQ ID NO: 145]; hu.25 [SEQ ID NO: 146]; hu.15 [SEQ ID NO: 147]; hu.16 [SEQ ID NO: 148]; hu.18 [SEQ ID NO: 149]; hu.7 [SEQ ID NO: 150]; hu11 [SEQ ID NO: 153]; hu.9 [SEQ ID NO: 155]; hu.10 [SEQ ID NO: 156]; hu.48 [SEQ ID NO: 157]; hu.44 [SEQ ID NO: 158]; hu.46 [SEQ ID NO: 159]; hu.43 [SEQ ID NO: 160]; hu.35 [SEQ ID NO: 164]; hu.24 [SEQ ID NO: 136]; rh.64 [SEQ ID NO: 99]; hu.41 [SEQ ID NO: 91]; hu.39 [SEQ ID NO: 102]; hu.67 [SEQ ID NO: 198]; hu.66 [SEQ ID NO: 197]; hu.51 [SEQ ID NO: 190]; hu.52 [SEQ ID NO: 191]; hu.49 [SEQ ID NO: 189]; hu.56 [SEQ ID NO: 192]; hu.57 [SEQ ID NO: 193]; hu.58 [SEQ ID NO: 194]; hu.63 [SEQ ID NO: 195]; hu.64 [SEQ ID NO: 196]; hu.60 [SEQ ID NO: 184]; hu.61 [SEQ ID NO: 185]; hu.53 [SEQ ID NO: 186]; hu.55 [SEQ ID NO: 187]; hu.54 [SEQ ID NO: 188]; hu.6 [SEQ ID NO: 84]; and rh.56 [SEQ ID NO: 152]. These capsid sequences are also reproduced in the Sequence Listing, which is incorporated by reference herein.

Figure 3B:
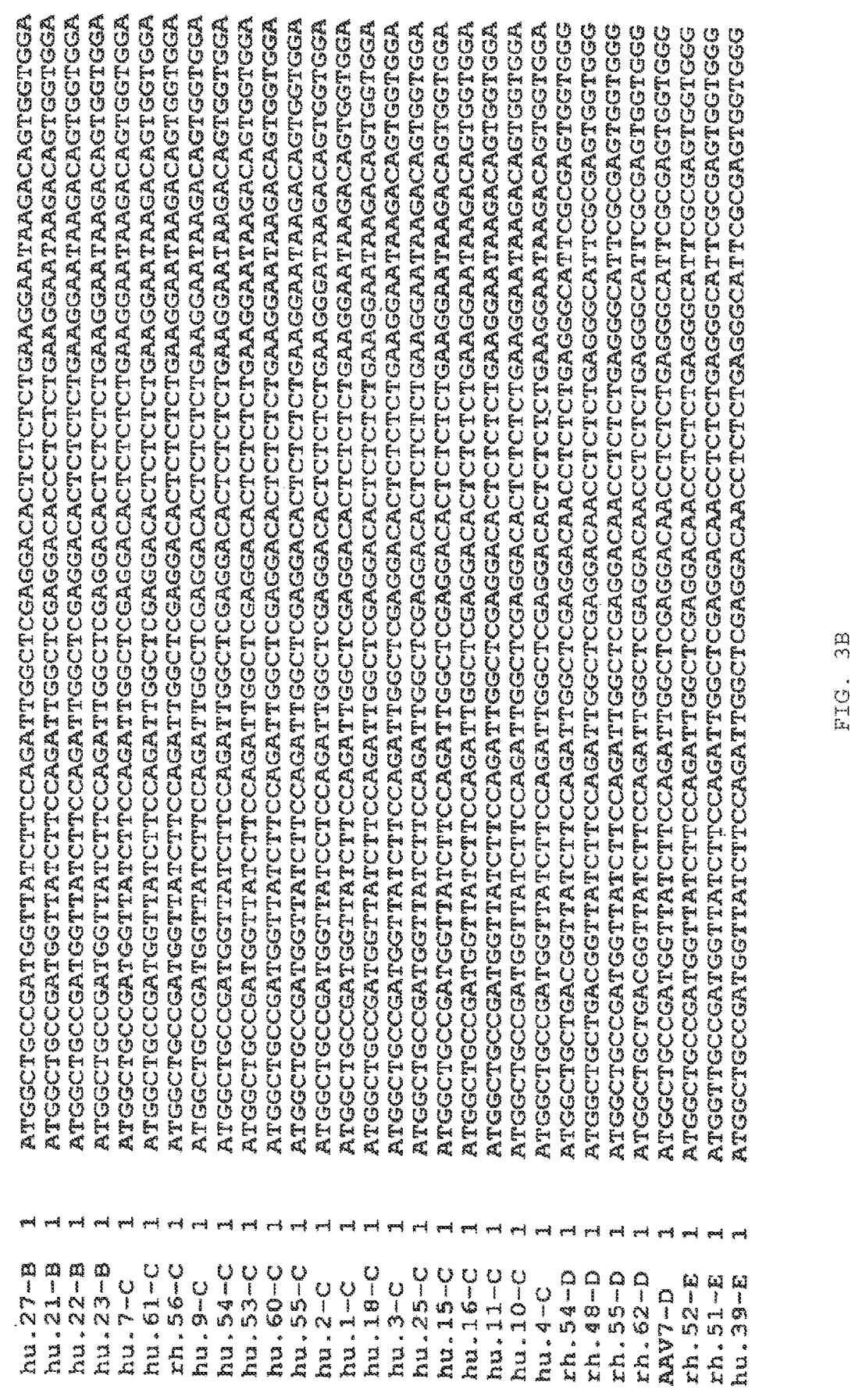
Figure 3E:
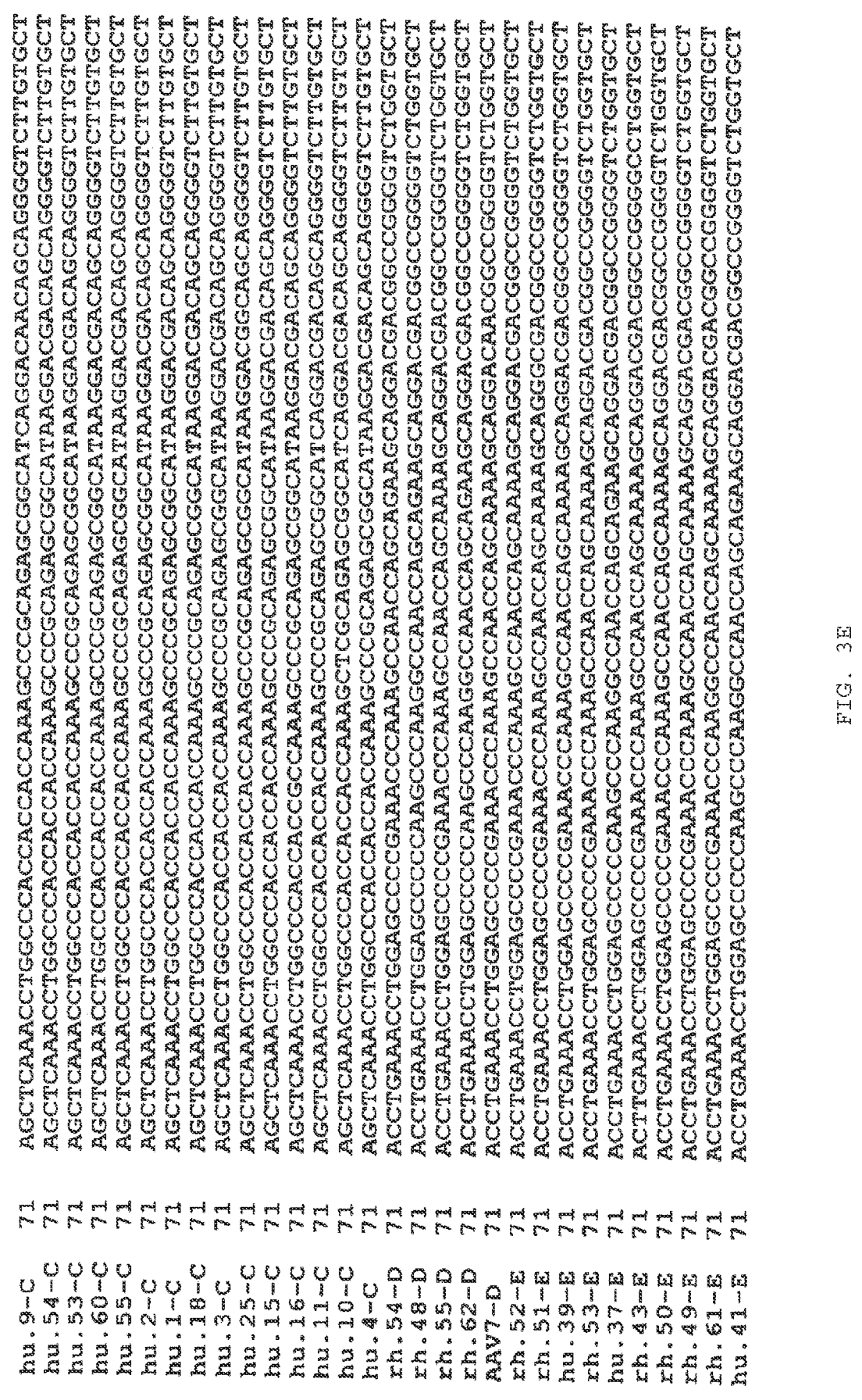
Figure 3F:
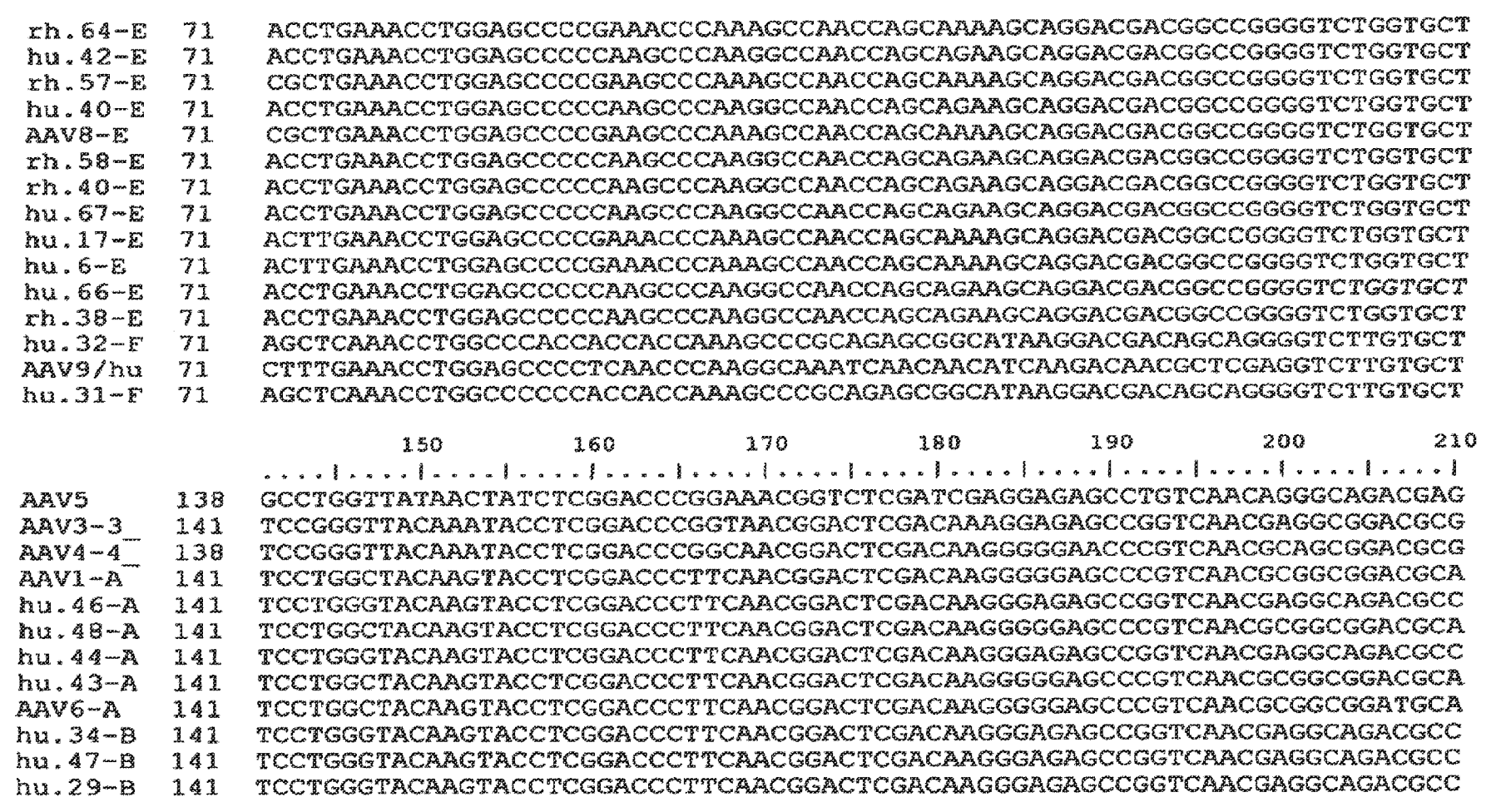
Figure 3G:
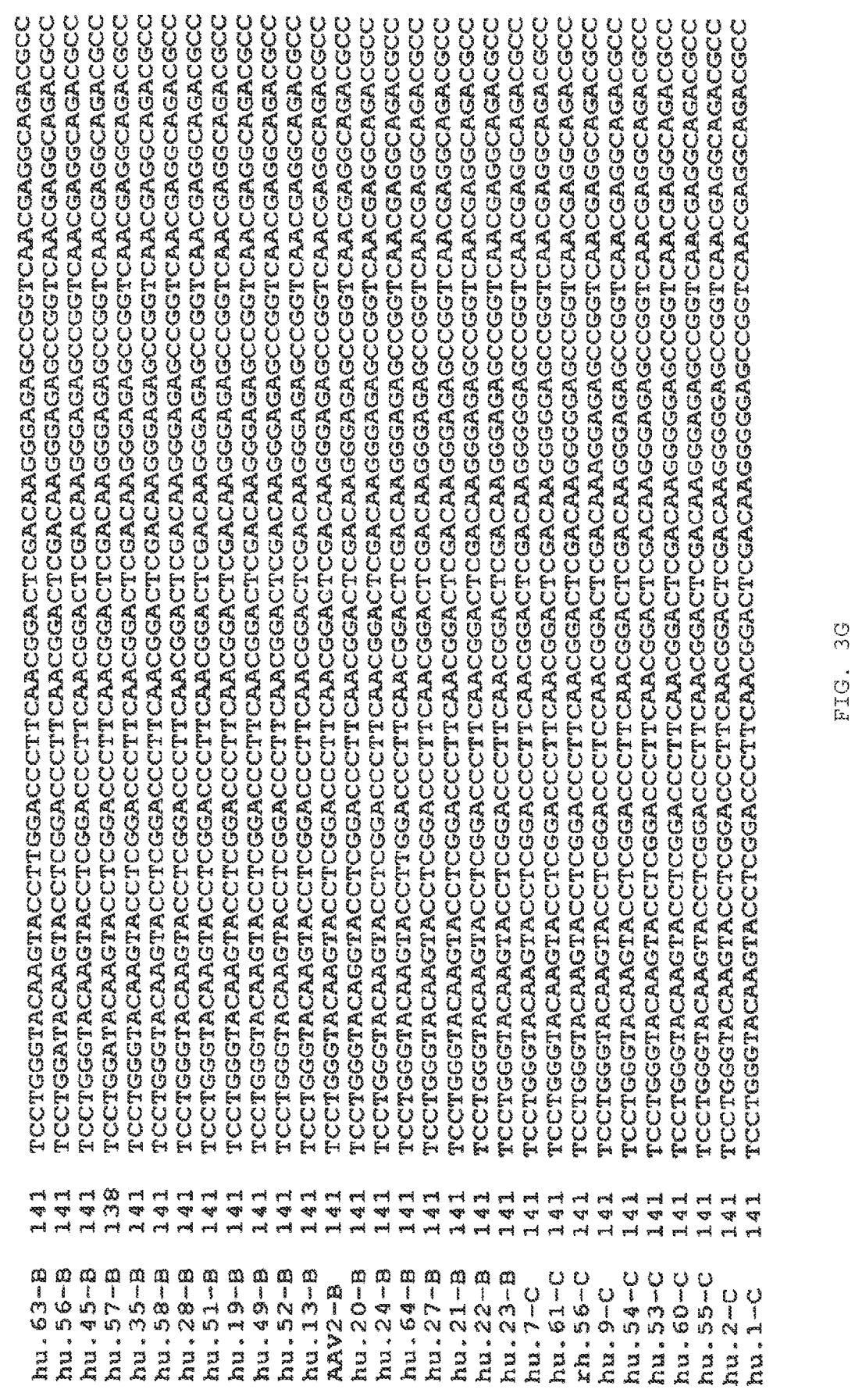
Figure 3H:
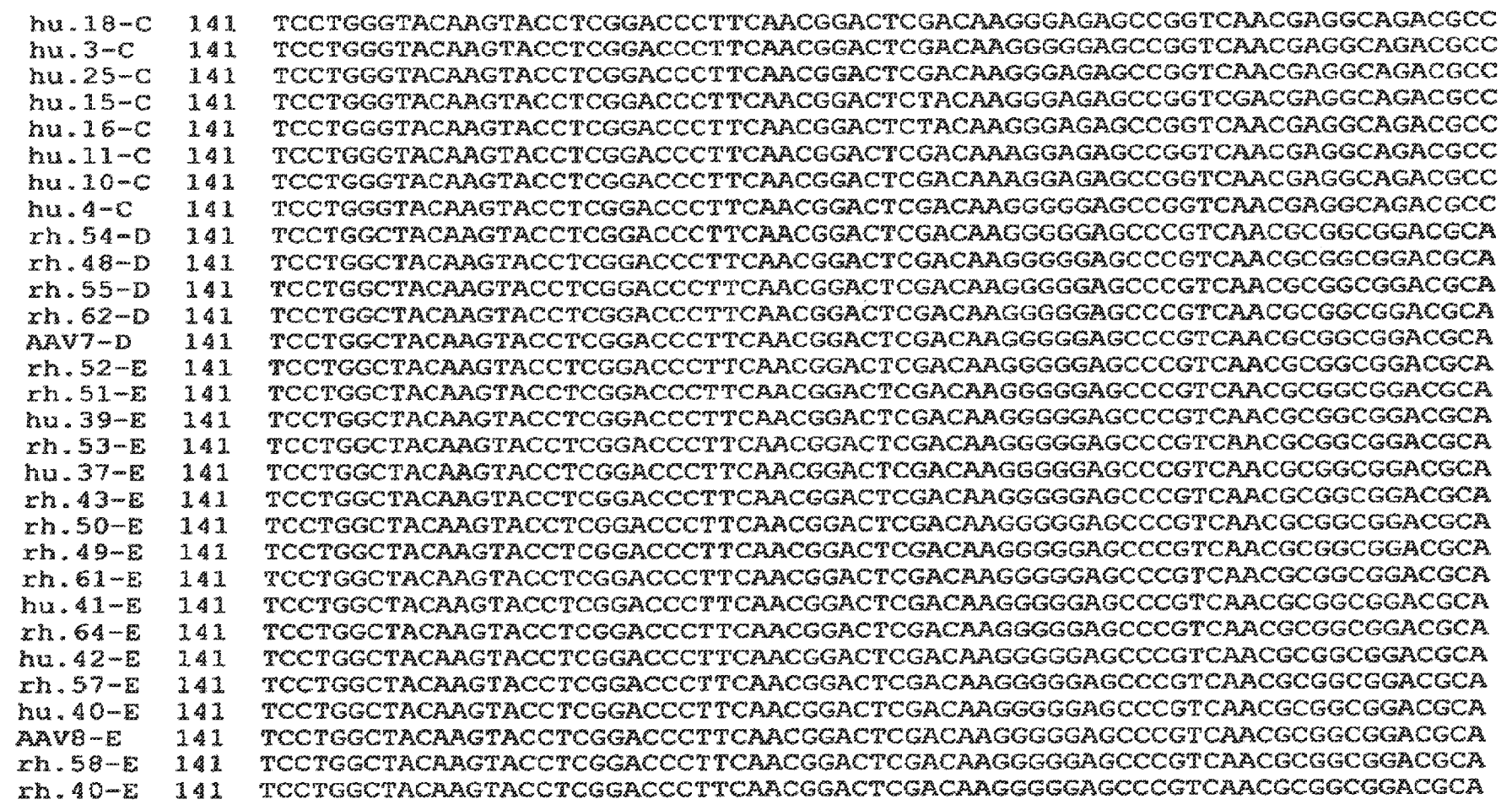
Figure 3K:
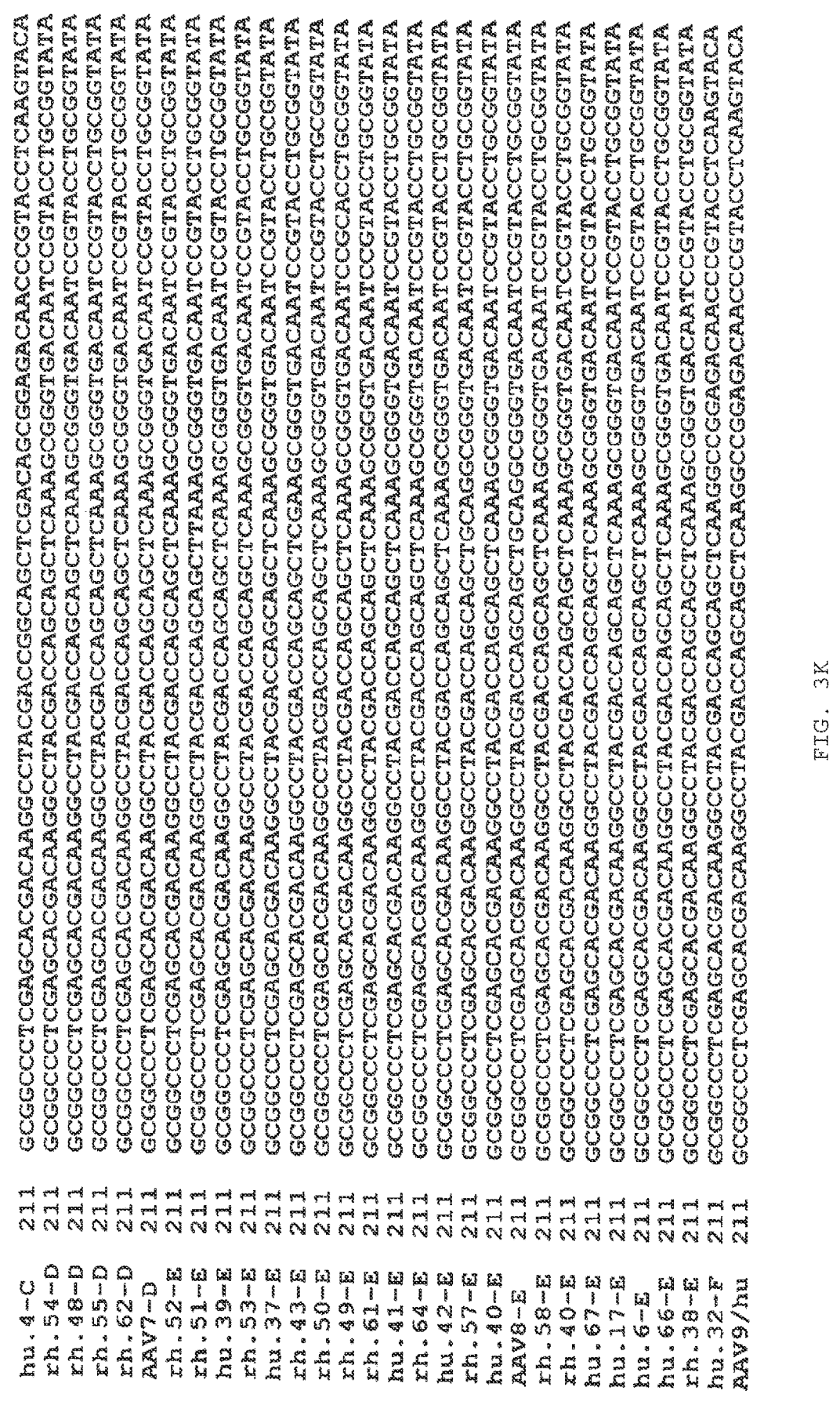
Figure 3L:
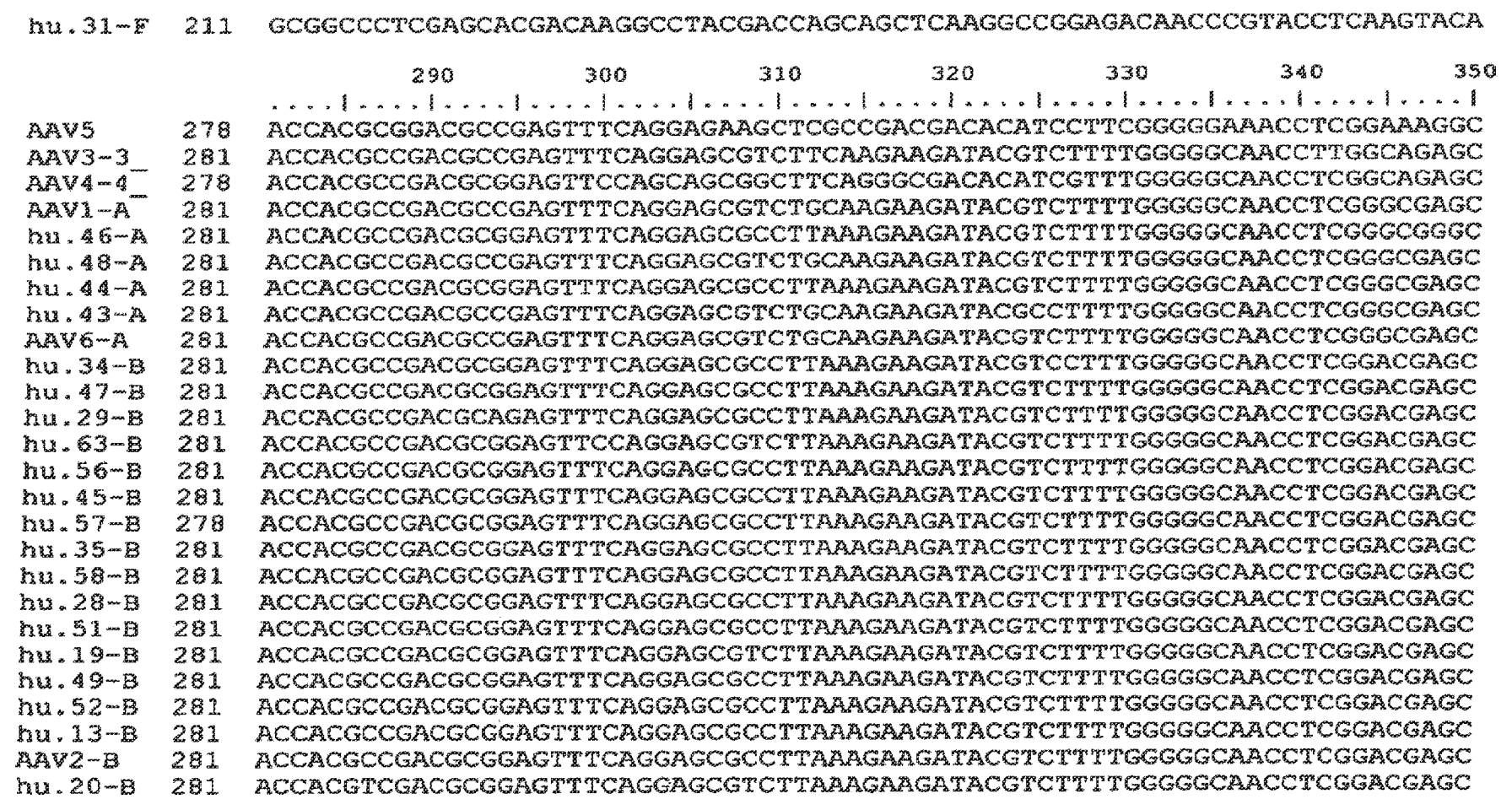
Figure 3N:
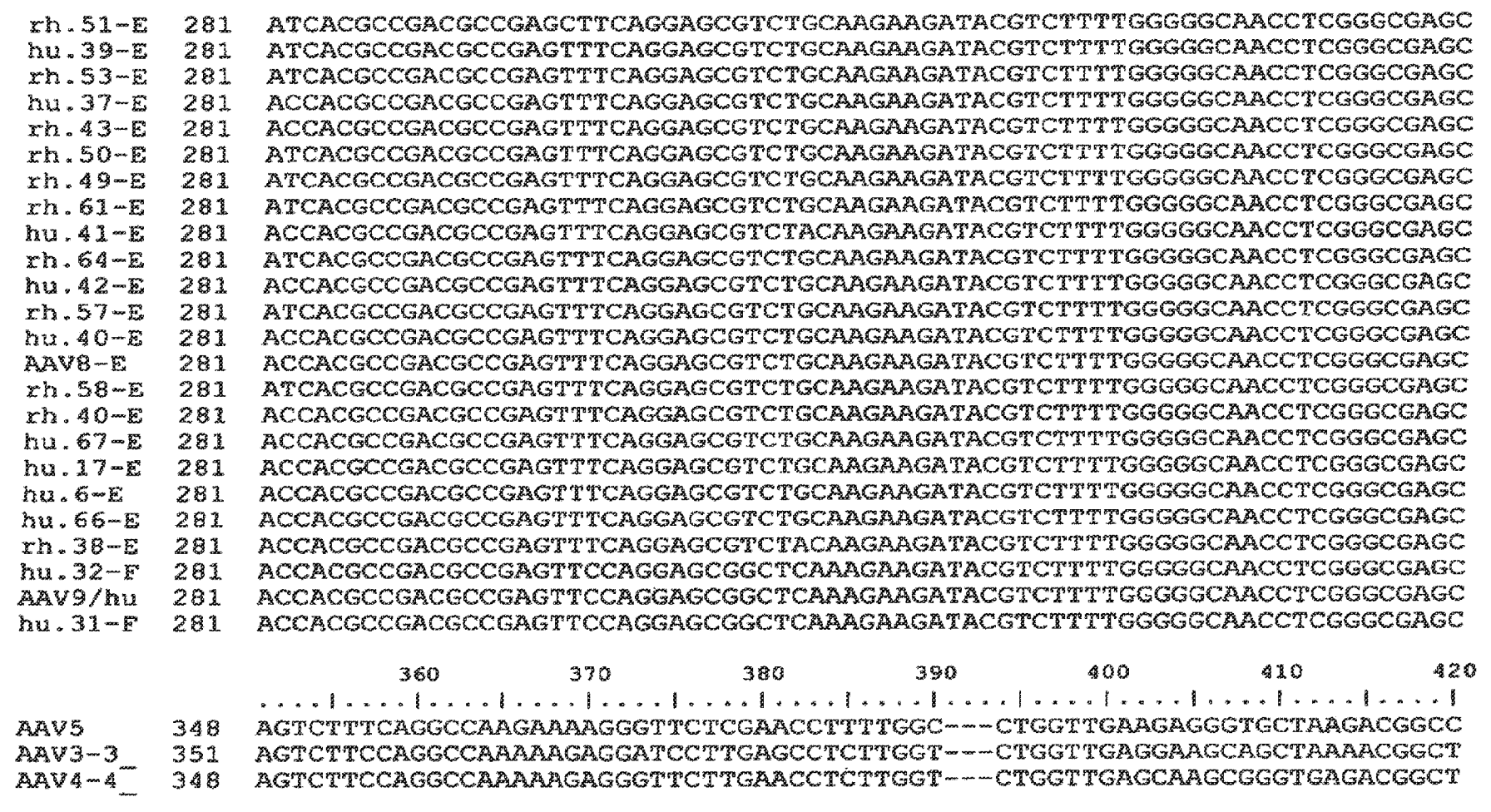
Figure 3P:
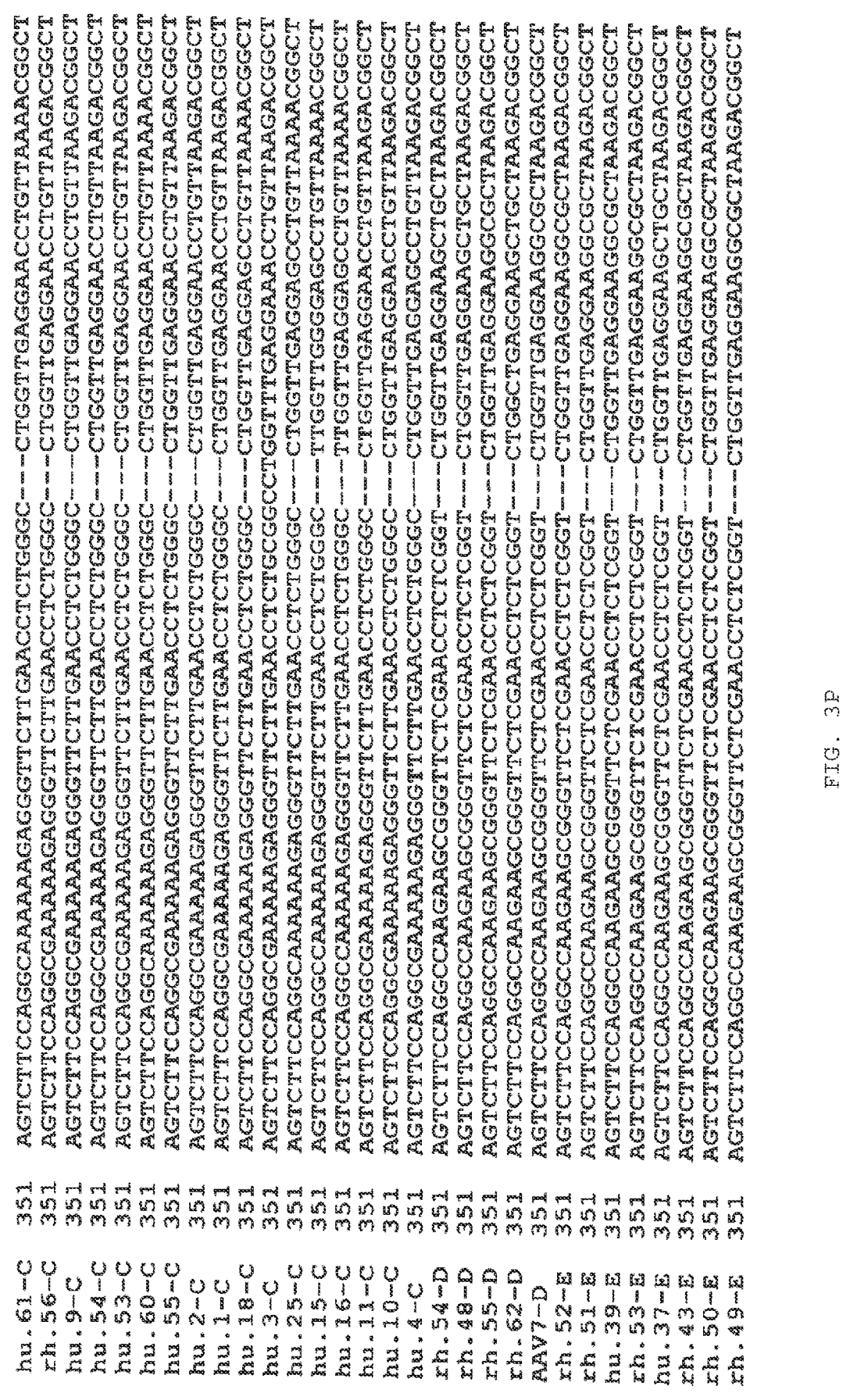
Figure 3R:
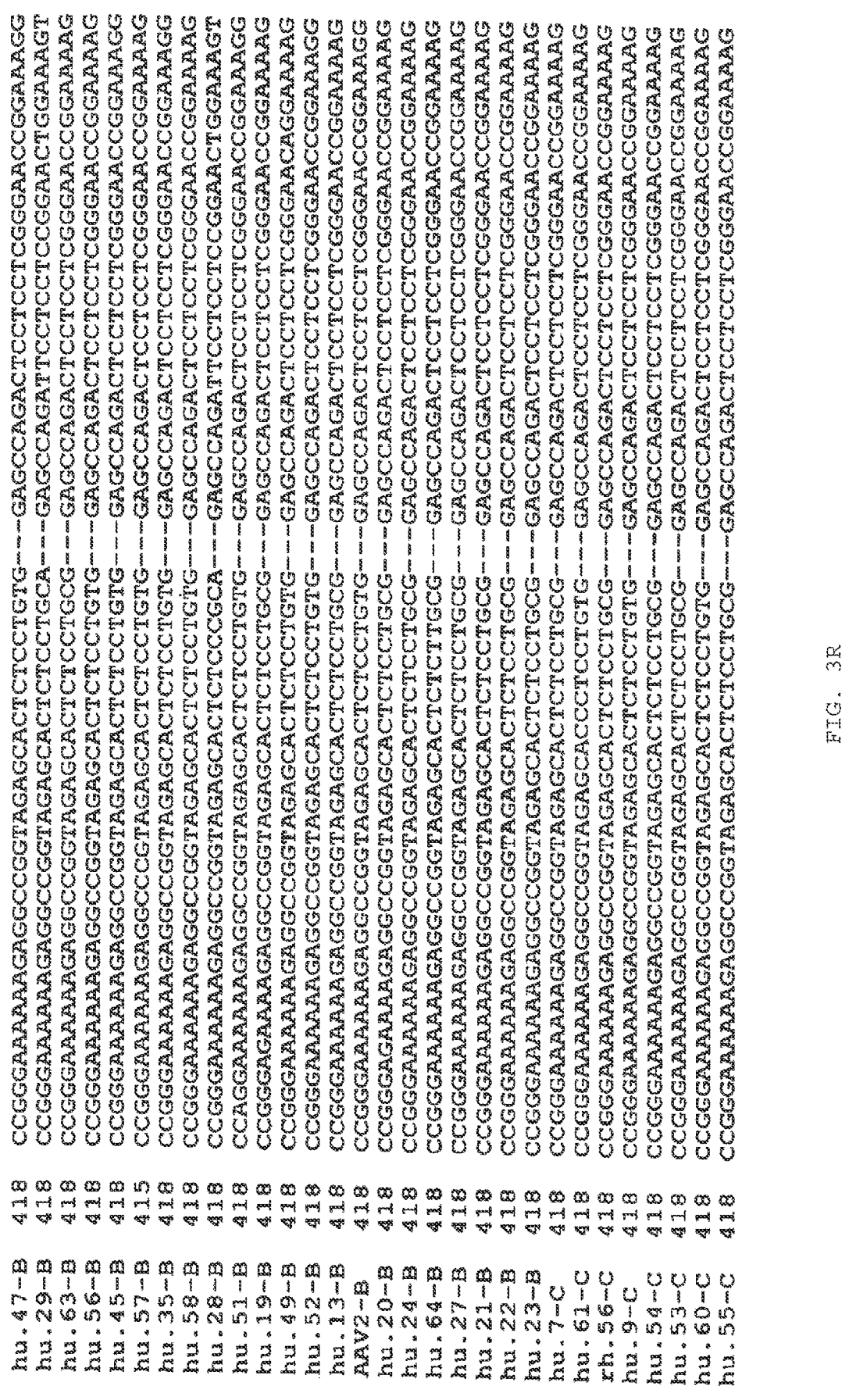
Figure 3S:
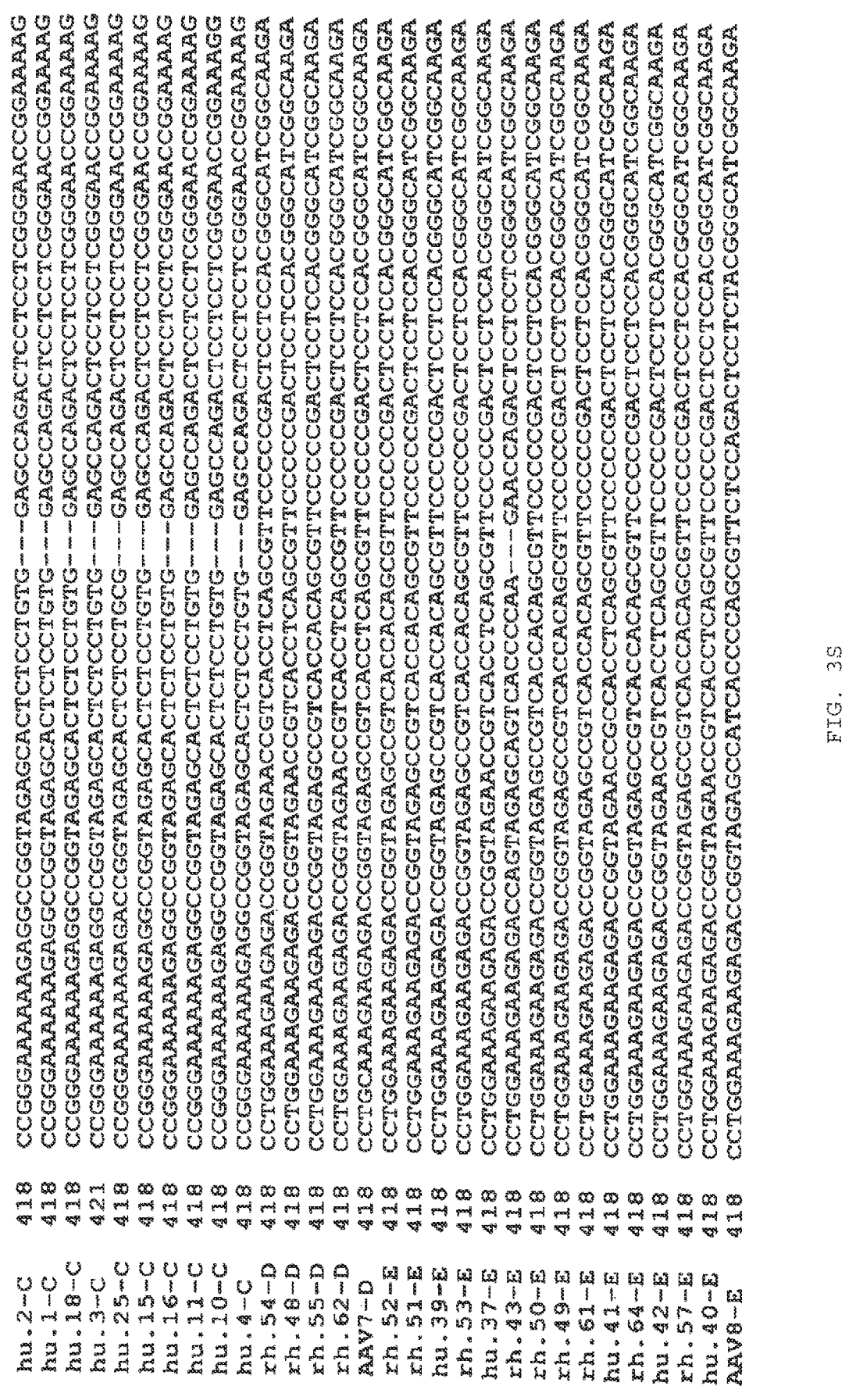
Figure 3U:
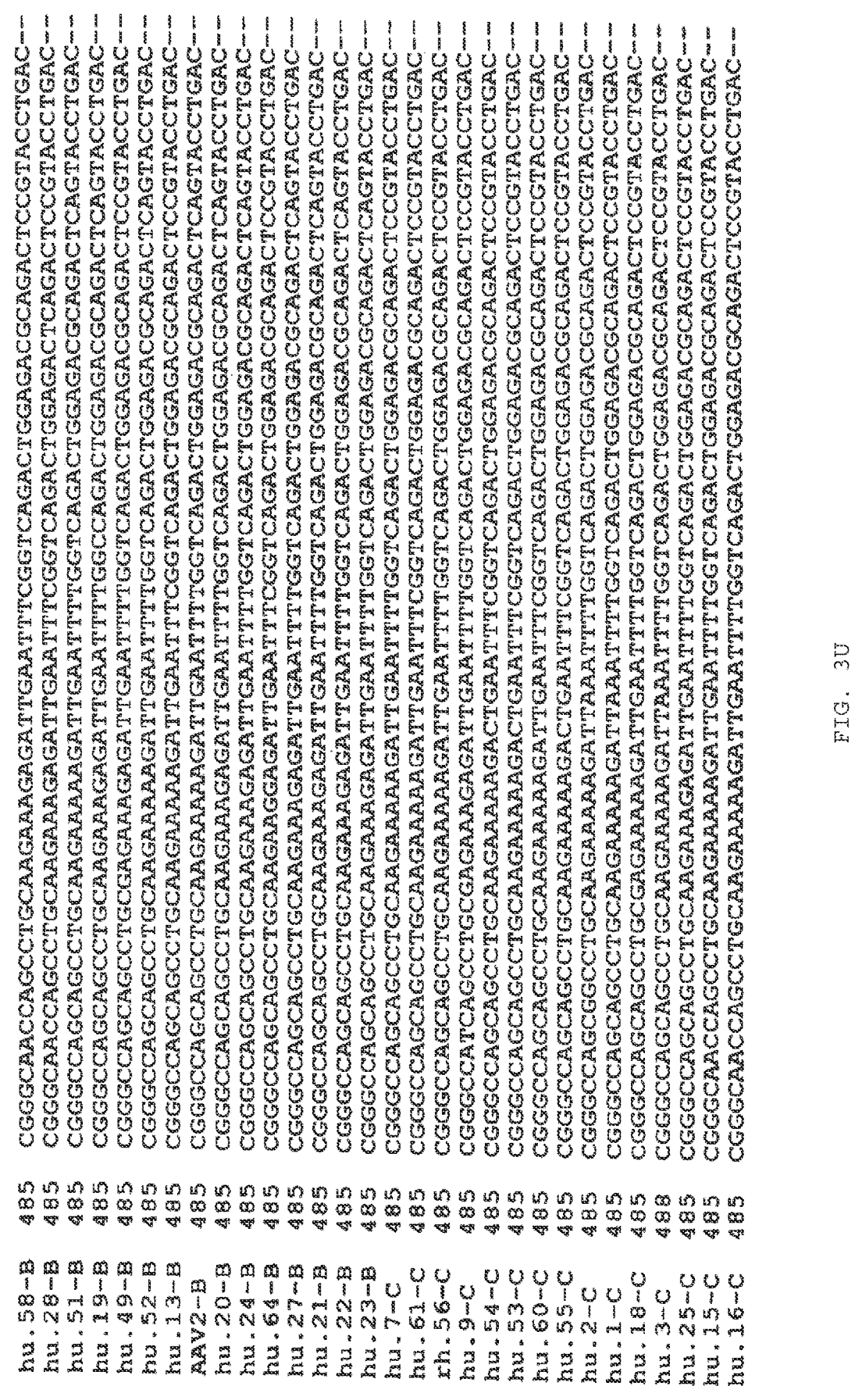
Figure 3V:
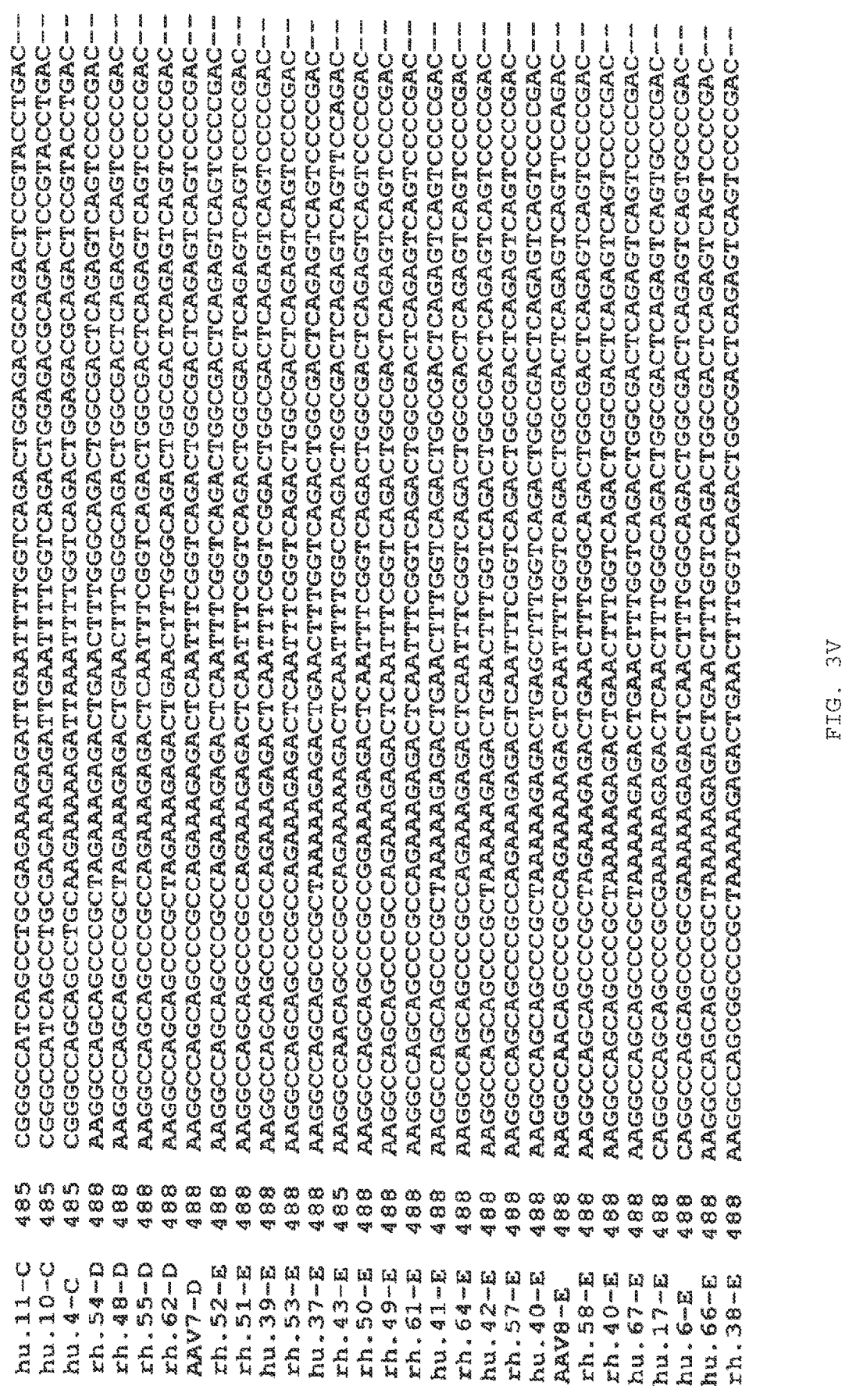
Figure 3X:
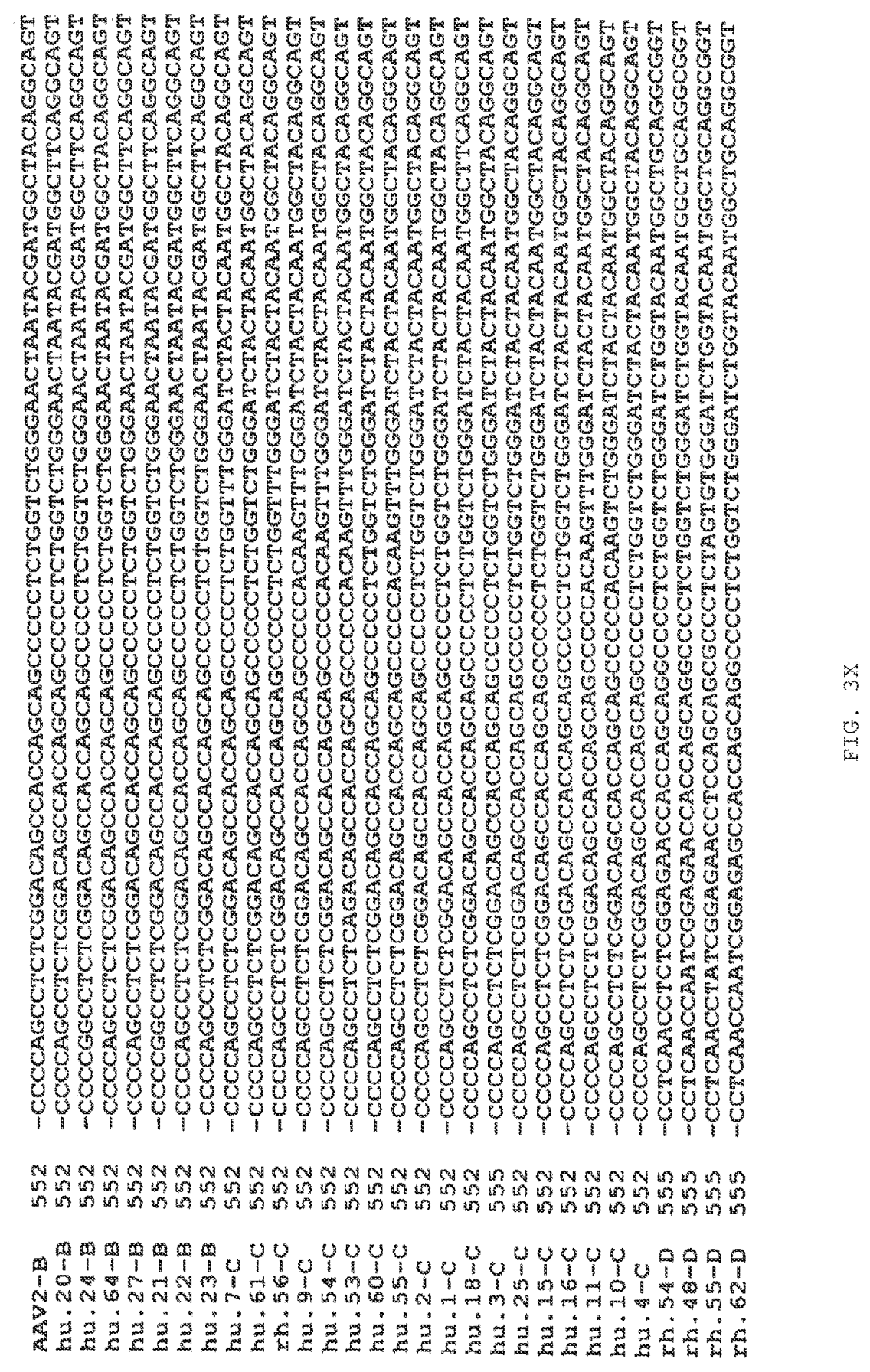
Figure 3Y:
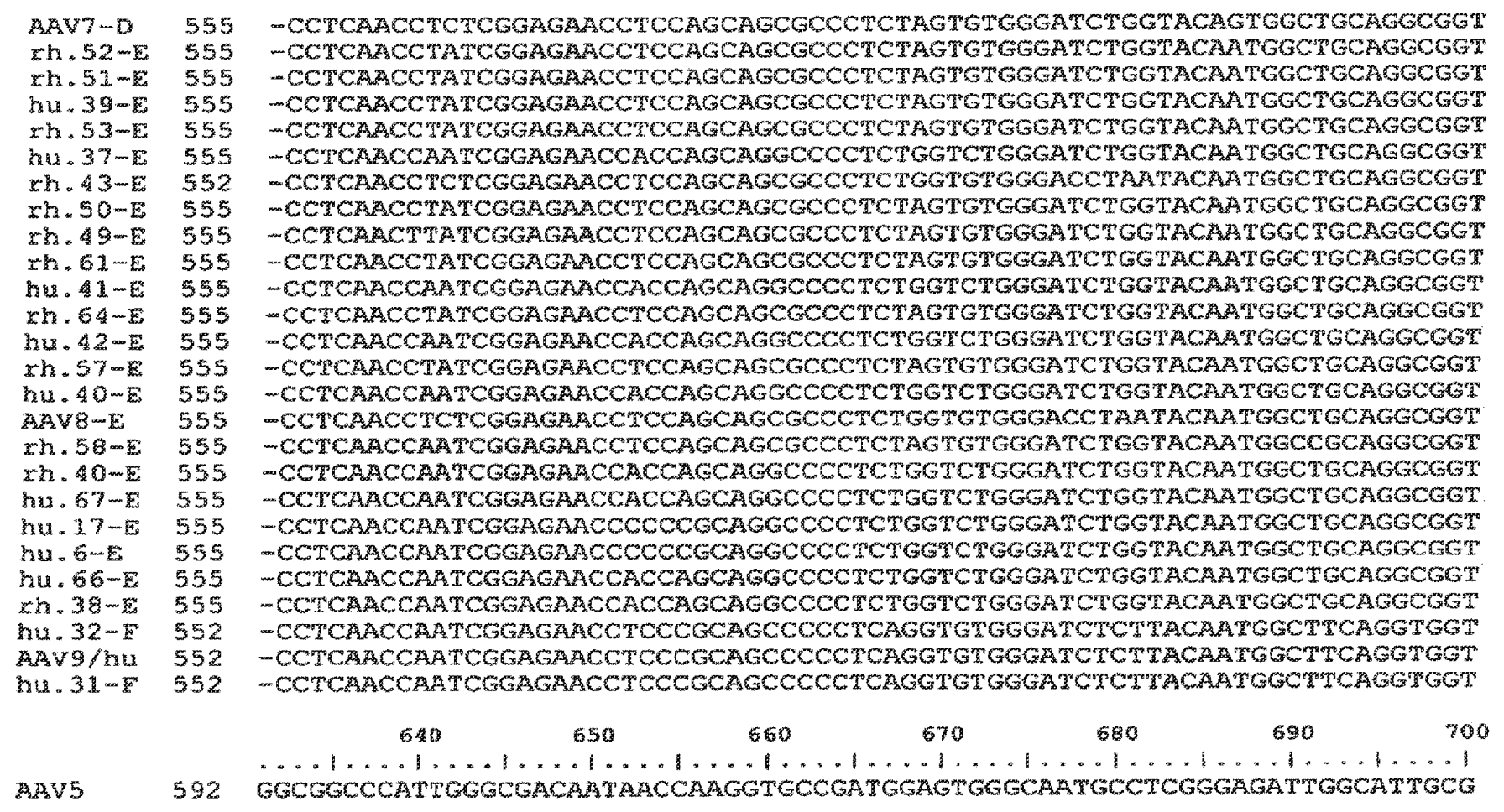
Figure 3Z:
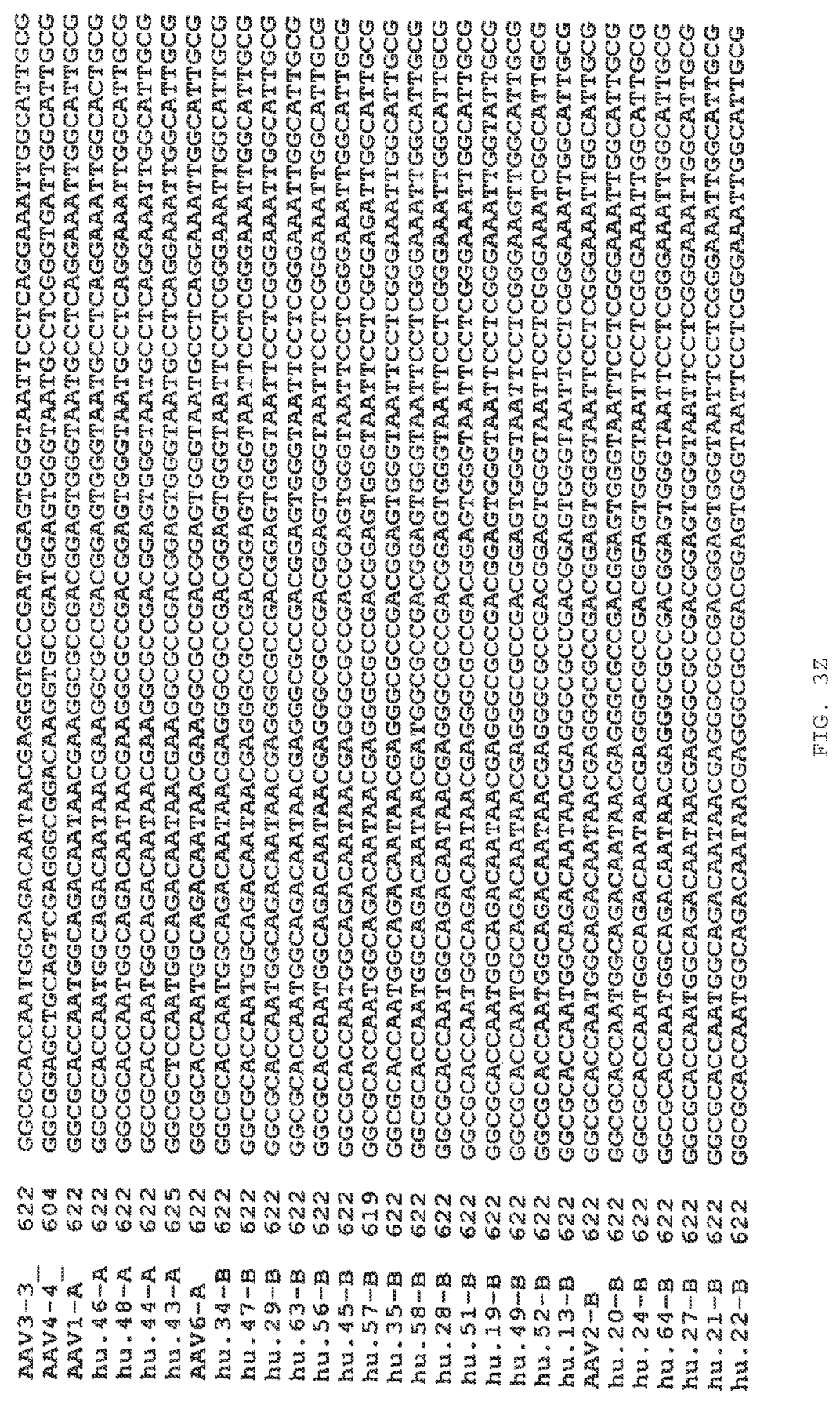

FIGS. 3A-3CN are an alignment of the nucleic acid sequences of AAV vp1 capsid proteins of the invention, with the numbering of the individual sequences reported, and previously published AAV5 (SEQ ID NO: 199); AAV3-3 (SEQ ID NO: 200); AAV4-4 (SEQ ID NO: 201); AAV1 (SEQ ID NO: 202); AAV6 (SEQ ID NO: 203); AAV2 (SEQ ID NO: 211); AAV7 (SEQ ID NO: 213) and AAV8 (SEQ ID NO: 214); rh. 25/42-15; 29.3/bb.1; cy.2; 29.5/bb.2; rh.32, rh.33, rh.34, rh.10; rh.24; rh14, rh.16, rh.17, rh.12, rh.18, rh.21 (formerly termed 41.10); rh.25 (formerly termed 41.15; GenBank accession AY530557); rh2; rh.31; cy.3; cy.5; rh.13; cy.4; cy.6; rh.22; rh.19; rh.35; rh.37; rh.36; rh.23; rh.8; and ch.5 [US Published Patent Application No. 2003/0138772 A1 (Jul. 24, 2003)]. The nucleic acid sequences of the invention include, hu.14/AAV9 (SEQ ID No: 3); LG-4/rh.38 (SEQ ID No: 7); LG-10/rh.40 (SEQ ID No: 14); N721-8/rh.43 (SEQ ID No: 43); 1-8/rh.49 (SEQ ID NO: 25); 2-4/rh.50 (SEQ ID No: 23); 2-5/rh.51 (SEQ ID No: 22); 3-9/rh.52 (SEQ ID No: 18); 3-11/rh.53 (SEQ ID NO: 17); 5-3/rh.57 (SEQ ID No: 26); 5-22/rh.58 (SEQ ID No: 27); 2-3/rh.61 (SEQ ID NO: 21); 4-8/rh.64 (SEQ ID No: 15); 3.1/hu.6 (SEQ ID NO: 5); 33.12/hu.17 (SEQ ID NO: 4); 106.1/hu.37 (SEQ ID No: 10); LG-9/hu.39 (SEQ ID No: 24); 114.3/hu.40 (SEQ ID No: 11); 127.2/hu.41 (SEQ ID NO:6); 127.5/hu.42 (SEQ ID No: 8); and hu.66 (SEQ ID NO: 173); 2-15/rh.62 (SEQ ID NO: 33); 1-7/rh.48 (SEQ ID NO: 32); 4-9/rh.54 (SEQ ID No: 40); 4-19/rh.55 (SEQ ID NO: 37); 52/hu.19 (SEQ ID NO: 62), 52.1/hu.20 (SEQ ID NO: 63), 54.5/hu.23 (SEQ ID No: 60), 54.2/hu.22 (SEQ ID No: 67), 54.7/hu.24 (SEQ ID No: 66), 54.1/hu.21 (SEQ ID No: 65), 54.4R/hu.27 (SEQ ID No: 64); 46.2/hu.28 (SEQ ID No: 68); 46.6/hu.29 (SEQ ID No: 69); 128.1/hu.43 (SEQ ID No: 80); 128.3/hu.44 (SEQ ID No: 81) and 130.4/hu.48 (SEQ ID NO: 78); 3.1/hu.9 (SEQ ID No: 58); 16.8/hu.10 (SEQ ID No: 56); 16.12/hu.11 (SEQ ID No: 57); 145.1/hu.53 (SEQ ID No: 176); 145.6/hu.55 (SEQ ID No: 178); 145.5/hu.54 (SEQ ID No: 177); 7.3/hu.7 (SEQ ID No: 55); 52/hu.19 (SEQ ID No: 62); 33.4/hu.15 (SEQ ID No: 50); 33.8/hu.16 (SEQ ID No: 51); 58.2/hu.25 (SEQ ID No: 49); 161.10/hu.60 (SEQ ID No: 170); H-5/hu.3 (SEQ ID No: 44); H-1/hu.1 (SEQ ID No: 46); 161.6/hu.61 (SEQ ID No: 174); hu.31 (SEQ ID No: 1); hu.32 (SEQ ID No: 2); hu.46 (SEQ ID NO: 82); hu.34 (SEQ ID NO: 72); hu.47 (SEQ ID NO: 77); hu.63 (SEQ ID NO: 204); hu.56 (SEQ ID NO: 205); hu.45 (SEQ ID NO: 76); hu.57 (SEQ ID NO: 206); hu.35 (SEQ ID NO: 73); hu.58 (SEQ ID NO: 207); hu.51 (SEQ ID NO: 208); hu.49 (SEQ ID NO: 209); hu.52 (SEQ ID NO: 210); hu.13 (SEQ ID NO: 71); hu.64 (SEQ ID NO: 212); rh.56 (SEQ ID NO: 54); hu.2 (SEQ ID NO: 48); hu.18 (SEQ ID NO: 52); hu.4 (SEQ ID NO: 47); and hu.67 (SEQ ID NO: 215). These sequences are also reproduced in the Sequence Listing, which is incorporated by reference herein.

FIGS. 4A-4D provide an evaluation of gene transfer efficiency of novel primate AAV-based vectors in vitro and in vivo. AAV vectors were pseudotyped as described [Gao et al, *Proc Natl Acad Sci USA*, 99:11854-11859 (Sep. 3, 2002)] with capsids of AAVs 1, 2, 5, 7, 8 and 6 and ch.5, rh.34, cy.5, rh.20, rh.8 and AAV9. For in vitro study, FIG. 4A, 84-32 cells (293 cells expressing E4 of adenovirus serotypes) seeded in a 95 well plate were infected with pseudotyped AAVCMVEGFP vectors at an MOI of $1 \times 10^4$ GC per cell. Relative EGFP transduction efficiency was estimated as percentage of green cells using a UV microscope at 48 hours post-infection and shown on the Y axis. For in vivo study, the vectors expressing the secreted reporter gene A1AT were administered to the liver (FIG. 4B), lung (FIG. 4C) and muscle (FIG. 4D) of NCR nude mice (4-6 weeks old) at a dose of $1 \times 10^{11}$ GC per animal by intraportal (FIG. 4B), intratracheal (FIG. 4C) and intramuscular injections (FIG. 4D), respectively. Serum A1AT levels (ng/mL) were compared at day 28 post gene transfer and presented on the Y axis. The X axis indicates the AAVs analyzed and the clades to which they belong.

DETAILED DESCRIPTION OF THE INVENTION

In any arsenal of vectors useful in therapy or prophylaxis, a variety of distinct vectors capable of carrying a macromolecule to a target cell is desirable, in order to permit selection of a vector source for a desired application. To date, one of the concerns regarding the use of AAV as vectors was the lack of a variety of different virus sources. One way in which the present invention overcomes this problem is by providing clades of AAV, which are useful for selecting phylogenetically related, or where desired for a selected regimen, phylogenetically distinct, AAV and for predicting function. The invention further provides novel AAV viruses.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. In the examples, AAV alignments are performed using the published AAV2 or AAV1 sequences as a reference point. However, one of skill in the art can readily select another AAV sequence as a reference.

Alignments are performed using any of a variety of publicly or commercially available Multiple Sequence Alignment Programs. Examples of such programs include, "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

The term "serotype" is a distinction with respect to an AAV having a capsid which is serologically distinct from other AAV serotypes. Serologic distinctiveness is determined on the basis of the lack of cross-reactivity between antibodies to the AAV as compared to other AAV.

Cross-reactivity is typically measured in a neutralizing antibody assay. For this assay polyclonal serum is generated against a specific AAV in a rabbit or other suitable animal model using the adeno-associated viruses. In this assay, the serum generated against a specific AAV is then tested in its ability to neutralize either the same (homologous) or a heterologous AAV. The dilution that achieves 50% neutralization is considered the neutralizing antibody titer. If for two AAVs the quotient of the heterologous titer divided by the homologous titer is lower than 16 in a reciprocal manner, those two vectors are considered as the same serotype. Conversely, if the ratio of the heterologous titer over the homologous titer is 16 or more in a reciprocal manner the two AAVs are considered distinct serotypes.

As defined herein, to form serotype 9, antibodies generated to a selected AAV capsid must not be cross-reactive with any of AAV 1, AAV2, AAV3, AAV4, AAV5, AAV6, AAV7 or AAV8. In one embodiment, the present invention provides an AAV capsid of a novel serotype, identified herein, as human AAV serotype 9.

As used throughout this specification and the claims, the terms "comprising" and "including" are inclusive of other components, elements, integers, steps and the like. Conversely, the term "consisting" and its variants are exclusive of other components, elements, integers, steps and the like.

I. Clades

In one aspect, the invention provides clades of AAV. A clade is a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence.

The Neighbor-Joining algorithm has been described extensively in the literature. See, e.g., M. Nei and S. Kumar, *Molecular Evolution and Phylogenetics* (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades.

While the clades defined herein are based primarily upon naturally occurring AAV vp1 capsids, the clades are not limited to naturally occurring AAV. The clades can encompass non-naturally occurring AAV, including, without limitation, recombinant, modified or altered, chimeric, hybrid, synthetic, artificial, etc., AAV which are phylogenetically related as determined using a Neighbor-Joining algorithm at least 75% (of at least 1000 replicates) and a Poisson correction distance measurement of no more than 0.05, based on alignment of the AAV vp1 amino acid sequence.

The clades described herein include Clade A (represented by AAV1 and AAV6), Clade B (represented by AAV2) and Clade C (represented by the AAV2-AAV3 hybrid), Clade D (represented by AAV7), Clade E (represented by AAV8), and Clade F (represented by human AAV9). These clades are represented by a member of the clade that is a previously described AAV serotype. Previously described AAV1 and AAV6 are members of a single clade (Clade A) in which 4 isolates were recovered from 3 humans. Previously described AAV3 and AAV5 serotypes are clearly distinct from one another, but were not detected in the screen described herein, and have not been included in any of these clades.

Clade B (AAV2) and Clade C (the AAV2-AAV3 hybrid) are the most abundant of those found in humans (22 isolates from 12 individuals for AAV2 and 17 isolates from 8 individuals for Clade C).

There are a large number of sequences grouped in either Clade D (AAV7) or Clade E (AAV8). Interestingly, both of these clades are prevalent in different species. Clade D is unique to rhesus and cynomolgus macaques with 15 members being isolated from 10 different animals. Clade E is interesting because it is found in both human and nonhuman primates: 9 isolates were recovered from 7 humans and 21 isolates were obtained in 9 different nonhuman primates including rhesus macaques, a baboon and a pigtail monkey.

In two other animals the hybrid nature of certain sequences was proven, although all sequences in this case seem to have originated through individual and different recombinations of two co-infecting viruses (in both animals a Clade D with a Clade E virus). None of these recombinants were identified in other animals or subjects.

Since Clade C (the AAV2-AAV3 hybrid) clade was identified in 6 different human subjects, the recombination event resulted in a fit progeny. In the case of the AAV7-AAV8 hybrids on the other hand, only few conclusions can be drawn as to the implication of recombination in AAV evolution. These recombination events show that AAV is capable of recombining, thereby creating in-frame genes and in some cases packagable and/or infectious capsid structures. Clade C (the AAV2-AAV3 hybrid clade) on the other hand is a group of viruses that has acquired a selective advantage through recombination that made them sustain certain environmental pressures.

A. Clade A (Represented by AAV1 and AAV6):

In another aspect, the invention provides Clade A, which is characterized by containing the previously published AAV1 and AAV6. See, e.g., International Publication No. WO 00/28061, 18 May 2000; Rutledge et al, *J Virol*, 72(1):309-319 (January 1998). In addition, this clade contains novel AAV including, without limitation, 128.1/hu. 43 [SEQ ID NOs: 80 and 160]; 128.3/hu. 44 [SEQ ID Nos: 81 and 158]; 130.4/hu.48 [SEQ ID NO: 78 and 157]; and hu.46 [SEQ ID NOs: 82 and 159]. The invention further provides a modified hu. 43 capsid [SEQ ID NO: 236] and a modified hu. 46 capsid [SEQ ID NO: 224].

In one embodiment, one or more of the members of this clade has a capsid with an amino acid identity of at least 85% identity, at least 90% identity, at least 95% identity, or at least 97% identity over the full-length of the vp1, the vp2, or the vp3 of the AAV1 and/or AAV6 capsid.

In another embodiment, the invention provides novel AAV of Clade A, provided that none of the novel AAV comprises a capsid of any of AAV1 or AAV6. These AAV may include, without limitation, an AAV having a capsid derived from one or more of 128.1/hu. 43 [SEQ ID Nos: 80 and 160]; modified hu.43 [SEQ ID NO: 236] 128.3/hu. 44 [SEQ ID Nos: 81 and 158]; hu.46 [SEQ ID NOs: 82 and 159]; modified hu. 46 [SEQ ID NO: 224]; and 130.4/hu.48 [SEQ ID NO: 78 and 157].

B. Clade B (AAV2 Clade):

In another embodiment, the invention provides a Clade B. This clade is characterized by containing, at a minimum, the previously described AAV2 and novel AAV of the invention including, 52/hu.19 [SEQ ID NOs: 62 and 133], 52.1/hu.20 [SEQ ID NOs: 63 and 134], 54.5/hu.23 [SEQ ID Nos: 60 and 137], 54.2/hu.22 [SEQ ID Nos: 67 and 138], 54.7/hu.24 [SEQ ID Nos: 66 and 136], 54.1/hu.21 [SEQ ID Nos: 65 and 135], 54.4R/hu.27 [SEQ ID Nos: 64 and 140]; 46.2/hu.28 [SEQ ID Nos: 68 and 130]; 46.6/hu.29 [SEQ ID Nos: 69 and 132]; modified hu. 29 [SEQ ID NO: 225]; 172.1/hu.63 [SEQ ID NO: 171 and 195; GenBank Accession No. AY530624]; 172.2/hu. 64 [SEQ ID NO: 172 and 196; GenBank Accession No. AY530625]; 24.5/hu.13 [SEQ ID NO: 71 and 129; GenBank Accession No. AY530578]; 145.6/hu.56 [SEQ ID NO: 168 and 192]; hu.57 [SEQ ID Nos: 169 and 193]; 136.1/hu.49 [SEQ ID NO: 165 and 189]; 156.1/hu.58 [SEQ ID NO: 179 and 194]; 72.2/hu.34 [SEQ ID NO: 72 and 125; GenBank Accession No. AY530598]; 72.3/hu.35 [SEQ ID NO: 73 and 164; GenBank Accession No. AY530599]; 130.1/hu.47 [SEQ ID NO: 77 and 128]; 129.1/hu.45 (SEQ ID NO: 76 and 127; GenBank Accession No. AY530608); 140.1/hu.51 [SEQ ID NO: 161 and 190; GenBank Accession No. AY530613]; and 140.2/hu.52 [SEQ ID NO: 167 and 191; GenBank Accession No. AY530614].

In one embodiment, one or more of the members of this clade has a capsid with an amino acid identity of at least 85% identity, at least 90% identity, at least 95% identity, or at least 97% identity over the full-length of the vp1, the vp2, or the vp3 of the AAV2 capsid.

In another embodiment, the invention provides novel AAV of Clade B, provided that none of the AAV has an AAV2 capsid. These AAV may include, without limitation, an AAV having a capsid derived from one or more of the following: 52/hu.19 [SEQ ID NOs: 62 and 133], 52.1/hu.20 [SEQ ID NOs: 63 and 134], 54.5/hu.23 [SEQ ID Nos: 60 and 137], 54.2/hu.22 [SEQ ID Nos: 67 and 138], 54.7/hu.24 [SEQ ID Nos: 66 and 136], 54.1/hu.21 [SEQ ID Nos: 65 and 135], 54.4R/hu.27 [SEQ ID Nos: 64 and 140]; 46.2/hu.28 [SEQ ID Nos: 68 and 130]; 46.6/hu.29 [SEQ ID Nos: 69 and 132]; modified hu. 29 [SEQ ID NO: 225]; 172.1/hu.63 [SEQ ID NO: 171 and 195]; 172.2/hu. 64 [SEQ ID NO: 172 and 196]; 24.5/hu.13 [SEQ ID NO: 71 and 129]; 145.6/hu.56 [SEQ ID NO: 168 and 192; GenBank Accession No. AY530618]; hu.57 [SEQ ID Nos: 169 and 193; GenBank Accession No. AY530619]; 136.1/hu.49 [SEQ ID NO: 165 and 189; GenBank Accession No. AY530612]; 156.1/hu.58 [SEQ ID NO: 179 and 194; GenBank Accession No. AY530620]; 72.2/hu.34 [SEQ ID NO: 72 and 125]; 72.3/hu.35 [SEQ ID NO: 73 and 164]; 129.1/hu.45 [SEQ ID NO: 76 and 127]; 130.1/hu.47 [SEQ ID NO: 77 and 128; GenBank Accession No. AY530610]; 140.1/hu.51 [SEQ ID NO: 161 and 190; GenBank Accession No. AY530613]; and 140.2/hu.52 [SEQ ID NO: 167 and 191; GenBank Accession No. AY530614].

C. Clade C (AAV2-AAV3 Hybrid Clade)

In another aspect, the invention provides Clade C, which is characterized by containing AAV that are hybrids of the previously published AAV2 and AAV3 such as H-6/hu.4; H-2/hu.2 [U.S. patent application 2003/0138772 (Jun. 24, 2003). In addition, this clade contains novel AAV including, without limitation, 3.1/hu.9 [SEQ ID Nos: 58 and 155]; 16.8/hu.10 [SEQ ID Nos: 56 and 156]; 16.12/hu.11 [SEQ ID Nos: 57 and 153]; 145.1/hu.53 [SEQ ID Nos: 176 and 186]; 145.6/hu.55 [SEQ ID Nos: 178 and 187]; 145.5/hu.54 [SEQ ID Nos: 177 and 188]; 7.3/hu.7 [SEQ ID Nos: 55 and 150; now deposited as GenBank Accession No. AY530628]; modified hu. 7 [SEQ ID NO: 226]; 33.4/hu.15 [SEQ ID Nos: 50 and 147]; 33.8/hu.16 [SEQ ID Nos: 51 and 148]; hu.18 [SEQ ID NOs: 52 and 149]; 58.2/hu.25 [SEQ ID Nos: 49 and 146]; 161.10/hu.60 [SEQ ID Nos: 170 and 184]; H-5/ hu.3 [SEQ ID Nos: 44 and 145]; H-1/hu.1 [SEQ ID Nos: 46 and 144]; and 161.6/hu.61 [SEQ ID Nos: 174 and 185].

In one embodiment, one or more of the members of this clade has a capsid with an amino acid identity of at least 85% identity, at least 90% identity, at least 95% identity, or at least 97% identity over the full-length of the vp1, the vp2, or the vp3 of the hu.4 and/or hu.2 capsid.

In another embodiment, the invention provides novel AAV of Clade C (the AAV2-AAV3 hybrid clade), provided that none of the novel AAV comprises a capsid of hu.2 or hu.4. These AAV may include, without limitation, an AAV having a capsid derived from one or more of 3.1/hu.9 [SEQ ID Nos: 58 and 155]; 16.8/hu.10 [SEQ ID Nos: 56 and 156]; 16.12/hu.11 [SEQ ID Nos: 57 and 153]; 145.1/hu.53 [SEQ ID Nos: 176 and 186]; 145.6/hu.55 [SEQ ID Nos: 178 and 187]; 145.5/hu.54 [SEQ ID Nos: 177 and 188]; 7.3/hu.7 [SEQ ID Nos: 55 and 150]; modified hu.7 [SEQ ID NO: 226]; 33.4/hu.15 [SEQ ID Nos: 50 and 147]; 33.8/hu.16 [SEQ ID Nos: 51 and 148]; 58.2/hu.25 [SEQ ID Nos: 49 and 146]; 161.10/hu.60 [SEQ ID Nos: 170 and 184]; H-5/hu.3 [SEQ ID Nos: 44 and 145]; H-1/hu.1 [SEQ ID Nos: 46 and 144]; and 161.6/hu.61 [SEQ ID Nos: 174 and 185].

D. Clade D (AAV7 Clade)

In another embodiment, the invention provides Clade D. This clade is characterized by containing the previously described AAV7 [G. Gao et al, Proc. Natl Acad. Sci USA, 99:11854-9 (Sep. 3, 2002). The nucleic acid sequences encoding the AAV7 capsid are reproduced in SEQ ID NO: 184; the amino acid sequences of the AAV7 capsid are reproduced in SEQ ID NO: 185. In addition, the clade contains a number of previously described AAV sequences, including: cy.2; cy.3; cy.4; cy.5; cy.6; rh.13; rh.37; rh. 36; and rh.35 [US Published Patent Application No. US 2003/0138772 A1 (Jul. 24 2003)]. Additionally, the AAV7 clade contains novel AAV sequences, including, without limitation, 2-15/rh.62 [SEQ ID Nos: 33 and 114]; 1-7/rh.48 [SEQ ID Nos: 32 and 115]; 4-9/rh.54 [SEQ ID Nos: 40 and 116]; and 4-19/rh.55 [SEQ ID Nos: 37 and 117]. The invention further includes modified cy. 5 [SEQ ID NO: 227]; modified rh.13 [SEQ ID NO: 228]; and modified rh. 37 [SEQ ID NO: 229].

In one embodiment, one or more of the members of this clade has a capsid with an amino acid identity of at least 85% identity, at least 90% identity, at least 95% identity, or at least 97% identity over the full-length of the vp1, the vp2, or the vp3 of the AAV7 capsid, SEQ ID NO: 184 and 185.

In another embodiment, the invention provides novel AAV of Clade D, provided that none of the novel AAV comprises a capsid of any of cy.2; cy.3; cy.4; cy.5; cy.6; rh.13; rh.37; rh. 36; and rh.35. These AAV may include, without limitation, an AAV having a capsid derived from one or more of the following 2-15/rh.62 [SEQ ID Nos: 33 and 114]; 1-7/rh.48 [SEQ ID Nos: 32 and 115]; 4-9/rh.54 [SEQ ID Nos: 40 and 116]; and 4-19/rh.55 [SEQ ID Nos: 37 and 117].

E. Clade E (AAV8 Clade)

In one aspect, the invention provides Clade E. This clade is characterized by containing the previously described AAV8 [G. Gao et al, Proc. Natl Acad. Sci USA, 99:11854-9 (Sep. 3, 2002)], 43.1/rh.2; 44.2/rh.10; rh. 25; 29.3/bb.1; and 29.5/bb.2 [US Published Patent Application No. US 2003/0138772 A1 (Jul. 24 2003)].

Further, the clade novel AAV sequences, including, without limitation, including, e.g., 30.10/pi.1 [SEQ ID NOs: 28 and 93], 30.12/pi.2 [SEQ ID NOs: 30 and 95, 30.19/pi.3 [SEQ ID NOs: 29 and 94], LG-4/rh.38 [SEQ ID Nos: 7 and 86]; LG-10/rh.40 [SEQ ID Nos: 14 and 92]; N721-8/rh.43 [SEQ ID Nos: 43 and 163]; 1-8/rh.49 [SEQ ID NOs: 25 and 103]; 2-4/rh.50 [SEQ ID Nos: 23 and 108]; 2-5/rh.51 [SEQ ID Nos: 22 and 104]; 3-9/rh.52 [SEQ ID Nos: 18 and 96]; 3-11/rh.53 [SEQ ID NOs: 17 and 97]; 5-3/rh.57 [SEQ ID Nos: 26 and 105]; 5-22/rh.58 [SEQ ID Nos: 27 and 58]; 2-3/rh.61 [SEQ ID NOs: 21 and 107]; 4-8/rh.64 [SEQ ID Nos: 15 and 99]; 3.1/hu.6 [SEQ ID NO: 5 and 84]; 33.12/hu.17 [SEQ ID NO: 4 and 83]; 106.1/hu.37 [SEQ ID Nos: 10 and 88]; LG-9/hu.39 [SEQ ID Nos: 24 and 102]; 114.3/hu. 40 [SEQ ID Nos: 11 and 87]; 127.2/hu.41 [SEQ ID NO: 6 and 91]; 127.5/hu.42 [SEQ ID Nos: 8 and 85]; hu. 66 [SEQ ID NOs: 173 and 197]; and hu.67 [SEQ ID NOs: 174 and 198]. This clade further includes modified rh. 2 [SEQ ID NO: 231]; modified rh. 58 [SEQ ID NO: 232]; modified rh. 64 [SEQ ID NO: 233].

In one embodiment, one or more of the members of this clade has a capsid with an amino acid identity of at least 85% identity, at least 90% identity, at least 95% identity, or at least 97% identity over the full-length of the vp1, the vp2, or the vp3 of the AAV8 capsid. The nucleic acid sequences encoding the AAV8 capsid are reproduced in SEQ ID NO: 186 and the amino acid sequences of the capsid are reproduced in SEQ ID NO:187.

In another embodiment, the invention provides novel AAV of Clade E, provided that none of the novel AAV comprises a capsid of any of AAV8, rh.8; 44.2/rh.10; rh. 25; 29.3/bb.1; and 29.5/bb.2 [US Published Patent Application No. US 2003/0138772 A1 (Jul. 24 2003)]. These AAV may include, without limitation, an AAV having a capsid derived from one or more of the following: 30.10/pi.1 [SEQ ID NOs: 28 and 93], 30.12/pi.2 [SEQ ID NOs: 30 and 95, 30.19/pi.3 [SEQ ID NOs: 29 and 94], LG-4/rh.38 [SEQ ID Nos: 7 and 86]; LG-10/rh.40 [SEQ ID Nos: 14 and 92]; N721-8/rh.43 [SEQ ID Nos: 43 and 163]; 1-8/rh.49 [SEQ ID NOs: 25 and 103]; 2-4/rh.50 [SEQ ID Nos: 23 and 108]; 2-5/rh.51 [SEQ ID Nos: 22 and 104]; 3-9/rh.52 [SEQ ID Nos: 18 and 96]; 3-11/rh.53 [SEQ ID NOs: 17 and 97]; 5-3/rh.57 [SEQ ID Nos: 26 and 105]; 5-22/rh.58 [SEQ ID Nos: 27 and 58]; modified rh. 58 [SEQ ID NO: 232]; 2-3/rh.61 [SEQ ID NOs: 21 and 107]; 4-8/rh.64 [SEQ ID Nos: 15 and 99]; modified rh. 64[SEQ ID NO: 233]; 3.1/hu.6 [SEQ ID NO: 5 and 84]; 33.12/hu.17 [SEQ ID NO: 4 and 83]; 106.1/hu.37 [SEQ ID Nos: 10 and 88]; LG-9/hu.39 [SEQ ID Nos: 24 and 102]; 114.3/hu. 40 [SEQ ID Nos: 11 and 87]; 127.2/hu.41 [SEQ ID NO: 6 and 91]; 127.5/hu.42 [SEQ ID Nos: 8 and 85]; hu. 66 [SEQ ID NOs: 173 and 197]; and hu.67 [SEQ ID NOs: 174 and 198]. F. Clade F (AAV 9 Clade)

This clade is identified by the name of a novel AAV serotype identified herein as hu.14/AAV9 [SEQ ID Nos: 3 and 123]. In addition, this clade contains other novel sequences including, hu.31 [SEQ ID NOs: 1 and 121]; and hu.32 [SEQ ID Nos: 2 and 122].

In one embodiment, one or more of the members of this clade has a capsid with an amino acid identity of at least 85% identity, at least 90% identity, at least 95% identity, or at least 97% identity over the full-length of the vp1, the vp2, or the vp3 of the AAV9 capsid, SEQ ID NO: 3 and 123.

In another embodiment, the invention provides novel AAV of Clade F, which include, without limitation, an AAV having a capsid derived from one or more of hu.14/AAV9 [SEQ ID Nos: 3 and 123], hu.31 [SEQ ID NOs: 1 and 121] and hu.32 [SEQ ID Nos: 1 and 122].

The AAV clades of the invention are useful for a variety of purposes, including providing ready collections of related AAV for generating viral vectors, and for generating targeting molecules. These clades may also be used as tools for a variety of purposes that will be readily apparent to one of skill in the art.

II. Novel AAV Sequences

The invention provides the nucleic acid sequences and amino acids of a novel AAV serotype, which is termed interchangeably herein as clone hu.14/28.4 and huAAV9. These sequences are useful for constructing vectors that are highly efficient in transduction of liver, muscle and lung. This novel AAV and its sequences are also useful for a variety of other purposes. These sequences are being submitted with GenBank and have been assigned the accession numbers identified herein.

The invention further provides the nucleic acid sequences and amino acid sequences of a number of novel AAV. Many of these sequence include those described above as members of a clade, as summarized below.

128.1/hu. 43 [SEQ ID Nos: 80 and 160 GenBank Accession No. AY530606; modified hu. 43 [SEQ ID NO: 236]; 128.3/hu. 44 [SEQ ID Nos: 81 and 158; GenBank Accession No. AY530607] and 130.4/hu.48 [SEQ ID NO: 78 and 157; GenBank Accession No. AY530611]; from the Clade A;

52/hu.19 [SEQ ID NOs: 62 and 133; GenBank Accession No. AY530584], 52.1/hu.20 [SEQ ID NOs: 63 and 134; GenBank Accession No. AY530586], 54.5/hu.23 [SEQ ID Nos: 60 and 137; GenBank Accession No. AY530589], 54.2/hu.22 [SEQ ID Nos: 67 and 138; GenBank Accession No. AY530588], 54.7/hu.24 [SEQ ID Nos: 66 and 136; GenBank Accession No. AY530590], 54.1/hu.21 [SEQ ID Nos: 65 and 135; GenBank Accession No. AY530587], 54.4R/hu.27 [SEQ ID Nos: 64 and 140; GenBank Accession No. AY530592]; 46.2/hu.28 [SEQ ID Nos: 68 and 130; GenBank Accession No. AY530593]; 46.6/hu.29 [SEQ ID Nos: 69 and 132; GenBank Accession No. AY530594]; modified hu. 29 [SEQ ID NO: 225]; 172.1/hu.63 [SEQ ID NO: 171 and 195]; and 140.2/hu.52 (SEQ ID NO: 167 and 191; from Clade B;

3.1/hu.9 [SEQ ID Nos: 58 and 155; GenBank Accession No. AY530626]; 16.8/hu.10 [SEQ ID Nos: 56 and 156; GenBank Accession No. AY530576]; 16.12/hu.11 [SEQ ID Nos: 57 and 153; GenBank Accession No. AY530577]; 145.1/hu.53 [SEQ ID Nos: 176 and 186; GenBank Accession No. AY530615]; 145.6/hu.55 [SEQ ID Nos: 178 and 187; GenBank Accession No. AY530617]; 145.5/hu.54 [SEQ ID Nos: 177 and 188; GenBank Accession No. AY530616]; 7.3/hu.7 [SEQ ID Nos: 55 and 150; GenBank Accession No. AY530628]; modified hu. 7 [SEQ ID NO: 226]; hu.18 [SEQ ID Nos: 52 and 149; GenBank Accession No. AY530583]; 33.4/hu.15 [SEQ ID Nos: 50 and 147; GenBank Accession No. AY530580]; 33.8/hu.16 [SEQ ID Nos: 51 and 148; GenBank Accession No. AY530581]; 58.2/hu.25 [SEQ ID Nos: 49 and 146; GenBank Accession No. AY530591]; 161.10/hu.60 [SEQ ID Nos: 170 and 184; GenBank Accession No. AY530622]; H-5/hu.3 [SEQ ID Nos: 44 and 145; GenBank Accession No. AY530595]; H-1/hu.1 [SEQ ID Nos: 46 and 144; GenBank Accession No. AY530575]; and 161.6/hu.61 [SEQ ID Nos: 174 and 185; GenBank Accession No. AY530623] from Clade C;

2-15/rh.62 [SEQ ID Nos: 33 and 114; GenBank Accession No. AY530573]; 1-7/rh.48 [SEQ ID Nos: 32 and 115; GenBank Accession No. AY530561]; 4-9/rh.54 [SEQ ID Nos: 40 and 116; GenBank Accession No. AY530567]; and 4-19/rh.55 [SEQ ID Nos: 37 and 117; GenBank Accession No. AY530568]; modified cy. 5 [SEQ ID NO: 227]; modified rh.13 [SEQ ID NO: 228]; and modified rh. 37 [SEQ ID NO: 229] from the Clade D;

30.10/pi.1 [SEQ ID NOs: 28 and 93; GenBank Accession No. AY53055], 30.12/pi.2 [SEQ ID NOs: 30 and 95; GenBank Accession No. AY 530554], 30.19/pi.3 [SEQ ID NOs: 29 and 94; GenBank Accession No. AY530555], LG-4/rh.38 [SEQ ID Nos: 7 and 86; GenBank Accession No. AY 530558]; LG-10/rh.40 [SEQ ID Nos: 14 and 92; GenBank Accession No. AY530559]; N721-8/rh.43 [SEQ ID Nos: 43 and 163; GenBank Accession No. AY530560]; 1-8/rh.49 [SEQ ID NOs: 25 and 103; GenBank Accession No. AY530561]; 2-4/rh.50 [SEQ ID Nos: 23 and 108; GenBank Accession No. AY530563]; 2-5/rh.51 [SEQ ID Nos: 22 and 104; GenBank Accession No. 530564]; 3-9/rh.52 [SEQ ID Nos: 18 and 96; GenBank Accession No. AY530565]; 3-11/rh.53 [SEQ ID Nos: 17 and 97; GenBank Accession No. AY530566]; 5-3/rh.57 [SEQ ID Nos: 26 and 105; GenBank Accession No. AY530569]; 5-22/rh.58 [SEQ ID Nos: 27 and 58; GenBank Accession No. 530570]; modified rh. 58 [SEQ ID NO: 232]; 2-3/rh.61 [SEQ ID Nos: 21 and 107; GenBank Accession No. AY530572]; 4-8/rh.64 [SEQ ID Nos: 15 and 99; GenBank Accession No. AY530574]; modified rh. 64[SEQ ID NO: 233]; 3.1/hu.6 [SEQ ID NO: 5 and 84; GenBank Accession No. AY530621]; 33.12/hu.17 [SEQ ID NO: 4 and 83; GenBank Accession No. AY530582]; 106.1/hu.37 [SEQ ID Nos: 10 and 88; GenBank Accession No. AY530600]; LG-9/hu.39 [SEQ ID Nos: 24 and 102; GenBank Accession No. AY530601]; 114.3/hu. 40 [SEQ ID Nos: 11 and 87; GenBank Accession No. AY530603]; 127.2/hu.41 [SEQ ID NO: 6 and 91; GenBank Accession No. AY530604]; 127.5/hu.42 [SEQ ID Nos: 8 and 85; GenBank Accession No. AY530605]; and hu. 66 [SEQ ID NOs: 173 and 197; GenBank Accession No. AY530626]; and hu.67 [SEQ ID NOs: 174 and 198; GenBank Accession No. AY530627]; and modified rh.2 [SEQ ID NO: 231]; from Clade E;

hu.14/AAV9 [SEQ ID Nos: 3 and 123; GenBank Accession No. AY530579], hu.31 [SEQ ID NOs: 1 and 121; AY530596] and hu.32 [SEQ ID Nos: 1 and 122; GenBank Accession No. AY530597] from Clade F.

In addition, the present invention provides AAV sequences, including, rh.59 [SEQ ID NO: 49 and 110]; rh.60 [SEQ ID NO: 31 and 120; GenBank Accession No. AY530571], modified ch.5 [SEQ ID NO: 234]; and modified rh. 8 [SEQ ID NO: 235], which are outside the definition of the clades described above.

Also provided are fragments of the AAV sequences of the invention. Each of these fragments may be readily utilized in a variety of vector systems and host cells. Among desirable AAV fragments are the cap proteins, including the vp1, vp2, vp3 and hypervariable regions. Where desired, the methodology described in published US Patent Publication No. US 2003/0138772 A1 (Jul. 24 2003)] can be used to obtain the rep sequences for the AAV clones identified above. Such rep sequences include, e.g., rep 78, rep 68, rep 52, and rep 40, and the sequences encoding these proteins. Similarly, other fragments of these clones may be obtained using the techniques described in the referenced patent publication, including the AAV inverted terminal repeat (ITRs), AAV P19 sequences, AAV P40 sequences, the rep binding site, and the terminal resolute site (TRS). Still other suitable fragments will be readily apparent to those of skill in the art.

The capsid and other fragments of the invention can be readily utilized in a variety of vector systems and host cells. Such fragments may be used alone, in combination with other AAV sequences or fragments, or in combination with elements from other AAV or non-AAV viral sequences. In one particularly desirable embodiment, a vector contains the AAV cap and/or rep sequences of the invention.

The AAV sequences and fragments thereof are useful in production of rAAV, and are also useful as antisense delivery vectors, gene therapy vectors, or vaccine vectors. The invention further provides nucleic acid molecules, gene delivery vectors, and host cells which contain the AAV sequences of the invention.

Suitable fragments can be determined using the information provided herein.

As described herein, the vectors of the invention containing the AAV capsid proteins of the invention are particularly well suited for use in applications in which the neutralizing antibodies diminish the effectiveness of other AAV serotype based vectors, as well as other viral vectors. The rAAV vectors of the invention are particularly advantageous in rAAV readministration and repeat gene therapy.

These and other embodiments and advantages of the invention are described in more detail below.

A. AAV Serotype 9/hu14 Sequences

The invention provides the nucleic acid sequences and amino acids of a novel AAV, which is termed interchangeable herein as clone hu.14 (formerly termed 28.4) and huAAV9. As defined herein, novel serotype AAV9 refers to AAV having a capsid which generates antibodies which cross-react serologically with the capsid having the sequence of hu. 14 [SEQ ID NO: 123] and which antibodies do not cross-react serologically with antibodies generated to the capsids of any of AAV1, AAV2, AAV3, AAV4, AAV5, AAV6, AAV7 or AAV8.

1. Nucleic Acid Sequences

The AAV9 nucleic acid sequences of the invention include the DNA sequences of SEQ ID NO: 3, which consists of 2211 nucleotides.

The nucleic acid sequences of the invention further encompass the strand which is complementary to SEQ ID NO: 3, as well as the RNA and cDNA sequences corresponding to SEQ ID NO: 3, and its complementary strand. Also included in the nucleic acid sequences of the invention are natural variants and engineered modifications of SEQ ID NO: 3 and its complementary strand. Such modifications include, for example, labels that are known in the art, methylation, and substitution of one or more of the naturally occurring nucleotides with a degenerate nucleotide.

Further included in this invention are nucleic acid sequences which are greater than about 90%, more preferably at least about 95%, and most preferably at least about 98 to 99%, identical or homologous to SEQ ID NO: 3.

Also included within the invention are fragments of SEQ ID NO: 3, its complementary strand, and cDNA and RNA complementary thereto. Suitable fragments are at least 15 nucleotides in length, and encompass functional fragments, i.e., fragments which are of biological interest. Such fragments include the sequences encoding the three variable proteins (vp) of the AAV9/HU.14 capsid which are alternative splice variants: vp1 [nt 1 to 2211 of SEQ ID NO: 3]; vp2 [about nt 411 to 2211 of SEQ ID NO: 3]; and vp 3 [about nt 609 to 2211 of SEQ ID NO: 3]. Other suitable fragments of SEQ ID NO: 3, include the fragment which contains the start codon for the AAV9/HU.14 capsid protein, and the fragments encoding the hypervariable regions of the vp1 capsid protein, which are described herein.

In addition to including the nucleic acid sequences provided in the figures and Sequence Listing, the present invention includes nucleic acid molecules and sequences which are designed to express the amino acid sequences, proteins and peptides of the AAV serotypes of the invention.

Thus, the invention includes nucleic acid sequences which encode the following novel AAV amino acid sequences and artificial AAV serotypes generated using these sequences and/or unique fragments thereof.

As used herein, artificial AAV serotypes include, without limitation, AAVs with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

2. HU.14/AAV9 Amino Acid Sequences, Proteins and Peptides

The invention further provides proteins and fragments thereof which are encoded by the hu.14/AAV9 nucleic acids of the invention, and hu.14/AAV9 proteins and fragments which are generated by other methods. As used herein, these proteins include the assembled capsid. The invention further encompasses AAV serotypes generated using sequences of the novel AAV serotype of the invention, which are generated using synthetic, recombinant or other techniques known to those of skill in the art. The invention is not limited to novel AAV amino acid sequences, peptides and proteins expressed from the novel AAV nucleic acid sequences of the invention, but encompasses amino acid sequences, peptides and proteins generated by other methods known in the art, including, e.g., by chemical synthesis, by other synthetic techniques, or by other methods. The sequences of any of the AAV capsids provided herein can be readily generated using a variety of techniques.

Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well-known solid phase peptide synthesis methods (Merrifield, *J. Am. Chem. Soc.*, 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

Particularly desirable proteins include the AAV capsid proteins, which are encoded by the nucleotide sequences identified above. The AAV capsid is composed of three proteins, vp1, vp2 and vp3, which are alternative splice variants. The full-length sequence provided in FIG. 2 is that of vp1. The AAV9/HU.14 capsid proteins include vp1 [amino acids (aa) 1 to 736 of SEQ ID NO: 123], vp2 [about aa 138 to 736 of SEQ ID NO: 123], vp3 [about aa 203 to 736 of SEQ ID NO: 123], and functional fragments thereof. Other desirable fragments of the capsid protein include the constant and variable regions, located between hypervariable regions (HVR). Other desirable fragments of the capsid protein include the HVR themselves.

An algorithm developed to determine areas of sequence divergence in AAV2 has yielded 12 hypervariable regions (HVR) of which 5 overlap or are part of the four previously described variable regions. [Chiorini et al, *J. Virol*, 73:1309-19 (1999); Rutledge et al, *J. Virol.*, 72:309-319] Using this algorithm and/or the alignment techniques described herein, the HVR of the novel AAV serotypes are determined. For example, the HVR are located as follows: HVR1, aa 146-

152; HVR2, aa 182-186; HVR3, aa 262-264; HVR4, aa 381-383; HVR5, aa 450-474; HVR6, aa 490-495; HVR7, aa 500-504; HVR8, aa 514-522; HVR9, aa 534-555; HVR10, aa 581-594; HVR11, aa 658-667; and HVR12, aa 705-719 [the numbering system is based on an alignment which uses the AAV2 vp1 as a point of reference]. Using the alignment provided herein performed using the Clustal X program at default settings, or using other commercially or publicly available alignment programs at default settings such as are described herein, one of skill in the art can readily determine corresponding fragments of the novel AAV capsids of the invention.

Still other desirable fragments of the AAV9/HU.14 capsid protein include amino acids 1 to 184 of SEQ ID NO: 123, amino acids 199 to 259; amino acids 274 to 446; amino acids 603 to 659; amino acids 670 to 706; amino acids 724 to 736 of SEQ ID NO: 123; aa 185-198; aa 260-273; aa447-477; aa495-602; aa660-669; and aa707-723. Additionally, examples of other suitable fragments of AAV capsids include, with respect to the numbering of AAV9 [SEQ ID NO: 123], aa 24-42, aa 25-28; aa 81-85; aa133-165; aa 134-165; aa 137-143; aa 154-156; aa 194-208; aa 261-274; aa 262-274; aa 171-173; aa 413-417; aa 449-478; aa 494-525; aa 534-571; aa 581-601; aa 660-671; aa 709-723. Using the alignment provided herein performed using the Clustal X program at default settings, or using other commercially or publicly available alignment programs at default settings, one of skill in the art can readily determine corresponding fragments of the novel AAV capsids of the invention.

Still other desirable AAV9/HU.14 proteins include the rep proteins include rep68/78 and rep40/52.

Suitably, fragments are at least 8 amino acids in length. However, fragments of other desired lengths may be readily utilized. Such fragments may be produced recombinantly or by other suitable means, e.g., chemical synthesis.

The invention further provides other AAV9/HU.14 sequences which are identified using the sequence information provided herein. For example, given the AAV9/HU.14 sequences provided herein, infectious AAV9/HU.14 may be isolated using genome walking technology (Siebert et al., 1995, *Nucleic Acid Research*, 23:1087-1088, Friezner-Degen et al., 1986, *J. Biol. Chem.* 261:6972-6985, BD Biosciences Clontech, Palo Alto, Calif.). Genome walking is particularly well suited for identifying and isolating the sequences adjacent to the novel sequences identified according to the method of the invention. This technique is also useful for isolating inverted terminal repeat (ITRs) of the novel AAV9/HU.14 serotype, based upon the novel AAV capsid and rep sequences provided herein.

The sequences, proteins, and fragments of the invention may be produced by any suitable means, including recombinant production, chemical synthesis, or other synthetic means. Such production methods are within the knowledge of those of skill in the art and are not a limitation of the present invention.

III. Production of rAAV with Novel AAV Capsids

The invention encompasses novel AAV capsid sequences of which are free of DNA and/or cellular material with these viruses are associated in nature. To avoid repeating all of the novel AAV capsids provided herein, reference is made throughout this and the following sections to the hu.14/AAV9 capsid. However, it should be appreciated that the other novel AAV capsid sequences of the invention can be used in a similar manner.

In another aspect, the present invention provides molecules that utilize the novel AAV sequences of the invention, including fragments thereof, for production of molecules useful in delivery of a heterologous gene or other nucleic acid sequences to a target cell.

In another aspect, the present invention provides molecules that utilize the AAV sequences of the invention, including fragments thereof, for production of viral vectors useful in delivery of a heterologous gene or other nucleic acid sequences to a target cell.

The molecules of the invention which contain AAV sequences include any genetic element (vector) which may be delivered to a host cell, e.g., naked DNA, a plasmid, phage, transposon, cosmid, episome, a protein in a non-viral delivery vehicle (e.g., a lipid-based carrier), virus, etc., which transfers the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

In one embodiment, the vectors of the invention contain, inter alia, sequences encoding an AAV capsid of the invention or a fragment thereof. In another embodiment, the vectors of the invention contain, at a minimum, sequences encoding an AAV rep protein or a fragment thereof. Optionally, vectors of the invention may contain both AAV cap and rep proteins. In vectors in which both AAV rep and cap are provided, the AAV rep and AAV cap sequences can originate from an AAV of the same clade. Alternatively, the present invention provides vectors in which the rep sequences are from an AAV source which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV source to form a chimeric AAV vector. Optionally, the vectors of the invention are vectors packaged in an AAV capsid of the invention. These vectors and other vectors described herein can further contain a minigene comprising a selected transgene which is flanked by AAV 5' ITR and AAV 3' ITR.

Thus, in one embodiment, the vectors described herein contain nucleic acid sequences encoding an intact AAV capsid which may be from a single AAV sequence (e.g., AAV9/HU.14). Such a capsid may comprise amino acids 1 to 736 of SEQ ID NO:123. Alternatively, these vectors contain sequences encoding artificial capsids which contain one or more fragments of the AAV9/HU.14 capsid fused to heterologous AAV or non-AAV capsid proteins (or fragments thereof). These artificial capsid proteins are selected from non-contiguous portions of the AAV9/HU.14 capsid or from capsids of other AAVs. For example, a rAAV may have a capsid protein comprising one or more of the AAV9/HU.14 capsid regions selected from the vp2 and/or vp3, or from vp 1, or fragments thereof selected from amino acids 1 to 184, amino acids 199 to 259; amino acids 274 to 446; amino acids 603 to 659; amino acids 670 to 706; amino acids 724 to 738 of the AAV9/HU.14 capsid, SEQ ID NO: 123. In another example, it may be desirable to alter the start codon of the vp3 protein to GTG. Alternatively, the rAAV may contain one or more of the AAV serotype 9 capsid protein hypervariable regions which are identified herein, or other fragment including, without limitation, aa 185-198; aa 260-273; aa447-477; aa495-602; aa660-669; and aa707-723 of the AAV9/HU.14 capsid. See, SEQ ID NO: 123. These modifications may be to increase expression, yield, and/or to improve purification in the selected expression systems, or for another desired purpose (e.g., to change tropism or alter neutralizing antibody epitopes).

The vectors described herein, e.g., a plasmid, are useful for a variety of purposes, but are particularly well suited for use in production of a rAAV containing a capsid comprising AAV sequences or a fragment thereof. These vectors, including rAAV, their elements, construction, and uses are described in detail herein.

In one aspect, the invention provides a method of generating a recombinant adeno-associated virus (AAV) having an AAV serotype 9 capsid, or a portion thereof. Such a method involves culturing a host cell which contains a nucleic acid sequence encoding an AAV serotype 9 capsid protein, or fragment thereof, as defined herein; a functional rep gene; a minigene composed of, at a minimum, AAV inverted terminal repeats (ITRs) and a transgene; and sufficient helper functions to permit packaging of the minigene into the AAV9/HU.14 capsid protein.

The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.*, 70:520-532 (1993) and U.S. Pat. No. 5,478,745.

Unless otherwise specified, the AAV ITRs, and other selected AAV components described herein, may be readily selected from among any AAV, including, without limitation, AAV1, AAV2, AAV3, AAV4, AAV5, AAV6, AAV7, AAV9 and one of the other novel AAV sequences of the invention. These ITRs or other AAV components may be readily isolated using techniques available to those of skill in the art from an AAV sequence. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

A. The Minigene

The minigene is composed of, at a minimum, a transgene and its regulatory sequences, and 5' and 3' AAV inverted terminal repeats (ITRs). In one desirable embodiment, the ITRs of AAV serotype 2 are used. However, ITRs from other suitable sources may be selected. It is this minigene that is packaged into a capsid protein and delivered to a selected host cell.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), enhanced GFP (EGFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal. Typically, suitable target sequences include oncologic targets and viral diseases. See, for examples of such targets the oncologic targets and viruses identified below in the section relating to immunogens.

The transgene may be used to correct or ameliorate gene deficiencies, which may include deficiencies in which normal genes are expressed at less than normal levels or deficiencies in which the functional gene product is not expressed. Alternatively, the transgene may provide a product to a cell which is not natively expressed in the cell type or in the host. A preferred type of transgene sequence encodes a therapeutic protein or polypeptide which is expressed in a host cell. The invention further includes using multiple transgenes. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. More often, when the transgene is large, consists of multi-subunits, or two transgenes are co-delivered, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [International Patent Publication No. WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)], the RU486-inducible system [Wang et al, *Nat. Biotech.*, 15:239-243 (1997) and Wang et al, *Gene Ther.*, 4:432-441 (1997)] and the rapamycin-inducible system [Magari et al, *J. Clin. Invest.*, 100:2865-2872 (1997)]. Other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a gene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). Examples of promoters that are tissue-specific are known for liver (albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Optionally, plasmids carrying therapeutically useful transgenes may also include selectable markers or reporter genes may include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available [see, e.g., Sambrook et al, and references cited therein].

The combination of the transgene, promoter/enhancer, and 5' and 3' AAV ITRs is referred to as a "minigene" for ease of reference herein. Provided with the teachings of this invention, the design of such a minigene can be made by resort to conventional techniques.

3. Delivery of the Minigene to a Packaging Host Cell

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3' AAV ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene (carrying the 5' AAV ITR-heterologous molecule-3' ITR) may be stably integrated into the genome of the host cell, either chromosomally or as an episome. In certain embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 µg to about 100 µg DNA, about 10 µg to about 50 µg DNA to about $1\times10^4$ cells to about $1\times10^{13}$ cells, or about $1\times10^5$ cells. However, the relative amounts of vector DNA to host cells may be adjusted, taking into consideration such factors as the selected vector, the delivery method and the host cells selected.

B. Rep and Cap Sequences

In addition to the minigene, the host cell contains the sequences which drive expression of a novel AAV capsid protein of the invention (or a capsid protein comprising a fragment thereof) in the host cell and rep sequences of the same source as the source of the AAV ITRs found in the minigene, or a cross-complementing source. The AAV cap and rep sequences may be independently obtained from an AAV source as described above and may be introduced into the host cell in any manner known to one in the art as described above. Additionally, when pseudotyping an AAV vector in (e.g., an AAV9/HU.14 capsid), the sequences encoding each of the essential rep proteins may be supplied by different AAV sources (e.g., AAV1, AAV2, AAV3, AAV4, AAV5, AAV6, AAV7, AAV8). For example, the rep78/68 sequences may be from AAV2, whereas the rep52/40 sequences may be from AAV8.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the chromosome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, E2a, and E4 ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, such as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See International Patent Publication No. WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

By "adenoviral DNA which expresses the E1a gene product", it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

D. Host Cells And Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it not carry any adenovirus gene other than E1, E2a and/or E4 ORF6; it not contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (International Patent Application Publication No. WO 99/15685), or those described in U.S. Pat. No. 5,658,785, may also be similarly employed. Another desirable host cell contains the minimum adenoviral DNA which is sufficient to express E4 ORF6. Yet other cell lines can be constructed using the novel AAV9 cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

The AAV9/HU.14 based vectors which are generated by one of skill in the art are beneficial for gene delivery to selected host cells and gene therapy patients since no neutralization antibodies to AAV9/HU.14 have been found in the human population. One of skill in the art may readily prepare other rAAV viral vectors containing the AAV9/HU.14 capsid proteins provided herein using a variety of techniques known to those of skill in the art. One may similarly prepare still other rAAV viral vectors containing AAV9/HU.14 sequence and AAV capsids from another source.

One of skill in the art will readily understand that the novel AAV sequences of the invention can be readily adapted for use in these and other viral vector systems for in vitro, ex vivo or in vivo gene delivery. Similarly, one of skill in the art can readily select other fragments of the AAV genome of the invention for use in a variety of rAAV and non-rAAV vector systems. Such vectors systems may include, e.g., lentiviruses, retroviruses, poxviruses, vaccinia viruses, and adenoviral systems, among others. Selection of these vector systems is not a limitation of the present invention.

Thus, the invention further provides vectors generated using the nucleic acid and amino acid sequences of the novel AAV of the invention. Such vectors are useful for a variety of purposes, including for delivery of therapeutic molecules and for use in vaccine regimens. Particularly desirable for delivery of therapeutic molecules are recombinant AAV containing capsids of the novel AAV of the invention. These, or other vector constructs containing novel AAV sequences of the invention may be used in vaccine regimens, e.g., for co-delivery of a cytokine, or for delivery of the immunogen itself.

IV. Recombinant Viruses and Uses Therefor

Using the techniques described herein, one of skill in the art can generate a rAAV having a capsid of an AAV of the invention or having a capsid containing one or more fragments of an AAV of the invention. In one embodiment, a full-length capsid from a single AAV, e.g., hu.14/AAV9 [SEQ ID NO: 123] can be utilized. In another embodiment, a full-length capsid may be generated which contains one or more fragments of the novel AAV capsid of the invention fused in frame with sequences from another selected AAV, or from heterologous (i.e., non-contiguous) portions of the same AAV. For example, a rAAV may contain one or more of the novel hypervariable region sequences of AAV9/HU.14. Alternatively, the unique AAV sequences of the invention may be used in constructs containing other viral or non-viral sequences. Optionally, a recombinant virus may carry AAV rep sequences encoding one or more of the AAV rep proteins.

A. Delivery of Viruses

In another aspect, the present invention provides a method for delivery of a transgene to a host which involves transfecting or infecting a selected host cell with a recombinant viral vector generated with the AAV9/HU.14 sequences (or functional fragments thereof) of the invention. Methods for delivery are well known to those of skill in the art and are not a limitation of the present invention.

In one desirable embodiment, the invention provides a method for AAV-mediated delivery of a transgene to a host. This method involves transfecting or infecting a selected host cell with a recombinant viral vector containing a selected transgene under the control of sequences that direct expression thereof and AAV9 capsid proteins.

Optionally, a sample from the host may be first assayed for the presence of antibodies to a selected AAV source (e.g., a serotype). A variety of assay formats for detecting neutralizing antibodies are well known to those of skill in the art. The selection of such an assay is not a limitation of the present invention. See, e.g., Fisher et al, *Nature Med.*, 3(3):306-312 (March 1997) and W. C. Manning et al, *Human Gene Therapy*, 9:477-485 (Mar. 1, 1998). The results of this assay may be used to determine which AAV vector containing capsid proteins of a particular source are preferred for delivery, e.g., by the absence of neutralizing antibodies specific for that capsid source.

In one aspect of this method, the delivery of vector with AAV capsid proteins of the invention may precede or follow delivery of a gene via a vector with a different AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of sources (and preferably, different serotypes) which differ from the first vector. For example, if a first vector has AAV9/HU.14 capsid proteins, subsequently administered vectors may have capsid proteins selected from among the other AAV, optionally, from another serotype or from another clade.

Optionally, multiple rAAV vectors can be used to deliver large transgenes or multiple transgenes by co-administration of rAAV vectors concatamerize in vivo to form a single vector genome. In such an embodiment, a first AAV may carry an expression cassette which expresses a single transgene (or a subunit thereof) and a second AAV may carry an expression cassette which expresses a second transgene (or a different subunit) for co-expression in the host cell. A first AAV may carry an expression cassette which is a first piece of a polycistronic construct (e.g., a promoter and transgene, or subunit) and a second AAV may carry an expression cassette which is a second piece of a polycistronic construct (e.g., transgene or subunit and a polyA sequence). These two pieces of a polycistronic construct concatamerize in vivo to form a single vector genome that co-expresses the transgenes delivered by the first and second AAV. In such embodiments, the rAAV vector carrying the first expression cassette and the rAAV vector carrying the second expression cassette can be delivered in a single pharmaceutical composition. In other embodiments, the two or more rAAV vectors are delivered as separate pharmaceutical compositions which can be administered substantially simultaneously, or shortly before or after one another.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 0.1 mL to about 100 mL of solution containing concentrations of from about $1 \times 10^9$ to $1 \times 10^{16}$ genomes virus vector. A preferred human dosage for delivery to large organs (e.g., liver, muscle, heart and lung) may be about $5 \times 10^{10}$ to $5 \times 10^{13}$ AAV genomes per 1 kg, at a volume of about 1 to 100 mL. A preferred dosage for delivery to eye is about $5 \times 10^9$ to $5 \times 10^{12}$ genome copies, at a volume of about 0.1 mL to 1 mL. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

Examples of therapeutic products and immunogenic products for delivery by the AAV-containing vectors of the invention are provided below. These vectors may be used for a variety of therapeutic or vaccinal regimens, as described herein. Additionally, these vectors may be delivered in combination with one or more other vectors or active ingredients in a desired therapeutic and/or vaccinal regimen.

B. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, argininosuccinate synthetase, argininosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product [e.g., a mini- or micro-dystrophin]. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Still other useful gene products include those used for treatment of hemophilia, including hemophilia B (including Factor IX) and hemophilia A (including Factor VIII and its variants, such as the light chain and heavy chain of the heterodimer and the B-deleted domain; U.S. Pat. No. 6,200,560 and U.S. Pat. No. 6,221,349). The Factor VIII gene codes for 2351 amino acids and the protein has six domains, designated from the amino to the terminal carboxy terminus as A1-A2-B-A3-C1-C2 [Wood et al, *Nature,* 312:330 (1984); Vehar et al., *Nature* 312:337 (1984); and Toole et al, *Nature,* 342:337 (1984)]. Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, the minigene comprises first 57 base pairs of the Factor VIII heavy chain which encodes the 10 amino acid signal sequence, as well as the human growth hormone (hGH) polyadenylation sequence. In alternative embodiments, the minigene further comprises the A1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding Factor VIII heavy chain and light chain are provided in a single minigene separated by 42 nucleic acids coding for 14 amino acids of the B domain [U.S. Pat. No. 6,200,560].

As used herein, a therapeutically effective amount is an amount of AAV vector that produces sufficient amounts of Factor VIII to decrease the time it takes for a subject's blood to clot. Generally, severe hemophiliacs having less than 1% of normal levels of Factor VIII have a whole blood clotting time of greater than 60 minutes as compared to approximately 10 minutes for non-hemophiliacs.

The present invention is not limited to any specific Factor VIII sequence. Many natural and recombinant forms of Factor VIII have been isolated and generated. Examples of naturally occurring and recombinant forms of Factor VII can be found in the patent and scientific literature including, U.S. Pat. No. 5,563,045, U.S. Pat. No. 5,451,521, U.S. Pat. No. 5,422,260, U.S. Pat. No. 5,004,803, U.S. Pat. No. 4,757,006, U.S. Pat. No. 5,661,008, U.S. Pat. No. 5,789,203, U.S. Pat. No. 5,681,746, U.S. Pat. No. 5,595,886, U.S. Pat. No. 5,045,455, U.S. Pat. No. 5,668,108, U.S. Pat. No. 5,633,150, U.S. Pat. No. 5,693,499, U.S. Pat. No. 5,587,310, U.S. Pat. No. 5,171,844, U.S. Pat. No. 5,149,637, U.S. Pat. No. 5,112,950, U.S. Pat. No. 4,886,876; International Patent Publication Nos. WO 94/11503, WO 87/07144, WO 92/16557, WO 91/09122, WO 97/03195, WO 96/21035, and WO 91/07490; European Patent Application Nos. EP 0 672 138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, and EP 0 160 457; Sanberg et al., XXth Int. Congress of the World Fed. Of Hemophilia (1992), and Lind et al., *Eur. J. Biochem.,* 232:19 (1995).

Nucleic acids sequences coding for the above-described Factor VIII can be obtained using recombinant methods or by deriving the sequence from a vector known to include the same. Furthermore, the desired sequence can be isolated directly from cells and tissues containing the same, using standard techniques, such as phenol extraction and PCR of cDNA or genomic DNA [See, e.g., Sambrook et al]. Nucleotide sequences can also be produced synthetically, rather than cloned. The complete sequence can be assembled from overlapping oligonucleotides prepared by standard methods and assembled into a complete coding sequence [See, e.g., Edge, *Nature* 292:757 (1981); Nambari et al, *Science,* 223: 1299 (1984); and Jay et al, *J. Biol. Chem.* 259:6311 (1984).

Furthermore, the invention is not limited to human Factor VIII. Indeed, it is intended that the present invention encompass Factor VIII from animals other than humans, including but not limited to companion animals (e.g., canine, felines, and equines), livestock (e.g., bovines, caprines and ovines), laboratory animals, marine mammals, large cats, etc.

The AAV vectors may contain a nucleic acid coding for fragments of Factor VIII which is itself not biologically active, yet when administered into the subject improves or restores the blood clotting time. For example, as discussed above, the Factor VIII protein comprises two polypeptide chains: a heavy chain and a light chain separated by a B-domain which is cleaved during processing. As demonstrated by the present invention, co-tranducing recipient cells with the Factor VIII heavy and light chains leads to the expression of biologically active Factor VIII. Because most hemophiliacs contain a mutation or deletion in only one of the chains (e.g., heavy or light chain), it may be possible to administer only the chain defective in the patient to supply the other chain.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

C. Immunogenic Transgenes

Suitably, the AAV vectors of the invention avoid the generation of immune responses to the AAV sequences contained within the vector. However, these vectors may nonetheless be formulated in a manner that permits the expression of a transgene carried by the vectors to induce an immune response to a selected antigen. For example, in order to promote an immune response, the transgene may be expressed from a constitutive promoter, the vector can be adjuvanted as described herein, and/or the vector can be put into degenerating tissue.

Examples of suitable immunogenic transgenes include those selected from a variety of viral families. Examples of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Other viral families include the astroviruses and the calcivirus family. The calcivirus family encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cat), feline enteric coronavirus (cat), canine coronavirus (dog), and human respiratory coronaviruses, which may cause the common cold and/or non-A, B or C hepatitis, and which include the putative cause of sudden acute respiratory syndrome (SARS). Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the arterivirus family and the rhabdovirus family. The rhabdovirus family includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. Another source of antigens is the bornavirus family. The reovirus family includes the genera reovirus, rotavirus (which causes acute gastroenteritis in children), orbiviruses, and cultivirus (Colorado Tick fever, Lebombo (humans), equine encephalosis, blue tongue). The retrovirus family includes the sub-family oncorivirinal which encompasses such human and veterinary diseases as feline leukemia virus, HTLVI and HTLVII, lentivirinal (which includes HIV, simian immunodeficiency virus, feline immunodeficiency virus, equine infectious anemia virus, and spumavirinal). The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family includes feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), human herpesviruses 6A, 6B and 7, Kaposi's sarcoma-associated herpesvirus and cercopithecine herpesvirus (B virus), infectious rhinotracheitis, Marek's disease virus, and rhadinovirus. The poxvirus family includes the sub-family chordopoxvirinae, which encompasses the genera orthopoxvirus (Variola major (Smallpox) and Vaccinia (Cowpox)), parapoxvirus, avipoxvirus, capripoxvirus, leporipoxvirus, suipoxvirus, and the subfamily entomopoxvirinae. The hepadnavirus family includes the Hepatitis B virus. One unclassified virus which may be suitable source of antigens is the Hepatitis delta virus, Hepatitis E virus, and prions. Another virus which is a source of antigens is Nipan Virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci (and the toxins produced thereby, e.g., enterotoxin B); and streptococci. Pathogenic gram-negative cocci include meningococcus; gonococcus. Pathogenic enteric gram-negative bacilli include enterobacteriaceae; *pseudomonas*, acinetobacteria and eikenella; melioidosis; *salmonella; shigella; haemophilus; moraxella; H. ducreyi* (which causes chancroid); *brucella* species (brucellosis); *Francisella tularensis* (which causes tularemia); *Yersinia pestis* (plague) and other *yersinia* (*pasteurella*); *streptobacillus moniliformis* and spirillum; Gram-positive bacilli include *listeria monocytogenes; erysipelothrix rhusiopathiae; Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism (*Clostridum botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis; histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever (*Coxiella burnetti*), and Rickettsialpox. Examples of *mycoplasma* and chlamydial infections include: *mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; Pneumocystis carinii; Trichans; Toxoplasma gondii;* babesiosis; giardiasis; trichinosis; filariasis; schistosomiasis; nematodes; trematodes or flukes; and cestode (tapeworm) infections.

Many of these organisms and/or the toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (melioidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In rheumatoid arthritis (RA), several specific variable regions of TCRs which are involved in the disease have been characterized. These TCRs include V-3, V-14, V-17 and V-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and V-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and V-16, V-3C, V-7, V-14, V-15, V-16, V-28 and V-12. Thus, delivery of a nucleic acid molecule that encodes at least one of these polypeptides will elicit an immune response that will target T cells involved in scleroderma.

Thus, a rAAV-derived recombinant viral vector of the invention provides an efficient gene transfer vehicle which can deliver a selected transgene to a selected host cell in vivo or ex vivo even where the organism has neutralizing antibodies to one or more AAV sources. In one embodiment, the rAAV and the cells are mixed ex vivo; the infected cells are cultured using conventional methodologies; and the transduced cells are re-infused into the patient.

These compositions are particularly well suited to gene delivery for therapeutic purposes and for immunization, including inducing protective immunity. Further, the compositions of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

The following examples illustrate several aspects and embodiments of the invention.

Example 1—Computational Analysis of Primate AAV Sequences

A. Collection of Primate Tissues

Sources of nonhuman primate tissues were described previously [N. Muzyczka, K. I. Berns, in *Fields Virology* D. M. Knipe, P. M. Howley, Eds. (Lippincott Williams & Wilkins, Philadelphia, 2001), vol. 2, pp. 2327-2359]. Human tissues were collected from either surgical procedures or postmortem examination or organ donors through two major national human tissue providers, Cooperative Human Tissue Network (CHTN) and National Disease Research Interchange (NDRI). Human tissues used for this study were comprised of 18 different tissue types that included colon, liver, lung, spleen, kidney, brain, small bowel, bone marrow, heart, lymph nodes, skeletal muscle, ovary, pancreas, stomach, esophagus, cervix, testis and prostate. The tissue samples came from a diverse group of individuals of different gender, races (Caucasian, African-American, Asian and Hispanic) and ages (23-83 years). Among 259 samples from 250 individuals analyzed, approximately 28% of tissues were associated with pathology.

B. Detection and Isolation of AAV Sequences

Total cellular DNAs were extracted from human and nonhuman primate tissues as described previously [R. W. Atchison, et al., *Science* 194, 754-756 (1965)]. Molecular prevalence and tissue distribution of AAVs in humans were determined by either signature or full-length cap PCR using the primers and conditions that were similar to those used for the nonhuman primate analysis. The same PCR cloning strategy used for the isolation and characterization of an expanded family of AAVs in nonhuman primates was deployed in the isolation of AAVs from selected human tissues. Briefly, a 3.1 kb fragment containing a part of rep and full length cap sequence was amplified from tissue DNAs by PCR and Topo-cloned (Invitrogen). The human AAV clones were initially analyzed by restriction mapping to help identify diversity of AAV sequences, which were subsequently subjected to full sequence analysis by SeqWright (SeqWright, Houston, Tex.) with an accuracy of 99.9%. A total of 67 capsid clones isolated from human tissues were characterized (hu.1-hu.67). From nonhuman primate tissues, 86 cap clones were sequenced, among which 70 clones were from rhesus macaques, 6 clones from cynomologus macaques, 3 clones from pigtailed macaques, 2 clones from a baboon and 5 clones from a chimpanzee.

C. Analysis of AAV Sequences

From all contiguous sequences, AAV capsid viral protein (vp1) open reading frames (ORFs) were analyzed. The AAV capsid VP1 protein sequences were aligned with the ClustalX1.81™ program [H. D. Mayor, J. L. Melnick, *Nature* 210, 331-332 (1966)] and an in-frame DNA alignment was produced with the BioEdit™ [U. Bantel-Schaal, H. Zur Hausen, *Virology* 134, 52-63 (1984)] software package. Phylogenies were inferred with the MEGA™ v2.1 and the TreePuzzle™ package. Neighbor-Joining, Maximum Parsimony, and Maximum Likelihood [M. Nei, S. Kumar, *Molecular Evolution and Phylogenetics* (Oxford University Press, New York, 2000); H. A. Schmidt, K. Strimmer, M. Vingron, A. von Haeseler, *Bioinformatics* 18, 502-4 (March, 2002); N. Saitou, M. Nei, *Mol Biol Evol* 4, 406-25 (July, 1987)] algorithms were used to confirm similar clustering of sequences in monophylic groups.

Clades were then defined from a Neighbor-Joining phylogenetic tree of all protein sequences. The amino-acid distances were estimated by making use of Poisson-correction. Bootstrap analysis was performed with a 1000 replicates. Sequences were considered monophylic when they had a connecting node within a 0.05 genetic distance. A group of sequences originating from 3 or more sources was considered a clade. The phylogeny of AAV was further evaluated for evidence of recombination through a sequential analysis. Homoplasy was screened for by implementation of the Split Decomposition algorithm [H. J. Bandelt, A. W. Dress, *Mol Phylogenet Evol* 1, 242-52 (September 1992)]. Splits that were picked up in this manner were then further analyzed for recombination making use of the Bootscan algorithm in the Simplot software [M. Nei and S. Kumar, *Molecular Evolution and Phylogenetics* (Oxford University Press, New York, 2000)]. A sliding window of 400 nt (10 nt/step) was used to obtain 100 bootstrap replicate neighbor-joining trees. Subsequently, Split Decomposition and Neighbor-Joining phylogenies were inferred from the putative recombination fragments. Significant improvement of bootstrap values, reduction of splits and regrouping of the hybrid sequences with their parental sources were considered the criterion for recombination.

A number of different cap sequences amplified from 8 different human subjects showed phylogenetic relationships to AAV2 (5') and AAV3 (3') around a common breakpoint at position 1400 of the Cap DNA sequence, consistent with recombination and the formation of a hybrid virus. This is the general region of the cap gene where recombination was detected from isolates from a mesenteric lymph node of a rhesus macaque [Gao et al., *Proc Natl Acad Sci USA* 100, 6081-6086 (May 13, 2002)]. An overall codon based Z-test for selection was performed implementing the Neib-Gojobori method [R. M. Kotin, *Hum Gene Ther* 5, 793-801 (July, 1994)].

The phylogenetic analyses were repeated excluding the clones that were positively identified as hybrids. In this analysis, goose and avian AAVs were included as outgroups [(I. Bossis, J. A. Chiorini, *J Virol* 77, 6799-810 (June 2003)]. FIG. 1 is a neighbor joining tree; similar relationships were obtained using maximum parsimony and maximum likelihood analyses.

This analysis demonstrated 11 phylogenetic groups, which are summarized in Table 1. The species origin of the 6 AAV clades and 5 individual AAV clones (or sets of clones) is represented by the number or sources from which the sequences were retrieved in the sampling. The total number of sequences gathered per species and per grouping is shown in between brackets. References for previously described sequences per clade are in the right column Rhesus—rhesus macaques; cyno—cynomologus macaques; chimp—chimpanzees; pigtail—pigtail macaques.

TABLE 1

Classification of the number of sources (sequences) per species and per clade or clone

| | Human | Rhesus | Cyno | Baboon | Chimp | Pigtail |
|---|---|---|---|---|---|---|
| Clade/representative | | | | | | |
| A/AAV1(AAV6) | 3(4) | | | | | |
| B/AAV2 | 12(22) | | | | | |
| C/AAV2-AAV3 hybrid | 8(17) | | | | | |
| D/AAV7 | | 5(10) | 5(5) | | | |
| E/AAV8 | 7(9) | 7(16) | | 1(2) | | 1(3) |
| F/AAV9 | 3(3) | | | | | |
| Clones | | | | | | |
| AAV3 | | | | | | |
| AAV4 | | 1(3) | | | | |
| AAV5 | | | | | | |
| Ch. 5 | | | | | 1(1) | |
| Rh. 8 | | 2(2) | | | | |

Since, as noted above, recombination is not implemented in the standard phylogenetic algorithms used, in order to build a proper phylogenetic tree, those sequences were excluded from the analysis, of which their recombinative ancestry was established. A neighbor-joining analysis of all non-recombined sequences is represented side by side with the clades that did evolve making use of recombination. A similar output was generated with the different algorithm used and with the nucleotide sequence as input.

Additional experiments were performed to evaluate the relationship of phylogenetic relatedness to function as measured by serologic activity and tropism, as described in the following examples.

Example 2—Serological Analysis of Novel Human AAVs

The last clade obtained as described in the preceding example was derived from isolates of 3 humans and did not contain a previously described serotype. Polyclonal antisera were generated against a representative member of this clade and a comprehensive study of serologic cross reactivity between the previously described serotypes was performed. This showed that the new human clade is serologically distinct from the other known serotypes and therefore is called Clade F (represented by AAV9).

Rabbit polyclonal antibodies against AAV serotypes 1-9 were generated by intramuscularly inoculating the animals with $1\times10^{13}$ genome copies each of AAV vectors together with an equal volume of incomplete Freud's adjuvant. The injections were repeated at day 34 to boost antibody titers. Serological cross reactivity between AAV 1-9 was determined by assessing the inhibitory effect of rabbit antisera on transduction of 293 cells by vectors carrying a reporter gene (AAVCMVEGFP, which carries enhanced green fluorescent protein) pseudotyped with capsids derived from different AAV sources. Transduction of 84-31 cells by AAVCMVEGFP vectors was assessed under a UV microscope. In assessing serologic relationships between two AAVs, the ability of both heterologous and homologous sera to neutralize vectors from each AAV were tested. If neutralization by the serum was at least 16-fold lower against heterologous vectors than homologous vectors in a reciprocal manner, the two AAVs are considered distinct serotypes. Neutralization titers were defined as described previously [(G. P. Gao et al., *Proc Natl Acad Sci USA* 99, 11854-9 (Sep. 3, 2002)].

with all other AAV serotypes compared in this study. Those findings provided the basis for us to name AAVhu.14 as a new serotype, AAV9.

Example 3—Evaluation of Primate AAVs as Gene Transfer Vectors

The biological tropisms of AAVs were studied by generating vector pseudotyped in which recombinant AAV2 genomes expressing either GFP or the secreted reporter gene α-1 antitrypsin (A1AT) were packaged with capsids derived from various clones and one representative member from each primate AAV clade for comparison. For instance, the data obtained from AAV1 was used to represent Clade A, followed by AAV2 for Clade B, Rh.34 for AAV4, AAV7 for Clade D, AAV8 for Clade E, and AAVHu.14 for Clade F. AAV5, AAVCh.5 and AAVRh.8 stand as single AAV genotypes for the comparison.

The vectors were evaluated for transduction efficiency in vitro, based on GFP transduction, and transduction efficiency in vivo in liver, muscle or lung (FIG. 4).

A. In Vitro

Vectors expressing enhanced green fluorescent protein (EGFP) were used to examine their in vitro transduction efficiency in 84-31 cells and to study their serological properties. For functional analysis, in vitro transduction of different AAVCMVEGFP vectors was measured in 84-31 cells that were seeded in a 96 well plate and infected with pseudotyped AAVCMVEGFP vectors at an MOI of $1\times10^{4}$ GC per cell. AAV vectors were pseudotyped with capsids of AAVs 1, 2, 5, 7, 8 and 6 other novel AAVs (Ch.5, Rh.34, Cy5, rh.20, Rh.8 and AAV9) using the technique described in G. Gao et al., *Proc Natl Acad Sci USA* 99, 11854-9 (Sep. 3, 2002). Relative EGFP transduction efficiency was scored as 0, 1, 2 and 3 corresponding to 0-10%, 10-30%, 30-70% and 70-100% of green cells estimated using a UV microscope at 48 hours post infection.

TABLE 2

Serologic evaluation of novel AAV vectors
Vector pseudotypes used in the neutralization assay

| from rabbit immunized with: | AAV2/1 | AAV2/2 | AAV2/3 | AAV2/4 | AAV2/5 | AAV2/6 | AAV2/7 | AAV2/8 | AAV2/9 |
|---|---|---|---|---|---|---|---|---|---|
| AAV2/1 | 1/163,840 | No NAB | No NAB | No NAB | 1/40,960 | 1/40,960 | 1/40 | No NAB | No NAB |
| AAV2/2 | 1/80 | 1/81,920 | 1/5,120 | 1/20 | No NAB | 1/80 | 1/40 | 1/40 | No NAB |
| AAV2/3 | 1/1,280 | 1/2,560 | 1/40,960 | 1/20 | 1/40 | 1/2,560 | 1/1,280 | 1/1,280 | No NAB |
| AAV2/4 | 1/20 | No NAB | No NAB | 1/1,280 | 1/40 | No NAB | No NAB | No NAB | 1/40 |
| AAV2/5 | 1/20,480 | No NAB | 1/80 | No NAB | 1/163,840 | 1/5,120 | 1/40 | No NAB | No NAB |
| AAV2/6 | 1/81,920 | No NAB | 1/640 | 1/40 | 1/40 | 1/327,680 | 1/40 | No NAB | 1/40 |
| AAV2/7 | 1/1,280 | 1/640 | 1/1,280 | 1/20 | No NAB | 1/1,280 | 1/163,840 | 1/5,120 | 1/80 |
| AAV2/8 | 1/20 | 1/1,280 | 1/1,280 | No NAB | 1/20 | No NAB | 1/640 | 1/327,680 | 1/2,560 |
| AAV2/9 | No NAB | No NAB | No NAB | No NAB | No NAB | No NAB | 1/20 | 1/640 | 1/20,480 |

These data confirm the phylogenetic groupings of the different clones and clades except for unanticipated serological reactivity of the structurally distinct AAV5 and AAV1 serotypes (i.e., ratio of heterologous/homologous titer were ¼ and ⅛ in reciprocal titrations).

The result further indicated that AAVhu.14 had a distinct serological property and did not have significant cross reactivity with antisera generated from any known AAV serotypes. The serological distinctiveness of AAVhu.14 was further supported by its uniqueness in the capsid structure which shared less than 85% amino acid sequence identity B. In Vivo For in vivo studies, human α-antitrypsin (A1AT) was selected as a sensitive and quantitative reporter gene in the vectors and expressed under the control of CMV-enhanced chicken β-actin promoter. Employment of the CB promoter enables high levels of tissue non-specific and constitutive A1AT gene transfer to be achieved and also permits use of the same vector preparation for gene transfer studies in any tissue of interest. Four to six week old NCR nude mice were treated with novel AAV vectors (AAVCBhA1AT) at a dose of $1\times10^{11}$ genome copies per animal through intraportal, intratracheal and intramuscular injections for liver, lung and muscle directed gene transfer, respectively. Serum samples were collected at different time points post gene transfer and A1AT concentrations were determined by an ELISA-based acid differences after a pairwise deletion of gaps by 750, the length of the VP1 protein sequence alignment.

|       | AAV1 | AAV2 | AAV3 | Ch. 5 | AAV4 | AAV5 | AAV7 | AAV8 | Rh. 8 | AAV9 |
|-------|------|------|------|-------|------|------|------|------|-------|------|
| AAV1  | 0    | 5    | ND   | 4     | 4    | 4    | 2    | 4    | 5     | 4    |
| AAV2  | *16.3* | 0  | ND   | 3     | 2    | 4    | 7    | 7    | 6     | 9    |
| AAV3  | *13.2* | *12.3* | 0 | ND   | ND   | ND   | ND   | ND   | ND    | ND   |
| Ch. 5 | *15.5* | *10.5* | *11.5* | 0 | 2   | 4    | 6    | 6    | 5     | 8    |
| AAV4  | *33.7* | *36.7* | *34.8* | *34.9* | 0 | 2 | 7    | 6    | 5     | 8    |
| AAV5  | *39.1* | *38.8* | *38.5* | *38.4* | *42.7* | 0 | 4  | 4    | 3     | 6    |
| AAV7  | *14.1* | *16.7* | *14.9* | *15.6* | *33.2* | *38.5* | 0 | 2 | 3     | 2    |
| AAV8  | *15.6* | *16.4* | *14*   | *15.6* | *33.2* | *38.9* | *11.6* | 0 | 1  | 2    |
| Rh. 8 | *14.1* | *15.2* | *14.3* | *14.4* | *33.7* | *39.6* | *12.1* | *8.8* | 0 | 3 |
| AAV9  | *17.2* | *17.3* | *15.6* | *14.8* | *34.5* | *39.7* | *17.5* | *14.3* | *12.5* | 0 | assay and scored as 0, 1, 2 and 3 relative to different serum A1AT levels at day 28 post gene transfer, depending on the route of vector administration (Liver: 0=A1AT<400 ng/ml, 1=A1AT 400-1000 ng/ml, 2=A1AT 1000-10,000 ng/ml, 3=A1AT>10,000 ng/ml; Lung: 0=A1AT<200 ng/ml, 1=A1AT 200-1000 ng/ml, 2=A1AT 1000-10,000 ng/ml, 3=A1AT>10,000 ng/ml; Muscle: 0=A1AT<100 ng/ml, 1=A1AT 100-1000 ng/ml, 2=A1AT 1000-10,000 ng/ml, 3=A1AT>10,000 ng/ml).

A human AAV, clone 28.4/hu.14 (now named AAV9), has the ability to transduce liver at a efficiency similar to AAV8, lung 2 logs better than AAV5 and muscle superior to AAV1, whereas the performance of two other human clones, 24.5 and 16.12 (hu.12 and hu.13) was marginal in all 3 target tissues. Clone N721.8 (AAVrh.43) is also a high performer in all three tissues.

To further analyze gene transfer efficiency of AAV9 and rh 43 in comparison with that of bench markers for liver (AAV8), lung (AAV5) and muscle (AAV1), a dose response experiment was carried out. Both new vectors demonstrated at least 10 fold more gene transfer than AAV1 in muscle, similar performance to AAV8 in liver and 2 logs more efficient than AAV5 in lung.

A group of AAVs demonstrated efficient gene transfer in all 3 tissues that was similar or superior to the performance of their bench marker in each tissue has emerged. To date, 3 novel AAVs have fallen into this category, two from rhesus (rh10 and 43) and one from human (hu.14 or AAV9). A direct comparison of relative gene transfer efficiency of those 3 AAVs to their bench markers in the murine liver, lung and muscle suggests that some primate AAVs with the best fitness might have evolved from rigorous biological selection and evolution as "super" viruses. These are particularly well suited for gene transfer applications.

C. Profiles of Biological Activity

Unique profiles of biological activity, in terms of efficiency of gene transfer, were demonstrated for the different AAVs with substantial concordance within members of a set of clones or clade. However, in vitro transduction did not predict the efficiency of gene transfer in vivo. An algorithm for comparing the biological activity between two different AAV pseudotypes was developed based on relative scoring of the level of transgene expression and a cumulative analysis of differences.

Cumulative differences of the gene transfer scores in vitro and in vivo between pairs of AAVs were calculated and presented in the table (ND=not determined) according to the following formula. Cumulative functional difference in terms of scores between vectors A and B=in vitro (A−B)+ lung (A−B)+liver (A−B)+muscle (A−B). The smaller the number, the more similar in function the AAVs. In the grey shaded area, the percentage difference in sequence is represented in bold italic. The percentage difference in cap structure was determined by dividing the number of amino- These studies point out a number of issues relevant to the study of parvoviruses in humans. The prevalence of endogenous AAV sequences in a wide array of human tissues suggests that natural infections with this group of viruses are quite common. The wide tissue distribution of viral sequences and the frequent detection in liver, spleen and gut indicate that transmission occurs via the gastrointestinal track and that viremia may be a feature of the infection.

The tremendous diversity of sequence present in both human and nonhuman primates has functional correlates in terms of tropism and serology, suggesting it is driven by real biological pressures such as immune escape. Clearly, recombination contributes to this diversity as evidenced by the second most common human clade, which is a hybrid of two previously described AAVs.

Inspection of the topology of the phylogenetic analysis reveals insight into the relationship between the evolution of the virus and its host restriction. The entire genus of dependoviruses appears to be derived from avian AAV consistent with Lukashov and Goudsmit [(V. V. Lukashov, J. Goudsmit, *J Virol* 75, 2729-40 (March, 2001)]. The AAV4 and AAV5 isolates diverged early from the subsequent development of the other AAVs. The next important node divides the species into two major monophilic groups. The first group contains clones isolated solely from humans and includes Clade B, AAV3 clone, Clade C and Clade A; the only exception to the species restriction of this group is the single clone from chimpanzees, called ch.5. The other monophilic group, representing the remaining members of the genus, is derived from both human and nonhuman primates. This group includes Clade D and the rh.8 clone, which were isolated exclusively from macaques, and the Clade F, which is human specific. The remaining clade within this group (i.e., Clade E) has members from both humans and a number of nonhuman primate species suggesting transmission of this clade across species barriers. It is interesting that the capsid structures of Clade E members isolated from some humans are essentially identical to some from nonhuman primates, indicating that very little host adaptation has occurred. Analysis of the biology of AAV8 derived vectors demonstrated a broad range of tissue tropism with high levels of gene transfer, which is consistent with a more promiscuous range of infectivity, and may explain its apparent zoonosis. An even greater range and efficiency of gene transfer was noted for the Clade F, highlighting the potential for cross species transmission, which to date has not been detected.

The presence of latent AAVs widely disseminated throughout human and nonhuman primates and their apparent predisposition to recombine and to cross species barriers raises important issues. This combination of events has the potential to lead to the emergence of new infectious agents with modified virulence. Assessing this potential is confounded by the fact that the clinical sequalae of AAV infections in primates has yet to be defined. In addition, the high prevalence of AAV sequences in liver may contribute to dissemination of the virus in the human population in the setting of allogeneic and xenogenic liver transplantation. Finally, the finding of endogenous AAVs in humans has implications in the use of AAV for human gene therapy. The fact that wild type AAV is so prevalent in primates without ever being associated with a malignancy suggests it is not particularly oncogenic. In fact, expression of AAV rep genes has been shown to suppress transformation P. L. Hermonat, *Virology* 172, 253-61 (September, 1989)].

Example 4—AAV 2/9 Vector for the Treatment of Cystic Fibrosis Airway Disease To date, CFTR gene transfer to the lung for the treatment of CF airway disease has been limited by poor vector performance combined with the significant barriers that the airway epithelium poses to effective gene transfer. The AAV2 genome packaged in the AAV9 capsid (AAV2/9) was compared to AAV2/5 in various airway model systems.

A 50 μl single dose of $1 \times 10^{11}$ genome copies (gc) of AAV2/9 expressing either the nuclear targeted β-galactosidase (nLacZ) gene or the green fluorescence protein (GFP) gene under the transcriptional control of the chicken β-actin promoter was instilled intranasally into nude and also C57Bl/6 mice. Twenty-one days later, the lung and nose were processed for gene expression. In control animals transduced with AAV2/9-GFP, no LacZ positive cells were seen. AAV2/9-nLacZ successfully transduced mainly airways, whereas AAV2/5-nLacZ transduced mainly alveoli and few airways. Across the nasal airway epithelium, both AAV2/5 and AAV2/9 transduced ciliated and non-ciliated epithelial cells.

Epithelial cell specific promoters are currently being evaluated to improve targeting to the airway cells in vivo. Based on the in vivo findings, the gene transfer efficiency of AAV2/9 to human airway epithelial cells was tested next. Airway epithelial cells were isolated from human trachea and bronchi and grown at air-liquid-interface (ALI) on collagen coated membrane supports. Once the cells polarized and differentiated, they were transduced with AAV2/9 or AAV2/5 expressing GFP from the apical as well as the basolateral side. Both AAV2/5 and AAV2/9 were successful at transducing epithelial cells from the basolateral surface. However, when applied onto the apical surface AAV2/9 resulted in a 10-fold increase in the number of transduced cells compared to AAV2/5. Currently, the gene transfer performance of AAV2/9 in the lungs and nasal airways of nonhuman primates is being evaluated.

This experiment demonstrates that AAV2/9 can efficiently transduce the airways of murine lung and well-differentiated human airway epithelial cells grown at ALI.

Example 5—Comparison of Direct Injection of AAV1(2/1) and AAV9(2/9) in Adult Rat Hearts Two adult (3 month old) rats received a single injection of $5 \times 10^{11}$ particles of AAV2/1 or AAV2/9 in the left ventricle The results were spectacular, with significantly more expression observed in the adult rat heart with AAV2/9 vectors as compared to AAV2/1, as assessed by lacZ histochemistry. AAV2/9 also shows superior gene transfer in neonatal mouse heart.

Example 6—AAV2/9 Vector for Hemophilia B Gene Therapy

In this study, AAV 2/9 vectors are shown to be more efficient and less immunogenic vectors for both liver and muscle-directed gene therapy for hemophilia B than the traditional AAV sources.

For a liver-directed approach, evaluation of the AAV2/9 pseudotyped vector was performed in mouse and dog hemophilic models. In immunocompetent hemophilia B mice (in C57BL/6 background), long-term superphysiological levels of canine Factor IX (cFIX, 41-70 μg/ml) and shortened activated partial thromboplastin time (aPTT) have been achieved following intraportal injection of $1 \times 10^{11}$ genome copies (GC)/mouse of AAV2/7, 2/8, and 2/9 vectors in which the cFIX is expressed under a liver specific promoter (LSP) and woodchuck hepatitis B post-transcriptional responsive element (WPRE). A 10-fold lower dose ($1 \times 10^{10}$ GC/mouse) of AAV2/8 vector generated normal level of cFIX and aPTT time. In University of North Caroline (UNC) hemophilia B dogs, it was previously demonstrated that administration of an AAV2/8 vector into a dog previously treated with an AAV2 vector was successful; cFIX expression peaked at 10 μg/ml day 6 after the $2^{nd}$ intraportal injection (dose=$5 \times 10^{12}$ GC/kg), then gradually decreased and stabilized around 700 ng/ml (16% of the normal level) throughout the study (1½ years). This level was about 3-fold higher than that from a hemophilia B dog that received a single injection of AAV2-cFIX at the similar dose. Recently, two naïve hemophilia B dogs were injected with AAV2/8 vectors intraportally at the dose of $5.25 \times 10^{12}$ GC/kg. cFIX levels in one dog (male) reached 30% of normal level (1.5 μg/ml) ten weeks after injection and has sustained at 1.3-1.5 μg/ml, while the second dog (female) maintained cFIX expression at about 10% of normal level. Whole blood clotting time (WBCT) and aPTT were both shortened after the injection, suggesting the antigen was biologically active. Liver enzymes (aspartate amino transferase (SGOT), alanine amino transferase (SGPT) in both dogs remained in the normal range after surgery. These AAV were also evaluated for muscle-targeted gene therapy of hemophilia B. AAV-CMV-cFIX-WPRE [an AAV carrying cFIX under the control of a CMV promoter and containing the WPRE] packaged with six different AAV sources were compared in immunocompetent hemophilia B mice (in C57BL/6 background) after intramuscular injection at the dose of $1 \times 10^{11}$ GC/mouse. cFIX gene expression and antibody formation were monitored. Highest expression was detected in the plasma of the mice injected with AAV2/8 vectors (1460±392 ng/ml at day 42), followed by AAV2/9 (773±171 ng/ml at day 42) and AAV2/7 (500±311 ng/ml at day 42). Levels were maintained for 5 months. Surprisingly, cFIX expression by AAV2/1 ranged from 0-253 ng/ml (average: 66±82 ng/ml). Anti-cFIX inhibitor (IgG) was detected in some of the AAV2/1-injected mice. cFIX expression levels in these mice correlated well with inhibitor levels. Further screening of inhibitor formation was performed on day 28 samples for all AAV. Hemophilia B mice showed highest inhibitor formation against AAV2/2, followed by AAV2/5, and AAV2/1. Only sporadic and low level inhibitors were detected in animals injected with AAV2/7, AAV2/8 and AAV2/9. Thus, the advantages of the new AAV serotype 2/9 vectors for muscle-directed gene therapy for hemophilia B as more efficient and safe vectors without eliciting any significant anti-FIX antibody formation are shown.

Example 7—Novel Rh.43 Vectors of Invention

A. Comparison of AAVrh.43 Based A1AT Expression Vector with AAV8 and AAV9 in Mouse Liver Directed Gene Transfer Novel AAVrh.43, which belongs to Clade E by phylogenetic analysis vector was compared to AAV8 and novel AAV9 for hA1AT levels after intraportal infusion to the mouse liver. More particularly, pseudotyped AAVrh.43, AAV2/8 and AAV2/9 vectors were compared in mouse liver-directed gene transfer. Pseudotyped vectors at doses of $1 \times 10^{11}$ GC, $3 \times 10^{10}$ GC and $1 \times 10^{10}$ GC per animal were administrated to 4-6 week old C57BL/6 mouse intramuscularly. Serum samples were collected from animals at day 28 post vector infusion for the human alpha 1 anti-trypsin (hA1AT) assay.

The data indicated that the novel AAVrh.43 vector had indeed a performance similar to that of AAV9 in the mouse model.

B. Nuclear Target LacZ Gene Transfer to Mouse Liver and Muscle Mediated by Pseudotyped AAV Vectors.

Novel AAV9 and AAVrh.43 based vectors of the invention were compared to AAV1 and AAV2-based vector. The vectors were injected at a dose of $1 \times 10^{11}$ GC per mouse either intraportally to target liver or intramuscularly to the right anterior tibialis muscle of C57BL/6 mice intramuscularly. The animals were sacrificed at day 28 post gene transfer and tissues of interest harvested for X-gal histochemical staining.

The AAVrh.43 vector demonstrated gene transfer efficiency that was close to AAV9 but at least 5 fold higher than AAV1. The property of AAVrh.43 was further analyzed in both liver and muscle using nuclear targeted LacZ gene as a reporter to visualize extend of gene transfer histochemically.

C. Comparison of AAVrh.43 Based A1AT Expression Vector with AAV5 in Mouse Lung Directed Gene Transfer A novel rh.43-based vector of the invention also demonstrated superb gene transfer potency in lung tissue. Different doses ($1 \times 10^{10}$, $3 \times 10^{10}$ and $1 \times 10^{11}$ GC per animal) of pseudotyped vectors were administrated to 4-6 week old C57BL/6 mouse lungs intratracheally. Serum samples were collected from animals at different time points for hA1AT assay.

This vector was compared to AAV5 at different doses for levels of hA1AT detected systematically after intratracheal instillation to the mouse lung. The data indicated that this novel vector was at lease 100 fold more efficient than AAV5 in the mouse model.

Example 8—Novel Human AAV Based Vectors in Mouse Models for Liver and Lung-Directed Gene Transfer The human clones, AAVhu.37, AAVhu.41 and AAVhu.47 were pseudotyped and examined for gene transfer potency in mouse tissues. AAVCBA1AT vectors pseudotyped with capsids of hu.37, hu.41 and hu.47 were prepared using the methods described herein and administrated to 4-6 week old C57BL/6 mouse through intraportal and intratracheal injections. Serum samples were collected from animals at day 14 post vector injection for hA1AT assay, which was performed in accordance with published techniques. AAVhu.47 belongs to AAV2 family (clade B) AAV2 and was isolated from a human bone marrow sample. AAVhu.37 and AAVhu.41 came from a human testis tissue and a human bone marrow sample respectively. Phylogenetically, they fall into the AAV 8 clade (clade E).

Serum A1AT analysis of injected animals indicated that AAV hu.41 and AAV hu.47 performed poorly in the three tissues tested. However, gene transfer potency of AAVhu.37 derived vector was similar to that of AAV8 in liver and AAV9 in lung All publications cited in this specification are incorporated herein by reference. While the invention has been described with reference to particularly preferred embodiments, it will be appreciated that modifications can be made without departing from the spirit of the invention.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10973928B2). An electronic copy of the "Sequence Listing" will also be available from the USPTO upon request and payment of the fee set forth in 37 CFR 1.19(b)(3).

The invention claimed is:

1. A recombinant adeno-associated virus (rAAV) having an AAV capsid comprising vp1 proteins, vp2 proteins, and vp3 proteins, wherein the vp3 proteins have the amino acid sequence of amino acids 203 to 736 of SEQ ID NO: 123 (AAV9 capsid protein) with 1 to 26 amino acid modifications, and wherein the AAV capsid has packaged therein a minigene having AAV inverted terminal repeats and a heterologous gene operably linked to regulatory sequences which direct expression of the heterologous gene in a host cell.

2. The rAAV according to claim 1, wherein the AAV vp3 capsid protein has an amino acid sequence which is at least 97% identical to the amino acids 203 to 736 of SEQ ID NO: 123.

3. A composition comprising the rAAV according to claim 1 and a physiologically compatible carrier.

4. A recombinant adeno-associated virus (rAAV) having an AAV capsid comprising vp1 proteins, vp2 proteins, and vp3 proteins, wherein the vp1 proteins have the amino acid sequence of amino acids 1 to 736 of SEQ ID NO: 123 (AAV9 capsid protein) with 1 to 37 amino acid modifications and wherein the AAV capsid has packaged therein a minigene having AAV inverted terminal repeats and a heterologous gene operably linked to regulatory sequences which direct expression of the heterologous gene in a host cell.

5. The rAAV according to claim 4, wherein the AAV vp1 capsid protein has an amino acid sequence which is at least 97% identical to the amino acids 1 to 736 of SEQ ID NO: 123.

6. The rAAV according to claim 4, wherein the AAV vp1 capsid protein has an amino acid sequence which is at least 99% identical to the amino acids 1 to 736 of SEQ ID NO: 123.

7. The rAAV according to claim 4, wherein the AAV vp3 capsid protein has an amino acid sequence which is at least 97% identical to the amino acids 203 to 736 of SEQ ID NO: 123.

8. The rAAV according to claim 4, wherein the AAV vp3 capsid protein has an amino acid sequence which is at least 99% identical to the amino acids 203 to 736 of SEQ ID NO: 123.

9. A recombinant adeno-associated virus (rAAV) having an AAV capsid comprising vp1 proteins, vp2 proteins, and vp3 proteins, wherein the vp2 proteins have the amino acid sequence of amino acids 138 to 736 of SEQ ID NO: 123 (AAV9 capsid protein) with 1 to 29 amino acid modifications, and wherein the AAV capsid has packaged therein a minigene having AAV inverted terminal repeats and a heterologous gene operably linked to regulatory sequences which direct expression of the heterologous gene in a host cell.

10. The rAAV according to claim 9, wherein the AAV vp2 capsid protein has an amino acid sequence which is at least 97% identical to the amino acids 138 to 736 of SEQ ID NO: 123.

11. The rAAV according to claim 9, wherein the AAV vp2 capsid protein has an amino acid sequence which is at least 99% identical to the amino acids 138 to 736 of SEQ ID NO: 123.

* * * * *